US012674171B2

(12) United States Patent
Green et al.

(10) Patent No.: US 12,674,171 B2
(45) Date of Patent: Jul. 7, 2026

(54) APTAMER AND RIBOZYME EQUILIBRIUM SHIFTING (ARES) RNA CIRCUITS AND USES THEREOF

(71) Applicant: TRUSTEES OF BOSTON UNIVERSITY, Boston, MA (US)

(72) Inventors: Alexander Arthur Green, Chestnut Hill, MA (US); McKayla Taylor Masity, Brighton, MA (US)

(73) Assignee: TRUSTEES OF BOSTON UNIVERSITY, Boston, MA (US)

( * ) Notice: Subject to any disclaimer, the term of this patent is extended or adjusted under 35 U.S.C. 154(b) by 0 days.

(21) Appl. No.: 19/092,639

(22) Filed: Mar. 27, 2025

(65) Prior Publication Data

US 2025/0304975 A1 Oct. 2, 2025

Related U.S. Application Data

(60) Provisional application No. 63/570,609, filed on Mar. 27, 2024.

(51) Int. Cl.
| | |
|---|---|
| *C12N 15/67* | (2006.01) |
| *C12N 15/113* | (2010.01) |
| *C12N 15/115* | (2010.01) |

(52) U.S. Cl.
CPC ............ *C12N 15/67* (2013.01); *C12N 15/113* (2013.01); *C12N 15/115* (2013.01); *C12N 2310/121* (2013.01); *C12N 2310/16* (2013.01); *C12N 2830/42* (2013.01); *C12N 2830/52* (2013.01); *C12N 2840/007* (2013.01)

(58) Field of Classification Search
None
See application file for complete search history.

(56) References Cited

U.S. PATENT DOCUMENTS

2011/0245326 A1 10/2011 Belmont et al.

OTHER PUBLICATIONS

Hirao et al., "The limits of specificity: An experimental analysis with RNA aptamers to MS2 coat protein variants" 4 Molecular Diversity 75-89 (Year: 1999).*
Biddlecome et al. "Delivery of self-amplifying RNA vaccines in in vitro reconstituted virus-like particles." Plos ONE. 14: Art. 6 (2019).
Fukunaga et al. "Small-molecule Aptamer for Regulating RNA functions in Mammalian Cells and Animals." Journal of American Chemical Society 145: Art. 14 (2023).
Athanassiou et al. "Structural mimicry of retroviral tat proteins by constrained ß-hairpin peptidomimetics: ligands with high affinity and selectivity for viral TAR RNA regulatory elements." Journal of the American Chemical Society 126.22: 6906-6913 (2004).

Bashor et al. "Engineering the next generation of cell-based therapeutics." Nature Reviews Drug Discovery 21.9: 655-675 (2022).
Bayer et al. "Arginine-rich motifs present multiple interfaces for specific binding by RNA." RNA 11.12: 1848-1857 (2005).
Bloom et al. "Self-amplifying RNA vaccines for infectious diseases." Gene therapy 28.3: 117-129 (2021).
Chai et al. "SELEX (Systematic Evolution of Ligands by EXponential Enrichment), as a powerful tool for deciphering the protein—DNA interaction space." Plant transcription factors: methods and protocols, Methods in Molecular Biology 754: 249-258 (2011).
Chehelgerdi et al. "The use of RNA-based treatments in the field of cancer immunotherapy." Molecular Cancer 22.1: 106 (2023).
Cocozaki et al. "The RNA-binding domain of bacteriophage P22 N protein is highly mutable, and a single mutation relaxes specificity toward λ." Journal of bacteriology 190.23: 7699-7708 (2008).
Dykstra et al. "Engineering synthetic RNA devices for cell control." Nature Reviews Genetics 23.4: 215-228 (2022).
Fenton et al. "Synthesis and biological evaluation of ionizable lipid materials for the in vivo delivery of messenger RNA to B lymphocytes." Advanced Materials 29.33: 1606944 (2017).
Fesnak et al. "Engineered T cells: the promise and challenges of cancer immunotherapy." Nature reviews cancer 16.9: 566-581 (2016).
Flynn et al. "Biomolecular sensors for advanced physiological monitoring." Nature Reviews Bioengineering 1.8: 560-575 (2023).
Geall et al. "Nonviral delivery of self-amplifying RNA vaccines." Proceedings of the National Academy of Sciences 109.36: 14604-14609 (2012).
Hincer et al. "Making the next generation of therapeutics: mRNA meets synthetic biology." ACS synthetic biology 12.9: 2505-2515 (2023).
Jacobs et al. "Implementation of the CRISPR-Cas9 system in fission yeast." Nature communications 5.1: 5344 (2014).
Jiang et al. "Current research status of tumor cell biomarker detection." Microsystems & Nanoengineering 9.1: 123 (2023).
Jiang et al. "Biosensors for point mutation detection." Frontiers in Bioengineering and Biotechnology 9: 797831 (2021).
Jimenez et al. "Chemistry and biology of self-cleaving ribozymes." Trends in biochemical sciences 40.11: 648-661 (2015).
Johansson et al. "A thermodynamic analysis of the sequence-specific binding of RNA by bacteriophage MS2 coat protein." Proceedings of the National Academy of Sciences 95.16: 9244-9249 (1998).
Karagyaur et al. "The power of gene technologies: 1001 ways to create a cell model." Cells 11.20: 3235 (2022).
Kim et al. "The potential of cell-penetrating peptides for mRNA delivery to cancer cells." Pharmaceutics 14.6: 1271 (2022).

(Continued)

*Primary Examiner* — Nancy J Leith
(74) *Attorney, Agent, or Firm* — Nixon Peabody LLP; Ronald I. Eisenstein; Alissa R. Young

(57) ABSTRACT

The technology described herein is directed to Aptamer and Ribozyme Equilibrium Shifting (ARES) regions, including ON-switches and OFF-switches, which can be harnessed to regulate the stability of RNA molecules. Also described herein are compositions comprising such RNA molecules and methods of using them to regulate translation of cargo polypeptides.

22 Claims, 52 Drawing Sheets
Specification includes a Sequence Listing.

(56)                    References Cited

OTHER PUBLICATIONS

Levenson et al. "Iron and ageing: an introduction to iron regulatory mechanisms." Ageing research reviews 3.3: 251-263 (2004).

Li et al. "The application of Aptamer in biomarker discovery." Biomarker research 11.1: 70 (2023).

Molla et al. "Revolutionizing Personalized Medicine: Synergy with Multi-Omics Data Generation, Main Hurdles, and Future Perspectives." Biomedicines 12.12: 2750 (2024).

Mustafina et al. "Design of mammalian ON-Riboswitches based on tandemly fused aptamer and ribozyme." ACS synthetic biology 9.1: 19-25 (2019).

Ono et al. "Sensing intracellular signatures with synthetic mRNAs." RNA biology 20.1: 588-602 (2023).

Peng et al. "Self-cleaving ribozymes: substrate specificity and synthetic biology applications." RSC Chemical Biology 2.5: 1370-1383 (2021).

Qin et al. "mRNA-based therapeutics: powerful and versatile tools to combat diseases." Signal transduction and targeted therapy 7.1: 166 (2022).

Rohner, et al. "Unlocking the promise of mRNA therapeutics." Nature biotechnology 40.11: 1586-1600 (2022).

Rossignoli et al. "Developing and characterizing a two-layered safety switch for cell therapies." Cancer Biology & Therapy 24.1: 2232146 (2023).

Sachdeva et al. "In vivo co-localization of enzymes on RNA scaffolds increases metabolic production in a geometrically dependent manner." Nucleic acids research 42.14: 9493-9503 (2014).

Saw et al. "Advancements in clinical RNA therapeutics: Present developments and prospective outlooks." Cell Reports Medicine 5(5): 101555 (2024).

Scott et al. "The hammerhead ribozyme: structure, catalysis, and gene regulation." Progress in molecular biology and translational science 120: 1-23 (2013).

Self et al. "Protein production is an early biomarker for RNA-targeted therapies." Annals of Clinical and Translational Neurology 5.12: 1492-1504 (2018).

Silva-Pilipich et al. "Self-amplifying RNA: a second revolution of mRNA vaccines against COVID-19." Vaccines 12.3: 318 (2024).

Strobel et al. "High-throughput identification of synthetic riboswitches by barcode-free amplicon-sequencing in human cells." Nature communications 11.1: 714 (2020).

Tinafar et al. "Synthetic biology goes cell-free." BMC biology 17.1.64: 1-14 (2019).

Van Hoecke et al. "How mRNA therapeutics are entering the monoclonal antibody field." Journal of Translational Medicine 17.1: 54 (2019).

Varshney, et al. "Identification of an RNA aptamer binding hTERT-derived peptide and inhibiting telomerase activity in MCF7 cells." Molecular and cellular biochemistry 427: 157-167 (2017).

Vlatkovic. "Non-immunotherapy application of LNP-mRNA: maximizing efficacy and safety." Biomedicines 9.5: 530 (2021).

Wang et al. "mRNA-based vaccines and therapeutics: an in-depth survey of current and upcoming clinical applications." Journal of biomedical science 30.1: 84 (2023).

Wiedermannova et al. "The expanding field of non-canonical RNA capping: new enzymes and mechanisms." Royal Society Open Science 8.5: 201979 (2021).

Wroblewska et al. "Mammalian synthetic circuits with RNA binding proteins for RNA-only delivery." Nature biotechnology 33.8: 839-841 (2015).

Xiang et al. "Massively parallel RNA device engineering in mammalian cells with RNA-Seq." Nature communications 10.1: 4327 (2019).

Xiang et al. "Suppression of FOXM1 transcriptional activities via a single-stranded DNA aptamer generated by SELEX." Scientific reports 7.1: 45377 (2017).

Yoon et al. "Targeted delivery of C/EBPα-saRNA by RNA aptamers shows anti-tumor effects in a mouse model of advanced PDAC." Molecular Therapy-Nucleic Acids 18: 142-154 (2019).

Yoon et al. "Blind SELEX approach identifies RNA aptamers that regulate EMT and inhibit metastasis." Molecular Cancer Research 15.7: 811-820 (2017).

Zadeh et al. "Nupack: Analysis and design of nucleic acid systems." Journal of computational chemistry 32.1: 170-173 (2011).

Zhao et al. "RNA-responsive elements for eukaryotic translational control." Nature biotechnology 40.4: 539-545 (2022).

Zhong et al. "A reversible RNA on-switch that controls gene expression of AAV-delivered therapeutics in vivo." Nature biotechnology 38.2: 169-175 (2020).

Zhu et al. "RNA circuits and RNA-binding proteins in T cells." Trends in immunology 44.10: 792-806 (2023).

* cited by examiner

MS2                    PP7                    BIV Tar

FIG. 21A

Aptamer and HHR is Formed

Stabilization Stems are formed Formed

APTAMER AND RIBOZYME EQUILIBRIUM SHIFTING (ARES) RNA CIRCUITS AND USES THEREOF

CROSS-REFERENCE TO RELATED APPLICATIONS

This application claims benefit under 35 U.S.C. § 119(e) of U.S. Provisional Application No. 63/570,609 filed Mar. 27, 2024, the contents of which are incorporated herein by reference in their entirety.

SEQUENCE LISTING

The instant application contains a Sequence Listing which has been submitted electronically in XML format and is hereby incorporated by reference in its entirety. Said XML copy, created on May 30, 2025, is named 701586-000131USPT_SL.xml and is 394,877 bytes in size.

TECHNICAL FIELD

The technology described herein relates to aptamer and ribozyme equilibrium shifting (ARES) RNA circuits and uses thereof.

BACKGROUND mRNA has gained significant attention for its vast potential in disease prevention and treatment. For example, the development of mRNA COVID vaccines has been a pivotal breakthrough, saving countless lives and highlighting one of mRNA's practical applications. Beyond vaccines, ongoing research explores many other mRNA applications, from protein replacement therapies to disease treatments. The appeal of mRNA lies in its numerous advantages, including rapid development, efficacy, potent immune response, safety profile, and versatility. However, while mRNA holds promise for disease treatments, these applications often present greater challenges than vaccines, as they may cause more pronounced side effects, including systemic reactions and immune responses. Enhanced precision in treatment localization and temporal regulation of mRNA therapies could mitigate many of these potential side effects, underscoring the need for advanced delivery systems and regulatory mechanisms.

In mRNA therapies, controlling the lifespan of mRNA is crucial for optimizing therapeutic outcomes and ensuring safety. Currently, mRNA stability is regulated through modifications such as the addition of cap structures and polyadenylation, which help protect mRNA from degradation and prolong its lifespan within cells. However, these mechanisms provide limited control over mRNA stability, necessitating the development of more precise regulatory strategies. There is thus great need for improved strategies to control the stability of mRNA therapies.

SUMMARY

In the past decade, mRNA devices and therapeutics have rapidly expanded as promising tools in the fight against various diseases. Despite their potential, these technologies are hindered by a significant limitation: the lack of precise spatial and temporal control. Described herein are compositions, methods and systems with the ability to control target gene expression spatially and temporally by merging RNA-binding proteins (RBPs) with self-cleaving ribozymes (e.g., hammerhead ribozyme, HHR) into an aptamer and ribozyme equilibrium shifting (ARES) RNA circuit, which can then be inserted into the UTR(s) of a gene to control mRNA stability. Depending on the placement of the aptamer and HHR a stabilizing or destabilizing switch can be developed with the RBP as the trigger. The ARES circuit allows for higher levels of cell-specific delivery and temporal control with the ARES stabilization and destabilizing switches. For the stabilizing switch, translation of a gene of interest (GOI) occurs only in the presence of the corresponding RBP; mRNA will be degraded in its absence. The destabilizing switch permits the translation of a GOI until a specific RBP is present, which then destabilizes and leads to the degradation of the mRNA. Boolean logic in the form of an AND, OR and more gates can also be demonstrated with ARES switches for further control of mRNA stability. This approach offers more precise spatial and temporal control over RNA therapeutics, as the selected RBP can either be a biomarker protein or an additional drug. This advancement results in enhanced efficacy and reduced side effects. Furthermore, the versatility of the RNA switches described herein permit their broad application across various healthcare scenarios.

RNA delivery vehicles such as lipid nanoparticles (LNPs) exist to deliver mRNA drugs in a cell-specific manner; however, they cannot target all cell types and can be cytotoxic. In contrast, the ARES switch described herein can target any cell type via biomarker proteins and is not inherently toxic. See e.g., Rohner et al. "Unlocking the promise of mRNA therapeutics." Nat Biotechnol. 40(11): 1586-1600 (2022).

eToeholds also attempt to deliver cell specificity through RNA triggers. RNA triggers are less ideal than proteins (as used in the systems described herein) for targeted mRNA drug delivery because proteins permit more precise and specific recognition of target cells or tissues, reducing the risk of off-target effects and improving therapeutic efficacy. eToehold also suffers from high leakage and difficulty expressing in high percentages of cells. See e.g., Zhao et al. "RNA-responsive elements for eukaryotic translational control." Nat Biotechnol. 40(4): 539-545 (2022).

Methods to extend mRNA lifespan have been developed including cap modifications, self-amplifying mRNA, and circularized RNA. These give some level of temporal control; however, they fail to provide adaptable control. See e.g., Wang et al. "mRNA-based vaccines and therapeutics: an in-depth survey of current and upcoming clinical applications." J Biomed Sci. 30(1): 84 (2023) (see e.g., FIG. 2 of Wang et al.).

Others have attempted to use Hammerhead ribozymes and aptamers to control when translation is ON or OFF. However, these systems were detecting a limited number of small molecules (e.g., tetracycline, guanine) not proteins; see e.g., Strobel et al. Nat. Commun. 11, 714 (2020).

The technology described herein is directed to ON-switch and OFF-switch aptamer ribozyme equilibrium shifting (ARES) domains that can control the stability of associated RNA molecules. One element of the ARES regions described herein include that they can sense any protein or peptide, including biomarkers. The ARES regions also allow for adaptable control where the RNA can be turned OFF or ON at any time and for any extended period of time.

Accordingly, in one aspect, described herein is an RNA molecule comprising: a) an open reading frame (ORF) encoding at least one cargo polypeptide; and b) at least one untranslated region (UTR) comprising at least one Aptamer and Ribozyme Equilibrium Shifting (ARES) region, which comprises: i) a protein-binding aptamer that specifically binds to a target protein; and ii) a ribozyme.

In some embodiments of any of the aspects, the aptamer is selected from the group consisting of: a MS2 aptamer, a PP7 aptamer, a bovine immunodeficiency virus (BIV) trans-activation response (Tar) aptamer, and a P22 aptamer.

In some embodiments of any of the aspects, the target protein is selected from: a) MS2 coat protein (MCP), which specifically binds to the MS2 aptamer; b) PP7 coat protein (PCP), which specifically binds to the PP7 aptamer; c) BIV trans-activator of transcription (Tat), which specifically binds to the BIV Tar aptamer; d) a P22 N protein, which specifically binds to the P22 aptamer.

In some embodiments of any of the aspects, the ribozyme is a self-cleaving ribozyme.

In some embodiments of any of the aspects, the self-cleaving ribozyme is selected from the group consisting of: hammerhead ribozyme (HHR), hepatitis delta virus (HDV) ribozyme, hairpin ribozyme, Varkud satellite (VS) ribozyme, glmS ribozyme, twister ribozyme, twister sister ribozyme, Pistol ribozyme, Hatchet ribozyme, and Hovlinc ribozyme.

In some embodiments of any of the aspects, the aptamer is 5' of the ribozyme in the ARES region.

In some embodiments of any of the aspects, the aptamer is 3' of the ribozyme in the ARES region.

In some embodiments of any of the aspects, the at least one ARES region is located in the UTR 5' of the ORF (5' UTR).

In some embodiments of any of the aspects, the at least one ARES region is located in the UTR 3' of the ORF (3' UTR).

In some embodiments of any of the aspects, at least one ARES region is located in 5' UTR, and at least one ARES region is located the 3' UTR.

In some embodiments of any of the aspects, the at least one ARES region modulates the stability of the RNA molecule and/or modulates translation of the at least one cargo polypeptide encoded by the ORF.

In some embodiments of any of the aspects, the at least one ARES region is an ON-switch ARES region structured such that either the aptamer or the ribozyme, but not both, can form at one time in the RNA molecule.

In some embodiments of any of the aspects, in an RNA molecule comprising an ON-switch ARES region: a) in the presence of the target protein, the aptamer is stabilized, the ribozyme cannot form, the RNA molecule is not cleaved, and the ORF can be translated (ON); and/or b) in the absence of the target protein, the aptamer is not stabilized, the ribozyme can form, the RNA molecule is cleaved, and the ORF cannot be translated (OFF).

In some embodiments of any of the aspects, the ON-switch ARES region comprises: a) the aptamer comprising: i) a first (a) region and a complementary (a*) region that can hybridize to the first (a) region; and ii) a primary second (b1) region and a complementary (b*) region that can hybridize to the primary second (b1) region or to a secondary second (b2) region in the ribozyme; and b) the ribozyme comprising: i) the secondary second (b2) region and the complementary (b*) region; and ii) a third (c) region and a complementary (c*) region that can hybridize to the third (c) region.

In some embodiments of any of the aspects, the ON-switch ARES region comprises from 5' to 3': a) the primary second (b1) region; b) the first (a) region; c) the complementary (a*) region that can hybridize to the first (a) region; d) the complementary (b*) region that can hybridize to the primary second (b1) region in the aptamer or to a secondary second (b2) region in the ribozyme; e) the third (c) region; f) the complementary (c*) region that can hybridize to the third (c) region; and g) the secondary second (b2) region.

In some embodiments of any of the aspects, the ON-switch ARES region comprises from 5' to 3': a) the secondary second (b2) region; b) the third (c) region; c) the complementary (c*) region that can hybridize to the third (c) region; d) the complementary (b*) region that can hybridize to the secondary second (b2) region in the ribozyme or to a primary second (b1) region in the aptamer; e) the first (a) region; f) the complementary (a*) region that can hybridize to the first (a) region; and g) the primary second (b1) region.

In some embodiments of any of the aspects, the RNA molecule further comprises at least one stabilization domain.

In some embodiments of any of the aspects, the RNA molecule further comprises at least one degradation domain.

In some embodiments of any of the aspects, the at least one ARES region is a stabilization/degradation ARES region, which comprises in the 3' UTR, from 5' to 3': a) a stabilization domain; b) an ON-switch ARES region as described herein; and c) a degradation domain.

In some embodiments of any of the aspects, in an RNA molecule comprising a stabilization/degradation ARES region: a) in the presence of the target protein, the aptamer is stabilized, the ribozyme cannot form, the RNA molecule is not cleaved, the degradation domain is retained, the RNA molecule is degraded, and the ORF cannot be translated (OFF); and/or b) in the absence of the target protein, the aptamer is not stabilized, the ribozyme can form, the RNA molecule is cleaved, the degradation domain is not retained, the stabilization domain protects the RNA molecule from degradation, and the ORF can be translated (ON).

In some embodiments of any of the aspects, the at least one ARES region is an OFF-switch ARES region structured such that either both the aptamer and the ribozyme, or at least one stabilization stem, can form at one time in the RNA molecule.

In some embodiments of any of the aspects, in an RNA molecule comprising an OFF-switch ARES region: a) in the presence of the target protein, the aptamer is stabilized, the ribozyme can form, the at least one stabilization stem cannot form, the RNA molecule is cleaved, and the ORF cannot be translated (OFF); and/or b) in the absence of the target protein, the aptamer is not stabilized, the ribozyme cannot form, the at least one stabilization stem can form, the RNA molecule is not cleaved, and the ORF can be translated (ON).

In some embodiments of any of the aspects, the OFF-switch ARES region comprises: a) the aptamer comprising: i) a first (a) region and a complementary (a*) region that can hybridize to the first (a) region; and ii) a primary second (b1) region and a primary complementary (b1*) region that can hybridize to the primary second (b1) region or to a secondary second (b2) region; b) the ribozyme comprising: i) the secondary second (b2) region and a secondary complementary (b2*) region that can hybridize to the secondary second (b2) region; and ii) a third (c) region and a complementary (c*) region that can hybridize to the third (c) region; and c) the at least one stabilization stem comprising: i) a fourth (d) region and a complementary (d*) region that can hybridize to the fourth (d) region; and ii) the secondary second (b2) region of the ribozyme and the primary complementary (b1*) region of the aptamer.

In some embodiments of any of the aspects, the OFF-switch ARES region comprises from 5' to 3': a) the primary second (b1) region; b) the first (a) region; c) the complementary (a*) region that can hybridize to the first (a) region;

d) the primary complementary (b1*) region that can hybridize to the primary second (b1) region or to a secondary second (b2) region; e) the fourth (d) region; f) the complementary (d*) region that can hybridize to the fourth (d) region; g) the secondary second (b2) region; h) the third (c) region; i) the complementary (c*) region that can hybridize to the third (c) region; and j) the secondary complementary (b2*) region that can hybridize to the secondary second (b2) region.

In some embodiments of any of the aspects, the OFF-switch ARES region comprises from 5' to 3': a) the secondary second (b2) region; b) the third (c) region; c) the complementary (c*) region that can hybridize to the third (a) region; d) the secondary complementary (b2*) region that can hybridize to the secondary second (b2) region or to a primary second (b1) region; e) the fourth (d) region; f) the complementary (d*) region that can hybridize to the fourth (d) region; g) the primary second (b1) region; h) the first (a) region; i) the complementary (a*) region that can hybridize to the first (a) region; and j) the primary complementary (b1*) region that can hybridize to the primary second (b1) region.

In some embodiments of any of the aspects, the OFF-switch ARES region comprises 2 stabilization stems.

In some embodiments of any of the aspects, the OFF-switch ARES region comprises: a) the aptamer comprising: i) a first (a) region and a complementary (a*) region that can hybridize to the first (a) region; and ii) a primary second (b1) region and a primary complementary (b1*) region that can hybridize to the primary second (b1) region or to a secondary second (b2) region; b) the ribozyme comprising: i) the secondary second (b2) region and a secondary complementary (b2*) region that can hybridize to the secondary second (b2) region; and ii) a third (c) region and a complementary (c*) region that can hybridize to the third (c) region; c) a first stabilization stem comprising: i) a primary fourth (d1) region and a complementary (d1*) region that can hybridize to the primary fourth (d1) region; and ii) the secondary second (b2) region of the ribozyme and the primary complementary (b1*) region of the aptamer; and d) a second stabilization stem comprising: i) a secondary fourth (d2) region and a complementary (d2*) region that can hybridize to the secondary fourth (d2) region; and ii) the primary second (b1) region of the aptamer and a tertiary complementary (b3*) region that can hybridize to the primary second (b1) region.

In some embodiments of any of the aspects, the OFF-switch ARES region comprises from 5' to 3': a) the tertiary complementary (b3*) region that can hybridize to the primary second (b1) region; b) the complementary (d2*) region that can hybridize to the secondary fourth (d2) region; c) the secondary fourth (d2) region; d) the primary second (b1) region; e) the first (a) region; f) the complementary (a*) region that can hybridize to the first (a) region; g) the primary complementary (b1*) region that can hybridize to the primary second (b1) region or to the secondary second (b2) region; h) the primary fourth (d1) region; i) the complementary (d1*) region that can hybridize to the primary fourth (d1) region; j) the secondary second (b2) region; k) the third (c) region; l) the complementary (c*) region that can hybridize to the third (c) region; and m) the secondary complementary (b2*) region that can hybridize to the secondary second (b2) region.

In some embodiments of any of the aspects, the OFF-switch ARES region comprises: a) the ribozyme comprising: i) a first (a) region and a complementary (a*) region that can hybridize to the first (a) region; and ii) a primary second (b1)

region and a primary complementary (b1*) region that can hybridize to the primary second (b1) region or to a secondary second (b2) region; b) the aptamer comprising: i) the secondary second (b2) region and a secondary complementary (b2*) region that can hybridize to the secondary second (b2) region; and ii) a third (c) region and a complementary (c*) region that can hybridize to the third (c) region; c) a first stabilization stem comprising: i) a primary fourth (d1) region and a complementary (d1*) region that can hybridize to the primary fourth (d1) region; and ii) the secondary second (b2) region of the aptamer and the primary complementary (b1*) region of the ribozyme; and d) a second stabilization stem comprising: i) a secondary fourth (d2) region and a complementary (d2*) region that can hybridize to the secondary fourth (d2) region; and ii) the primary second (b1) region of the ribozyme and a tertiary complementary (b3*) region that can hybridize to the primary second (b1) region.

In some embodiments of any of the aspects, the OFF-switch ARES region comprises from 5' to 3': a) the tertiary complementary (b3*) region that can hybridize to the primary second (b1) region; b) the complementary (d2*) region that can hybridize to the secondary fourth (d2) region; c) the secondary fourth (d2) region; d) the primary second (b1) region; e) the first (a) region; f) the complementary (a*) region that can hybridize to the first (a) region; g) the primary complementary (b1*) region that can hybridize to the primary second (b1) region or to the secondary second (b2) region; h) the primary fourth (d1) region; i) the complementary (d1*) region that can hybridize to the primary fourth (d1) region; j) the secondary second (b2) region; k) the third (c) region; l) the complementary (c*) region that can hybridize to the third (c) region; and m) the secondary complementary (b2*) region that can hybridize to the secondary second (b2) region.

In some embodiments of any of the aspects, the at least cargo polypeptide is selected from: a) a detectable marker (e.g., a fluorescent polypeptide); b) an antigen (e.g., severe acute respiratory syndrome coronavirus 2 (SARS-CoV-2) spike gene, respiratory syncytial virus (RSV) F protein, influenza hemagglutinin, a tumor associated antigen (e.g., New York esophageal squamous cell carcinoma 1 for melanoma, kallikrein-2 for prostate cancer); an antibody (e.g., a monoclonal antibody; e.g.., an anti-claudin 18 isoform 2 (anti-CLDN18.2, which is specific for tumors) antibody, anti-cytotoxic T-lymphocyte-associated protein 4 (anti-CTLA-4) or anti-glucocorticoid-induced tumor necrosis factor receptor (TNFR)-related protein (anti-GITR) antibodies, which are specific for melanoma); c) a cytokine (e.g., interleukin-2 (IL-2), interleukin-7 (IL-7), interleukin-12 (IL-12), Tumor necrosis factor receptor superfamily, member 4 (TNFRSF4) ligand (OX40L), interleukin-23 (IL-23)); d) a cell therapy protein (e.g., claudin-6 (CLDN6), a chimeric antigen receptor (CAR) protein, a T cell receptor); e) a tumor suppressor protein (e.g., tumor protein 53 (p53), breast cancer gene 1 (BRCA1), breast cancer gene 2 (BRCA2)); f) a programmed cell death protein (e.g., B-cell lymphoma 2 (Bcl-2)-associated X protein (Bax), a caspase); g) a site-specific nuclease (e.g., Cas9; a prime editing enzyme (e.g., Prime Editor 2 (PE2), Prime Editor 3 (PE3), Prime Editor 4 (PE4), Prime Editor 5 (PE5), Prime Editor 2 Max (PE2max), Prime Editor 3 Max (PE3max), and the like); h) a therapeutic protein (e.g., vascular endothelial growth factor (VEGF), Glucagon-like peptide-1, insulin); or i) an oncogene (e.g., mutant forms of Kirsten rat sarcoma virus oncogene homolog (KRAS), Harvey Rat sarcoma viral oncogene homolog (HRAS), Epidermal Growth Factor Receptor (EGFR), Human Epidermal growth factor Receptor 2 (HER2), Platelet-derived growth factor receptor A (PDGFR), myelocytomatosis (MYC), Breast Cancer Gene 1 (BRCA1), Breast Cancer Gene 2 (BRCA2), Abelson murine leukemia (ABL) proto-oncogene 1 (ABL1), Vascular Endothelial Growth Factor (VEGF)).

In some embodiments of any of the aspects, the RNA molecule is a messenger RNA (mRNA), further comprising a 5' cap and a 3' polyA tail.

In one aspect, described herein is a self-amplifying RNA (saRNA) comprising an RNA as described herein, which further comprises a second open reading frame encoding an RNA-dependent RNA polymerase.

In one aspect, described herein is a self-amplifying RNA (saRNA) comprising from 5' to 3': a) a 5' conserved sequence element (CSE); b) a first open reading frame (ORF) encoding an RNA-dependent RNA polymerase (RdRP), operably linked to a promoter in the 5' CSE; c) a subgenomic promoter (SGP); d) a second ORF encoding at least one cargo polypeptide, operably linked to the SGP; and e) a 3' CSE; and wherein the 5' CSE, a region between the first and second ORFs, and/or the 3' CSE further comprises at least one Aptamer and Ribozyme Equilibrium Shifting (ARES) region in a sense or anti-sense orientation, wherein the ARES region comprises: i) a protein-aptamer that specifically binds to a target protein; and ii) a ribozyme.

In some embodiments of any of the aspects, when the ARES region is in the sense orientation, the ARES region is functional in the saRNA.

In some embodiments of any of the aspects, when the ARES region is in the anti-sense orientation, the ARES region is functional when the saRNA is delivered to a cell, the RdRP is translated from the saRNA, and the RdRP synthesizes a reverse complementary negative strand of the saRNA.

In one aspect, described herein is a polynucleotide comprising an RNA molecule as described herein or an saRNA as described herein.

In one aspect, described herein is a vector comprising a polynucleotide as described herein.

In one aspect, described herein is a combination comprising: a) an RNA molecule as described herein or an saRNA as described herein; and b) a target protein as described herein.

In some embodiments of any of the aspects, the target protein is linked to a polypeptide of interest.

In one aspect, described herein is a cell comprising an RNA molecule as described herein, an saRNA as described herein, a polynucleotide as described herein, a vector as described herein, and/or a combination as described herein.

In one aspect, described herein is a pharmaceutical composition comprising an RNA molecule as described herein, an saRNA as described herein, a polynucleotide as described herein, a vector as described herein, a combination as described herein, or a cell as described herein.

In one aspect, described herein is a method of modulating the translation of at least one cargo polypeptide, the method comprising contacting a cell with an RNA molecule as described herein, an saRNA as described herein, a polynucleotide as described herein, a vector as described herein, a combination as described herein, or a pharmaceutical composition as described herein.

In some embodiments of any of the aspects, the method further comprises contacting the cell with the target protein.

In some embodiments of any of the aspects, the cell expresses the target protein.

In one aspect, described herein is a method of modulating the translation of at least one cargo polypeptide in a subject in need thereof, the method comprising administering to the subject an effective amount of an RNA molecule as described herein, an saRNA as described herein, a polynucleotide as described herein, a vector as described herein, a combination as described herein, a cell as described herein, or a pharmaceutical composition as described herein.

In some embodiments of any of the aspects, the method further comprises administering to the subject an effective amount of the target protein.

In some embodiments of any of the aspects, a target cell in the subject expresses the target protein.

In some embodiments of any of the aspects, the RNA molecule comprises an ON-switch ARES region as described herein.

In some embodiments of any of the aspects, in an RNA molecule comprising an ON-switch ARES region: a) in the presence of the target protein, the at least one cargo polypeptide is translated (ON); and/or b) in the absence of the target protein, the at least one cargo polypeptide is not translated (OFF).

In some embodiments of any of the aspects, the RNA molecule comprises a stabilization/degradation ARES region as described herein.

In some embodiments of any of the aspects, the RNA molecule comprises an OFF-switch ARES region as described herein.

In some embodiments of any of the aspects, in an RNA molecule comprising a stabilization/degradation ARES region or an OFF-switch ARES region: a) in the presence of the target protein, the at least one cargo polypeptide is not translated (OFF); and/or b) in the absence of the target protein, the at least one cargo polypeptide is translated (ON).

BRIEF DESCRIPTION OF THE DRAWINGS

FIG. 1A-1H are a series of schematics showing exemplary ARES regions. FIG. 1A shows an exemplary ON-switch ARES region where the aptamer is 5' of the ribozyme. FIG. 1B shows an exemplary ON-switch ARES region where the ribozyme is 5' of the aptamer. FIG. 1C shows an exemplary stabilization/degradation ARES region where the aptamer is 5' of the ribozyme. FIG. 1D shows an exemplary stabilization/degradation ARES region where the ribozyme is 5' of the aptamer. FIG. 1E shows an exemplary OFF-switch ARES region with a single stabilization stem where the aptamer is 5' of the ribozyme. FIG. 1F shows an exemplary OFF-switch ARES region with a single stabilization stem where the ribozyme is 5' of the aptamer. FIG. 1G shows an exemplary OFF-switch ARES region with two stabilization stems where the aptamer is 5' of the ribozyme. FIG. 1H shows an exemplary OFF-switch ARES region with two stabilization stems where the ribozyme is 5' of the aptamer.

FIG. 5A. The ON/OFF ratio of each ARES ON switch tested with the BIV Tat trigger RBP. Left bars show ON/OFF ratios above 2.0, middle bars show ON/OFF ratios between 2-1.5. The ON/OFF ratios below 1.5 are to the right. FIG. 5B. The ON/OFF ratios of the ARES ON switches plotted against their Gibbs free energy of the HHR forming (kcal/mol). FIG. 5C. The ON/OFF ratios of the ARES ON switches plotted against their Gibbs free energy of the aptamer forming (kcal/mol). FIG. 5D. The percent leakage of the ARES ON switches plotted against their Gibbs free energy of the HHR forming (kcal/mol).

FIG. 6A. ON/OFF ratios for 46 P22N ARES ON switches. FIG. 6B. ON/OFF ratios for 12 MCP ARES ON switches. In FIG. 6A-6B, left bars show ON/OFF ratios above 2.0, middle bars show ON/OFF ratios between 2-1.5, and right bars show ON/OFF ratios below.

FIG. 7A. Schematic showing the concatenation of ARES ON switches in the 3' UTR. FIG. 7B. The normalized GFP MFI of the negative control (left bar) an ARES ON switch (middle bar), and two ARES ON switches concatenated (right bar) all with no RBP present.

FIG. 9A Models of BIV Tat ARES OFF switch with varying "a", "b", "c", and "d" domain lengths. The top left image shows the aptamer and HHR formed, top right and bottom left are intermediate structures and the bottom right shows the middle stem loop formed. Each nucleotide position shows its thermodynamic likelihood based on the equilibrium probability scale. FIG. 9B ON/OFF ratios of all 83 OFF switches. FIG. 9C. The normalized GFP MFI of the negative control (left bar), best OFF switch without BIV Tat (middle bar), best OFF switch with BIV Tat (right bar).

(FIG. 17A) A HHR positioned in the 3' UTR self-cleaves, removing the poly-A tail and triggering RNA degradation. (FIG. 17B) A HHR positioned in the 5' UTR self-cleaves, removing the 5' cap and leading to RNA degradation. (FIG. 17C) Structures of three distinct aptamers: MS2, PP7, and BIV-Tar. The black bar regions are utilized in the ARES switch in the "a" and "b" domains.

(FIG. 18A) Schematic representation of the ARES ON switch in the 3' UTR. Both aptamer and HHR structures can form. When the RNA-binding protein (RBP) is present, it binds and stabilizes the mRNA, leading to payload expression. In the absence of RBP, the HHR self-cleaves, triggering mRNA degradation. (FIG. 18B) Gibbs free energy of aptamer formation versus the ON/OFF ratio for 46 PP7 ARES ON switches. The trend line represents a linear fit with an R-squared value of 0.72. (FIG. 18C) Defect level of the HHR versus the percent leakage of 46 PP7 ARES ON switches in the absence of RBP. The trend line represents a fitted Hill function with an R-squared value of 0.56. (FIG. 18D) Normalized mCherry mean fluorescence intensity (MFI) of the best-performing MS2, PP7, and BIV-TAR (BT) ARES ON switches with (gray triangles) and without (black circles) their respective RBP.

(FIG. 19A) Schematic representation of the ARES ON switch in the 5' UTR. (FIG. 19B) Percentage of mCherry (ARES reporter) positive cells for the best-performing MS2 and PP7 designs in the 5' UTR. Black circles indicate the absence of RBP, while gray triangles indicate the presence of RBP. (FIG. 19C) Schematic of the flipped ARES ON switch design, where the HHR is positioned upstream of the aptamer. (FIG. 19D) Percentage of mCherry (ARES reporter) positive cells for the best-performing MS2 and PP7 flipped designs. Black circles indicate the absence of RBP, while triangles indicate the presence of RBP.

(FIG. 20A) Schematic representation of multiple ARES ON switches within the same mRNA. ARES switches can be concatenated in the 3' UTR or placed in different UTRs. (FIG. 20B) Normalized mCherry MFI of concatenated MS2 ARES switches in the 3' UTR in the absence of RBP. (FIG. 20C) Normalized mCherry MFI of concatenated MS2 ARES switches in the 3' UTR with (gray triangle) and without (black circle) RBP. (FIG. 20D) Normalized mCherry MFI of concatenated MS2 and PP7 ARES switches in the 3' UTR under different conditions: without RBP (circle), with MCP only (star), with PCP only (diamond), or with both RBPs (triangle). (FIG. 20E) Percentage of mCherry-positive cells for designs incorporating an MS2 ARES switch in the 5' UTR and a PP7 ARES switch in the 3' UTR under different conditions: without RBP (circle), with MCP only (star), with PCP only (diamond), or with both RBPs (triangle).

FIG. 21A-21D: The ARES OFF Switch in the 3' UTR. (FIG. 21A) Schematic representation of the first ARES OFF switch design in the 3' UTR. Both aptamer and HHR structures form at the same time or the stabilizing stem. When the RNA-binding protein (RBP) is present, it binds the aptamer leading to the HHR cleavage, triggering mRNA degradation. In the absence of RBP payload expression is on. (FIG. 21B) Percent GFP (reporter) positive cells of the best-performing BT ARES OFF switch with (gray triangle) and without (black circle) RBP. (FIG. 21C) Schematic representation of the second ARES OFF switch design in the 3' UTR. Both aptamer and HHR structures form at the same time or two stabilizing stems. When the RNA-binding protein (RBP) is present, it binds the aptamer leading to the HHR cleavage, triggering mRNA degradation. In the absence of RBP payload expression is on. (FIG. 21D) Normalized mCherry MFI of the best-performing MS2 ARES OFF switch with (gray triangle) and without (black circle) RBP.

(FIG. 23A) The amplification cycle of saRNA. Upon entry into the cell, translation of the RNA-dependent RNA polymerase (RdRp) (nsP1-4) begins. The RdRp first recognizes the active promoter sequence (black arrows) at the 3' end of the positive-sense strand. Synthesis of the negative-sense strand by RdRp generates two new promoter sequences, which are then used to synthesize both the full-length positive-sense strand and the subgenomic strand. The subgenomic strand is responsible for payload production. Asterisks (*) indicate reverse complement sequences. (FIG. 23B) Integration sites (A, B, C, D) for ARES switches in the saRNA.

Figure 1A:
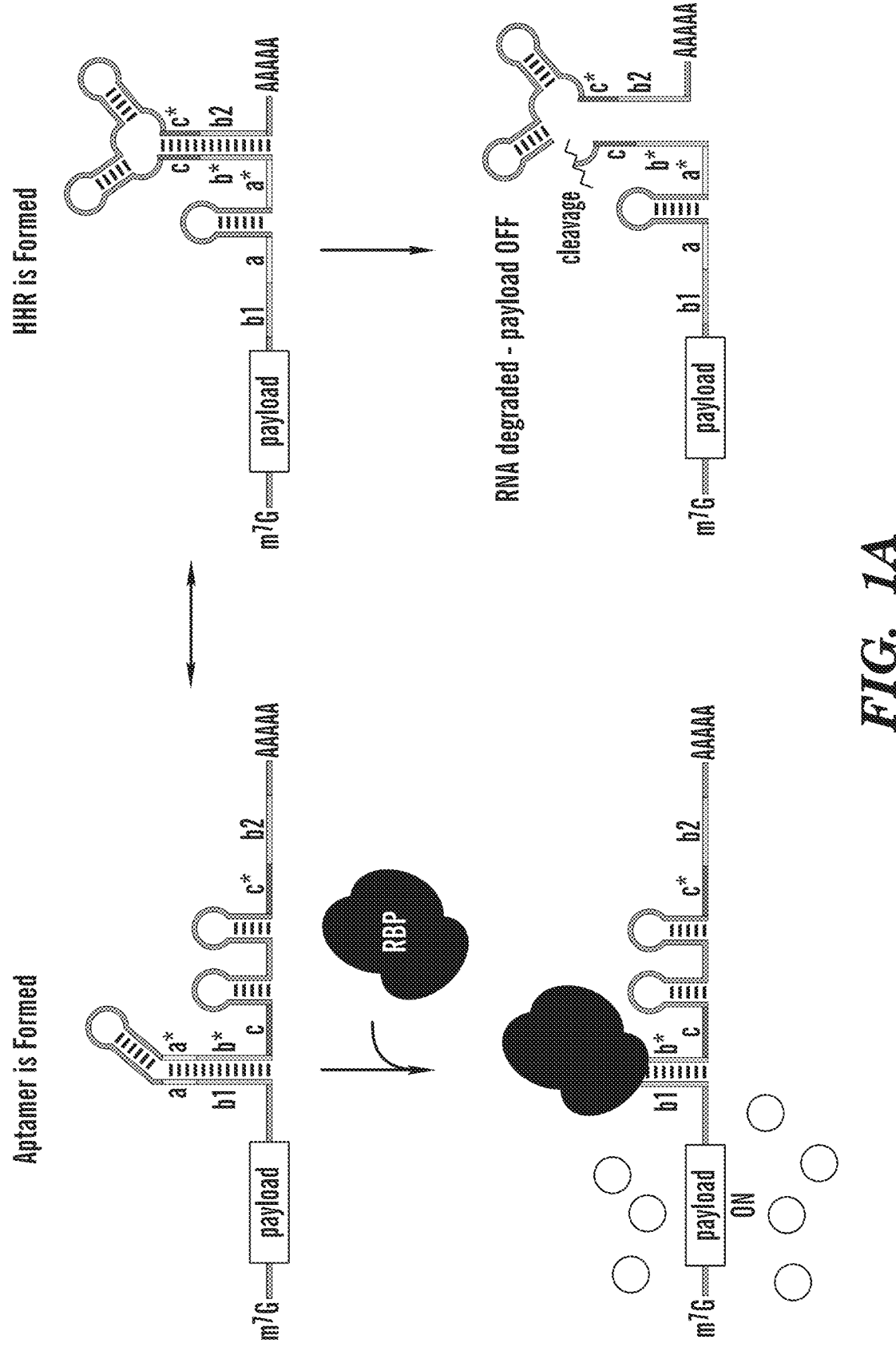

DETAILED DESCRIPTION mRNA devices and therapeutics have rapidly expanded as promising tools in the fight against various diseases. Despite their potential, these technologies are hindered by a significant limitation: the lack of precise spatial and temporal control. Presently, the specific delivery of mRNA relies on delivery vehicles, but such systems cannot achieve cell-specific delivery. Additionally, temporal control has been achieved through the addition of cap structures, degradation tags, and similar methods; however, this only extends or shortens lifespan and does not give adaptable control. To tackle these issues, described herein are systems that merge RNA binding proteins (RBPs) with self-cleaving ribozymes (e.g., hammerhead ribozyme, HHR) into an aptamer and ribozyme equilibrium shifting (ARES) RNA circuit, which can then be inserted into the UTR of a gene to control mRNA stability. Depending on the placement of the aptamer and HHR, a stabilizing or destabilizing switch can be developed with the RBP as the trigger.

First, described herein is a stabilization or ON-switch ARES region, where translation of a gene of interest (GOI) occurs only in the presence of the corresponding RBP; mRNA is degraded in its absence. Second, described herein is a destabilizing or OFF-switch ARES region, permitting translation of a GOI until a specific RBP is present, which then destabilizes and leads to the degradation of the mRNA. Third, described herein is higher-order control in the form of logic gates. These gates utilize developed stabilizing and destabilizing switches to form AND, OR, and A AND NOT B logic. This approach offers more precise spatial and temporal control over RNA therapeutics, as the selected RBP can be, for example, a biomarker protein or an additional drug. This advancement results in enhanced efficacy and reduced side effects. Furthermore, the versatility of the RNA switches described herein permit their broad application across various healthcare scenarios. Fourth, described herein are stabilization/degradation ARES regions, which can function as an OFF switch. Fifth, described herein are self-amplifying RNAs comprising at least one of the ARES regions described herein.

As such, embodiments of the technology described herein relate to RNA molecules comprising at least one ARES region described herein, for example at least one ON-switch ARES region, at least one OFF-switch ARES region, and/or at least one stabilization and degradation ARES region. In multiple aspects, described herein is an RNA molecule comprising a) an open reading frame (ORF) encoding at least one cargo polypeptide; and b) at least one untranslated region (UTR) comprising at least one Aptamer and Ribozyme Equilibrium Shifting (ARES) region. In some embodiments, the ARES region comprises i) at least one a protein-binding aptamer that specifically binds to a protein; and ii) at least one ribozyme, as described further herein.

In some embodiments, an RNA molecule comprises at least one ARES region as described herein (e.g., 1, 2, 3, 4, 5, or more ARES regions, which can be the same or different ARES regions), which is located in the UTR 5' of the ORF (5' UTR). In some embodiments, an RNA molecule comprises at least one ARES region as described herein (e.g., 1, 2, 3, 4, 5, or more ARES regions, which can be the same or different ARES regions), which is located in the UTR 3' of the ORF (3' UTR). In some embodiments, an RNA molecule comprises at least one ARES region as described herein (e.g., 1, 2, 3, 4, 5, or more ARES regions, which can be the same or different ARES regions), which is located in the UTR 5' of the ORF (5' UTR), and at least one ARES region as described herein (e.g., 1, 2, 3, 4, 5, or more ARES regions, which can be the same or different ARES regions), which is located in the UTR 3' of the ORF (3' UTR).

In some embodiments, as discussed further herein, the at least one ARES region modulates the stability of the RNA molecule. In some embodiments, as discussed further herein, the at least one ARES region modulates translation of the at least one cargo polypeptide encoded by the ORF. In some embodiments, as discussed further herein, the at least one ARES region modulates the stability of the RNA molecule and modulates translation of the at least one cargo polypeptide encoded by the ORF.

In multiple aspects, described herein is an RNA molecule that comprises two different ARES domains (see e.g., Table 1). In some embodiments, the first ARES region comprises an aptamer that specifically binds to a first target protein, and the second ARES region comprises an aptamer that specifically binds to a second target protein. In some embodiments, the first ARES region comprises an aptamer that specifically binds to a first target protein, and the second ARES region comprises an aptamer that specifically binds to the first target protein. As an example, an RNA molecule that comprises two ON-switch ARES regions, where each ARES region comprises an aptamer that specifically binds to a different target protein, can be referred to herein as an "AND logic gate" (see e.g., FIG. 14). As another example, an RNA molecule that comprises two OFF-switch ARES regions (or two stabilization/degradation ARES regions; or an OFF-switch ARES region and a stabilization/degradation ARES region), where each ARES region comprises an aptamer that specifically binds to a different target protein, can be referred to herein as a "NOR logic gate" (see e.g., FIG. 15). As a further example, an RNA molecule that comprises an OFF-switch ARES region and an OFF-switch ARES region (or a stabilization/degradation ARES region), where each ARES region comprises an aptamer that specifically binds to a different target protein, can be referred to herein as an "A AND NOT B logic gate" (see e.g., FIG. 16).

TABLE 1

Exemplary Combinations of ARES regions in an RNA molecule

| First ARES region | Second ARES region |
|---|---|
| ON-Switch ARES region | ON-Switch ARES region |
| ON-Switch ARES region | Stabilization/degradation ARES region |
| ON-Switch ARES region | OFF-Switch ARES region |
| Stabilization/degradation ARES region | ON-Switch ARES region |
| Stabilization/degradation ARES region | Stabilization/degradation ARES region |

TABLE 1-continued

Exemplary Combinations of ARES regions in an RNA molecule

| First ARES region | Second ARES region |
|---|---|
| Stabilization/degradation ARES region | OFF-Switch ARES region |
| OFF-Switch ARES region | ON-Switch ARES region |
| OFF-Switch ARES region | Stabilization/degradation ARES region |
| OFF-Switch ARES region | OFF-Switch ARES region |

Aptamers and Target Proteins

In multiple aspects, described herein are ARES regions, which comprise at least one protein-binding aptamer (e.g., 1, 2, 3, 4, 5, 6, 7, 8, 9, 10, or more aptamers, which can be the same or different aptamers). As used herein, the term "protein-binding aptamer" refers to a single-stranded nucleic acid molecule (e.g., single-stranded RNA, ssRNA) that can hybridize to itself to form at least one stem and loop secondary structure (e.g., a hairpin) that is configured to specifically bind to at least one target protein (e.g., 1, 2, 3, 4, 5, 6, 7, 8, 9, 10, or more target proteins, which can be the same or different target proteins). The target protein binding to the aptamer can stabilize the formation of the aptamer and influence the formation of other secondary structures in the ARES region (e.g., ribozymes, stabilization loops, etc.), as described further herein. In some embodiments, the target protein is an RNA-binding protein (RBP).

The ARES regions described herein can comprise any aptamer known in the art or discovered to be capable of specifically binding to a target protein. Non-limiting examples of protein-binding aptamers and their associated target proteins include a portion of a viral genome (e.g., an RNA recognition site) that binds to a viral capsid protein, a viral coat protein, or another viral protein. For example, the MS2 aptamer from the MS2 bacteriophage (e.g., SEQ ID NO: 1) specifically binds to MS2 coat protein (MCP, SEQ ID NO: 5). As another example, the PP7 aptamer from the PP7 bacteriophage (e.g., SEQ ID NO: 2) specifically binds to PP7 coat protein (PCP, SEQ ID NO: 6). As a third example, the bovine immunodeficiency virus (BIV) Tar aptamer (e.g., SEQ ID NO: 3) specifically binds to BIV trans-activator of transcription (Tat, SEQ ID NO: 7). As a fourth example, the P22 aptamer from the bacteriophage P22, also referred to as the BoxB aptamer, (e.g., SEQ ID NO: 4) specifically binds to P22 N protein (SEQ ID NO: 8).

TABLE 2

Exemplary protein-binding aptamer sequences and their associated target proteins

| Protein-binding aptamer | Exemplary Sequence | Aptamer SEQ ID NO: | Associated target protein | Target Protein SEQ ID NO: |
|---|---|---|---|---|
| MS2 | GCACGAGCAUCAGCCGUGC | 1 | MCP | 5 |
| PP7 | GGCACAGAAGAUAUGGCUUCGUGCC | 2 | PCP | 6 |
| BIV Tar | GGCUCGUGUAGCUCAUUAGCUCCGAGCC | 3 | BIV Tat | 7 |
| P22 (also referred to as BoxB) | GGUGCGCUGACAAAGCGCGCC | 4 | P22 N | 8 |

15

In some embodiments, the protein-binding aptamer comprises one of SEQ ID NOs: 1-4 or a nucleic acid sequence that is at least 70%, at least 75%, at least 80%, at least 85%, at least 90%, at least 90%, at least 91%, at least 92%, at least 93%, at least 94%, at least 95%, at least 96%, at least 97%, at least 98%, or at least 99% identical to one of SEQ ID NOs: 1-4, which maintains its functions (e.g., stem-loop formation, target protein binding), or a functional fragment thereof.

In some embodiments, the target protein comprises one of SEQ ID NOs: 5-8 or an amino acid sequence that is at least 70%, at least 75%, at least 80%, at least 85%, at least 90%, at least 90%, at least 91%, at least 92%, at least 93%, at least 94%, at least 95%, at least 96%, at least 97%, at least 98%, or at least 99% identical to one of SEQ ID NOs: 5-8, which maintains its function (e.g., RNA binding), or a functional fragment thereof.

```
SEQ ID NO: 5, MCP:
MASNFTQFVLVDNGGTGDVTVAPSNFANGIAEWISSNSRSQAYKVTCSV

RQSSAQNRKYTIKVEVPKGAWRSYLNMELTIPIFATNSDCELIVKAMQG

LLKDGNPIPSAIAANSGIY

SEQ ID NO: 6, PCP:
MSKTIVLSVGEATRTLTEIQSTADRQIFEEKVGPLVGRLRLTASLRQNG

AKTAYRVNLKLDQADVVDSGLPKVRYTQVWSHDVTIVANSTEASRKSLY

DLTKSLVATSQVEDLVVNLVPLG

SEQ ID NO: 7, BIV Tat:
SGPRPRGTRGKGRRIRR

SEQ ID NO: 8, P22 N protein:
NAKTRRHERRRKLAIER
```

In some embodiments, the target protein is encoded by a nucleic acid comprising one of SEQ ID NOs: 373-376 or a nucleic acid sequence that is at least 70%, at least 75%, at least 80%, at least 85%, at least 90%, at least 90%, at least 91%, at least 92%, at least 93%, at least 94%, at least 95%, at least 96%, at least 97%, at least 98%, or at least 99% identical to one of SEQ ID NOs: 373-376, which maintains its function when translated as a polypeptide (e.g., RNA binding), or a codon-optimized version thereof, or a functional fragment thereof.

```
SEQ ID NO: 373, MCP nucleic acid:
ATGGCCTCTAACTTTACCCAATTCGTCCTCGTCGATAATGGCGGCACAG

GAGATGTGACAGTGGCTCCTAGTAATTTCGCAAATGGCATCGCTGAATG

GATTTCCAGTAACAGCCGCAGCCAGGCTTATAAGGTGACCTGTTCCGTT

CGGCAGTCCTCAGCACAAAACCGGAAATATACAATAAAGGTGGAAGTAC

CTAAAGGCGCTTGGCGCTCTTACCTCAATATGGAATTAACAATTCCCAT

ATTTGCAACGAATTCCGATTGCGAGTTGATCGTCAAGGCAATGCAGGGG

CTCCTGAAAGACGGGAATCCCATCCCTAGTGCAATTGCCGCTAATTCTG

GAATCTAT

SEQ ID NO: 374, PCP nucleic acid:
ATGTCCAAGACTATCGTCTTATCAGTTGGAGAGGCGACCCGCACCTTAA

CCGAGATCCAATCCACTGCCGATAGACAAATCTTCGAGGAGAAGGTCGG

CCCACTCGTGGGTCGGTTGCGCCTTACAGCTAGTCTGCGGCAGAATGGT
```

16

```
-continued
GCCAAGACCGCCTACAGAGTCAACCTTAAACTGGATCAAGCTGATGTGG

TGGATAGCGGCCTTCCGAAGGTTCGTTATACGCAGGTGTGGAGTCATGA

CGTTACAATCGTGGCGAACTCTACTGAAGCCTCTCGGAAGAGCTTGTAC

GACCTTACTAAGAGCTTAGTGGCGACGTCCCAGGTCGAAGACCTGGTTG

TAAACCTGGTACCTCTGGGC

SEQ ID NO: 375, BIV Tat nucleic acid:
AGTGGACCGAGACCAAGAGGAACACGCGGAAAGGGCAGGCGGATCCGAC

GG

SEQ ID NO: 376, P22 N nucleic acid:
AATGCCAAGACTCGACGGCATGAGAGAAGGCGGAAACTGGCTATCGAAC

GG
```

In some embodiments, the aptamer specifically binds to a target protein, which is specifically produced by cells infected by a bacterium or virus or fungus, and not by healthy, uninfected cells. In some embodiments, the aptamer specifically binds to a target protein, which is specifically produced by cells associated with a disease or disorder, and not by healthy cells. In some embodiments, the aptamer specifically binds to a target protein, which is a mutant variant of a naturally occurring polypeptide. For example, an aptamer can specifically bind to a mutant variant of a naturally occurring polypeptide expressed by cancer cells but does not bind to the naturally occurring polypeptide expressed by non-cancerous cells.

Further non-limiting examples of target proteins to which the aptamer can specifically bind include: a) a detectable marker (e.g., a fluorescent polypeptide); b) an antigen (e.g., severe acute respiratory syndrome coronavirus 2 (SARS-CoV-2) spike gene, respiratory syncytial virus (RSV) F protein, influenza hemagglutinin, a tumor associated antigen (e.g., New York esophageal squamous cell carcinoma 1 for melanoma, kallikrein-2 for prostate cancer); an antibody (e.g., a monoclonal antibody; e.g.., an anti-claudin 18 isoform 2 (anti-CLDN18.2, which is specific for tumors) antibody, anti-cytotoxic T-lymphocyte-associated protein 4 (anti-CTLA-4) or anti-glucocorticoid-induced tumor necrosis factor receptor (TNFR)-related protein (anti-GITR) antibodies, which are specific for melanoma); c) a cytokine (e.g., IL-2, IL-7, IL-12, OX40L, IL-23); d) a cell therapy protein (e.g., claudin-6 (CLDN6), a chimeric antigen receptor (CAR) protein, a T cell receptor); e) a tumor suppressor protein (e.g., tumor protein 53 (p53), breast cancer gene 1 (BRCA1), breast cancer gene 2 (BRCA2)); f) a programmed cell death protein (e.g., Bax, a caspase); g) a site-specific nuclease (e.g., Cas9; a prime editing enzyme (e.g., PE2, PE3, PE4, PE5, PE2max, PE3max, and the like); h) a therapeutic protein (e.g., vascular endothelial growth factor (VEGF), Glucagon-like peptide-1, insulin); or i) an oncogene (e.g., mutant forms of KRAS, HRAS, EGFR, HER2, PDGFR, MYC, BRCA1, BRCA2, ABL1, VEGF).

In some embodiments, the aptamer comprises Iron responsive element (IRE), and the target protein comprises Iron responsive protein (IRP); see e.g., Levenson et al. "Iron and ageing: an introduction to iron regulatory mechanisms." Ageing Res Rev. 3(3): 251-263 (2004).

In some embodiments, aptamers (e.g., RNA aptamers) can be selected for particular target proteins using a techniques, including but not limited to, Systematic Evolution of Ligands by EXponential enrichment (SELEX).

In some embodiments, the aptamer is located 5' of the ribozyme in the ARES region. In some embodiments, the aptamer is located 3' of the ribozyme in the ARES region.

Ribozymes

In multiple aspects, described herein are ARES regions, which comprise at least ribozyme (e.g., 1, 2, 3, 4, 5, 6, 7, 8, 9, 10, or more ribozymes, which can be the same or different ribozymes). As used herein, the term "ribozyme" refers to an RNA-comprising nucleic acid, which is capable of functioning as an enzyme. Any ribozyme known in the art or discovered can be used in the ARES regions described herein. In some embodiments, the ribozyme is a self-cleaving ribozyme, that is the ribozyme is capable of cleaving itself (i.e., endonucleolytic cleavage). Non-limiting examples of self-cleaving ribozymes include hammerhead ribozyme (HHR), hepatitis delta virus (HDV) ribozyme, hairpin ribozyme, Varkud satellite (VS) ribozyme, glmS ribozyme, twister ribozyme, twister sister ribozyme, Pistol ribozyme, Hatchet ribozyme, and Hovlinc ribozyme; for more details about self-cleaving ribozymes, see e.g., Jimenez et al. "Chemistry and Biology of Self-Cleaving Ribozymes." Trends Biochem Sci. 40(11): 648-661 (2015); Peng et al. "Self-cleaving ribozymes: substrate specificity and synthetic biology applications." RSC Chem Biol. 2(5): 1370-1383 (2021); the contents of each of which are incorporated herein by reference in their entirety.

In some embodiments, the self-cleaving ribozyme comprises a hammerhead ribozyme (HHR). A HHR comprises a catalytic core of conserved nucleotides, which is flanked by three helices; two of the helices can form tertiary interactions that can permit self-cleavage. HHRs occur in many species' genomes, including in subviral plant pathogens.

In some embodiments, the hammerhead ribozyme (HHR) comprises SEQ ID NO: 370 or an nucleic acid sequence that is at least 70%, at least 75%, at least 80%, at least 85%, at least 90%, at least 90%, at least 91%, at least 92%, at least 93%, at least 94%, at least 95%, at least 96%, at least 97%, at least 98%, or at least 99% identical to SEQ ID NO: 370, , which maintains its function (e.g., self-cleavage), or a functional fragment thereof.

```
SEQ ID NO: 370, hammerhead ribozyme (HHR):
GCGCGTCCTGGATTCGCGGAAACGCGTACATCCAGCTGACGAGTCCCAA

ATAGGACGAAACGCGC
```

In some embodiments, the ribozyme is located 5' of the aptamer in the ARES region. In some embodiments, the ribozyme is located 3' of the aptamer in the ARES region.

ON-Switch ARES Regions

In multiple aspects, described herein are ON-switch ARES region. As used herein, the term "ON-switch ARES region" refers to an ARES region which can turn the translation of at least one cargo polypeptide ON in the presence of a target protein that specifically binds to the protein-binding aptamer. Specifically, in an RNA molecule comprising an ON-switch ARES region, in the presence of the target protein, the aptamer is stabilized, the ribozyme (e.g., self-cleaving ribozyme) cannot form, the RNA molecule is not cleaved (e.g., by the self-cleaving ribozyme), and the ORF encoding the at least one cargo polypeptide can be translated (ON). Furthermore, in an RNA molecule comprising an ON-switch ARES region, the aptamer is not stabilized, the self-cleaving ribozyme can form, the RNA molecule is cleaved (e.g., by the self-cleaving ribozyme), and the ORF encoding the at least one cargo polypeptide cannot be translated (OFF). In some embodiments, the ON-switch ARES region is structured such that either the aptamer or the ribozyme, but not both, can form at one time in the RNA molecule. For example, the ON-switch ARES region can be structured such that the aptamer and the ribozyme share at least one region.

In one aspect, described herein is an ON-switch ARES region comprising: a) at least one aptamer comprising: i) a first (a) region and a complementary (a*) region that can hybridize to the first (a) region; and ii) a primary second (b1) region and a complementary (b*) region that can hybridize to the primary second (b1) region or to a secondary second (b2) region in the ribozyme; and b) at least one ribozyme comprising: i) the secondary second (b2) region and the complementary (b*) region; and ii) a third (c) region and a complementary (c*) region that can hybridize to the third (c) region.

In some embodiments, in an ON-switch ARES region, the aptamer and ribozyme share at least one region (e.g., the complementary (b*) region).

In some embodiments, the aptamer is 5' of the ribozyme in the ON-switch ARES region (see e.g., FIG. 1A). In some embodiments, the ON-switch ARES region comprises from 5' to 3': a) the primary second (b1) region; b) the first (a) region; c) the complementary (a*) region that can hybridize to the first (a) region; d) the complementary (b*) region that can hybridize to the primary second (b1) region in the aptamer or to a secondary second (b2) region in the ribozyme; e) the third (c) region; f) the complementary (c*) region that can hybridize to the third (c) region; and g) the secondary second (b2) region.

Figure 1B:
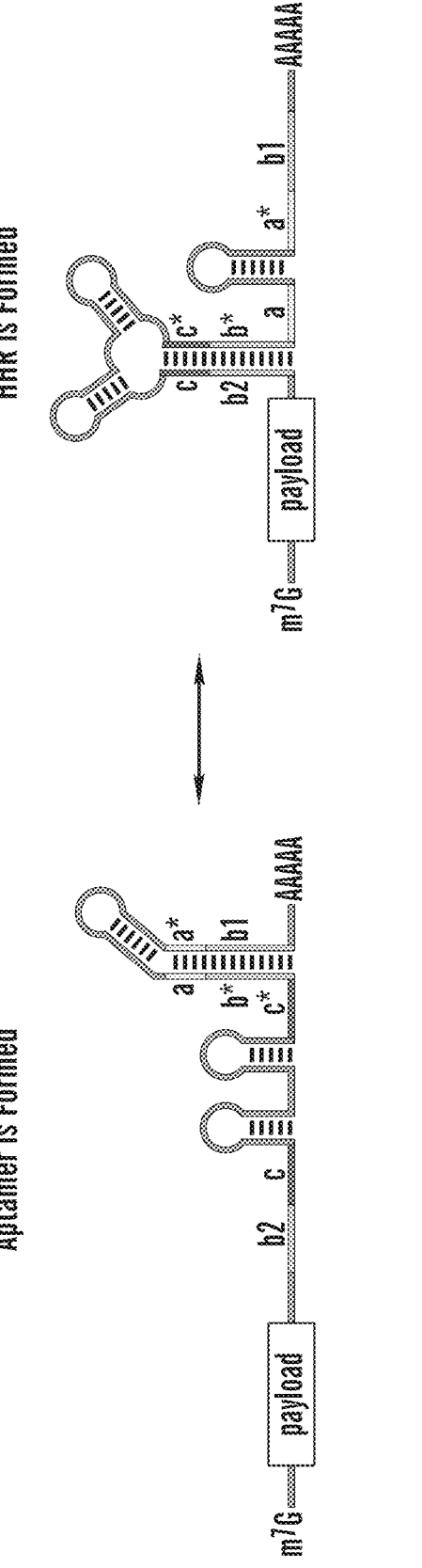

In some embodiments, the ribozyme is 5' of the aptamer in the ON-switch ARES region (see e.g., FIG. 1B). In some embodiments, the ON-switch ARES region comprises from 5' to 3': a) the secondary second (b2) region; b) the third (c) region; c) the complementary (c*) region that can hybridize to the third (c) region; d) the complementary (b*) region that can hybridize to the secondary second (b2) region in the ribozyme or to a primary second (b1) region in the aptamer; e) the first (a) region; f) the complementary (a*) region that can hybridize to the first (a) region; and g) the primary second (b1) region.

In some embodiments, the ON-switch ARES region comprises a sequence selected from Table 4 (Exemplary MS2 ON switches), Table 6 (Exemplary PP7 ON switches), Table 7 (Exemplary BIV Tar ON switches), Table 9 (Exemplary P22N ON switches), or Table 10 (Exemplary High-Performing ON and OFF switches).

In some embodiments, the ON-switch ARES region comprises one of SEQ ID NOs: 9-26, 122-218, or 313-369 or a nucleic acid sequence that is at least 70%, at least 75%, at least 80%, at least 85%, at least 90%, at least 90%, at least 91%, at least 92%, at least 93%, at least 94%, at least 95%, at least 96%, at least 97%, at least 98%, or at least 99% identical to one of SEQ ID NOs: 9-26, 122-218, or 313-369, which maintains its function (e.g., ON-switch ARES region).

In some embodiments, the ON-switch ARES region comprises an MS2 aptamer 5' of an HHR. In some embodiments, the ON-switch ARES region comprises one of SEQ ID NOs: 9-23, or a nucleic acid sequence that is at least 70%, at least 75%, at least 80%, at least 85%, at least 90%, at least 90%, at least 91%, at least 92%, at least 93%, at least 94%, at least 95%, at least 96%, at least 97%, at least 98%, or at least 99% identical to one of SEQ ID NOs: 9-23, which maintains its function (e.g., ON-switch ARES region).

In some embodiments, the ON-switch ARES region comprises an HHR 5' of an MS2 aptamer. In some embodiments, the ON-switch ARES region comprises one of SEQ ID NOs: 24-26, or a nucleic acid sequence that is at least 70%, at least 75%, at least 80%, at least 85%, at least 90%, at least 90%, at least 91%, at least 92%, at least 93%, at least 94%, at least 95%, at least 96%, at least 97%, at least 98%, or at least 99% identical to one of SEQ ID NOs: 24-26, which maintains its function (e.g., ON-switch ARES region).

In some embodiments, the ON-switch ARES region comprises a PP7 aptamer 5' of an HHR. In some embodiments, the ON-switch ARES region comprises one of SEQ ID NOs: 122-168, or a nucleic acid sequence that is at least 70%, at least 75%, at least 80%, at least 85%, at least 90%, at least 90%, at least 91%, at least 92%, at least 93%, at least 94%, at least 95%, at least 96%, at least 97%, at least 98%, or at least 99% identical to one of SEQ ID NOs: 122-168, which maintains its function (e.g., ON-switch ARES region).

In some embodiments, the ON-switch ARES region comprises an HHR 5' of a PP7 aptamer. In some embodiments, the ON-switch ARES region comprises one of SEQ ID NOs: 169-172, or a nucleic acid sequence that is at least 70%, at least 75%, at least 80%, at least 85%, at least 90%, at least 90%, at least 91%, at least 92%, at least 93%, at least 94%, at least 95%, at least 96%, at least 97%, at least 98%, or at least 99% identical to one of SEQ ID NOs: 169-172, which maintains its function (e.g., ON-switch ARES region).

In some embodiments, the ON-switch ARES region comprises a BIV Tar aptamer 5' of an HHR. In some embodiments, the ON-switch ARES region comprises one of SEQ ID NOs: 173-218, or a nucleic acid sequence that is at least 70%, at least 75%, at least 80%, at least 85%, at least 90%, at least 90%, at least 91%, at least 92%, at least 93%, at least 94%, at least 95%, at least 96%, at least 97%, at least 98%, or at least 99% identical to one of SEQ ID NOs: 173-218, which maintains its function (e.g., ON-switch ARES region). In some embodiments, the ON-switch ARES region comprises an HHR 5' of a BIV Tar aptamer.

In some embodiments, the ON-switch ARES region comprises a P22 aptamer 5' of an HHR. In some embodiments, the ON-switch ARES region comprises one of SEQ ID NOs: 313-369, or a nucleic acid sequence that is at least 70%, at least 75%, at least 80%, at least 85%, at least 90%, at least 90%, at least 91%, at least 92%, at least 93%, at least 94%, at least 95%, at least 96%, at least 97%, at least 98%, or at least 99% identical to one of SEQ ID NOs: 313-369, which maintains its function (e.g., ON-switch ARES region). In some embodiments, the ON-switch ARES region comprises an HHR 5' of a P22 aptamer.

In some embodiments, the ON-switch ARES region is a high-performing ON-switch ARES region. In some embodiments, the ON-switch ARES region comprises one of SEQ ID NOs: 10, 12, 18, 22, 24, 122, 130, 136, 149, 157, 169, 204, 214, 394, or a nucleic acid sequence that is at least 70%, at least 75%, at least 80%, at least 85%, at least 90%, at least 90%, at least 91%, at least 92%, at least 93%, at least 94%, at least 95%, at least 96%, at least 97%, at least 98%, or at least 99% identical to one of SEQ ID NOs: 10, 12, 18, 22, 24, 122, 130, 136, 149, 157, 169, 204, 214, 394, which maintains its function (e.g., ON-switch ARES region).

Stabilization and Degradation ARES Regions

In multiple aspects, described herein are ARES region that comprise at least one stabilization domain (e.g., 1, 2, 3, 4, 5, 6, 7, 8, 9, 10, or more stabilization domains, which can be the same or stabilization domains) and/or at least one degradation domain (e.g., 1, 2, 3, 4, 5, 6, 7, 8, 9, 10, or more degradation domains, which can be the same or degradation domains). As used herein, the term "stabilization domain" or "stabilizing domain" refers to a nucleic acid sequence (e.g., ssRNA) that increases the half-life of a nucleic acid (e.g., RNA molecule) that comprises it. As used herein, the term "degradation domain" or "destabilization domain" or "destabilizing domain" refers to a nucleic acid sequence (e.g., ssRNA) that decreases the half-life of a nucleic acid (e.g., RNA molecule) that comprises it and/or increase the degradation rate of a nucleic acid (e.g., RNA molecule) that comprises it. For more details about stabilization domains and degradation domains, see e.g., Wroblewska et al. (2015). "Mammalian synthetic circuits with RNA binding proteins for RNA-only delivery." Nature biotechnology, 33(8), 839-841, the contents of which are incorporated herein by reference in their entirety.

In some embodiments, an RNA molecule comprises a stabilization/degradation ARES region. In some embodiments, the stabilization/degradation ARES region is in the 3' UTR of the RNA molecule. In some embodiments, the stabilization/degradation ARES region is in the 5' UTR of the RNA molecule. In some embodiments, the stabilization/degradation ARES region comprises at least one stabilization domain, at least one ONE-switch ARES region as described herein, and at least one degradation domain.

In some embodiments, in an RNA molecule comprising a stabilization/degradation ARES region, in the presence of the target protein, the aptamer is stabilized, the ribozyme (e.g., self-cleaving ribozyme) cannot form, the RNA molecule is not cleaved (e.g., by the self-cleaving ribozyme), the degradation domain is retained, the RNA molecule is degraded, and the ORF encoding the at least one cargo polypeptide cannot be translated (OFF). In some embodiments, in an RNA molecule comprising a stabilization/degradation ARES region, in the absence of the target protein, the aptamer is not stabilized, the ribozyme (e.g., self-cleaving ribozyme) can form, the RNA molecule is cleaved (e.g., by the self-cleaving ribozyme), the degradation domain is not retained, the stabilization domain protects the RNA molecule from degradation, and the ORF encoding the at least one cargo polypeptide can be translated (ON).

In one aspect, described herein is a stabilization/degradation ARES region comprising from 5' to 3': a) a stabilization domain; b) an ON-switch ARES region structured such that either the aptamer or the ribozyme, but not both, can form at one time in the RNA molecule; and c) a degradation domain.

In one aspect, described herein is a stabilization/degradation ARES region comprising from 5' to 3': a) a stabilization domain; b) an ON-switch ARES region as described herein; and c) a degradation domain. In one aspect, described herein is an ON-switch ARES region comprising: a) a stabilization domain; b) at least one aptamer comprising: i) a first (a) region and a complementary (a*) region that can hybridize to the first (a) region; and ii) a primary second (b1) region and a complementary (b*) region that can hybridize to the primary second (b1) region or to a secondary second (b2) region in the ribozyme; c) at least one ribozyme comprising: i) the secondary second (b2) region and the complementary (b*) region; and ii) a third (c) region and a complementary (c*) region that can hybridize to the third (c) region; and d) at least one degradation domain.

Figure 1C:
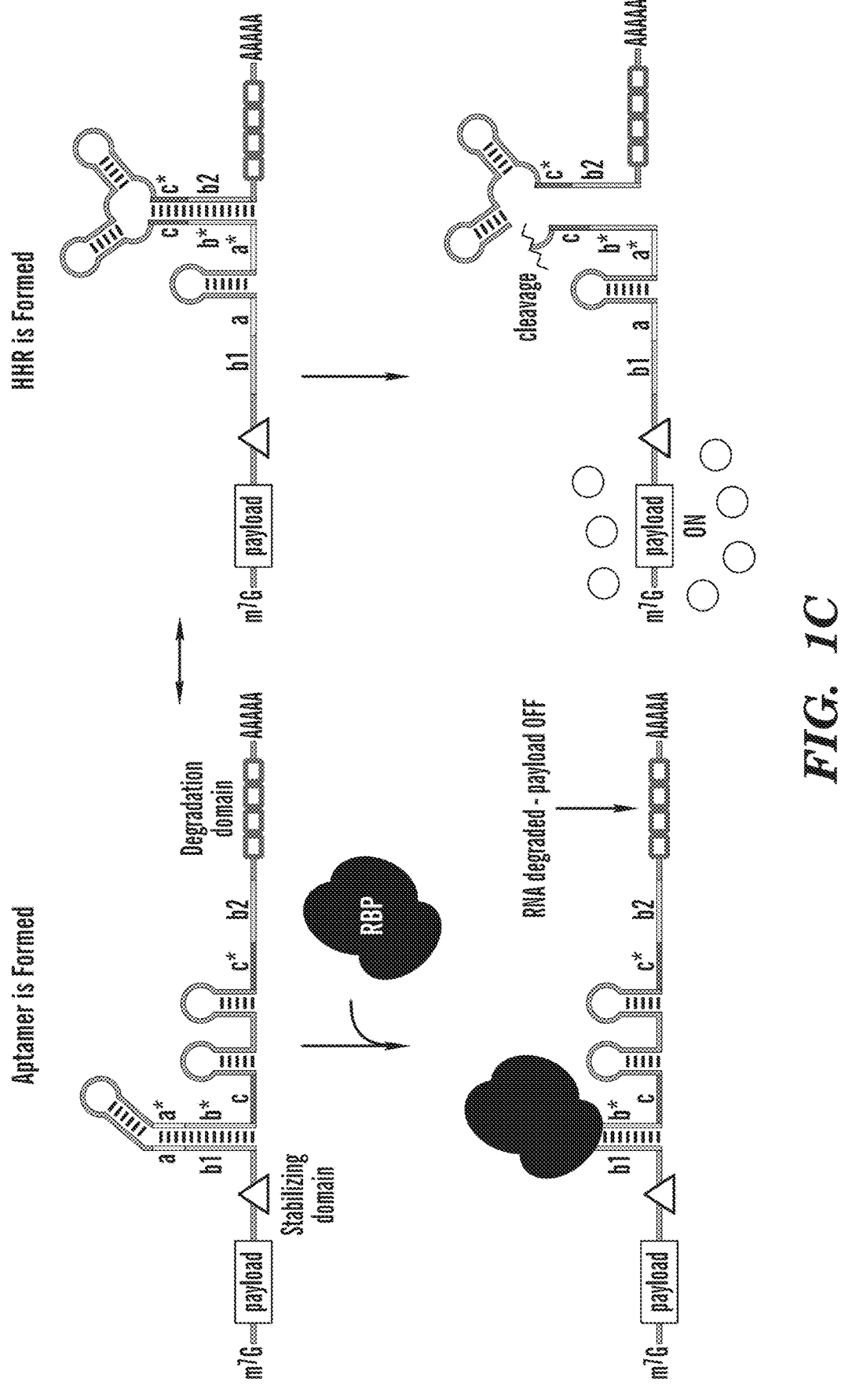

In some embodiments, the aptamer is 5' of the ribozyme in the stabilization/degradation ARES region (see e.g., FIG. 1C). In some embodiments, the stabilization/degradation ARES region comprises from 5' to 3': a) the stabilization domain; b) the primary second (b1) region; c) the first (a) region; d) the complementary (a*) region that can hybridize to the first (a) region; e) the complementary (b*) region that can hybridize to the primary second (b1) region in the aptamer or to a secondary second (b2) region in the ribozyme; f) the third (c) region; g) the complementary (c*) region that can hybridize to the third (c) region; h) the secondary second (b2) region; and i) the degradation domain.

Figure 1D:
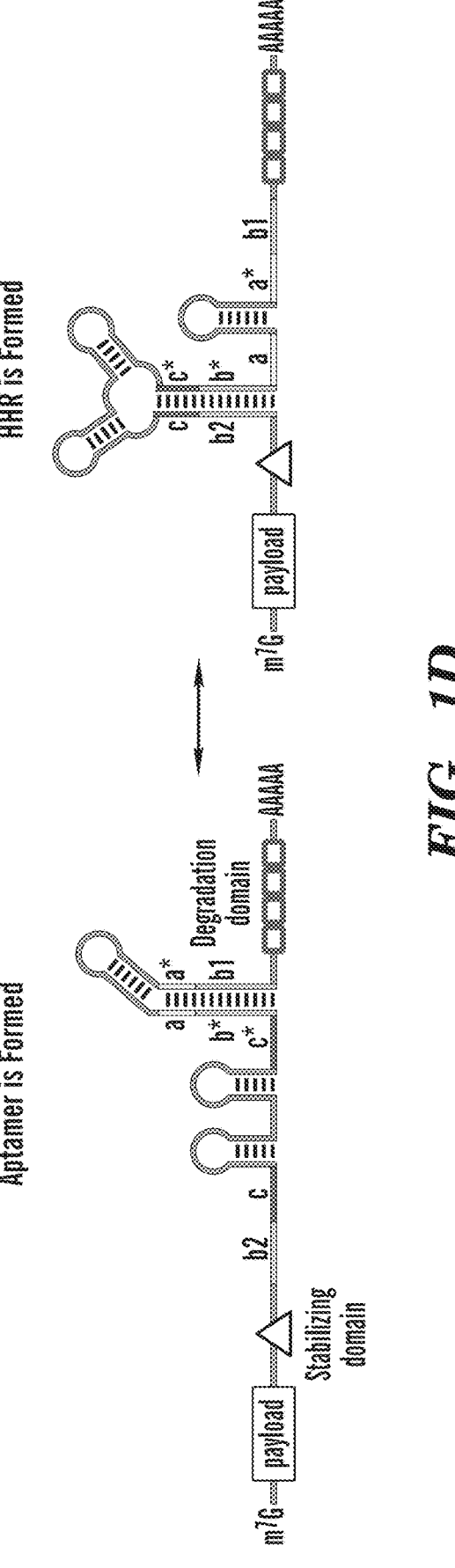

In some embodiments, the ribozyme is 5' of the aptamer in the stabilization/degradation (see e.g., FIG. 1D). In some embodiments, the stabilization/degradation ARES region comprises from 5' to 3': a) the stabilization domain; b) the secondary second (b2) region; c) the third (c) region; d) the complementary (c*) region that can hybridize to the third (c) region; e) the complementary (b*) region that can hybridize to the secondary second (b2) region in the ribozyme or to a primary second (b1) region in the aptamer; f) the first (a) region; g) the complementary (a*) region that can hybridize to the first (a) region; h) the primary second (b1) region; and i) the degradation domain.

In some embodiments, the stabilization domain comprises SEQ ID NO: 371 or an nucleic acid sequence that is at least 70%, at least 75%, at least 80%, at least 85%, at least 90%, at least 90%, at least 91%, at least 92%, at least 93%, at least 94%, at least 95%, at least 96%, at least 97%, at least 98%, or at least 99% identical to SEQ ID NO: 371, which maintains its function (e.g., stabilization of an RNA molecule), or a functional fragment thereof.

SEQ ID NO: 371, stabilization domain:
GATTCGTCAGTAGGGTTGTAAAGGTTTTTCTTTTCCTGAGAAAACAACC

TTTTGTTTTCTCAGGTTTTGCTTTTTGGCCTTTCCCTAGCTTTAAAAAA

AAAAAAGCAAAA

In some embodiments, the degradation domain comprises 30 repeats of TAAGTTAT (SEQ ID NO: 372). In some embodiments, the degradation domain comprises at least 5, at least 10, at least 15, at least 20, at least 25, or at least 30 repeats of TAAGTTAT. In some embodiments, the degradation domain comprises SEQ ID NO: 372 or an nucleic acid sequence that is at least 70%, at least 75%, at least 80%, at least 85%, at least 90%, at least 90%, at least 91%, at least 92%, at least 93%, at least 94%, at least 95%, at least 96%, at least 97%, at least 98%, or at least 99% identical to SEQ ID NO: 372, which maintains its function (e.g., destabilization of an RNA molecule and/or degradation of an RNA molecule), or a functional fragment thereof.

SEQ ID NO: 372, degradation domain:
TAAGTTATTAAGTTATTAAGTTATTAAGTTATTAAGTTATTAAGTTATT

AAGTTATTAAGTTATTAAGTTATTAAGTTATTAAGTTATTAAGTTATTA

AGTTATTAAGTTATTAAGTTATTAAGTTATTAAGTTATTAAGTTATTAA

GTTATTAAGTTATTAAGTTATTAAGTTATTAAGTTATTAAGTTATTAAG

TTATTAAGTTATTAAGTTATTAAGTTATTAAGTTATTAAGTTATTAAGTTAT

OFF-Switch ARES Regions

In multiple aspects, described herein are OFF-switch ARES region. As used herein, the term "OFF-switch ARES region" refers to an ARES region which can turn the translation of at least one cargo polypeptide OFF in the presence of a target protein that specifically binds to the protein-binding aptamer. Specifically, in an RNA molecule comprising an OFF-switch ARES region, in the presence of the target protein, the aptamer is stabilized, the ribozyme (e.g., self-cleaving ribozyme) can form, at least one stabilization stem cannot form, the RNA molecule is cleaved (e.g., by the self-cleaving ribozyme), and the ORF encoding the at least one cargo polypeptide cannot be translated (OFF). Furthermore, in an RNA molecule comprising an OFF-switch ARES region, in the absence of the target protein, the aptamer is not stabilized, the ribozyme (e.g., self-cleaving ribozyme) cannot form, at least one stabilization stem can form, the RNA molecule is not cleaved (e.g., by the self-cleaving ribozyme), and the ORF encoding the at least one cargo polypeptide can be translated (ON). In some embodiments, the OFF-switch ARES region is structured such that either both the aptamer and the ribozyme, or at least one stabilization stem, can form at one time in the RNA molecule.

In some embodiments, the OFF-switch ARES region comprises at least one stabilization stem (e.g., 1, 2, 3, 4, 5, 6, 7, 8, 9, 10, or more stabilization stems, which can be the same or different stabilization stems). As used herein, the term "stabilization stem" or "ON stem" refers to a secondary structure that can form in the OFF-switch ARES region, which prevents the formation of the aptamer and the ribozyme. Since the self-cleaving ribozyme cannot form when the at least one stabilization stem is present, the OFF-switch ARES region is "ON" when the at least one stabilization stem is formed. In some embodiments, the at least one stabilization stem has more a stable secondary structure that is preferred to the less stable structures of the aptamer and ribozyme, when the target protein is not present. When the target protein is present, its binding to the aptamer stabilizes the aptamer and allows the ribozyme to form, and the at least one stabilization stem is not formed. In some embodiments, the at least one stabilization stem shares at least one region with the aptamer and/or ribozyme, such that either the at least one stabilization stem, or both the aptamer and the ribozyme, can form at one time in the RNA molecule.

In some embodiments, the OFF-switch ARES region comprises one stabilization stem. In one aspect, described herein is an OFF-switch ARES region comprising: a) at least one aptamer comprising: i) a first (a) region and a complementary (a*) region that can hybridize to the first (a) region; and ii) a primary second (b1) region and a primary complementary (b1*) region that can hybridize to the primary second (b1) region or to a secondary second (b2) region; b) at least one ribozyme comprising: i) the secondary second (b2) region and a secondary complementary (b2*) region that can hybridize to the secondary second (b2) region; and ii) a third (c) region and a complementary (c*) region that can hybridize to the third (c) region; and c) at least one stabilization stem comprising: i) a fourth (d) region and a complementary (d*) region that can hybridize to the fourth (d) region; and ii) the secondary second (b2) region of the ribozyme and the primary complementary (b1*) region of the aptamer.

In some embodiments, in an OFF-switch ARES region with a single stabilization stem, the 5' to 3' order is: aptamer, stabilization stem, and ribozyme. In some embodiments, in an OFF-switch ARES region with a single stabilization stem, the 5' to 3' order is: ribozyme, stabilization stem, and aptamer. In some embodiments, in an OFF-switch ARES region, the aptamer and stabilization stem share at least one region (e.g., the primary complementary (b1*) region). In some embodiments, in an OFF-switch ARES region, the ribozyme and stabilization stem share at least one region (e.g., the secondary second (b2) region).

Figure 1E:
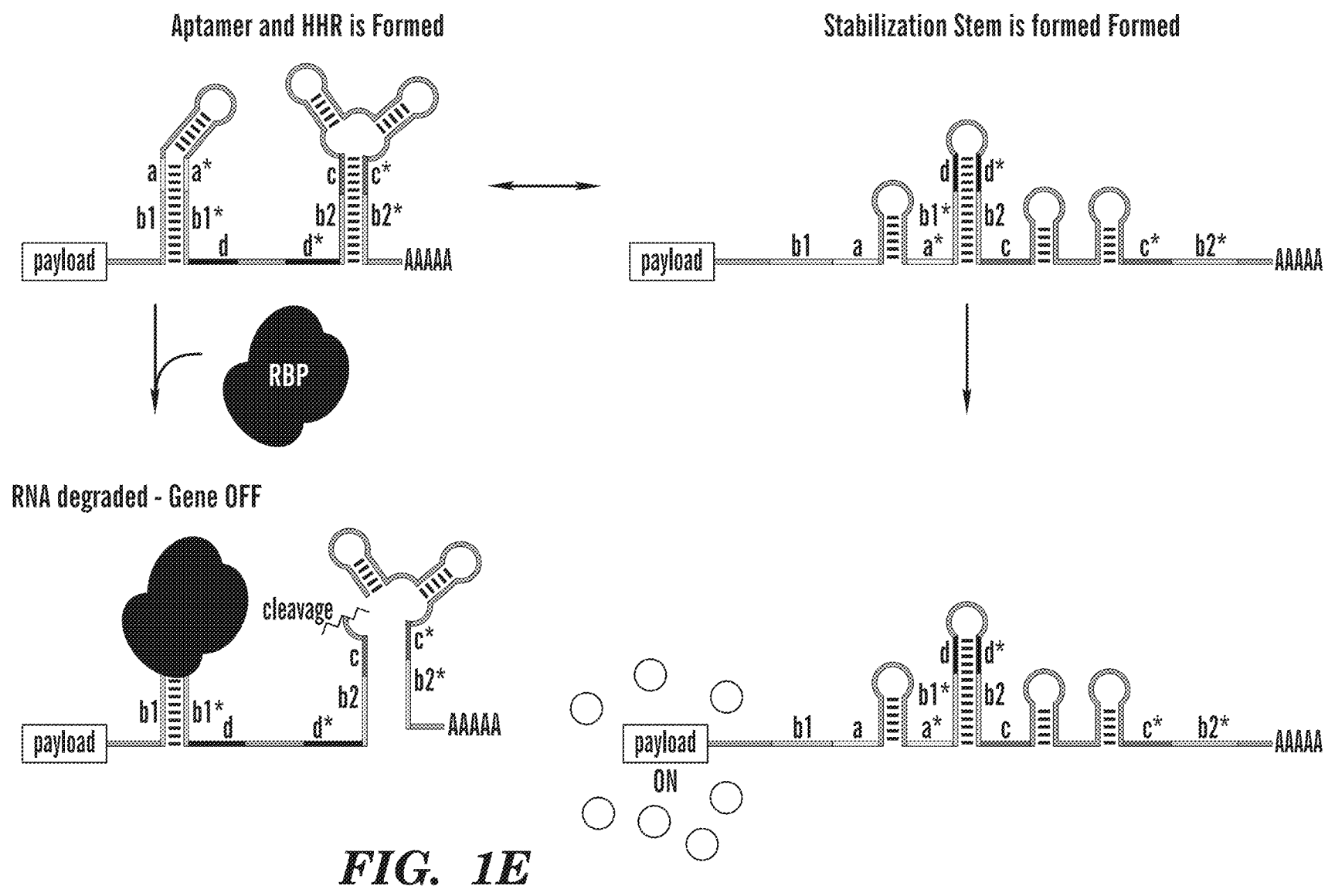

In some embodiments, the aptamer is 5' of the ribozyme in the OFF-switch ARES region with a single stabilization stem (see e.g., FIG. 1E). In some embodiments, the OFF-switch ARES region comprises from 5' to 3': a) the primary second (b1) region; b) the first (a) region; c) the complementary (a*) region that can hybridize to the first (a) region; d) the primary complementary (b1*) region that can hybridize to the primary second (b1) region or to a secondary second (b2) region; e) the fourth (d) region; f) the complementary (d*) region that can hybridize to the fourth (d) region; g) the secondary second (b2) region; h) the third (c) region; i) the complementary (c*) region that can hybridize to the third (c) region; and j) the secondary complementary (b2*) region that can hybridize to the secondary second (b2) region.

Figure 1F:
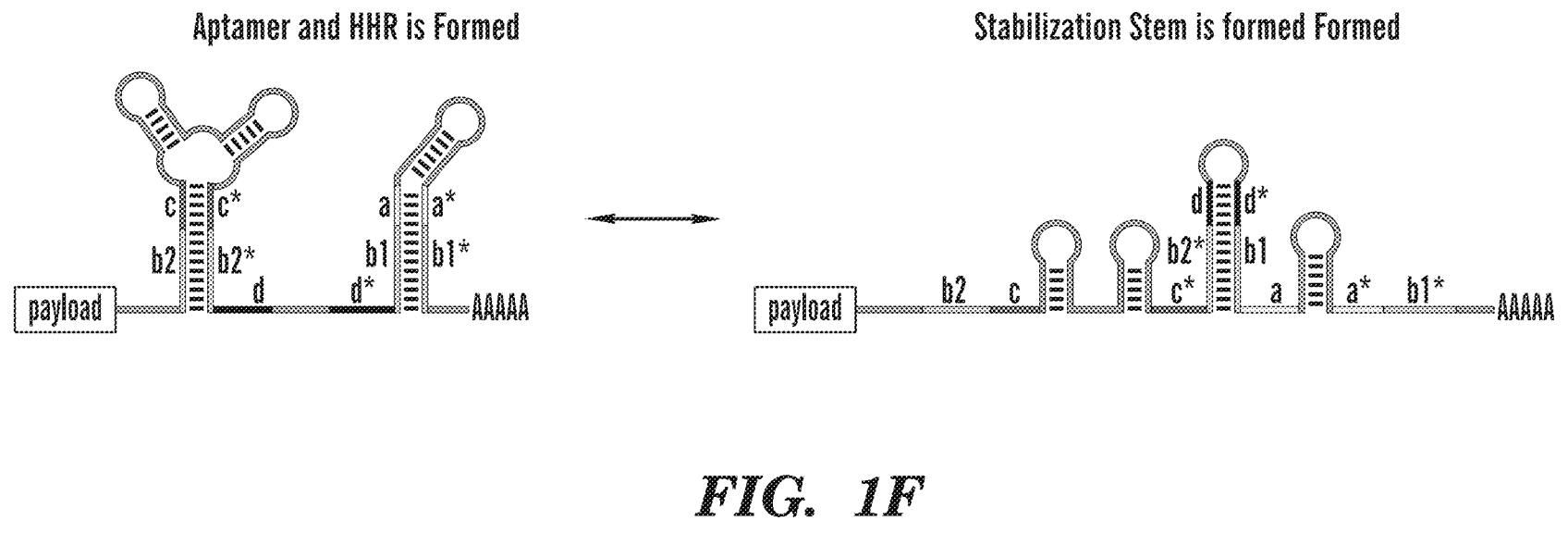

In some embodiments, the ribozyme is 5' of the aptamer in the OFF-switch ARES region with a single stabilization stem (see e.g., FIG. 1F). In some embodiments, the OFF-switch ARES region comprises from 5' to 3': a) the secondary second (b2) region; b) the third (c) region; c) the complementary (c*) region that can hybridize to the third (a) region; d) the secondary complementary (b2*) region that can hybridize to the secondary second (b2) region or to a primary second (b1) region; e) the fourth (d) region; f) the complementary (d*) region that can hybridize to the fourth (d) region; g) the primary second (b1) region; h) the first (a) region; i) the complementary (a*) region that can hybridize to the first (a) region; and j) the primary complementary (b1*) region that can hybridize to the primary second (b1) region.

In some embodiments, the OFF-switch ARES region comprises two stabilization stems. In one aspect, described herein is an OFF-switch ARES region comprising: a) an aptamer comprising: i) a first (a) region and a complementary (a*) region that can hybridize to the first (a) region; and ii) a primary second (b1) region and a primary complementary (b1*) region that can hybridize to the primary second (b1) region or to a secondary second (b2) region; b) a ribozyme comprising: i) the secondary second (b2) region and a secondary complementary (b2*) region that can hybridize to the secondary second (b2) region; and ii) a third (c) region and a complementary (c*) region that can hybridize to the third (c) region; c) a first stabilization stem comprising: i) a primary fourth (d1) region and a complementary (d1*) region that can hybridize to the primary fourth (d1) region; and ii) the secondary second (b2) region of the ribozyme and the primary complementary (b1*) region of the aptamer; and d) a second stabilization stem comprising: i) a secondary fourth (d2) region and a complementary (d2*) region that can hybridize to the secondary fourth (d2) region; and ii) the primary second (b1) region of the aptamer and a tertiary complementary (b3*) region that can hybridize to the primary second (b1) region (see e.g., FIG. 1G).

In some embodiments, in an OFF-switch ARES region with two stabilization stems, the 5' to 3' order is: second stabilization stem, aptamer, first stabilization stem, and ribozyme. In some embodiments, in an OFF-switch ARES region with two stabilization stems, the aptamer and the first stabilization stem share at least one region (e.g., the primary complementary (b1*) region). In some embodiments, in an OFF-switch ARES region with two stabilization stems, the aptamer and the second stabilization stem share at least one region (e.g., the primary second (b1) region). In some embodiments, in an OFF-switch ARES region with two stabilization stems, the ribozyme and stabilization stem share at least one region (e.g., the secondary second (b2) region).

Figure 1G:
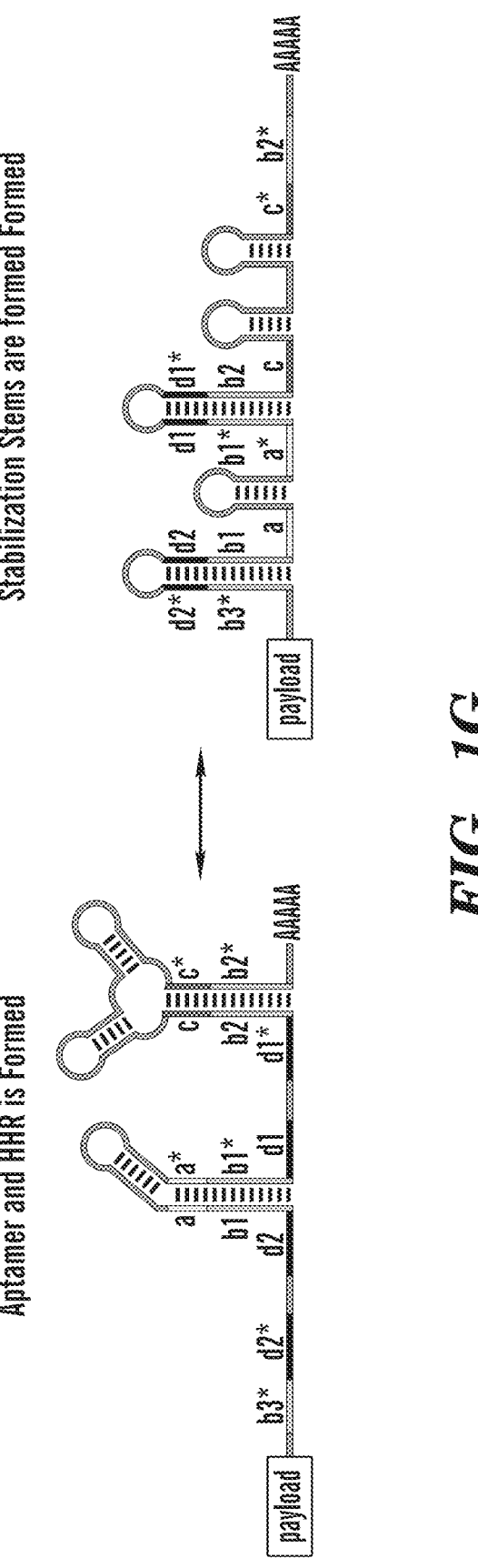

In some embodiments, the aptamer is 5' of the ribozyme in the OFF-switch ARES region with two stabilization stems (see e.g., FIG. 1G). In some embodiments, the OFF-switch ARES region comprises from 5' to 3': a) the tertiary complementary (b3*) region that can hybridize to the primary second (b1) region; b) the complementary (d2*) region that can hybridize to the secondary fourth (d2) region; c) the secondary fourth (d2) region; d) the primary second (b1) region; e) the first (a) region; f) the complementary (a*) region that can hybridize to the first (a) region; g) the primary complementary (b1*) region that can hybridize to the primary second (b1) region or to the secondary second (b2) region; h) the primary fourth (d1) region; i) the complementary (d1*) region that can hybridize to the primary fourth (d1) region; j) the secondary second (b2) region; k) the third (c) region; l) the complementary (c*) region that can hybridize to the third (c) region; and m) the secondary complementary (b2*) region that can hybridize to the secondary second (b2) region.

Figure 1H:
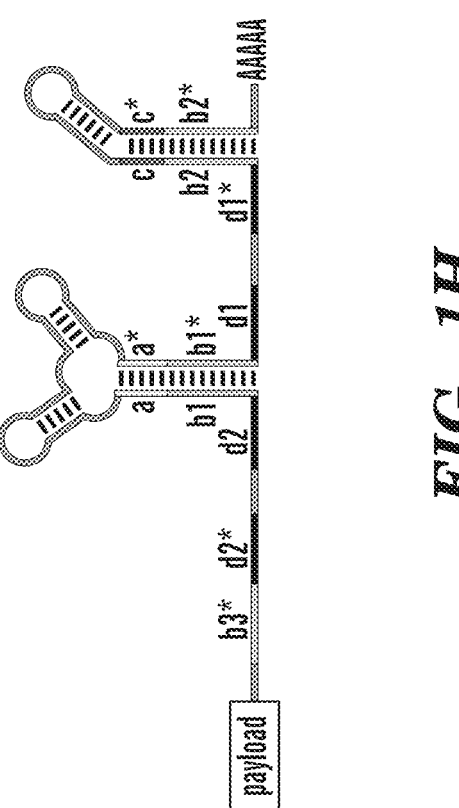

In one aspect, described herein is an OFF-switch ARES region comprising: a) a ribozyme comprising: i) a first (a) region and a complementary (a*) region that can hybridize to the first (a) region; and ii) a primary second (b1) region and a primary complementary (b1*) region that can hybridize to the primary second (b1) region or to a secondary second (b2) region; b) an aptamer comprising: i) the secondary second (b2) region and a secondary complementary (b2*) region that can hybridize to the secondary second (b2) region; and ii) a third (c) region and a complementary (c*) region that can hybridize to the third (c) region; c) a first stabilization stem comprising: i) a primary fourth (d1) region and a complementary (d1*) region that can hybridize to the primary fourth (d1) region; and ii) the secondary second (b2) region of the aptamer and the primary complementary (b1*) region of the ribozyme; and d) a second stabilization stem comprising: i) a secondary fourth (d2) region and a complementary (d2*) region that can hybridize to the secondary fourth (d2) region; and ii) the primary second (b1) region of the ribozyme and a tertiary complementary (b3*) region that can hybridize to the primary second (b1) region (see e.g., FIG. 1H).

In some embodiments, in an OFF-switch ARES region with two stabilization stems, the 5' to 3' order is: second stabilization stem, ribozyme, first stabilization stem, and aptamer. In some embodiments, in an OFF-switch ARES region with two stabilization stems, the ribozyme and the first stabilization stem share at least one region (e.g., the primary complementary (b1*) region). In some embodiments, in an OFF-switch ARES region with two stabilization stems, the ribozyme and the second stabilization stem share at least one region (e.g., the primary second (b1) region). In some embodiments, in an OFF-switch ARES region with two stabilization stems, the aptamer and stabilization stem share at least one region (e.g., the secondary second (b2) region).

In some embodiments, the ribozyme is 5' of the aptamer in the OFF-switch ARES region with two stabilization stems (see e.g., FIG. 1H). In some embodiments, the OFF-switch ARES region comprises from 5' to 3': a) the tertiary complementary (b3*) region that can hybridize to the primary second (b1) region; b) the complementary (d2*) region that can hybridize to the secondary fourth (d2) region; c) the secondary fourth (d2) region; d) the primary second (b1) region; e) the first (a) region; f) the complementary (a*) region that can hybridize to the first (a) region; g) the primary complementary (b1*) region that can hybridize to the primary second (b1) region or to the secondary second (b2) region; h) the primary fourth (d1) region; i) the complementary (d1*) region that can hybridize to the primary fourth (d1) region; j) the secondary second (b2) region; k) the third (c) region; 1) the complementary (c*) region that can hybridize to the third (c) region; and m) the secondary complementary (b2*) region that can hybridize to the secondary second (b2) region.

In some embodiments, the OFF-switch ARES region comprises a sequence selected from Table 5 (Exemplary MS2 OFF switches, with 2 stabilization stems), Table 8 (Exemplary BIV Tar OFF switches, with 1 stabilization stem), or Table 10 (Exemplary High-Performing ON and OFF switches).

In some embodiments, the OFF-switch ARES region comprises one of SEQ ID NOs: 27-121 or 219-312 or a nucleic acid sequence that is at least 70%, at least 75%, at least 80%, at least 85%, at least 90%, at least 90%, at least 91%, at least 92%, at least 93%, at least 94%, at least 95%, at least 96%, at least 97%, at least 98%, or at least 99% identical to one of SEQ ID NOs: 27-121 or 219-312, which maintains its function (e.g., OFF-switch ARES region).

In some embodiments, the OFF-switch ARES region comprises an MS2 aptamer 5' of an HHR (e.g., with 2 stabilization stems). In some embodiments, the OFF-switch ARES region comprises one of SEQ ID NOs: 27-121, or a nucleic acid sequence that is at least 70%, at least 75%, at least 80%, at least 85%, at least 90%, at least 90%, at least 91%, at least 92%, at least 93%, at least 94%, at least 95%, at least 96%, at least 97%, at least 98%, or at least 99% identical to one of SEQ ID NOs: 27-121, which maintains its function (e.g., OFF-switch ARES region). In some embodiments, the OFF-switch ARES region comprises an HHR 5' of an MS2 aptamer. In some embodiments, the OFF-switch ARES region comprises a PP7 aptamer 5' of an HHR. In some embodiments, the OFF-switch ARES region comprises an HHR 5' of a PP7 aptamer.

In some embodiments, the OFF-switch ARES region comprises a BIV Tar aptamer 5' of an HHR (e.g., with 1 stabilization stem). In some embodiments, the OFF-switch ARES region comprises one of SEQ ID NOs: 219-312, or a nucleic acid sequence that is at least 70%, at least 75%, at least 80%, at least 85%, at least 90%, at least 90%, at least 91%, at least 92%, at least 93%, at least 94%, at least 95%, at least 96%, at least 97%, at least 98%, or at least 99% identical to one of SEQ ID NOs: 219-312, which maintains its function (e.g., OFF-switch ARES region). In some embodiments, the OFF-switch ARES region comprises an HHR 5' of a BIV Tar aptamer. In some embodiments, the OFF-switch ARES region comprises a P22 aptamer 5' of an HHR. In some embodiments, the OFF-switch ARES region comprises an HHR 5' of a P22 aptamer.

In some embodiments, the OFF-switch ARES region is a high-performing OFF-switch ARES region. In some embodiments, the OFF-switch ARES region comprises one of SEQ ID NO: 41 or SEQ ID NO: 263, or a nucleic acid sequence that is at least 70%, at least 75%, at least 80%, at least 85%, at least 90%, at least 90%, at least 91%, at least 92%, at least 93%, at least 94%, at least 95%, at least 96%, at least 97%, at least 98%, or at least 99% identical to one of SEQ ID NO: 41 or SEQ ID NO: 263, which maintains its function (e.g., OFF-switch ARES region).

Self-Amplifying RNAs

In some aspects, the RNA molecules described herein are comprised by a self-amplifying RNA (saRNA). As used herein, the terms "self-amplifying RNA" or "saRNA" or "self-replicating RNA" or "srRNA" are used interchangeably and refer to a positive sense RNA (e.g., +ssRNA; e.g., genome), which encodes machinery for its own replication (e.g., an RNA-dependent RNA polymerase, RdRP) and is thus capable of undergoing replication activity that results in reverse complementary negative sense strands (e.g., anti-sense; e.g., -ssRNA; e.g., anti-genome) and replicate strands (e.g., +ssRNA) from the original positive sense RNA strand. In some embodiments, the saRNA is derived from a viral genome. In some embodiments, the saRNA is derived from an alphaviral genome.

In one aspect, described herein is a self-amplifying RNA (saRNA) comprising an RNA molecule as described herein (which comprises an open reading frame encoding at least one cargo polypeptide, and at least one ARES region as described herein), where the saRNA further comprises an additional open reading frame encoding an RNA-dependent RNA polymerase.

In some embodiments, the saRNA comprises from 5' to 3': a) a 5' conserved sequence element (CSE); b) a first open reading frame (ORF) encoding an RNA-dependent RNA polymerase (RdRP), operably linked to a promoter in the 5' CSE; c) a subgenomic promoter (SGP); d) a second ORF encoding at least one cargo polypeptide, operably linked to the SGP; and e) a 3' CSE. In some embodiments, the 5' CSE, a region between the first and second ORFs, and/or the 3' CSE further comprises at least one ARES region as described herein (e.g., 1, 2, 3, 4, 5, 6, 7, 8, 9, 10, or more ARES regions, which can be the same or different ARES regions; e.g., an ON-switch ARES region, a stabilization/degradation ARES region, and/or an OFF-switch ARES region). In some embodiments, the at least one ARES region is in a sense orientation in the saRNA, such that the ARES region is functional in the saRNA (e.g., in the positive sense saRNA; e.g., prior and after replication of the saRNA by the encoded RdRP). In some embodiments, the at least one ARES region is in an anti-sense orientation in the saRNA, such that the ARES region is not functional in the saRNA (e.g., in the positive sense saRNA; e.g., not functional prior to replication of the saRNA by the encoded RdRP), and the antisense-orientation ARES region is functional when the saRNA is delivered to a cell, the RdRP is translated from the saRNA, and the RdRP synthesizes a reverse complementary negative strand of the saRNA.

In some embodiments, the first open reading frame (ORF), which encodes an RNA-dependent RNA polymerase (RdRP), specifically encodes non-structural protein 1 (nsp 1), non-structural protein 2 (nsp2), non-structural protein 3 (nsp3), and/or non-structural protein 4 (nsp4), each derived from at least one virus (e.g., an alphavirus).

In some embodiments, the saRNAs described herein are derived from at least one alphavirus. Non-limiting examples of alphaviruses include: Aura Virus (AURAV), Barmah Forest Virus (BFV), Bebaru virus, Caaingua virus, Cabassou virus, Chikungunya Virus (CHIKV), Eastern Equine Encephalitis Virus (EEEV), Eliat virus, Everglades Virus (EVEV), Fort Morgan virus, Getah Virus (GETV), Highlands J Virus (HJV), Madariaga virus, Mayaro Virus (MAYV), Middleburg Virus (MIDV), Mosso das Pedras virus, Mucambo Virus (MUCV), Ndumu virus, O'nyong nyong virus (ONNV), Pixuna virus, Rio Negro Virus (RNV), Ross River Virus (RRV), Salmon pancreas disease virus, Semliki Forest Virus (SFV), Sindbis Virus (SIN), Southern elephant seal virus, Tonate Virus (TONV), Trocara virus, Una Virus (UNAV), Venezuela Equine Encephalitis Virus (VEEV), Western Equine Encephalitis Virus (WEEV), and Whataroa virus.

Alphavirus is a genus of RNA viruses, the sole genus in the Togaviridae family. Alphaviruses belong to group IV of the Baltimore classification of viruses, with a positive-sense, single-stranded RNA genome. The alphaviruses are small, spherical, enveloped viruses with a genome of a single strand of positive-sense RNA. The total genome length ranges between 11,000 and 12,000 nucleotides, and the genome resembles mRNA with a 5' cap and a 3' poly-A tail. The four non-structural protein genes are encoded in the 5' two-thirds of the genome, while the three structural proteins are translated from a subgenomic mRNA colinear with the 3' one-third of the genome. There are two open reading frames (ORFs) in the genome, nonstructural and structural. The first is non-structural and encodes proteins (nsP1-nsP4) necessary for transcription and replication of viral RNA. The second encodes three structural proteins: the core nucleocapsid protein C, and the envelope proteins P62 and E1.

In some embodiments of any of the aspects, the saRNAs described herein do not comprise structural proteins derived from at least one alphavirus. In some embodiments of any of the aspects, the saRNAs described herein do not comprise capsid or envelope proteins derived from at least one alphavirus.

In some embodiments, chemical modifications (e.g., modified bases) may be introduced into the saRNA containing the ARES region(s) (e.g., in the sense direction) such that the modification disrupts the function of the ribozyme and ensures the complete saRNA is delivered into the cell without any ribozyme cleavage. As the saRNA is replicated in the cell, the RdRp will eventually synthesize positive sense saRNA copies that do not comprise chemical modifications (e.g., modified bases) and contain an active ribozyme so that the ARES regulatory functions are activated. Non-limiting examples of such modified bases include 5-hydroxymethylcytidine, 5-methylcytidine, and/or 5-methyluridine.

In some embodiments, the saRNA comprises a sequence selected from Table 11 (Exemplary saRNA sequences).

In some embodiments, the saRNA comprises one of SEQ ID NOs: 377-393 or a nucleic acid sequence that is at least 70%, at least 75%, at least 80%, at least 85%, at least 90%, at least 90%, at least 91%, at least 92%, at least 93%, at least 94%, at least 95%, at least 96%, at least 97%, at least 98%, or at least 99% identical to one of SEQ ID NOs: 377-393, which maintains its function (e.g., self-amplification; ARES region function), or a functional fragment thereof.

Nucleic Acids and Vectors

Described herein in multiple aspects are RNA molecules comprising at least one ARES region, which regulates the translation of at least one cargo polypeptide (also referred to herein as "payload" or "gene") encoded in a ORF of the RNA molecule. In some embodiments, the RNA molecule comprises at least one open reading frame (ORF; e.g., 1, 2, 3, 4, 5, 6, 7, 8, 9, 10, or more ORFs, which can be the same or different ORFs). In some embodiments, each ORF encodes at least one cargo polypeptide (e.g., 1, 2, 3, 4, 5, 6, 7, 8, 9, 10, or more cargo polypeptides, which can be the same or different cargo polypeptides).

It is contemplated herein that any cargo polypeptide known or to be discovered can be encoded by the at least one ORF of the RNA molecule. In some embodiments, the cargo polypeptide is an enzyme, a structural protein, or an immune protein. Further non-limiting examples of such cargo polypeptides include: a) a detectable marker (e.g., a fluorescent polypeptide); b) an antigen (e.g., severe acute respiratory syndrome coronavirus 2 (SARS-CoV-2) spike gene, respiratory syncytial virus (RSV) F protein, influenza hemagglutinin, a tumor associated antigen (e.g., New York esophageal squamous cell carcinoma 1 for melanoma, kallikrein-2 for prostate cancer); an antibody (e.g., a monoclonal antibody; e.g.., an anti-claudin 18 isoform 2 (anti-CLDN18.2, which is specific for tumors) antibody, anti-cytotoxic T-lymphocyte-associated protein 4 (anti-CTLA-4) or anti-glucocorticoid-induced tumor necrosis factor receptor (TNFR)-related protein (anti-GITR) antibodies, which are specific for melanoma); c) a cytokine (e.g., IL-2, IL-7, IL-12, OX40L, IL-23); d) a cell therapy protein (e.g., claudin-6 (CLDN6), a chimeric antigen receptor (CAR) protein, a T cell receptor); e) a tumor suppressor protein (e.g., tumor protein 53 (p53), breast cancer gene 1 (BRCA1), breast cancer gene 2 (BRCA2)); f) a programmed cell death protein (e.g., Bax, a caspase); g) a site-specific nuclease (e.g., Cas9; a prime editing enzyme (e.g., PE2, PE3, PE4, PE5, PE2max, PE3max, and the like); h) a therapeutic protein (e.g., vascular endothelial growth factor (VEGF), Glucagon-like peptide-1, insulin); or i) an oncogene (e.g., mutant forms of KRAS, HRAS, EGFR, HER2, PDGFR, MYC, BRCA1, BRCA2, ABL1, VEGF).

In some embodiments, the RNA molecule described herein is a messenger RNA (mRNA) molecule. In some embodiments, the RNA molecule described herein comprises a 5' cap (e.g., a 7-methylguanylate cap). In some embodiments, the RNA molecule described herein comprises a 3' polyA (i.e., polyadenylated) tail. The 5' cap and the 3' polyA tail help to increase the stabilization of the RNA molecule, increase the RNA molecule's transport from the nucleus into the cytoplasm, and help to allow the RNA molecule to be translated by a ribosome during protein synthesis.

In some embodiments, the RNA molecules described herein can be encoded and/or expressed by nucleic acids and/or vectors. Accordingly, in one aspect described herein is a nucleic acid (e.g., a polynucleotide) encoding or comprising an RNA molecule as described herein. In another aspect described herein is a vector encoding or comprising an RNA molecule as described herein.

In some embodiments of any of the aspects, the nucleic acid encoding or comprising an RNA molecule as described herein comprises DNA. In some embodiments of any of the aspects, the nucleic acid encoding an RNA molecule as described herein consists essentially of DNA. In some embodiments of any of the aspects, the nucleic acid encoding an RNA molecule as described herein consists of DNA.

In some embodiments of any of the aspects, a DNA molecule encoding an RNA molecule as described herein comprises at least one regulatory sequence upstream of the encoded RNA molecule. In some embodiments of any of the aspects, a DNA molecule encoding an RNA molecule as described herein comprises a promoter for transcription of the RNA molecule using an RNA polymerase. In some embodiments of any of the aspects, a DNA molecule encoding an RNA molecule as described herein comprises a T7 promoter.

When the nucleic acid molecule that encodes any of the RNA molecules described herein is expressed in a cell, a variety of transcription control sequences (e.g., promoter/enhancer sequences) can be used to direct its expression. The promoter can be a native promoter, e.g., the promoter of the at least one cargo polypeptide in its endogenous context, which provides normal regulation of expression of the cargo polypeptide. In some embodiments the promoter can be constitutive, i.e., the promoter is unregulated allowing for continual transcription of the RNA molecule. A variety of conditional promoters also can be used, such as promoters controlled by the presence or absence of a molecule.

The precise nature of the regulatory sequences needed for expression can vary between species or cell types, but in general can include, as necessary, 5' non-transcribed and 5' non-translated sequences involved with the initiation of transcription and translation respectively, such as a TATA box, capping sequence, CAAT sequence, and the like. In particular, such 5' non-transcribed regulatory sequences can include a promoter region which includes a promoter sequence for transcriptional control of the encoded RNA molecule. Regulatory sequences can also include enhancer sequences or upstream activator sequences as desired.

As used herein, an RNA-encoding sequence and regulatory sequences are said to be "operably" joined when they are covalently linked in such a way as to place the transcription of the RNA-encoding sequence under the influence or control of the regulatory sequences. If it is desired that at least one cargo polypeptide encoded in the RNA molecule be translated into a functional protein, two DNA sequences are said to be operably joined if induction of a promoter in the 5' regulatory sequences results in the transcription of the RNA molecule and if the nature of the linkage between the two DNA sequences does not (1) result in the introduction of a frame-shift mutation, (2) interfere with the ability of the promoter region to direct the transcription of the RNA molecule, or (3) interfere with the ability of the at least one cargo polypeptide encoded in the RNA molecule to be translated into a protein.

A nucleic acid molecule that encodes an RNA molecule as described herein can be introduced into a cell or cells using methods and techniques that are standard in the art. For example, nucleic acid molecules can be introduced by standard protocols such as transformation including chemical transformation and electroporation, transduction, particle bombardment, etc. Expressing the nucleic acid molecule encoding an RNA molecule as described herein can also be accomplished by integrating the nucleic acid molecule into the genome.

In some embodiments, one or more of the RNA molecules described herein is expressed in a recombinant expression vector or plasmid. As used herein, the term "vector" refers to a polynucleotide sequence suitable for transferring nucleic acids (e.g., RNA molecules as described herein) into a host cell. The vector can encompass any genetic element that is capable of replication when associated with the proper control elements and that can transfer nucleic acid sequences to cells. The term "vector" includes a plasmid, a cloning vector, an expression vector, naked DNA, a mini-chromosome, a chromosome, a transposon, a cosmid, a virus, virion, phage, and the like. See, for example, U.S. Pat. Nos. 4,980,285; 5,631,150; 5,707,828; 5,759,828; 5,888,783 and, 5,919,670, and, Sambrook et al, Molecular Cloning: A Laboratory Manual, 2nd Ed., Cold Spring Harbor Press (1989). One type of vector is a "plasmid," which refers to a circular double stranded DNA loop into which additional DNA segments are ligated. Another type of vector is a viral vector, wherein additional DNA segments are ligated into the viral genome. Certain vectors are capable of autonomous replication in a host cell into which they are introduced (e.g., bacterial vectors having a bacterial origin of replication and episomal mammalian vectors). Moreover, certain vectors are capable of directing the expression of encoded RNA molecules to which they are operatively linked. Such vectors are referred to herein as "expression vectors". In general, expression vectors of utility in recombinant DNA techniques are often in the form of plasmids. In the present specification, "plasmid" and "vector" are used interchangeably as the plasmid is the most commonly used form of vector. However, the technology is intended to include such other forms of expression vectors, such as viral vectors (e.g., replication defective retroviruses, adenoviruses and adeno-associated viruses), which serve equivalent functions.

In some embodiments of any of the aspects, the vector is recombinant, e.g., it comprises sequences originating from at least two different sources. In some embodiments of any of the aspects, the vector comprises sequences originating from at least two different species. In some embodiments of any of the aspects, the vector comprises sequences originating from at least two different genes, e.g., it comprises a fusion protein or a nucleic acid encoding an expression product which is operably linked to at least one non-native (e.g., heterologous) genetic control element (e.g., a promoter, suppressor, activator, enhancer, response element, or the like).

In some embodiments of any of the aspects, the vector or nucleic acid described herein is codon-optimized, e.g., the native or wild-type sequence of the nucleic acid sequence has been altered or engineered to include alternative codons such that altered or engineered nucleic acid encodes the same polypeptide expression product as the native/wild-type sequence, but will be transcribed and/or translated at an improved efficiency in a desired expression system. In some embodiments of any of the aspects, the expression system is an organism other than the source of the native/wild-type sequence (or a cell obtained from such organism). In some embodiments of any of the aspects, the vector and/or nucleic acid sequence described herein is codon-optimized for expression in a mammal or mammalian cell, e.g., a mouse, a murine cell, or a human cell. In some embodiments of any of the aspects, the vector and/or nucleic acid sequence described herein is codon-optimized for expression in a human cell. In some embodiments of any of the aspects, the vector and/or nucleic acid sequence described herein is codon-optimized for expression in a yeast or yeast cell. In some embodiments of any of the aspects, the vector and/or nucleic acid sequence described herein is codon-optimized for expression in a bacterial cell. In some embodiments of any of the aspects, the vector and/or nucleic acid sequence described herein is codon-optimized for expression in an *E. coli* cell.

A cloning vector is one which is able to replicate autonomously or integrated in the genome in a host cell, and which is further characterized by one or more endonuclease restriction sites at which the vector can be cut in a determinable fashion and into which a desired DNA sequence (e.g., encoding an RNA molecule as described herein) can be ligated such that the new recombinant vector retains its ability to replicate in the host cell. In the case of plasmids, replication of the desired sequence can occur many times as the plasmid increases in copy number within the host cell such as a host bacterium or just a single time per host before the host reproduces by mitosis. In the case of phage, replication can occur actively during a lytic phase or passively during a lysogenic phase.

An expression vector is one into which a desired DNA sequence (e.g., encoding an RNA molecule as described herein) can be inserted by restriction and ligation such that it is operably joined to regulatory sequences and can be expressed as an RNA molecule. Vectors can further contain one or more marker sequences suitable for use in the identification of cells which have or have not been transformed or transformed or transfected with the vector. Markers include, for example, genes encoding proteins which increase or decrease either resistance or sensitivity to antibiotics or other compounds (e.g., ampicillin resistance), genes which encode enzymes whose activities are detectable by standard assays known in the art (e.g., β-galactosidase, luciferase or alkaline phosphatase), and genes which visibly affect the phenotype of transformed or transfected cells, hosts, colonies or plaques (e.g., green fluorescent protein). In certain embodiments, the vectors used herein are capable of autonomous replication and expression of the RNA molecules present in the DNA segments to which they are operably joined. The sequences expressed will often, but not necessarily, be heterologous to the cell. An expression vector may comprise additional elements, for example, the expression vector may have two replication systems, thus allowing it to be maintained in two organisms, for example in human cells for expression and in a prokaryotic host for cloning and amplification.

Expression vectors containing all the necessary elements for expression are commercially available and known to those skilled in the art. See, e.g., Sambrook et al., *Molecular Cloning: A Laboratory Manual*, Second Edition, Cold Spring Harbor Laboratory Press, 1989. Cells are genetically engineered by the introduction into the cells of heterologous DNA (or RNA). That heterologous DNA (or RNA) is placed under operable control of transcriptional elements to permit the expression of the heterologous DNA in the host cell.

As used herein, the term "viral vector" refers to a nucleic acid vector construct that includes at least one element of viral origin and has the capacity to be packaged into a viral vector particle. The viral vector can contain the nucleic acid encoding a polypeptide as described herein in place of non-essential viral genes. The vector and/or particle may be utilized for the purpose of transferring any nucleic acids into cells either in vitro or in vivo. Numerous forms of viral vectors are known in the art. Non-limiting examples of a viral vector of this invention include an AAV vector, an adenovirus vector, a lentivirus vector, a retrovirus vector, a herpesvirus vector, an alphavirus vector, a poxvirus vector, a baculovirus vector, and a chimeric virus vector.

It should be understood that the vectors described herein can, in some embodiments, be combined with other suitable compositions and therapies. In some embodiments, the vector is episomal. The use of a suitable episomal vector provides a means of maintaining the nucleic acid of interest (e.g., RNA molecules as described herein) in the subject in high copy number extra chromosomal DNA thereby eliminating potential effects of chromosomal integration.

Nucleic Acid Modifications

In some embodiments of any of the aspects, a nucleic acid (e.g., an RNA molecule as described herein, or a DNA molecule encoding such an RNA molecule) is chemically modified to enhance stability or other beneficial characteristics. The nucleic acids described herein may be synthesized and/or modified by methods well established in the art, such as those described in "Current protocols in nucleic acid chemistry," Beaucage, S. L. et al. (Edrs.), John Wiley & Sons, Inc., New York, NY, USA, which is hereby incorporated herein by reference. Modifications include, for example, (a) end modifications, e.g., 5' end modifications (phosphorylation, conjugation, inverted linkages, etc.) 3' end modifications (conjugation, DNA nucleotides, inverted linkages, etc.), (b) base modifications, e.g., replacement with stabilizing bases, destabilizing bases, or bases that base pair with an expanded repertoire of partners, removal of bases (abasic nucleotides; 1',2'-dideoxyribose abasic nucleotides), or conjugated bases, (c) sugar modifications (e.g., at the 2' position or 4' position) or replacement of the sugar, as well as (d) backbone modifications, including modification or replacement of the phosphodiester linkages. Specific examples of nucleic acid compounds useful in the embodiments described herein include, but are not limited to nucleic acids containing modified backbones or no natural internucleoside linkages. nucleic acids having modified backbones include, among others, those that do not have a phosphorus atom in the backbone. For the purposes of this specification, and as sometimes referenced in the art, modified nucleic acids that do not have a phosphorus atom in their internucleoside backbone can also be considered to be oligonucleosides. In some embodiments of any of the aspects, the modified nucleic acid will have a phosphorus atom in its internucleoside backbone.

Modified nucleic acid backbones can include, for example, phosphorothioates, chiral phosphorothioates, phosphorodithioates, phosphotriesters, aminoalkylphosphotriesters, methyl and other alkyl phosphonates including 3'-alkylene phosphonates and chiral phosphonates, phosphinates, phosphoramidates including 3'-amino phosphoramidate and aminoalkylphosphoramidates, thionophosphoramidates, thionoalkylphosphonates, thionoalkylphosphotriesters, and boranophosphates having normal 3'-5' linkages, 2'-5' linked analogs of these, and those) having inverted polarity wherein the adjacent pairs of nucleoside units are linked 3'-5' to 5'-3' or 2'-5' to 5'-2'. Various salts, mixed salts and free acid forms are also included. Modified nucleic acid backbones that do not include a phosphorus atom therein have backbones that are formed by short chain alkyl or cycloalkyl internucleoside linkages, mixed heteroatoms and alkyl or cycloalkyl internucleoside linkages, or one or more short chain heteroatomic or heterocyclic internucleoside linkages. These include those having morpholino linkages (formed in part from the sugar portion of a nucleoside); siloxane backbones; sulfide, sulfoxide and sulfone backbones; formacetyl and thioformacetyl backbones; methylene formacetyl and thioformacetyl backbones; alkene containing backbones; sulfamate backbones; methyleneimino and methylenehydrazino backbones; sulfonate and sulfonamide backbones; amide backbones; others having mixed N, O, S and CH2 component parts, and oligonucleosides with heteroatom backbones, and in particular —CH2-NH—CH2-, —CH2-N(CH3)-O—CH2-[known as a methylene (methylimino) or MMI backbone], —CH2-O—N(CH3)-CH2-, —CH2-N(CH3)-N(CH3)-CH2- and —N(CH3)-CH2-CH2-[wherein the native phosphodiester backbone is represented as —O—P—O—CH2-].

In other nucleic acid mimetics, both the sugar and the internucleoside linkage, i.e., the backbone, of the nucleotide units are replaced with novel groups. The base units are maintained for hybridization with an appropriate nucleic acid target compound. One such oligomeric compound, an RNA mimetic that has been shown to have excellent hybridization properties, is referred to as a peptide nucleic acid (PNA). In PNA compounds, the sugar backbone of an RNA is replaced with an amide containing backbone, in particular an aminoethylglycine backbone. The nucleobases are retained and are bound directly or indirectly to aza nitrogen atoms of the amide portion of the backbone.

The nucleic acid can also be modified to include one or more locked nucleic acids (LNA). A locked nucleic acid is a nucleotide having a modified ribose moiety in which the ribose moiety comprises an extra bridge connecting the 2' and 4' carbons. This structure effectively "locks" the ribose in the 3'-endo structural conformation. The addition of locked nucleic acids to siRNAs has been shown to increase siRNA stability in serum, and to reduce off-target effects (Elmen, J. et al., (2005) Nucleic Acids Research 33(1):439-

447; Mook, OR. et al., (2007) Mol. Canc. Ther. 6(3):833-843; Grunweller, A. et al., (2003) Nucleic Acids Research 31(12):3185-3193).

Modified nucleic acids can also contain one or more substituted sugar moieties. The nucleic acids described herein can include one of the following at the 2' position: OH; F; O—, S—, or N-alkyl; O-, S-, or N-alkenyl; O—, S- or N-alkynyl; or O-alkyl-O-alkyl, wherein the alkyl, alkenyl and alkynyl may be substituted or unsubstituted C1 to C10 alkyl or C2 to C10 alkenyl and alkynyl. Exemplary suitable modifications include O[(CH2)nO]mCH3, O(CH2)nOCH3, O(CH2)nNH2, O(CH2) nCH3, O(CH2)nONH2, and O(CH2)nON[(CH2)nCH3)]2, where n and m are from 1 to about 10. In some embodiments of any of the aspects, nucleic acids include one of the following at the 2' position: C1 to C10 lower alkyl, substituted lower alkyl, alkaryl, aralkyl, O-alkaryl or O-aralkyl, SH, SCH$_3$, OCN, Cl, Br, CN, CF$_3$, OCF$_3$, SOCH$_3$, SO$_2$CH$_3$, ONO$_2$, NO$_2$, N$_3$, NH$_2$, heterocycloalkyl, heterocycloalkaryl, aminoalkylamino, polyalkylamino, substituted silyl, an RNA cleaving group, a reporter group, an intercalator, a group for improving the pharmacokinetic properties of a nucleic acid, or a group for improving the pharmacodynamic properties of a nucleic acid, and other substituents having similar properties. In some embodiments of any of the aspects, the modification includes a 2' methoxyethoxy (2'-O—CH$_2$CH$_2$OCH$_3$, also known as 2'-O-(2-methoxyethyl) or 2'-MOE) (Martin et al., Helv. Chim. Acta, 1995, 78:486-504) i.e., an alkoxy-alkoxy group. Another exemplary modification is 2'-dimethylaminooxyethoxy, i.e., a O(CH2)2ON(CH3)2 group, also known as 2'-DMAOE, as described in examples herein below, and 2'-dimethylaminoethoxyethoxy (also known in the art as 2'-O-dimethylaminoethoxyethyl or 2'-DMAEOE), i.e., 2'-O—CH2-O—CH2-N(CH2)2, also described in examples herein below.

Other modifications include 2'-methoxy (2'-OCH3), 2'-aminopropoxy (2'-OCH2CH2CH2NH2) and 2'-fluoro (2'-F). Similar modifications can also be made at other positions on the nucleic acid, particularly the 3' position of the sugar on the 3' terminal nucleotide or in 2-5' linked dsRNAs and the 5' position of 5' terminal nucleotide. Nucleic acids may also have sugar mimetics such as cyclobutyl moieties in place of the pentofuranosyl sugar.

A nucleic acid can also include nucleobase (often referred to in the art simply as "base") modifications or substitutions. As used herein, "unmodified" or "natural" or "canonical" nucleobases include the purine bases adenine (A) and guanine (G), and the pyrimidine bases thymine (T), cytosine (C) and uracil (U). Modified or "non-canonical" nucleobases can include other synthetic and natural nucleobases including but not limited to as inosine, isocytosine, isoguanine, 5-methylcytosine (5-me-C), 5-hydroxymethyl cytosine, xanthine, hypoxanthine, 2-aminoadenine, 6-methyl and other alkyl derivatives of adenine and guanine, 2-propyl and other alkyl derivatives of adenine and guanine, 2-thiouracil, 2-thiothymine and 2-thiocytosine, 5-halouracil and cytosine, 5-propynyl uracil and cytosine, 6-azo uracil, cytosine and thymine, 5-uracil (pseudouracil), 4-thiouracil, 8-halo, 8-amino, 8-thiol, 8-thioalkyl, 8-hydroxyl anal other 8-substituted adenines and guanines, 5-halo, particularly 5-bromo, 5-trifluoromethyl and other 5-substituted uracils and cytosines, 7-methylguanine and 7-methyladenine, 8-azaguanine and 8-azaadenine, 7-deazaguanine and 7-daazaadenine and 3-deazaguanine and 3-deazaadenine. Certain of these nucleobases are particularly useful for increasing the binding affinity of the inhibitory nucleic acids featured in the invention. These include 5-substituted pyrimidines, 6-azapyrimi-dines and N-2, N-6 and 0-6 substituted purines, including 2-aminopropyladenine, 5-propynyluracil and 5-propynylcytosine. 5-methylcytosine substitutions have been shown to increase nucleic acid duplex stability by 0.6-1.2° C. (Sanghvi, Y. S., Crooke, S. T. and Lebleu, B., Eds., dsRNA Research and Applications, CRC Press, Boca Raton, 1993, pp. 276-278) and are exemplary base substitutions, even more particularly when combined with 2'-O-methoxyethyl sugar modifications. In some embodiments of any of the aspects, modified nucleobases can include d5SICS and dNAM, which are a non-limiting example of unnatural nucleobases that can be used separately or together as basepairs (see e.g., Leconte et. al. J. Am. Chem. Soc.2008, 130, 7, 2336-2343; Malyshev et. al. PNAS. 2012. 109 (30) 12005-12010). In some embodiments of any of the aspects, the nucleic acid comprises any modified nucleobases known in the art, i.e., any nucleobase that is modified from an unmodified and/or natural nucleobase.

The preparation of the modified nucleic acids, backbones, and nucleobases described above are well known in the art.

Another modification of a nucleic acid featured in the invention involves chemically linking to the nucleic acid to one or more ligands, moieties or conjugates that enhance the activity, cellular distribution, pharmacokinetic properties, or cellular uptake of the nucleic acid. Such moieties include but are not limited to lipid moieties such as a cholesterol moiety (Letsinger et al., Proc. Natl. Acid. Sci. USA, 1989, 86: 6553-6556), cholic acid (Manoharan et al., Biorg. Med. Chem. Let., 1994, 4:1053-1060), a thioether, e.g., beryl-S-tritylthiol (Manoharan et al., Ann. N.Y. Acad. Sci., 1992, 660:306-309; Manoharan et al., Biorg. Med. Chem. Let., 1993, 3:2765-2770), a thiocholesterol (Oberhauser et al., Nucl. Acids Res., 1992, 20:533-538), an aliphatic chain, e.g., dodecandiol or undecyl residues (Saison-Behmoaras et al., EMBO J, 1991, 10:1111-1118; Kabanov et al., FEBS Lett., 1990, 259:327-330; Svinarchuk et al., Biochimie, 1993, 75:49-54), a phospholipid, e.g., di-hexadecyl-rac-glycerol or triethyl-ammonium 1,2-di-O-hexadecyl-rac-glycero-3-phosphonate (Manoharan et al., Tetrahedron Lett., 1995, 36:3651-3654; Shea et al., Nucl. Acids Res., 1990, 18:3777-3783), a polyamine or a polyethylene glycol chain (Manoharan et al., Nucleosides & Nucleotides, 1995, 14:969-973), or adamantane acetic acid (Manoharan et al., Tetrahedron Lett., 1995, 36:3651-3654), a palmityl moiety (Mishra et al., Biochim. Biophys. Acta, 1995, 1264:229-237), or an octadecylamine or hexylamino-carbonyloxycholesterol moiety (Crooke et al., J. Pharmacol. Exp. Ther., 1996, 277:923-937).

Combinations, Cells, and Compositions

In multiple aspects, described herein are combinations of RNA molecules and target proteins. For example, in one aspect, described herein is a combination comprising: (a) an RNA molecule comprising at least one ARES region that comprises an MS2 aptamer, and (b) MCP. In one aspect, described herein is a combination comprising: (a) an RNA molecule comprising at least one ARES region that comprises an PP7 aptamer, and (b) PCP. In one aspect, described herein is a combination comprising: (a) an RNA molecule comprising at least one ARES region that comprises a BIV Tar aptamer, and (b) BIV Tat protein. In one aspect, described herein is a combination comprising: (a) an RNA molecule comprising at least one ARES region that comprises an P22 aptamer, and (b) a P22 N protein. In embodiments where the RNA molecule comprises a plurality of ARES regions, each with a different associated target protein, the combination can thus comprise at least one of the associated target proteins (see e.g., Table 2). In some embodiments, the RNA molecule in such a combination is an saRNA as described herein.

In some embodiments, the target protein is linked (e.g., covalently, with or with a linker peptide, such as a glycine-serine linker peptide) to a polypeptide of interest. In some embodiments, the polypeptide of interest increases the steric hindrance of the target protein when it specifically binds to the aptamer, e.g., to increase inhibition of the function of a nearby ribozyme (e.g., to decrease the self-cleaving function of a nearby ribozyme in the ARES region). In some embodiments, the polypeptide of interest is an inert polypeptide, e.g., it is not an enzyme, or does not exhibit a function other than its steric hindrance. In some embodiments, the polypeptide of interest (e.g., linked to the target protein) comprises Maltose Binding Peptide (MBP). For example, in some embodiments, the polypeptide of interest linked to the target protein comprises MBP-MCP, MBP-PCP, MBP-BIV tat, or MBP-P22N. In some embodiments, the polypeptide of interest (e.g., linked to the target protein) comprises adenosine deaminase acting on RNA (ADAR). For example, in some embodiments, the polypeptide of interest linked to the target protein comprises ADAR-MCP, ADAR-PCP, ADAR-BIV tat, or ADAR-P22N.

In some embodiments, any polypeptide known or to be discovered can be linked to the target protein. In some embodiments, the polypeptide of interest, which is linked to the target protein, is an enzyme, a structural protein, or an immune protein. Further non-limiting examples of such a polypeptide of interest, which is linked to the target protein, include: a) a detectable marker (e.g., a fluorescent polypeptide); b) an antigen (e.g., severe acute respiratory syndrome coronavirus 2 (SARS-CoV-2) spike gene, respiratory syncytial virus (RSV) F protein, influenza hemagglutinin, a tumor associated antigen (e.g., New York esophageal squamous cell carcinoma 1 for melanoma, kallikrein-2 for prostate cancer); an antibody (e.g., a monoclonal antibody; e.g.., an anti-claudin 18 isoform 2 (anti-CLDN18.2, which is specific for tumors) antibody, anti-cytotoxic T-lymphocyte-associated protein 4 (anti-CTLA-4) or anti-glucocorticoid-induced tumor necrosis factor receptor (TNFR)-related protein (anti-GITR) antibodies, which are specific for melanoma); c) a cytokine (e.g., IL-2, IL-7, IL-12, OX40L, IL-23); d) a cell therapy protein (e.g., claudin-6 (CLDN6), a chimeric antigen receptor (CAR) protein, a T cell receptor); e) a tumor suppressor protein (e.g., tumor protein 53 (p53), breast cancer gene 1 (BRCA1), breast cancer gene 2 (BRCA2)); f) a programmed cell death protein (e.g., Bax, a caspase); g) a site-specific nuclease (e.g., Cas9; a prime editing enzyme (e.g., PE2, PE3, PE4, PE5, PE2max, PE3max, and the like); h) a therapeutic protein (e.g., vascular endothelial growth factor (VEGF), Glucagon-like peptide-1, insulin); or i) an oncogene (e.g., mutant forms of KRAS, HRAS, EGFR, HER2, PDGFR, MYC, BRCA1, BRCA2, ABL1, VEGF).

In some embodiments, RNA molecules, target proteins, and combinations thereof, described herein can be comprised by cells, such as eukaryotic cells. In some embodiments, the RNA molecule in such a cell is an saRNA as described herein. The RNA molecules, target proteins, and combinations thereof, or cells comprising such RNA molecules, target proteins, and combinations thereof, can be comprised by compositions, such as pharmaceutical compositions, as described further herein. In some embodiments, the RNA molecule in such a composition is an saRNA as described herein.

In one aspect described herein is a pharmaceutical composition comprising an RNA molecule as described herein and a pharmaceutically acceptable carrier. In one aspect described herein is a pharmaceutical composition comprising an RNA molecule as described herein, a target protein as described herein, and a pharmaceutically acceptable carrier. In one aspect described herein is a pharmaceutical composition comprising a nucleic acid or vector comprising or expressing an RNA molecule as described herein and a pharmaceutically acceptable carrier. In one aspect described herein is a pharmaceutical composition comprising a cell comprising or expressing an RNA molecule as described herein and a pharmaceutically acceptable carrier. In some embodiments, the RNA molecule in such a pharmaceutical composition is an saRNA as described herein. In some embodiments, a pharmaceutical composition comprising a target protein as described herein is provided in a separate administration than the pharmaceutical composition comprising an RNA molecule as described herein; the two pharmaceutical compositions can be provided contemporaneously or at different times.

Formulations

In some embodiments, the technology described herein relates to a pharmaceutical composition comprising an RNA molecule as described herein, and optionally a pharmaceutically acceptable carrier. In some embodiments, the active ingredients of the pharmaceutical composition comprise an RNA molecule as described herein. In some embodiments, the active ingredients of the pharmaceutical composition consist essentially of an RNA molecule as described herein. In some embodiments, the active ingredients of the pharmaceutical composition consist of an RNA molecule as described herein.

In some embodiments, the technology described herein relates to a pharmaceutical composition comprising a target protein as described herein, and optionally a pharmaceutically acceptable carrier. In some embodiments, the active ingredients of the pharmaceutical composition comprise a target protein as described herein. In some embodiments, the active ingredients of the pharmaceutical composition consist essentially of a target protein as described herein. In some embodiments, the active ingredients of the pharmaceutical composition consist of a target protein as described herein.

Pharmaceutically acceptable carriers and diluents include saline, aqueous buffer solutions, solvents and/or dispersion media. The use of such carriers and diluents is well known in the art. Some non-limiting examples of materials which can serve as pharmaceutically-acceptable carriers include: (1) sugars, such as lactose, glucose and sucrose; (2) starches, such as corn starch and potato starch; (3) cellulose, and its derivatives, such as sodium carboxymethyl cellulose, methylcellulose, ethyl cellulose, microcrystalline cellulose and cellulose acetate; (4) powdered tragacanth; (5) malt; (6) gelatin; (7) lubricating agents, such as magnesium stearate, sodium lauryl sulfate and talc; (8) excipients, such as cocoa butter and suppository waxes; (9) oils, such as peanut oil, cottonseed oil, safflower oil, sesame oil, olive oil, corn oil and soybean oil; (10) glycols, such as propylene glycol; (11) polyols, such as glycerin, sorbitol, mannitol and polyethylene glycol (PEG); (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) pH buffered solutions; (21) polyesters, polycarbonates and/or polyanhydrides; (22) bulking agents, such as polypeptides and amino acids; (23) serum component, such as serum albumin, HDL and LDL; (24) $C_2$-$C_{12}$ alcohols; and (25) other non-toxic compatible substances employed in pharmaceutical formulations. Wetting agents, coloring agents, release agents, coating agents, sweetening agents, flavoring agents, perfuming agents, preservative and antioxidants can also be present in the formulation. The terms such as "excipient", "carrier", "pharmaceutically acceptable carrier" or the like are used interchangeably herein. In some embodiments, the carrier inhibits the degradation of the active agent, e.g. RNA molecules and/or target proteins as described herein.

In some embodiments, the pharmaceutical composition comprising RNA molecules and/or target proteins as described herein can be a parenteral dose form (i.e., administered or occurring elsewhere in the body than the mouth and alimentary canal). Since administration of parenteral dosage forms typically bypasses the patient's natural defenses against contaminants, parenteral dosage forms are preferably sterile or capable of being sterilized prior to administration to a patient. Examples of parenteral dosage forms include, but are not limited to, solutions ready for injection, dry products ready to be dissolved or suspended in a pharmaceutically acceptable vehicle for injection, suspensions ready for injection, and emulsions.

Suitable vehicles that can be used to provide parenteral dosage forms of RNA molecules and/or target proteins as disclosed within are well known to those skilled in the art. Non-limiting examples include, without limitation: sterile water; water for injection USP; saline solution; glucose solution; aqueous vehicles such as but not limited to, sodium chloride injection, Ringer's injection, dextrose injection, dextrose and sodium chloride injection, and lactated Ringer's injection; water-miscible vehicles such as, but not limited to, ethyl alcohol, polyethylene glycol, and propylene glycol; and non-aqueous vehicles such as, but not limited to, corn oil, cottonseed oil, peanut oil, sesame oil, ethyl oleate, isopropyl myristate, and benzyl benzoate.

Pharmaceutical compositions comprising RNA molecules and/or target proteins as described herein can also be formulated to be suitable for oral administration, for example as discrete dosage forms, such as, but not limited to, tablets (including without limitation scored or coated tablets), pills, caplets, capsules, chewable tablets, powder packets, cachets, troches, wafers, aerosol sprays, or liquids, such as but not limited to, syrups, elixirs, solutions or suspensions in an aqueous liquid, a non-aqueous liquid, an oil-in-water emulsion, or a water-in-oil emulsion. Such compositions contain a predetermined amount of the pharmaceutically acceptable salt of the disclosed compounds, and may be prepared by methods of pharmacy well known to those skilled in the art. See generally, Remington: The Science and Practice of Pharmacy, 21st Ed., Lippincott, Williams, and Wilkins, Philadelphia PA. (2005).

In some embodiments of any of the aspects, the RNA molecule and/or target protein as described herein is formulated as lipid nanoparticles (LNP). In some embodiments of any of the aspects, the lipid nanoparticle comprises a targeting moiety, specific for a cell or tissue of interest. As a non-limiting example, the LNP can be conjugated to an antibody. In some embodiments, the LNPs are formulated with a lipid:oligonucleotide weight ratio of about 10:1. In some embodiments, lipids in the LNPs comprise ionizable lipids, cholesterol, phospholipids, and/or polyethylene glycol lipids. Further non-limiting examples of lipids for use in LNP formulations include SM-102, DMG-PEG2K, DOPE, and cholesterol.

Dosing

In some embodiments, the methods described herein comprise administering an effective amount of compositions described herein, e.g. comprising the RNA molecule and/or target protein as described herein, to a subject in order to alleviate a symptom of a disease or disorder. As used herein, "alleviating a symptom of a disease or disorder" is ameliorating any condition or symptom associated with the disease or disorder. As compared with an equivalent untreated control, such reduction is by at least 5%, 10%, 20%, 40%, 50%, 60%, 80%, 90%, 95%, 99% or more as measured by any standard technique. A variety of means for administering the compositions described herein to subjects are known to those of skill in the art.

In some embodiments of any of the aspects, the RNA molecule is formulated at a dose of about 10 µg to about 1000 µg, about 10 µg to about 100 µg, about 10 µg to about 20 µg, about 20 µg to about 30 µg, about 30 µg to about 40 µg, about 40 µg to about 50 µg, about 50 µg to about 60 µg, about 60 µg to about 70 µg, about 70 µg to about 80 µg, about 80 µg to about 90 µg, about 90 µg to about 100 µg, about 100 µg to about 1000 µg, about 100 µg to about 200 µg, about 200 µg to about 300 µg, about 300 µg to about 400 µg, about 400 µg to about 500 µg, about 500 µg to about 600 µg, about 600 µg to about 700 µg, about 700 µg to about 800 µg, about 800 µg to about 900 µg, or about 900 µg to about 1000 µg; see e.g., Qin et al. "mRNA-based therapeutics: powerful and versatile tools to combat diseases." Signal Transduct Target Ther. 7(1): 166 (2022). In some embodiments of any of the aspects, the target protein, e.g., if administered to a subject as a non-endogenous protein, is formulated at a dose of about 2× the molar concentration of RNA molecule.

The term "effective amount" as used herein refers to the amount of RNA molecule and/or target protein needed to alleviate at least one or more symptom of the disease or disorder, and relates to a sufficient amount of pharmacological composition to provide the desired effect. The term "therapeutically effective amount" therefore refers to an amount of RNA molecule and/or target protein that is sufficient to provide a particular alleviating effect when administered to a typical subject. An effective amount as used herein, in various contexts, would also include an amount sufficient to delay the development of a symptom of the disease, alter the course of a symptom disease (for example but not limited to, slowing the progression of a symptom of the disease), or reverse a symptom of the disease. Thus, it is not generally practicable to specify an exact "effective amount". However, for any given case, an appropriate "effective amount" can be determined by one of ordinary skill in the art using only routine experimentation.

Effective amounts, toxicity, and therapeutic efficacy can be determined by standard pharmaceutical procedures in cell cultures or experimental animals, e.g., for the ED50 (the dose therapeutically effective in 50% of the population). The dosage can vary depending upon the dosage form employed and the route of administration utilized. A therapeutically effective dose can be estimated initially from cell culture assays. Also, a dose can be formulated in animal models to achieve a circulating plasma concentration range that includes the IC50 (i.e., the concentration of RNA molecule and/or target protein, which achieves a half-maximal inhibition of symptoms) as determined in cell culture, or in an appropriate animal model. Levels in plasma can be measured, for example, by high performance liquid chromatography. The effects of any particular dosage can be monitored by a suitable bioassay. The dosage can be determined by a physician and adjusted, as necessary, to suit observed effects of the treatment.

The dosage ranges for the administration of RNA molecule and/or target protein, according to the methods described herein depend upon, for example, the form of RNA molecule and/or target protein, its potency, and the extent to which symptoms, markers, or indicators of a disease or disorder are desired to be reduced. The dosage should not be so large as to cause adverse side effects. Generally, the dosage will vary with the age, condition, and sex of the patient and can be determined by one of skill in the art. The dosage can also be adjusted by the individual physician in the event of any complication.

The efficacy of RNA molecule and/or target protein in, e.g. the treatment of a disease or disorder can be determined by the skilled clinician. However, a treatment is considered "effective treatment," as the term is used herein, if one or more of the signs or symptoms of a disease or disorder are altered in a beneficial manner, other clinically accepted symptoms are improved, or even ameliorated, or a desired response is induced e.g., by at least 10% following treatment according to the methods described herein. Efficacy can be assessed, for example, by measuring a marker, indicator, symptom, and/or the incidence of a disease or disorder treated or any other measurable parameter appropriate. Efficacy can also be measured by a failure of an individual to worsen as assessed by hospitalization, or need for medical interventions (i.e., progression of the disease is halted). Methods of measuring these indicators are known to those of skill in the art and/or are described herein. Treatment includes any treatment of a disease in an individual or an animal (some non-limiting examples include a human or an animal) and includes: (1) inhibiting the disease, e.g., preventing a worsening of symptoms (e.g. pain or inflammation); or (2) relieving the severity of the disease, e.g., causing regression of symptoms. An effective amount for the treatment of a disease means that amount which, when administered to a subject in need thereof, is sufficient to result in effective treatment as that term is defined herein, for that disease. Efficacy of an agent can be determined by assessing physical indicators of a condition or desired response. It is well within the ability of one skilled in the art to monitor efficacy of administration and/or treatment by measuring any one of such parameters, or any combination of parameters. Efficacy can be assessed in animal models of a disease or disorder. When using an experimental animal model, efficacy of treatment is evidenced when a statistically significant change in a marker is observed.

With respect to duration and frequency of treatment, it is typical for skilled clinicians to monitor subjects in order to determine when the treatment is providing therapeutic benefit, and to determine whether to increase or decrease dosage, increase or decrease administration frequency, discontinue treatment, resume treatment, or make other alterations to the treatment regimen.

In certain embodiments, an effective dose of a composition comprising an RNA molecule and/or target protein as described herein can be administered to a patient once. In certain embodiments, an effective dose of a composition comprising an RNA molecule and/or target protein as described herein can be administered to a patient repeatedly.

The dosing schedule can vary from once a week to daily depending on a number of clinical factors, such as the subject's sensitivity to the RNA molecule and/or target protein as described herein. The desired dose or amount can be administered at one time or divided into subdoses, e.g., 2-4 subdoses and administered over a period of time, e.g., at appropriate intervals through the day or other appropriate schedule. In some embodiments, administration can be one or more doses and/or treatments daily over a period of weeks or months. Examples of dosing and/or treatment schedules are administration daily, twice daily, three times daily or four or more times daily over a period of 1 week, 2 weeks, 3 weeks, 4 weeks, 1 month, 2 months, 3 months, 4 months, 5 months, or 6 months, or more. A composition comprising an RNA molecule and/or target protein as described herein can be administered over a period of time, such as over a 5 minute, 10 minute, 15 minute, 20 minute, or 25 minute period.

In some embodiments, after an initial treatment regimen, the treatments can be administered on a less frequent basis. For example, after treatment biweekly for three months, treatment can be repeated once per month, for six months or a year or longer.

Administration

A variety of means for administering the compositions described herein to subjects are known to those of skill in the art. Such methods can include, but are not limited to oral, parenteral, intravenous (IV), intramuscular (IM), subcutaneous (SC), transdermal, airway (aerosol), pulmonary, cutaneous, topical, injection, intraosseous (IO), intraperitoneal (IP), intrarectal, intravaginal, intraarticular (IA), or intratumoral administration. Administration can be local or systemic.

In some embodiments of any of the aspects, an RNA molecule and/or target protein as described herein is administered as a monotherapy, e.g., another treatment for the disease or disorder is not administered to the subject.

In some embodiments of any of the aspects, the methods described herein can further comprise administering a second agent and/or treatment to the subject, e.g. as part of a combinatorial therapy. Non-limiting examples of a second agent and/or treatment can include a cancer therapy selected from the group consisting of radiation therapy, surgery, gemcitabine, cisplatin, paclitaxel, carboplatin, bortezomib, AMG479, vorinostat, rituximab, temozolomide, rapamycin, ABT-737, PI-103; alkylating agents such as thiotepa and CYTOXAN® cyclophosphamide; alkyl sulfonates such as busulfan, improsulfan and piposulfan; aziridines such as benzodopa, carboquone, meturedopa, and uredopa; ethylenimines and methylmelamines including altretamine, triethylenemelamine, trietylenephosphoramide, triethylenethiophosphoramide and trimethylol melamine; acetogenins (especially bullatacin and bullatacinone); a camptothecin (including the synthetic analogue topotecan); bryostatin; callystatin; CC-1065 (including its adozelesin, carzelesin and bizelesin synthetic analogues); cryptophycins (particularly cryptophycin 1 and cryptophycin 8); dolastatin; duocarmycin (including the synthetic analogues, KW-2189 and CB1-TM1); eleutherobin; pancratistatin; a sarcodictyin; spongistatin; nitrogen mustards such as chlorambucil, chlornaphazine, cholophosphamide, estramustine, ifosfamide, mechlorethamine, mechlorethamine oxide hydrochloride, melphalan, novembichin, phenesterine, prednimustine, trofosfamide, uracil mustard; nitrosoureas such as carmustine, chlorozotocin, fotemustine, lomustine, nimustine, and ranimustine; antibiotics such as the enediyne antibiotics (e.g., calicheamicin, especially calicheamicin gammaII and calicheamicin omegaII (see, e.g., Agnew, Chem. Intl. Ed. Engl., 33: 183-186 (1994)); dynemicin, including dynemicin A; bisphosphonates, such as clodronate; an esperamicin; as well as neocarzinostatin chromophore and related chromoprotein enediyne antibiotic chromophores), aclacinomycins, actinomycin, authramycin, azaserine, bleomycins, cactinomycin, carabicin, caminomycin, carzinophilin, chromomycins, dactinomycin, daunorubicin, detorubicin, 6-diazo-5-oxo-L-norleucine, ADRIAMYCIN® doxorubicin (including morpholino-doxorubicin, cyanomorpholino-doxorubicin, 2-pyrrolino-doxorubicin and deoxydoxorubicin), epirubicin, esorubicin, idarubicin, marcellomycin, mitomycins such as mitomycin C, mycophenolic acid, nogalamycin, olivomycins, peplomycin, potfiromycin, puromycin, quelamycin, rodorubicin, streptonigrin, streptozocin, tubercidin, ubenimex, zinostatin, zorubicin; anti-metabolites such as methotrexate and 5-fluorouracil (5-FU); folic acid analogues such as denopterin, methotrexate, pteropterin, trimetrexate; purine analogs such as fludarabine, 6-mercaptopurine, thiamiprine, thioguanine; pyrimidine analogs such as ancitabine, azacitidine, 6-azauridine, carmofur, cytarabine, dideoxyuridine, doxifluridine, enocitabine, floxuridine; androgens such as calusterone, dromostanolone propionate, epitiostanol, mepitiostane, testolactone; anti-adrenals such as aminoglutethimide, mitotane, trilostane; folic acid replenisher such as frolinic acid; aceglatone; aldophosphamide glycoside; aminolevulinic acid; eniluracil; amsacrine; bestrabucil; bisantrene; edatraxate; defofamine; demecolcine; diaziquone; elformithine; elliptinium acetate; an epothilone; etoglucid; gallium nitrate; hydroxyurea; lentinan; lonidainine; maytansinoids such as maytansine and ansamitocins; mitoguazone; mitoxantrone; mopidanmol; nitraerine; pentostatin; phenamet; pirarubicin; losoxantrone; podophyllinic acid; 2-ethylhydrazide; procarbazine; PSK® polysaccharide complex (JHS Natural Products, Eugene, Oreg.); razoxane; rhizoxin; sizofuran; spirogermanium; tenuazonic acid; triaziquone; 2,2',2''-trichlorotriethylamine; trichothecenes (especially T-2 toxin, verracurin A, roridin A and anguidine); urethan; vindesine; dacarbazine; mannomustine; mitobronitol; mitolactol; pipobroman; gacytosine; arabinoside ("Ara-C"); cyclophosphamide; thiotepa; taxoids, e.g., TAXOL® paclitaxel (Bristol-Myers Squibb Oncology, Princeton, N.J.), ABRAXANE® Cremophor-free, albumin-engineered nanoparticle formulation of paclitaxel (American Pharmaceutical Partners, Schaumberg, Ill.), and TAXOTERE® doxetaxel (Rhone-Poulenc Rorer, Antony, France); chloranbucil; GEMZAR® gemcitabine; 6-thioguanine; mercaptopurine; methotrexate; platinum analogs such as cisplatin, oxaliplatin and carboplatin; vinblastine; platinum; etoposide (VP-16); ifosfamide; mitoxantrone; vincristine; NAVELBINE® vinorelbine; novantrone; teniposide; edatrexate; daunomycin; aminopterin; xeloda; ibandronate; irinotecan (Camptosar, CPT-11) (including the treatment regimen of irinotecan with 5-FU and leucovorin); topoisomerase inhibitor RFS 2000; difluoromethylomithine (DMFO); retinoids such as retinoic acid; capecitabine; combretastatin; leucovorin (LV); oxaliplatin, including the oxaliplatin treatment regimen (FOLFOX); lapatinib (Tykerb®); inhibitors of PKC-alpha, Raf, H-Ras, EGFR (e.g., erlotinib (Tarceva®)) and VEGF-A that reduce cell proliferation (e.g., pazopanib, sunitinib, sorafenib, regorafenib, cabozantinib, lenvatinib, ponatinib, ziv-aflibercept, axitinib, tivozanib, vandetanib, ramucirumab); and pharmaceutically acceptable salts, acids or derivatives of any of the above.

In some embodiments of any of the aspects, the cancer treatment method further comprises administering an immune checkpoint inhibitor. In some embodiments of any of the aspects, the immune checkpoint inhibitor comprises an immune checkpoint inhibitor antibody. In some embodiments of any of the aspects, the checkpoint inhibitor immunotherapy is an inhibitor of a checkpoint molecule selected from the group consisting of: programmed cell death 1 (PD-1), programmed death-ligand 1 (PD-L1), cytotoxic T-lymphocyte-associated protein 4 (CTLA-4), Adenosine A2A receptor (A2AR), CD276, CD39, CD73, B7 family immune checkpoint molecules, V-set domain-containing T-cell activation inhibitor 1 (B7H4), B and T Lymphocyte Attenuator (BTLA), Indoleamine 2,3-dioxygenase (IDO), Killer-cell Immunoglobulin-like Receptor (KIR), Lymphocyte Activation Gene-3 (LAG-3), nicotinamide adenine dinucleotide phosphate NADPH oxidase isoform 2 (NOX2), T-cell Immunoglobulin domain and Mucin domain 3 (TIM-3), T cell immunoreceptor with Ig and ITIM domains (TIGIT), V-domain Ig suppressor of T cell activation (VISTA), and Sialic acid-binding immunoglobulin-type lectin 7 (SIGLEC7).

Non-limiting examples of immune checkpoint inhibitors (ICIs) include: pembrolizumab (Keytruda®), nivolumab (Opdivo®), cemiplimab (Libtayo®), spartalizumab, camrelizumab (AiRuiKa™), sintilimab (TYVYT®), tislelizumab, toripalimab (Tuoyi™), dostarlimab (JEMPERLI), INCMGA00012, AMP-224, AMP-514 (MED10608), atezolizumab (Tecentriq®), avelumab (Bavencio®), envafolimab (KN035), cosibelimab (CK-301), AUNP12, CA-170, BMS-986189, BMS-936559 (MDX-1105), durvalumab (IMFINZI®), tremelimumab, and ipilimumab (Yervoy®). See e.g., US Patents U.S. Pat. Nos. 5,811,097, 5,855,887, 6,051,227, 6,682,736, 6,984,720, 7,595,048, 7,605,238, 7,943,743, 8,008,449, 8,217,149, 8,354,509, 8,383,796, 8,728,474, 8,735,553, 8,779,105, 8,779,108, 8,907,053, 8,900,587, 8,952,136, 9,067,999, 9,073,994, 9,683,048, 9,987,500, U.S. Ser. No. 10/160,736, U.S. Ser. No. 10/316, 089, U.S. Ser. No. 10/441,655, U.S. Ser. No. 10/590,199, U.S. Ser. No. 11/225,522, US Patent Publication US2014341917; Storz et al., MAbs. 2016 January; 8(1): 10-26; the contents of each of which are incorporated herein by reference in their entireties.

One of skill in the art can readily identify a chemotherapeutic agent of use (e.g. see Physicians' Cancer Chemotherapy Drug Manual 2014, Edward Chu, Vincent T. DeVita Jr., Jones & Bartlett Learning; Principles of Cancer Therapy, Chapter 85 in Harrison's Principles of Internal Medicine, 18th edition; Therapeutic Targeting of Cancer Cells: Era of Molecularly Targeted Agents and Cancer Pharmacology, Chs. 28-29 in Abeloff's Clinical Oncology, 2013 Elsevier; and Fischer D S (ed): The Cancer Chemotherapy Handbook, 4th ed. St. Louis, Mosby-Year Book, 2003).

In addition, the methods of treatment can further include the use of radiation or radiation therapy. Further, the methods of treatment can further include the use of surgical treatments.

The methods described herein can further comprise administering a second agent and/or treatment to the subject, e.g. as part of a combinatorial therapy. By way of non-limiting example, if a subject is to be treated for pain or inflammation according to the methods described herein, the subject can also be administered a second agent and/or treatment known to be beneficial for subjects suffering from pain or inflammation. Examples of such agents and/or treatments include, but are not limited to, non-steroidal anti-inflammatory drugs (NSAIDs—such as aspirin, ibuprofen, or naproxen); corticosteroids, including glucocorticoids (e.g. cortisol, prednisone, prednisolone, methylprednisolone, dexamethasone, betamethasone, triamcinolone, and beclometasone); methotrexate; sulfasalazine; leflunomide; anti-TNF medications; cyclophosphamide; pro-resolving drugs; mycophenolate; or opiates (e.g. endorphins, enkephalins, and dynorphin), steroids, analgesics, barbiturates, oxycodone, morphine, lidocaine, and the like.

Uses

In multiple aspects, described herein are uses of the RNA molecules described herein. For example, described herein are methods of modulating the translation of at least one cargo polypeptide. In some embodiments, the method comprises contacting a cell with an RNA molecule as described herein. In some embodiments, the method comprises contacting a cell with an saRNA as described herein. In some embodiments, the method comprises contacting a cell with a polynucleotide as described herein. In some embodiments, the method comprises contacting a cell with a vector as described herein. In some embodiments, the method comprises contacting a cell with a combination (e.g. of an RNA molecule and an associated target protein) as described herein. In some embodiments, the method comprises contacting a cell with a pharmaceutical composition as described herein.

In some embodiments, the method further comprises contacting the cell with at least one target protein (e.g., each associated with the at least one aptamer in the at least one ARES region of the RNA molecule).

In some embodiments, the cell already expresses at least one target protein (e.g., the RNA molecule can help to sense the presence in the cell of the at least one target protein which is associated with the at least one aptamer in the at least one ARES region of the RNA molecule).

In additional aspects, described herein are method of modulating the translation of at least one cargo polypeptide in a subject in need thereof. For example, the translation of the at least one cargo polypeptide can treat an associated disease or disorder in the subject. In some embodiments, the method comprises administering to the subject an effective amount of an RNA molecule as described herein. In some embodiments, the method comprises administering to the subject an effective amount of an saRNA as described herein. In some embodiments, the method comprises administering to the subject an effective amount of a polynucleotide as described herein. In some embodiments, the method comprises administering to the subject an effective amount of a vector as described herein. In some embodiments, the method comprises administering to the subject an effective amount of a combination (e.g. of an RNA molecule and an associated target protein) as described herein. In some embodiments, the method comprises administering to the subject an effective amount of a cell as described herein. In some embodiments, the method comprises administering to the subject an effective amount of a pharmaceutical composition as described herein.

In some embodiments, the method further comprises administering to the subject an effective amount of at least one target protein (e.g., each associated with the at least one aptamer in the at least one ARES region of the RNA molecule).

In some embodiments, a target cell in the subject expresses at least one target protein (e.g., the RNA molecule can help to sense the presence in the target cell of the subject the at least one target protein, which is associated with the at least one aptamer in the at least one ARES region of the RNA molecule).

In some embodiments, the RNA molecule provided in the method comprises at least one ON-switch ARES region as described herein. In some embodiments, with an RNA molecule comprising an ON-switch ARES region, in the presence of the target protein, the at least one cargo polypeptide encoded by the provided RNA molecule is translated (ON). In some embodiments, with an RNA molecule comprising an ON-switch ARES region, in the absence of the target protein, the at least one cargo polypeptide encoded by the provided RNA molecule is not translated (OFF).

In some embodiments, the RNA molecule provided in the method comprises at least one stabilization/degradation ARES region as described herein. In some embodiments, the RNA molecule provided in the method comprises at least one OFF-switch ARES region. In some embodiments, with an RNA molecule comprising a stabilization/degradation ARES region or an OFF-switch ARES region, in the presence of the target protein, the at least one cargo polypeptide encoded by the provided RNA molecule is not translated (OFF). In some embodiments, with an RNA molecule comprising a stabilization/degradation ARES region or an OFF-switch ARES region, in the absence of the target protein, the at least one cargo polypeptide encoded by the provided RNA molecule is translated (ON).

Exemplary uses and applications of RNA molecules comprising at least ARES region as described herein, include but are not limited to the following: therapeutics (e.g., targeted protein therapy, engineered immune cells (e.g., to treat cancer), personalized medicine, temporal control (e.g., kill switch)); synthetic biology (e.g., metabolic engineering, cellular logic systems); diagnostics (e.g., biosensors; in vitro or in vivo); vaccines; conditional expression systems (e.g., tools for studying gene function).

Exemplary uses in therapeutic gene regulation include targeted protein therapy and personalized medicine. In targeted protein therapy, RNA molecules described herein (e.g., comprising at least one ARES region described herein) permit precise control over therapeutic gene expression in response to disease-related proteins. For example, if a tumor marker protein is detected in cancer, an RNA molecule described herein (e.g., comprising at least one ARES region described herein) can activate or repress a therapeutic gene, delivering drugs or immune-modulatory proteins directly to the site of the tumor. In personalized medicine, by tailoring an RNA molecule described herein (e.g., comprising at least one ARES region described herein) to detect specific biomarkers (proteins), treatments can be customized for individual patients, offering highly personalized therapeutic strategies that respond to their unique biomolecular profiles.

Exemplary uses in cell-based therapies include engineered immune cells. In immunotherapy, particularly CAR-T cell therapy, an RNA molecule described herein (e.g., comprising at least one ARES region described herein) permit engineered immune cells to activate or suppress certain functions based on the presence of target proteins on tumor cells. This would allow for more precise targeting of cancer cells and minimize off-target effects.

Exemplary uses in synthetic biology include metabolic engineering and cellular logic systems. In metabolic engineering, an RNA molecule described herein (e.g., comprising at least one ARES region described herein) can regulate the production of specific metabolites or biofuels in response to the detection of certain proteins. With cellular logic systems, an RNA molecule described herein (e.g., comprising at least one ARES region described herein) can be used to build logic gates that control cellular behavior based on multiple protein inputs. This could allow the creation of sophisticated biosensors or "smart" cells that make decisions based on protein signals, permitting complex biological systems for applications like biosensing or advanced diagnostics.

Exemplary uses in diagnostics include biosensors. An RNA molecule described herein (e.g., comprising at least one ARES region described herein) can serve as highly sensitive biosensor mRNAs for detecting disease-associated proteins (e.g., viral or bacterial markers). When these proteins are present, the RNA molecule described herein (e.g., comprising at least one ARES region described herein) would activate a reporter gene, signaling the presence of the target protein. In some embodiments, following detection by the biosensor mRNA of a disease-associated protein, a disease-associated treatment can be administered (e.g., by the biosensor mRNA itself as the at least encoded cargo polypeptide; e.g., by a clinical following detection of a positive signal from the biosensor mRNA).

Exemplary uses in gene expression control in vaccines include protein-based vaccine modulation and therapeutic vaccines. In protein-based vaccine modulation, an RNA molecule described herein (e.g., comprising at least one ARES region described herein) can help regulate the expression of antigens or immune modulators in vaccines, triggering the production of these proteins only in response to specific proteins that indicate a pathogen is present in the body. This ensures more precise immune system activation. With therapeutic vaccines, an RNA molecule described herein (e.g., comprising at least one ARES region described herein) can be used to create mRNA-based therapeutic vaccines where the expression of the therapeutic protein (such as an antibody) is activated only in the presence of certain disease-related proteins.

Exemplary uses in protein replacement therapy inducible protein production. For inducible protein production, in patients with genetic diseases caused by protein deficiencies (e.g., cystic fibrosis or certain metabolic disorders), an RNA molecule described herein (e.g., comprising at least one ARES region described herein) can be used to regulate the expression of missing or malfunctioning proteins in the patient. The switch could activate protein production when a disease-related protein is present, ensuring controlled expression and minimizing side effects.

Exemplary uses in gene silencing and activation include regulated gene knockdown and conditional expression systems. In regulated gene knockdown, an RNA molecule described herein (e.g., comprising at least one ARES region described herein) can be used to regulate gene expression in research or therapy by silencing genes in response to specific proteins. This could help in studies of gene function or in therapeutic strategies to silence disease-causing genes, such as oncogenes. For conditional expression systems, an RNA molecule described herein (e.g., comprising at least one ARES region described herein) can permit conditional expression of genes in cell culture or animal models, providing tools for studying gene function in a controlled manner. For example, researchers could use an RNA molecule described herein (e.g., comprising at least one ARES region described herein) to express a protein only when a specific protein in the environment is present.

Definitions

For convenience, the meaning of some terms and phrases used in the specification, examples, and appended claims, are provided below. Unless stated otherwise, or implicit from context, the following terms and phrases include the meanings provided below. The definitions are provided to aid in describing particular embodiments, and are not intended to limit the claimed invention, because the scope of the invention is limited only by the claims. Unless otherwise defined, all technical and scientific terms used herein have the same meaning as commonly understood by one of ordinary skill in the art to which this invention belongs. If there is an apparent discrepancy between the usage of a term in the art and its definition provided herein, the definition provided within the specification shall prevail.

The terms "decrease", "reduced", "reduction", or "inhibit" are all used herein to mean a decrease by a statistically significant amount. In some embodiments, "reduce," "reduction" or "decrease" or "inhibit" typically means a decrease by at least 10% as compared to a reference level (e.g. the absence of a given treatment or agent) and can include, for example, a decrease by at least about 10%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, at least about 95%, at least about 98%, at least about 99%, or more. As used herein, "reduction" or "inhibition" does not encompass a complete inhibition or reduction as compared to a reference level. "Complete inhibition" is a 100% inhibition as compared to a reference level. A decrease can be preferably down to a level accepted as within the range of normal, e.g., for an individual without a given disorder.

The terms "increased", "increase", "enhance", or "activate" are all used herein to mean an increase by a statistically significant amount. In some embodiments, the terms "increased", "increase", "enhance", or "activate" can mean an increase of at least 10% as compared to a reference level, for example an increase of at least about 20%, or at least about 30%, or at least about 40%, or at least about 50%, or at least about 60%, or at least about 70%, or at least about 80%, or at least about 90% or up to and including a 100% increase or any increase between 10-100% as compared to a reference level, or at least about a 2-fold, or at least about a 3-fold, or at least about a 4-fold, or at least about a 5-fold or at least about a 10-fold increase, or any increase between 2-fold and 10-fold or greater as compared to a reference level. In the context of a marker or symptom, an "increase" is a statistically significant increase in such level.

As used herein, a "subject" means a human or animal. Usually the animal is a vertebrate such as a primate, rodent, domestic animal or game animal. Primates include chimpanzees, cynomolgus monkeys, spider monkeys, and macaques, e.g., Rhesus. Rodents include mice, rats, woodchucks, ferrets, rabbits and hamsters. Domestic and game animals include cows, horses, pigs, deer, bison, buffalo, feline species, e.g., domestic cat, canine species, e.g., dog, fox, wolf, avian species, e.g., chicken, emu, ostrich, and fish, e.g., trout, catfish and salmon. In some embodiments, the subject is a mammal, e.g., a primate, e.g., a human. The terms, "individual," "patient" and "subject" are used interchangeably herein.

Preferably, the subject is a mammal. The mammal can be a human, non-human primate, mouse, rat, dog, cat, horse, or cow, but is not limited to these examples. Mammals other than humans can be advantageously used as subjects that represent animal models of a disease or disorder. A subject can be male or female.

A subject can be one who has been previously diagnosed with or identified as suffering from or having a condition in need of treatment or one or more complications related to such a condition, and optionally, have already undergone treatment for the condition or the one or more complications related to the condition. Alternatively, a subject can also be one who has not been previously diagnosed as having the condition or one or more complications related to the condition. For example, a subject can be one who exhibits one or more risk factors for the condition or one or more complications related to the condition or a subject who does not exhibit risk factors.

A "subject in need" of treatment for a particular condition can be a subject having that condition, diagnosed as having that condition, or at risk of developing that condition.

As used herein, the terms "protein" and "polypeptide" are used interchangeably to designate a series of amino acid residues, connected to each other by peptide bonds between the alpha-amino and carboxy groups of adjacent residues. The terms "protein", and "polypeptide" refer to a polymer of amino acids, including modified amino acids (e.g., phosphorylated, glycated, glycosylated, etc.) and amino acid analogs, regardless of its size or function. "Protein" and "polypeptide" are often used in reference to relatively large polypeptides, whereas the term "peptide" is often used in reference to small polypeptides, but usage of these terms in the art overlaps. The terms "protein" and "polypeptide" are used interchangeably herein when referring to a gene product and fragments thereof. Thus, exemplary polypeptides or proteins include gene products, naturally occurring proteins, homologs, orthologs, paralogs, fragments and other equivalents, variants, fragments, and analogs of the foregoing.

In the various embodiments described herein, it is further contemplated that variants (naturally occurring or otherwise), alleles, homologs, conservatively modified variants, and/or conservative substitution variants of any of the particular polypeptides described are encompassed. As to amino acid sequences, one of skill will recognize that individual substitutions, deletions or additions to a nucleic acid, peptide, polypeptide, or protein sequence which alters a single amino acid or a small percentage of amino acids in the encoded sequence is a "conservatively modified variant" where the alteration results in the substitution of an amino acid with a chemically similar amino acid and retains the desired activity of the polypeptide. Such conservatively modified variants are in addition to and do not exclude polymorphic variants, interspecies homologs, and alleles consistent with the disclosure.

A given amino acid can be replaced by a residue having similar physiochemical characteristics, e.g., substituting one aliphatic residue for another (such as Ile, Val, Leu, or Ala for one another), or substitution of one polar residue for another (such as between Lys and Arg; Glu and Asp; or Gln and Asn). Other such conservative substitutions, e.g., substitutions of entire regions having similar hydrophobicity characteristics, are well known. Polypeptides comprising conservative amino acid substitutions can be tested to confirm that a desired activity of a native or reference polypeptide is retained.

Amino acids can be grouped according to similarities in the properties of their side chains (in A. L. Lehninger, in Biochemistry, second ed., pp. 73-75, Worth Publishers, New York (1975)): (1) non-polar: Ala (A), Val (V), Leu (L), Ile (I), Pro (P), Phe (F), Trp (W), Met (M); (2) uncharged polar: Gly (G), Ser (S), Thr (T), Cys (C), Tyr (Y), Asn (N), Gln (Q); (3) acidic: Asp (D), Glu (E); (4) basic: Lys (K), Arg (R), His (H). Alternatively, naturally occurring residues can be divided into groups based on common side-chain properties: (1) hydrophobic: Norleucine, Met, Ala, Val, Leu, Ile; (2) neutral hydrophilic: Cys, Ser, Thr, Asn, Gln; (3) acidic: Asp, Glu; (4) basic: His, Lys, Arg; (5) residues that influence chain orientation: Gly, Pro; (6) aromatic: Trp, Tyr, Phe. Non-conservative substitutions will entail exchanging a member of one of these classes for another class. Particular conservative substitutions include, for example; Ala into Gly or into Ser; Arg into Lys; Asn into Gln or into His; Asp into Glu; Cys into Ser; Gln into Asn; Glu into Asp; Gly into Ala or into Pro; His into Asn or into Gln; Ile into Leu or into Val; Leu into Ile or into Val; Lys into Arg, into Gln or into Glu; Met into Leu, into Tyr or into Ile; Phe into Met, into Leu or into Tyr; Ser into Thr; Thr into Ser; Trp into Tyr; Tyr into Trp; and/or Phe into Val, into Ile or into Leu.

In some embodiments, the nucleic acids described herein (e.g., an aptamer and/or ribozyme) can be a functional fragment of one of the full-length (e.g., wild-type or reference) nucleic acids (e.g., an aptamer and/or ribozyme) described herein. The functional fragment can comprise at least 10%, at least 20%, at least 30%, at least 40%, at least 50%, at least 60%, at least 70%, at least 80%, at least 90%, at least 91%, at least 92%, at least 93%, at least 94%, at least 95%, at least 96%, at least 97%, at least 98%, at least 99%, or more of the nucleotide sequence of the full-length (e.g., wild-type or reference) nucleic acid. As used herein, a "functional fragment" is a fragment or segment of a nucleic acid which retains at least 50%, at least 60%, at least 70%, at least 80%, at least 90%, at least 91%, at least 92%, at least 93%, at least 94%, at least 95%, at least 96%, at least 97%, at least 98%, at least 99%, or more of the full-length (e.g., wild-type or reference) nucleic acid's activity. For example, a functional fragment of an aptamer sequence described herein retains at least 50%, at least 60%, at least 70%, at least 80%, at least 90%, at least 91%, at least 92%, at least 93%, at least 94%, at least 95%, at least 96%, at least 97%, at least 98%, at least 99%, or more of the full-length (e.g., wild-type or reference) aptamer's ability to specifically bind a target protein. As another example, a functional fragment of a ribozyme sequence described herein retains at least 50%, at least 60%, at least 70%, at least 80%, at least 90%, at least 91%, at least 92%, at least 93%, at least 94%, at least 95%, at least 96%, at least 97%, at least 98%, at least 99%, or more of the full-length (e.g., wild-type or reference) ribozyme's enzymatic function (e.g., ability to cleave itself if a self-cleaving ribozyme). A functional fragment can comprise conservative substitutions of the nucleic acid sequences disclosed herein.

In some embodiments, the polypeptide described herein (or a nucleic acid encoding such a polypeptide) can be a functional fragment of one of the full-length (e.g., wild-type or reference) amino acid sequences described herein. The functional fragment can comprise at least 10%, at least 20%, at least 30%, at least 40%, at least 50%, at least 60%, at least 70%, at least 80%, at least 90%, at least 91%, at least 92%, at least 93%, at least 94%, at least 95%, at least 96%, at least 97%, at least 98%, at least 99%, or more of the amino acid sequence of the full-length (e.g., wild-type or reference) polypeptide. As used herein, a "functional fragment" is a fragment or segment of a polypeptide which retains at least 50%, at least 60%, at least 70%, at least 80%, at least 90%, at least 91%, at least 92%, at least 93%, at least 94%, at least 95%, at least 96%, at least 97%, at least 98%, at least 99%, or more of the full-length (e.g., wild-type or reference) polypeptide's activity. A functional fragment can comprise conservative substitutions of the sequences disclosed herein.

In some embodiments, the polypeptide described herein can be a variant of a polypeptide sequence described herein. In some embodiments, the variant is a conservatively modified variant. Conservative substitution variants can be obtained by mutations of native nucleotide sequences, for example. A "variant," as referred to herein, is a polypeptide substantially homologous to a native or reference polypeptide, but which has an amino acid sequence different from that of the native or reference polypeptide because of one or a plurality of deletions, insertions or substitutions. Variant polypeptide-encoding DNA sequences encompass sequences that comprise one or more additions, deletions, or substitutions of nucleotides when compared to a native or reference DNA sequence, but that encode a protein or fragment thereof that retains activity of the native or reference polypeptide. A wide variety of, for example, PCR-based, site-specific mutagenesis approaches are known in the art and can be applied by the ordinarily skilled artisan to generate and test artificial variants.

A variant amino acid or DNA sequence can be at least 80%, at least 85%, at least 90%, at least 91%, at least 92%, at least 93%, at least 94%, at least 95%, at least 96%, at least 97%, at least 98%, at least 99%, or more, identical to a native or reference sequence. The degree of homology (percent identity) between a native and a mutant sequence can be determined, for example, by comparing the two sequences using freely available computer programs commonly employed for this purpose on the world wide web (e.g. BLASTp or BLASTn with default settings).

A variant amino acid sequence can be at least 50%, at least 60%, at least 70%, at least 80%, at least 90%, at least 91%, at least 92%, at least 93%, at least 94%, at least 95%, at least 96%, at least 97%, at least 98%, at least 99%, or more, similar to a native or reference sequence. As used herein, "similarity" refers to an identical amino acid or a conservatively substituted amino acid, as described herein. Accordingly, the percentage of "sequence similarity" is the percentage of amino acids which is either identical or conservatively changed; e.g., "sequence similarity"=(% sequence identity)+(% conservative changes). It should be understood that a sequence that has a specified percent similarity to a reference sequence necessarily encompasses a sequence with the same specified percent identity to that reference sequence. The skilled person will be aware of various computer programs, using different mathematical algorithms, that are available to determine the identity or similarity between two sequences. For instance, use can be made of a computer program employing the Needleman and Wunsch algorithm (Needleman et al. (1970)); the GAP program in the Accelrys GCG software package (Accelerys Inc., San Diego U.S.A.); the algorithm of E. Meyers and W. Miller (Meyers et al. (1989)) which has been incorporated into the ALIGN program (version 2.0); or more preferably the BLAST (Basic Local Alignment Tool using default parameters); see e.g., U.S. Pat. No. 10,023,890, the content of which is incorporated by reference herein in its entirety.

Alterations of the native amino acid sequence can be accomplished by any of a number of techniques known to one of skill in the art. Mutations can be introduced, for example, at particular loci by synthesizing oligonucleotides containing a mutant sequence, flanked by restriction sites enabling ligation to fragments of the native sequence. Following ligation, the resulting reconstructed sequence encodes an analog having the desired amino acid insertion, substitution, or deletion. Alternatively, oligonucleotide-directed site-specific mutagenesis procedures can be employed to provide an altered nucleotide sequence having particular codons altered according to the substitution, deletion, or insertion required. A wide variety of, site-specific mutagenesis approaches, e.g., Kunkel's method, cassette mutagenesis, PCR site-directed mutagenesis (e.g., traditional PCR, primer extension, or inverse PCR), whole plasmid mutagenesis, in vivo site-directed mutagenesis, CRISPR/Cas-guided mutagenesis, are known in the art and can be applied by the ordinarily skilled artisan to introduce mutations into specific nucleic acid loci. Techniques for making such alterations are very well established and include, for example, those disclosed by Walder et al. (Gene 42:133, 1986); Bauer et al. (Gene 37:73, 1985); Craik (BioTechniques, January 1985, 12-19); Smith et al. (Genetic Engineering: Principles and Methods, Plenum Press, 1981); Braman, Jeff, ed. (2002) In Vitro Mutagenesis Protocols, Methods in Molecular Biology, Vol. 182 (2nd ed.); Khudyakov and Fields (2002), Artificial DNA: Methods and Applications, CRC Press; Hsu et al. (2014), Cell 157 (6): 1262-78; Cerchione et al. (2020) PLOS ONE 15 (4): e0231716; and U.S. Pat. Nos. 4,518,584 and 4,737,462, which are herein incorporated by reference in their entireties. Any cysteine residue not involved in maintaining the proper conformation of the polypeptide also can be substituted, generally with serine, to improve the oxidative stability of the molecule and prevent aberrant crosslinking. Conversely, cysteine bond(s) can be added to the polypeptide to improve its stability or facilitate oligomerization.

As used herein, the term "nucleic acid" or "nucleic acid sequence" refers to any molecule, preferably a polymeric molecule, incorporating units of ribonucleic acid, deoxyribonucleic acid or an analog thereof. The nucleic acid can be either single-stranded or double-stranded. A single-stranded nucleic acid can be one nucleic acid strand of a denatured double-stranded DNA. Alternatively, it can be a single-stranded nucleic acid not derived from any double-stranded DNA. In one aspect, the nucleic acid can be DNA. In another aspect, the nucleic acid can be RNA. Suitable DNA can include, e.g., genomic DNA, vector DNA, or cDNA. Suitable RNA can include, e.g., mRNA, saRNA.

As used herein, the term "hybridize" refers to the process by which single strands of polynucleotides form a double-stranded structure through hydrogen bonding between the constituent bases. It is understood herein that the two polynucleotides that can hybridize to each other can be in separate nucleic acid molecules or can be in separate regions of a single nucleic acid molecule. The ability of two polynucleotides to hybridize with each other is based on the degree of complementarity of the two polynucleotides, which in turn is based on the fraction of matched complementary nucleotide pairs. In some embodiments, the two polynucleotides that can hybridize to each other comprise at least 80%, at least 85%, at least 90%, at least 91%, at least 92%, at least 93%, at least 94%, at least 95%, at least 96%, at least 97%, at least 98%, at least 99%, or more matched complementary nucleotide pairs. The more nucleotides in a given polynucleotide that are complementary to another polynucleotide, the more stringent the conditions can be for hybridization and the more specific will be the binding between the two polynucleotides. Increased stringency may be achieved by elevating the temperature, increasing the ratio of co-solvents, lowering the salt concentration, and combinations thereof.

As used herein, the terms "complementary," "complement," and "complementary nucleic acid sequence" refer to the nucleic acid strand that is related to the base sequence in another nucleic acid strand by the Watson-Crick base-pairing rules. In general, two polynucleotides are complementary when one polynucleotide can bind another polynucleotide in an anti-parallel sense wherein the 3'-end of each polynucleotide binds to or is aligned with the 5'-end of the other polynucleotide and each A, T(U), G, and C of one polynucleotide is then aligned with a T(U), A, C, and G, respectively, of the other polynucleotide. Polynucleotides that comprise RNA bases can also include complementary G/U or U/G basepairs. Two complementary strands may comprise complementary regions comprising all or one or more portions of one or both strands.

The term "expression" refers to the cellular processes involved in producing RNA and proteins and as appropriate, secreting proteins, including where applicable, but not limited to, for example, transcription, transcript processing, translation and protein folding, modification and processing. Expression can refer to the transcription and stable accumulation of sense (e.g., mRNA) or antisense RNA derived from a nucleic acid fragment or fragments and/or to the translation of mRNA into a polypeptide.

"Expression products" include RNA transcribed from a gene, and polypeptides obtained by translation of mRNA transcribed from a gene. The term "gene" refers to the nucleic acid sequence which is transcribed (DNA) to RNA in vitro or in vivo when operably linked to appropriate regulatory sequences. The gene may or may not include regions preceding and following a coding region, e.g. 5' untranslated (5' UTR) or "leader" sequences and 3' UTR or "trailer" sequences, as well as intervening sequences (introns) between individual coding segments (exons).

In some embodiments of any of the aspects, a polypeptide, nucleic acid (e.g., an RNA molecule), or cell as described herein can be engineered. As used herein, "engineered" refers to the aspect of having been manipulated by the hand of man. For example, a nucleic acid (e.g., an RNA molecule) is considered to be "engineered" when at least one aspect of the nucleic acid, e.g., its sequence, has been manipulated by the hand of man to differ from the aspect as it exists in nature. As another example, a polypeptide is considered to be "engineered" when at least one aspect of the polypeptide, e.g., its sequence, has been manipulated by the hand of man to differ from the aspect as it exists in nature. As is common practice and is understood by those in the art, progeny of an engineered cell are typically still referred to as "engineered" even though the actual manipulation was performed on a prior entity.

In some embodiments of any of the aspects, the RNA molecule and/or target protein described herein is exogenous. In some embodiments of any of the aspects, the RNA molecule and/or target protein described herein is ectopic. In some embodiments of any of the aspects, the RNA molecule and/or target protein described herein is not endogenous.

The term "exogenous" refers to a substance present in a cell other than its native source. The term "exogenous" when used herein can refer to a nucleic acid (e.g. an RNA molecule as described herein) or a polypeptide that has been introduced by a process involving the hand of man into a biological system such as a cell or organism in which it is not normally found and one wishes to introduce the nucleic acid or polypeptide into such a cell or organism. Alternatively, "exogenous" can refer to a nucleic acid or a polypeptide that has been introduced by a process involving the hand of man into a biological system such as a cell or organism in which it is found in relatively low amounts and one wishes to increase the amount of the nucleic acid or polypeptide in the cell or organism, e.g., to create ectopic expression or levels. In contrast, the term "endogenous" refers to a substance that is native to the biological system or cell. As used herein, "ectopic" refers to a substance that is found in an unusual location and/or amount. An ectopic substance can be one that is normally found in a given cell, but at a much lower amount and/or at a different time. Ectopic also includes a substance, such as a polypeptide or nucleic acid that is not naturally found or expressed in a given cell in its natural environment.

As used herein, the terms "treat," "treatment," "treating," or "amelioration" refer to therapeutic treatments, wherein the object is to reverse, alleviate, ameliorate, inhibit, slow down or stop the progression or severity of a condition associated with a disease or disorder. The term "treating" includes reducing or alleviating at least one adverse effect or symptom of a condition, disease or disorder. Treatment is generally "effective" if one or more symptoms or clinical markers are reduced. Alternatively, treatment is "effective" if the progression of a disease is reduced or halted. That is, "treatment" includes not just the improvement of symptoms or markers, but also a cessation of, or at least slowing of, progress or worsening of symptoms compared to what would be expected in the absence of treatment. Beneficial or desired clinical results include, but are not limited to, alleviation of one or more symptom(s), diminishment of extent of disease, stabilized (i.e., not worsening) state of disease, delay or slowing of disease progression, amelioration or palliation of the disease state, remission (whether partial or total), and/or decreased mortality, whether detectable or undetectable. The term "treatment" of a disease also includes providing relief from the symptoms or side-effects of the disease (including palliative treatment).

As used herein, the term "pharmaceutical composition" refers to the active agent in combination with a pharmaceutically acceptable carrier e.g. a carrier commonly used in the pharmaceutical industry. The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio. In some embodiments of any of the aspects, a pharmaceutically acceptable carrier can be a carrier other than water. In some embodiments of any of the aspects, a pharmaceutically acceptable carrier can be a cream, emulsion, gel, liposome, nanoparticle, and/or ointment. In some embodiments of any of the aspects, a pharmaceutically acceptable carrier can be an artificial or engineered carrier, e.g., a carrier that the active ingredient would not be found to occur in or within nature.

As used herein, the term "administering," refers to the placement of a composition or compound as disclosed herein into a subject by a method or route which results in at least partial delivery of the composition, compound, or metabolite thereof at a desired site. Pharmaceutical compositions comprising the compounds disclosed herein can be administered by any appropriate route which results in an effective treatment in the subject. In some embodiments, administration comprises physical human activity, e.g., an injection, act of ingestion, an act of application, and/or manipulation of a delivery device or machine. Such activity can be performed, e.g., by a medical professional and/or the subject being treated.

As used herein, "contacting" refers to any suitable means for delivering, or exposing, an agent to at least one cell. Exemplary delivery methods include, but are not limited to, direct delivery to cell culture medium, transfection, transduction, perfusion, injection, or other delivery method known to one skilled in the art. In some embodiments, contacting comprises physical human activity, e.g., an injection; an act of dispensing, mixing, and/or decanting; and/or manipulation of a delivery device or machine. "Contacting" of a cell can be performed in vitro, ex vivo, or in vivo.

In some embodiments of any of the aspects, the cells can be maintained in culture. As used herein, "maintaining" refers to continuing the viability of a cell or population of cells. A maintained population of cells will have at least a subpopulation of metabolically active cells.

As used herein, the term "specific binding" or "specifically binds" refers to a chemical or physical interaction between two molecules, compounds, cells and/or particles wherein the first entity binds to the second, target entity (e.g., the aptamer and its associated target protein) with greater specificity and affinity than it binds to a third entity which is a non-target. In some embodiments, specific binding can refer to an affinity of the first entity for the second target entity which is at least 10 times, at least 50 times, at least 100 times, at least 500 times, at least 1000 times or greater than the affinity for the third non-target entity.

The term "statistically significant" or "significantly" refers to statistical significance and generally means a two standard deviation (2SD) or greater difference or a p-value of less than 0.05.

Other than in the operating examples, or where otherwise indicated, all numbers expressing quantities of ingredients or reaction conditions used herein should be understood as modified in all instances by the term "about." The term "about" when used in connection with percentages can mean±1%.

As used herein, the term "comprising" means that other elements can also be present in addition to the defined elements presented. The use of "comprising" indicates inclusion rather than limitation.

The term "consisting of" refers to compositions, methods, and respective components thereof as described herein, which are exclusive of any element not recited in that description of the embodiment.

As used herein the term "consisting essentially of" refers to those elements required for a given embodiment. The term permits the presence of additional elements that do not materially affect the basic and novel or functional characteristic(s) of that embodiment of the invention.

As used herein, the term "corresponding to" refers to an amino acid or nucleotide at the enumerated position in a first polypeptide or nucleic acid, or an amino acid or nucleotide that is equivalent to an enumerated amino acid or nucleotide in a second polypeptide or nucleic acid. Equivalent enumerated amino acids or nucleotides can be determined by alignment of candidate sequences using degree of homology programs known in the art, e.g., BLAST.

The singular terms "a," "an," and "the" include plural referents unless context clearly indicates otherwise. Similarly, the word "or" is intended to include "and" unless the context clearly indicates otherwise. Although methods and materials similar or equivalent to those described herein can be used in the practice or testing of this disclosure, suitable methods and materials are described below. The abbreviation, "e.g." is derived from the Latin exempli gratia, and is used herein to indicate a non-limiting example. Thus, the abbreviation "e.g." is synonymous with the term "for example."

Groupings of alternative elements or embodiments of the invention disclosed herein are not to be construed as limitations. Each group member can be referred to and claimed individually or in any combination with other members of the group or other elements found herein. One or more members of a group can be included in, or deleted from, a group for reasons of convenience and/or patentability. When any such inclusion or deletion occurs, the specification is herein deemed to contain the group as modified thus fulfilling the written description of all Markush groups used in the appended claims.

Unless otherwise defined herein, scientific and technical terms used in connection with the present application shall have the meanings that are commonly understood by those of ordinary skill in the art to which this disclosure belongs. It should be understood that this invention is not limited to the particular methodology, protocols, and reagents, etc., described herein and as such can vary. The terminology used herein is for the purpose of describing particular embodiments only, and is not intended to limit the scope of the present invention, which is defined solely by the claims. Definitions of common terms in cell biology, immunology, and molecular biology can be found in The Merck Manual of Diagnosis and Therapy, 20th Edition, published by Merck Sharp & Dohme Corp., 2018 (ISBN 0911910190, 978-0911910421); Robert S. Porter et al. (eds.), The Encyclopedia of Molecular Cell Biology and Molecular Medicine, published by Blackwell Science Ltd., 1999-2012 (ISBN 9783527600908); and Robert A. Meyers (ed.), Molecular Biology and Biotechnology: a Comprehensive Desk Reference, published by VCH Publishers, Inc., 1995 (ISBN 1-56081-569-8); Immunology by Werner Luttmann, published by Elsevier, 2006; Janeway's Immunobiology, Kenneth Murphy, Allan Mowat, Casey Weaver (eds.), W. W. Norton & Company, 2016 (ISBN 0815345054, 978-0815345053); Lewin's Genes XI, published by Jones & Bartlett Publishers, 2014 (ISBN-1449659055); Michael Richard Green and Joseph Sambrook, Molecular Cloning: A Laboratory Manual, 4th ed., Cold Spring Harbor Laboratory Press, Cold Spring Harbor, N.Y., USA (2012) (ISBN 1936113414); Davis et al., Basic Methods in Molecular Biology, Elsevier Science Publishing, Inc., New York, USA (2012) (ISBN 044460149X); Laboratory Methods in Enzymology: DNA, Jon Lorsch (ed.) Elsevier, 2013 (ISBN 0124199542); Current Protocols in Molecular Biology (CPMB), Frederick M. Ausubel (ed.), John Wiley and Sons, 2014 (ISBN 047150338X, 9780471503385), Current Protocols in Protein Science (CPPS), John E. Coligan (ed.), John Wiley and Sons, Inc., 2005; and Current Protocols in Immunology (CPI) (John E. Coligan, ADA M Kruisbeek, David H Margulies, Ethan M Shevach, Warren Strobe, (eds.) John Wiley and Sons, Inc., 2003 (ISBN 0471142735, 9780471142737), the contents of which are all incorporated by reference herein in their entireties.

Other terms are defined herein within the description of the various aspects of the invention.

All patents and other publications; including literature references, issued patents, published patent applications, and co-pending patent applications; cited throughout this application are expressly incorporated herein by reference for the purpose of describing and disclosing, for example, the methodologies described in such publications that might be used in connection with the technology described herein. These publications are provided solely for their disclosure prior to the filing date of the present application. Nothing in this regard should be construed as an admission that the inventors are not entitled to antedate such disclosure by virtue of prior invention or for any other reason. All statements as to the date or representation as to the contents of these documents is based on the information available to the applicants and does not constitute any admission as to the correctness of the dates or contents of these documents.

The description of embodiments of the disclosure is not intended to be exhaustive or to limit the disclosure to the precise form disclosed. While specific embodiments of, and examples for, the disclosure are described herein for illustrative purposes, various equivalent modifications are possible within the scope of the disclosure, as those skilled in the relevant art will recognize. For example, while method steps or functions are presented in a given order, alternative embodiments may perform functions in a different order, or functions may be performed substantially concurrently. The teachings of the disclosure provided herein can be applied to other procedures or methods as appropriate. The various embodiments described herein can be combined to provide further embodiments. Aspects of the disclosure can be modified, if necessary, to employ the compositions, functions and concepts of the above references and application to provide yet further embodiments of the disclosure. Moreover, due to biological functional equivalency considerations, some changes can be made in protein structure without affecting the biological or chemical action in kind or amount. These and other changes can be made to the disclosure in light of the detailed description. All such modifications are intended to be included within the scope of the appended claims.

Specific elements of any of the foregoing embodiments can be combined or substituted for elements in other embodiments. Furthermore, while advantages associated with certain embodiments of the disclosure have been described in the context of these embodiments, other embodiments may also exhibit such advantages, and not all embodiments need necessarily exhibit such advantages to fall within the scope of the disclosure.

Some embodiments of the technology described herein can be defined according to any of the following numbered paragraphs:

1. An RNA molecule comprising:
   a) an open reading frame (ORF) encoding at least one cargo polypeptide; and
   b) at least one untranslated region (UTR) comprising at least one Aptamer and Ribozyme Equilibrium Shifting (ARES) region, which comprises:
      i) a protein-binding aptamer that specifically binds to a target protein; and
      ii) a ribozyme.
2. The RNA molecule of paragraph 1, wherein the aptamer is selected from the group consisting of: a MS2 aptamer, a PP7 aptamer, a bovine immunodeficiency virus (BIV) transactivation response (Tar) aptamer, and a P22 aptamer.
3. The RNA molecule of paragraph 1 or 2, wherein the target protein is selected from:
   a) MS2 coat protein (MCP), which specifically binds to the MS2 aptamer;
   b) PP7 coat protein (PCP), which specifically binds to the PP7 aptamer;
   c) BIV trans-activator of transcription (Tat), which specifically binds to the BIV Tar aptamer;
   d) a P22 N protein, which specifically binds to the P22 aptamer.
4. The RNA molecule of any one of paragraphs 1-3, wherein the ribozyme is a self-cleaving ribozyme.
5. The RNA molecule of paragraph 4, wherein the self-cleaving ribozyme is selected from the group consisting of: hammerhead ribozyme (HHR), hepatitis delta virus (HDV) ribozyme, hairpin ribozyme, Varkud satellite (VS) ribozyme, glmS ribozyme, twister ribozyme, twister sister ribozyme, Pistol ribozyme, Hatchet ribozyme, and Hovlinc ribozyme.
6. The RNA molecule of any one of paragraphs 1-5, wherein the aptamer is 5' of the ribozyme in the ARES region.
7. The RNA molecule of any one of paragraphs 1-6, wherein the aptamer is 3' of the ribozyme in the ARES region.
8. The RNA molecule of any one of paragraphs 1-7, wherein the at least one ARES region is located in the UTR 5' of the ORF (5' UTR).
9. The RNA molecule of any one of paragraphs 1-8, wherein the at least one ARES region is located in the UTR 3' of the ORF (3' UTR).
10. The RNA molecule of any one of paragraphs 1-9, wherein at least one ARES region is located in 5' UTR, and at least one ARES region is located the 3' UTR.

11. The RNA molecule of any one of paragraphs 1-10, wherein the at least one ARES region modulates the stability of the RNA molecule and/or modulates translation of the at least one cargo polypeptide encoded by the ORF.
12. The RNA molecule of any one of paragraphs 1-11, wherein the at least one ARES region is an ON-switch ARES region structured such that either the aptamer or the ribozyme, but not both, can form at one time in the RNA molecule.
13. The RNA molecule of paragraph 12, wherein in an RNA molecule comprising an ON-switch ARES region:
   a) in the presence of the target protein, the aptamer is stabilized, the ribozyme cannot form, the RNA molecule is not cleaved, and the ORF can be translated (ON); and/or
   b) in the absence of the target protein, the aptamer is not stabilized, the ribozyme can form, the RNA molecule is cleaved, and the ORF cannot be translated (OFF).
14. The RNA molecule of paragraph 12 or 13, wherein the ON-switch ARES region comprises:
   a) the aptamer comprising:
      i) a first (a) region and a complementary (a*) region that can hybridize to the first (a) region; and
      ii) a primary second (b1) region and a complementary (b*) region that can hybridize to the primary second (b1) region or to a secondary second (b2) region in the ribozyme; and
   b) the ribozyme comprising:
      i) the secondary second (b2) region and the complementary (b*) region; and
      ii) a third (c) region and a complementary (c*) region that can hybridize to the third (c) region.
15. The RNA molecule of paragraph 14, wherein the ON-switch ARES region comprises from 5' to 3':
   a) the primary second (b1) region;
   b) the first (a) region;
   c) the complementary (a*) region that can hybridize to the first (a) region;
   d) the complementary (b*) region that can hybridize to the primary second (b1) region in the aptamer or to a secondary second (b2) region in the ribozyme;
   e) the third (c) region;
   f) the complementary (c*) region that can hybridize to the third (c) region; and
   g) the secondary second (b2) region.
16. The RNA molecule of paragraph 14, wherein the ON-switch ARES region comprises from 5' to 3':
   a) the secondary second (b2) region;
   b) the third (c) region;
   c) the complementary (c*) region that can hybridize to the third (c) region;
   d) the complementary (b*) region that can hybridize to the secondary second (b2) region in the ribozyme or to a primary second (b1) region in the aptamer;
   e) the first (a) region;
   f) the complementary (a*) region that can hybridize to the first (a) region; and
   g) the primary second (b1) region.
17. The RNA molecule of any one of paragraphs 1-16, which further comprises at least one stabilization domain.
18. The RNA molecule of any one of paragraphs 1-17, which further comprises at least one degradation domain.

19. The RNA molecule of any one of paragraphs 1-18, wherein the at least one ARES region is a stabilization/degradation ARES region, which comprises in the 3' UTR, from 5' to 3':
a) a stabilization domain;
b) the ON-switch ARES region of any one of paragraphs 12-16; and
c) a degradation domain.

20. The RNA molecule of paragraph 19, wherein in an RNA molecule comprising a stabilization/degradation ARES region:
a) in the presence of the target protein, the aptamer is stabilized, the ribozyme cannot form, the RNA molecule is not cleaved, the degradation domain is retained, the RNA molecule is degraded, and the ORF cannot be translated (OFF); and/or
b) in the absence of the target protein, the aptamer is not stabilized, the ribozyme can form, the RNA molecule is cleaved, the degradation domain is not retained, the stabilization domain protects the RNA molecule from degradation, and the ORF can be translated (ON).

21. The RNA molecule of any one of paragraphs 1-20, wherein the at least one ARES region is an OFF-switch ARES region structured such that either both the aptamer and the ribozyme, or at least one stabilization stem, can form at one time in the RNA molecule.

22. The RNA molecule of paragraph 21, wherein in an RNA molecule comprising an OFF-switch ARES region:
a) in the presence of the target protein, the aptamer is stabilized, the ribozyme can form, the at least one stabilization stem cannot form, the RNA molecule is cleaved, and the ORF cannot be translated (OFF); and/or
b) in the absence of the target protein, the aptamer is not stabilized, the ribozyme cannot form, the at least one stabilization stem can form, the RNA molecule is not cleaved, and the ORF can be translated (ON).

23. The RNA molecule of paragraph 21 or 22, wherein the OFF-switch ARES region comprises:
a) the aptamer comprising:
i) a first (a) region and a complementary (a*) region that can hybridize to the first (a) region; and
ii) a primary second (b1) region and a primary complementary (b1*) region that can hybridize to the primary second (b1) region or to a secondary second (b2) region;
b) the ribozyme comprising:
i) the secondary second (b2) region and a secondary complementary (b2*) region that can hybridize to the secondary second (b2) region; and
ii) a third (c) region and a complementary (c*) region that can hybridize to the third (c) region; and
c) the at least one stabilization stem comprising:
i) a fourth (d) region and a complementary (d*) region that can hybridize to the fourth (d) region; and
ii) the secondary second (b2) region of the ribozyme and the primary complementary (b1*) region of the aptamer.

24. The RNA molecule of paragraph 23, wherein the OFF-switch ARES region comprises from 5' to 3':
a) the primary second (b1) region;
b) the first (a) region;
c) the complementary (a*) region that can hybridize to the first (a) region;

d) the primary complementary (b1*) region that can hybridize to the primary second (b1) region or to a secondary second (b2) region;
e) the fourth (d) region;
f) the complementary (d*) region that can hybridize to the fourth (d) region;
g) the secondary second (b2) region;
h) the third (c) region;
i) the complementary (c*) region that can hybridize to the third (c) region; and
j) the secondary complementary (b2*) region that can hybridize to the secondary second (b2) region.

25. The RNA molecule of paragraph 23, wherein the OFF-switch ARES region comprises from 5' to 3':
a) the secondary second (b2) region;
b) the third (c) region;
c) the complementary (c*) region that can hybridize to the third (a) region;
d) the secondary complementary (b2*) region that can hybridize to the secondary second (b2) region or to a primary second (b1) region;
e) the fourth (d) region;
f) the complementary (d*) region that can hybridize to the fourth (d) region;
g) the primary second (b1) region;
h) the first (a) region;
i) the complementary (a*) region that can hybridize to the first (a) region; and
j) the primary complementary (b1*) region that can hybridize to the primary second (b1) region.

26. The RNA molecule of paragraph 21 or 22, wherein the OFF-switch ARES region comprises 2 stabilization stems.

27. The RNA molecule of paragraph 26, wherein the OFF-switch ARES region comprises:
a) the aptamer comprising:
i) a first (a) region and a complementary (a*) region that can hybridize to the first (a) region; and
ii) a primary second (b1) region and a primary complementary (b1*) region that can hybridize to the primary second (b1) region or to a secondary second (b2) region;
b) the ribozyme comprising:
i) the secondary second (b2) region and a secondary complementary (b2*) region that can hybridize to the secondary second (b2) region; and
ii) a third (c) region and a complementary (c*) region that can hybridize to the third (c) region;
c) a first stabilization stem comprising:
i) a primary fourth (d1) region and a complementary (d1*) region that can hybridize to the primary fourth (d1) region; and
ii) the secondary second (b2) region of the ribozyme and the primary complementary (b1*) region of the aptamer; and
d) a second stabilization stem comprising:
i) a secondary fourth (d2) region and a complementary (d2*) region that can hybridize to the secondary fourth (d2) region; and
ii) the primary second (b1) region of the aptamer and a tertiary complementary (b3*) region that can hybridize to the primary second (b1) region.

28. The RNA molecule of paragraph 27, wherein the OFF-switch ARES region comprises from 5' to 3':
a) the tertiary complementary (b3*) region that can hybridize to the primary second (b1) region;

b) the complementary (d2*) region that can hybridize to the secondary fourth (d2) region;

c) the secondary fourth (d2) region;

d) the primary second (b1) region;

e) the first (a) region;

f) the complementary (a*) region that can hybridize to the first (a) region;

g) the primary complementary (b1*) region that can hybridize to the primary second (b1) region or to the secondary second (b2) region;

h) the primary fourth (d1) region;

i) the complementary (d1*) region that can hybridize to the primary fourth (d1) region;

j) the secondary second (b2) region;

k) the third (c) region;

l) the complementary (c*) region that can hybridize to the third (c) region; and m) the secondary complementary (b2*) region that can hybridize to the secondary second (b2) region.

29. The RNA molecule of paragraph 26, wherein the OFF-switch ARES region comprises:

a) the ribozyme comprising:

i) a first (a) region and a complementary (a*) region that can hybridize to the first (a) region; and ii) a primary second (b1) region and a primary complementary (b1*) region that can hybridize to the primary second (b1) region or to a secondary second (b2) region;

b) the aptamer comprising:

i) the secondary second (b2) region and a secondary complementary (b2*) region that can hybridize to the secondary second (b2) region; and ii) a third (c) region and a complementary (c*) region that can hybridize to the third (c) region;

c) a first stabilization stem comprising:

i) a primary fourth (d1) region and a complementary (d1*) region that can hybridize to the primary fourth (d1) region; and ii) the secondary second (b2) region of the aptamer and the primary complementary (b1*) region of the ribozyme; and d) a second stabilization stem comprising:

i) a secondary fourth (d2) region and a complementary (d2*) region that can hybridize to the secondary fourth (d2) region; and ii) the primary second (b1) region of the ribozyme and a tertiary complementary (b3*) region that can hybridize to the primary second (b1) region.

30. The RNA molecule of paragraph 29, wherein the OFF-switch ARES region comprises from 5' to 3':

a) the tertiary complementary (b3*) region that can hybridize to the primary second (b1) region;

b) the complementary (d2*) region that can hybridize to the secondary fourth (d2) region;

c) the secondary fourth (d2) region;

d) the primary second (b1) region;

e) the first (a) region;

f) the complementary (a*) region that can hybridize to the first (a) region;

g) the primary complementary (b1*) region that can hybridize to the primary second (b1) region or to the secondary second (b2) region;

h) the primary fourth (d1) region;

i) the complementary (d1*) region that can hybridize to the primary fourth (d1) region;

j) the secondary second (b2) region;

k) the third (c) region;

l) the complementary (c*) region that can hybridize to the third (c) region; and m) the secondary complementary (b2*) region that can hybridize to the secondary second (b2) region.

31. The RNA molecule of any one of paragraphs 1-30, wherein the at least cargo polypeptide is selected from:

a) a detectable marker (e.g., a fluorescent polypeptide);

b) an antigen (e.g., severe acute respiratory syndrome coronavirus 2 (SARS-CoV-2) spike gene, respiratory syncytial virus (RSV) F protein, influenza hemagglutinin, a tumor associated antigen (e.g., New York esophageal squamous cell carcinoma 1 for melanoma, kallikrein-2 for prostate cancer); an antibody (e.g., a monoclonal antibody; e.g.., an anti-claudin 18 isoform 2 (anti-CLDN18.2, which is specific for tumors) antibody, anti-cytotoxic T-lymphocyte-associated protein 4 (anti-CTLA-4) or anti-glucocorticoid-induced tumor necrosis factor receptor (TNFR)-related protein (anti-GITR) antibodies, which are specific for melanoma);

c) a cytokine (e.g., IL-2, IL-7, IL-12, OX40L, IL-23);

d) a cell therapy protein (e.g., claudin-6 (CLDN6), a chimeric antigen receptor (CAR) protein, a T cell receptor);

e) a tumor suppressor protein (e.g., tumor protein 53 (p53), breast cancer gene 1 (BRCA1), breast cancer gene 2 (BRCA2));

f) a programmed cell death protein (e.g., Bax, a caspase);

g) a site-specific nuclease (e.g., Cas9; a prime editing enzyme (e.g., PE2, PE3, PE4, PE5, PE2max, PE3max, and the like);

h) a therapeutic protein (e.g., vascular endothelial growth factor (VEGF), Glucagon-like peptide-1, insulin); or i) an oncogene (e.g., mutant forms of KRAS, HRAS, EGFR, HER2, PDGFR, MYC, BRCA1, BRCA2, ABL1, VEGF).

32. The RNA molecule of any one of paragraphs 1-31, which is a messenger RNA (mRNA), further comprising a 5' cap and a 3' polyA tail.

33. A self-amplifying RNA (saRNA) comprising the RNA molecule of any one of paragraphs 1-32, which further comprises a second open reading frame encoding an RNA-dependent RNA polymerase.

34. A self-amplifying RNA (saRNA) comprising from 5' to 3':

a) a 5' conserved sequence element (CSE);

b) a first open reading frame (ORF) encoding an RNA-dependent RNA polymerase (RdRP), operably linked to a promoter in the 5' CSE;

c) a subgenomic promoter (SGP);

d) a second ORF encoding at least one cargo polypeptide, operably linked to the SGP; and e) a 3' CSE; and wherein the 5' CSE, a region between the first and second ORFs, and/or the 3' CSE further comprises at least one Aptamer and Ribozyme Equilibrium Shifting (ARES) region in a sense or anti-sense orientation, wherein the ARES region comprises:

i) a protein-aptamer that specifically binds to a target protein; and ii) a ribozyme.

35. The saRNA of paragraph 33 or 34, wherein when the ARES region is in the sense orientation, the ARES region is functional in the saRNA.

36. The saRNA of paragraph 33 or 34, wherein when the ARES region is in the anti-sense orientation, the ARES region is functional when the saRNA is delivered to a cell, the RdRP is translated from the saRNA, and the RdRP synthesizes a reverse complementary negative strand of the saRNA.

37. A polynucleotide comprising the RNA molecule of any one of paragraphs 1-32 or the saRNA of any one of paragraphs 33-36.

38. A vector comprising the polynucleotide of paragraph 37.

39. A combination comprising:
   a) the RNA molecule of any one of paragraphs 1-32 or the saRNA of any one of paragraphs 33-36; and
   b) a target protein.

40. The combination of paragraph 39, wherein the target protein is linked to a polypeptide of interest.

41. A cell comprising the RNA molecule of any one of paragraphs 1-32, the saRNA of any one of paragraphs 33-36, the polynucleotide of paragraph 37, the vector of paragraph 38, and/or the combination of paragraph 39 or 40.

42. A pharmaceutical composition comprising the RNA molecule of any one of paragraphs 1-32, the saRNA of any one of paragraphs 33-36, the polynucleotide of paragraph 37, the vector of paragraph 38, the combination of paragraph 39 or 40, or the cell of paragraph 41.

43. A method of modulating the translation of at least one cargo polypeptide, the method comprising contacting a cell with the RNA molecule of any one of paragraphs 1-32, the saRNA of any one of paragraphs 33-36, the polynucleotide of paragraph 37, the vector of paragraph 38, the combination of paragraph 39 or 40, or the pharmaceutical composition of paragraph 42.

44. The method of paragraph 43, further comprising contacting the cell with the target protein.

45. The method of paragraph 43 or 44, wherein the cell expresses the target protein.

46. A method of modulating the translation of at least one cargo polypeptide in a subject in need thereof, the method comprising administering to the subject an effective amount of the RNA molecule of any one of paragraphs 1-32, the saRNA of any one of paragraphs 33-36, the polynucleotide of paragraph 37, the vector of paragraph 38, the combination of paragraph 39 or 40, the cell of paragraph 41, or the pharmaceutical composition of paragraph 42.

47. The method of paragraph 46, further comprising administering to the subject an effective amount of the target protein.

48. The method of paragraph 46 or 47, wherein a target cell in the subject expresses the target protein.

49. The method of any one of paragraphs 43-48, wherein the RNA molecule comprises the ON-switch ARES region of any one of paragraphs 12-16.

50. The method of paragraph 49, wherein in an RNA molecule comprising an ON-switch ARES region:
   a) in the presence of the target protein, the at least one cargo polypeptide is translated (ON); and/or
   b) in the absence of the target protein, the at least one cargo polypeptide is not translated (OFF).

51. The method of any one of paragraphs 43-50, wherein the RNA molecule comprises the stabilization/degradation ARES region of any one of paragraphs 19-20.

52. The method of any one of paragraphs 43-51, wherein the RNA molecule comprises the OFF-switch ARES region of any one of paragraphs 21-30.

53. The method of paragraph 51 or 52, wherein in an RNA molecule comprising a stabilization/degradation ARES region or an OFF-switch ARES region:
   a) in the presence of the target protein, the at least one cargo polypeptide is not translated (OFF); and/or
   b) in the absence of the target protein, the at least one cargo polypeptide is translated (ON).

The technology described herein is further illustrated by the following examples which in no way should be construed as being further limiting.

EXAMPLES

Example 1: Aptamer and Ribozyme Equilibrium Shifting (ARES) RNA Circuits for Cell-Specific Targeting and Temporal Control of mRNA Therapeutics RNA therapeutics hold immense promise for the future of healthcare, potentially revolutionizing treatments for various diseases, including genetic disorders and cancers.[1,2] However, there is a critical need to develop systems that provide precise spatial and temporal control over these therapies to maximize their efficacy and minimize potential side effects. Current site-specific control methods such as lipid nanoparticles (LNPs) are used for targeted drug delivery, but they lack highly specific cell types and tissue targeting.[3,4] Methods to control mRNA lifespan, the addition of cap structures, polyadenylation, and degradation tags, exist but do not provide adaptable control over the system, resulting in highly variable lifespans for the therapeutics.[5] To fully realize the potential of RNA therapeutics, the focus must now shift to pioneering novel solutions that refine targeting accuracy and control mRNA lifespan.

To address these challenges, described herein is the development of RNA switches designed to regulate mRNA life span in response to proteins present in the environment. These switches leverage a previously optimized hammerhead ribozyme (HHR) and RNA binding proteins (RBPs). The HHR possesses self-cleaving properties that can cause mRNA to be degraded. RBPs, on the other hand, can specifically bind to RNA aptamers and affect the cleavage activity of the HHR.[6,7] Without wishing to be bound by theory, it is hypothesized that by combining HHR and RBP aptamers into an aptamer ribozyme equilibrium shifting (ARES) RNA circuit, generalizable mRNA stabilizing and destabilizing switches can be achieved and controlled with RBPs. If successful, this approach would provide more precise spatial and temporal control over RNA therapeutics, leading to enhanced efficacy and minimized side effects. Additionally, the versatility of the proposed RNA switches would facilitate their widespread application in healthcare.

Section 1: Attain cell-specific and temporal control of translation through mRNA stabilizing switch triggered by RBPs. Thus far, several exogenous RBP-aptamer pairs have been designed and screened through to identify mRNA stabilizing switches. In these switches mRNA structures remain stable when an RBP is present, allowing for normal translation. However, in the absence of the RBP, an HHR in proximity to the aptamer is thermodynamically favored to form and will self-cleave. This leads to the degradation of the mRNA before translation. Several exogenous RBPs and their aptamers have proved successful including BIV Tat, P22N, and MCP. To further validate these systems cell-specific control and temporal control will be tested. This will be accomplished with stable cell lines that produce the RBPs on a constitutively active prompter and an inducible promoter. Furthermore, to demonstrate disease-specific applications, an ON switch utilizing an aptamer corresponding to an RBP relevant to pancreatic cancer will be developed. Subsequently, it will be demonstrated that this switch facilitates translation solely in pancreatic cancer cells, underscoring its potential for targeted therapeutic interventions.

Section 2: Achieve cell-specific and temporal control of translation by utilizing an mRNA destabilizing switch triggered by RBPs. A translational OFF switch has been achieved with the BIV Tat RBP where translation occurs normally without the RBP, but when the RBP is present, an HHR is thermodynamically favored to form, destabilizing the mRNA, and leading to decreased translational levels. To build on this, the library of OFF switches and their corresponding RBPs will be expanded. The switches will then be tested for cell-specific and temporal control using stable cell lines that produce the RBPs on a constitutively active prompter and an inducible promoter.

Section 3: Demonstrate increased control of translation using stabilizing and destabilizing switches with logic gates. This section will showcase higher-order logic by implementing an AND gate, requiring the presence of two or more RBPs for translation to occur with the use of two or more stabilizing switches. Moreover, higher-order logic will be implemented in the form of a NOR gate, requiring the presence of one or more RBPs to halt translation with the use of two or more destabilizing switches. Stabilizing and destabilizing switches will then be combined to demonstrate A AND NOT B logic.

Strategy mRNA has gained significant attention over the past decade for its vast potential in disease prevention and treatment.[1,2] The development of mRNA COVID vaccines has been a pivotal breakthrough, saving countless lives and highlighting one of mRNA's practical applications.[8] Beyond vaccines, ongoing research explores many other mRNA applications, from protein replacement therapies to disease treatments. The appeal of mRNA lies in its numerous advantages, including rapid development, efficacy, potent immune response, safety profile, and versatility.[9] However, while mRNA holds promise for disease treatments, these applications often present greater challenges than vaccines, as they may cause more pronounced side effects, including systemic reactions and immune responses.[10] Enhanced precision in treatment localization and temporal regulation of mRNA therapies could mitigate many of these potential side effects, underscoring the need for advanced delivery systems and regulatory mechanisms.

In mRNA therapies, controlling the lifespan of mRNA is crucial for optimizing therapeutic outcomes and ensuring safety. Currently, mRNA stability is regulated through modifications such as the addition of cap structures and polyadenylation, which help protect mRNA from degradation and prolong its lifespan within cells. However, these mechanisms provide limited control over mRNA stability, necessitating the development of more precise regulatory strategies.[5] Introducing proteins that act as termination switches or stabilizers offers a means to exert tighter control over mRNA lifespan, permitting researchers to modulate protein expression levels with greater accuracy. This enhanced control is essential for managing potential safety risks associated with the overexpression of therapeutic proteins, ensuring controlled responses to treatment, and providing flexibility in therapy design.[11,12] By fine-tuning mRNA stability through the incorporation of regulatory proteins, researchers can advance the development of mRNA-based therapies and expand their clinical applicability across various diseases.

In addition to controlling mRNA stability, leveraging proteins for cell-specific delivery of mRNA therapies is crucial for optimizing therapeutic efficacy and minimizing off-target effects. Currently, targeted delivery of mRNA therapies is being achieved through various strategies such as lipid nanoparticles, cell-penetrating peptides, or antibody-mediated targeting.[3,4,13,14] However, these approaches may still suffer from limitations such as off-target effects and inefficient delivery to specific cell types. Targeting specific cell types or tissues can enhance the precision of treatment, ensuring that therapeutic proteins are delivered directly to the intended site of action. By harnessing proteins such as biomarker proteins for cell-specific delivery, researchers can enhance the therapeutic index of mRNA therapies, improve patient outcomes, and reduce the potential for adverse events, ultimately advancing the clinical utility of this promising therapeutic modality.[15,16]

Figure 2:
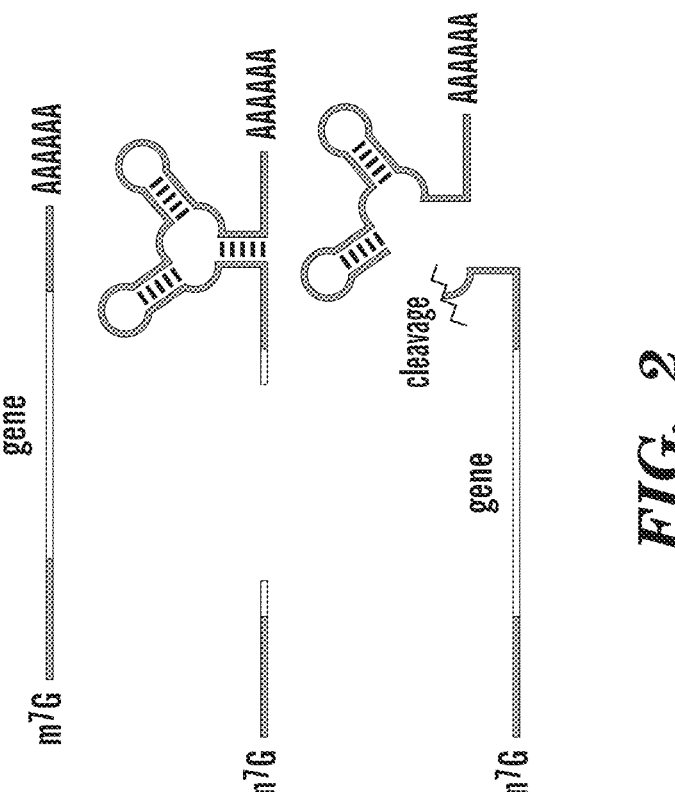
FIG. 2 is a schematic of a hammerhead ribozyme (HHR) in the 3' UTR of an mRNA. The HHR self-cleaves leaving the 3' UTR exposed to degradation and leads to an end in translation.

To regulate mRNA stability, whether through proteins or alternative methods, a means of modulating stability must first be established. Hammerhead ribozymes (HHR) can aid with this modularity. HHR are RNA sequences capable of forming distinct secondary and tertiary structures. When combined with the appropriate magnesium levels, these structures trigger a self-cleavage reaction.[17,18,19] There are many forms of self-cleaving ribozymes, but previous works have optimized the type III HHR for fast cleavage kinetics.[6] A typical mRNA strand possesses several key features, including a 3' polyadenylate (poly-A) tail, shielding it from degradation in the cytoplasm. Placing an HHR downstream of the encoded gene but before the poly-A tail enables it to cleave the poly-A tail from the mRNA strand, initiating its degradation before translation (FIG. 2). In essence, HHR cleavage destabilizes the mRNA strand, halting translation.[6]

To regulate mRNA with proteins, a connection between them is essential, a role fulfilled by RNA binding proteins (RBPs). RBPs are proteins or peptides capable of binding to specific RNA structures known as aptamers.[7] RBPs can occur naturally, exemplified by viral peptides like BIV Tat, P22N, and MCP.[20,21,22,23] Alternatively, RNA aptamers can be selected for particular proteins using techniques like Systematic Evolution of Ligands by EXponential enrichment (SELEX).[24] This versatility allows RBPs involved in mRNA stability regulation to be either exogenous or biomarker proteins specific to diseases or cell types. Depending on the placement of aptamers within mRNA strands, RBPs can also disrupt nearby RNA structures.[9] Described herein is the strategically positioning of Hammerhead ribozymes (HHR) and RNA aptamers in the 3' UTR of mRNA strands, which can regulate mRNA stability and consequently translation. By integrating HHR and RBP aptamers into an aptamer ribozyme equilibrium shifting (ARES) RNA circuit, one can achieve generalizable switches for mRNA stabilization and destabilization, controlled by RBPs.

Approach

Figure 3:
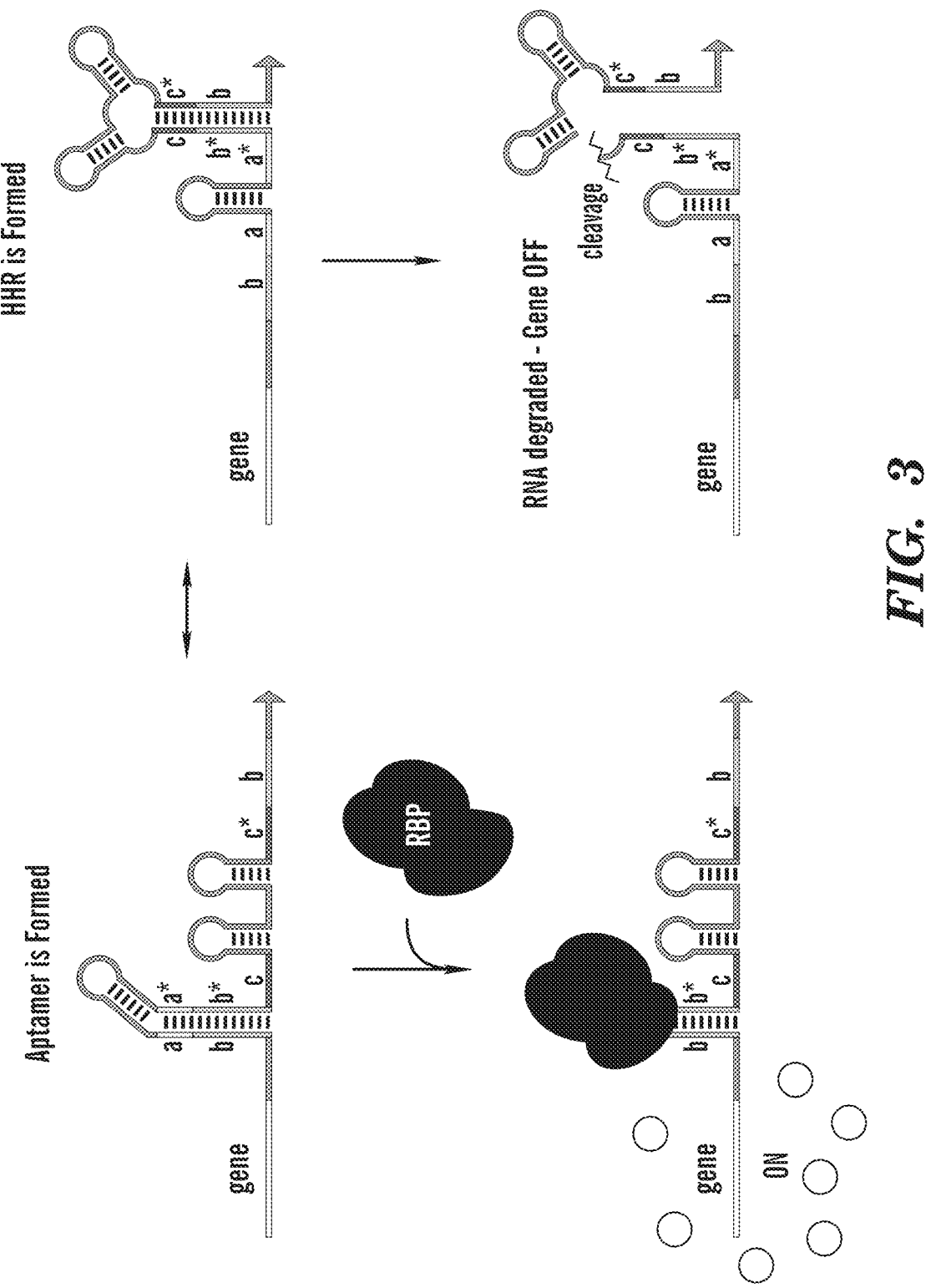
FIG. 3 is a schematic representing an exemplary ARES ON switch. Both an aptamer and HHR structure can form from the RNA sequence but only one structure is fully formed at a time due to the shared "b" domain. Domains "a" and "c" make the aptamer and HHR structure more or less thermodynamically favored to form. When a RBP corresponding to the aptamer structure is present it binds the aptamer, stabilizing the mRNA. When the RBP is not present, the HHR forms and self-cleaves, leaving the mRNA open to degradation, stopping further translation.

Described herein is the development of several RNA stabilizing switches that act as translational ON switches. These ON switches are placed in the 3' UTR of a gene before the poly-A tail and can be turned on with the presence of the corresponding RBP. All the switches that have been developed and tested follow the same general mRNA design pattern that capitalizes on an aptamer ribozyme equilibrium shift (ARES) (FIG. 3). In these designs, the ARES region comprises an aptamer upstream followed directly by an HHR. Part of the base stem of the aptamer and the base stem of the ribozyme share the same domain (domain "b"). This means that the downstream end of the aptamer base stem is the same as the upstream HHR base stem. By sharing this region both structures are likely to form, however, at any moment only the aptamer or the HHR can be fully formed. There is an additional domain at the top of the aptamer base stem (domain "a") that can be shortened or lengthened or its sequence composition modified (e.g., change the GC content without modifying the length) to increase the thermodynamic likelihood that the aptamer is formed compared to the HHR. These additional paired bases also serve as a toehold to shift the mRNA structure into the aptamer formation. This means that the base pairing in domain "a" increases the probability of the rest of the aptamer base stem forming with domain "b" as it brings the paired bases in stem "b" closer together and makes their pairing more favorable. Similar to domain "a", there is also domain "c" which is found at the top of the HHR base stem which provides the HHR with a toehold and, depending on its length, or sequence composition, or combination of length and sequence composition, serves to increase or decrease the probability of the HHR being formed over the aptamer structure. When the corresponding RBP to the aptamer is present, it can bind the aptamer structure, shifting the equilibrium of the ARES system away from the HHR and allowing for normal translation to occur. When the RBP is not present and the HHR is formed, a self-cleavage reaction occurs separating the poly-A tail from the mRNA strand, leading to the degradation of the mRNA stand.

Figure 4:
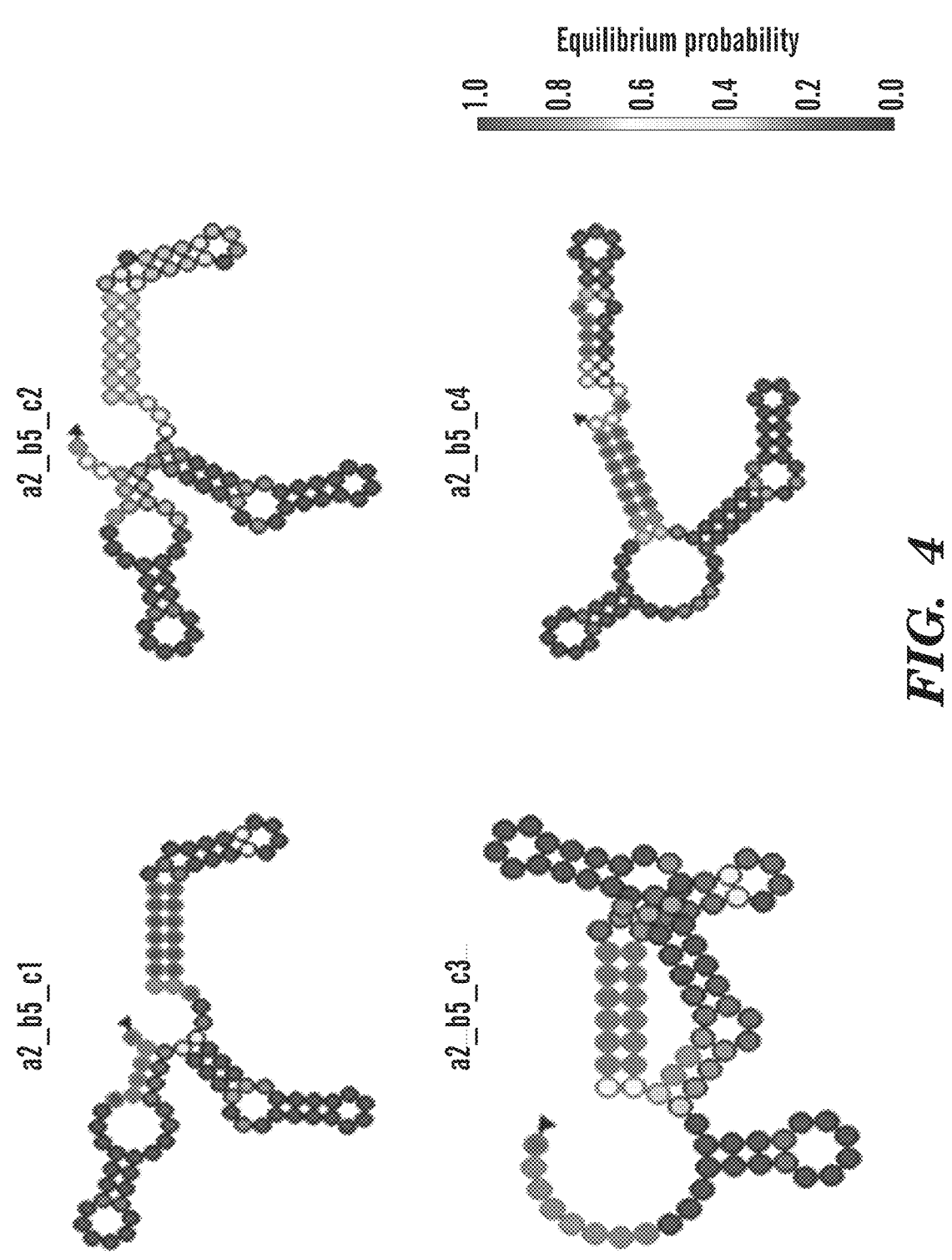
FIG. 4 shows models of an ARES ON switch with varying "a", "b", and "c" domain lengths. The upper left image shows the aptamer formed, upper right and lower left are intermediate structures and the bottom right shows the HHR formed. Each nucleotide position shows its thermodynamic likelihood based on the equilibrium probability scale.

When first designing the ARES switches the optimal lengths of domain "a", "b", and "c" were unknown. Furthermore, it was not understood how much the aptamer or HHR structure should be favored over the other. To gain a better idea of how these domains would affect the equilibrium shifting mechanism and which ones might be the most optimal ON switch, the programs MATLAB and NUPACK were used to generate models of RNA strands that varied the three domains with the aptamer BIV Tar that corresponds to the RBP BIV Tat (BT). The "a" and "c" domains ranged from 0-4 nucleotides (nt) and the "b" domain ranged from 5-7 nt. These lengths were chosen so that the overall stem length ("a" and "b" or "b" and "c") was short enough to allow the equilibrium shifting between the two formations to be fast. Furthermore, the lengths of "a" and "c" were chosen to give a slight advantage to their corresponding structures but not so overpowering that only one structure would form. The model output showed a range of structures, some of which favored the HHR forming, the aptamer forming, or an intermediate structure (FIG. 4). From these models, it is hypothesized that switches favoring the HHR formation would result in cleavage and RNA degradation before the aptamer could form and be stabilized by the RBP. On the other side, designs that favored the aptamer forming would allow for translation without the RBP present as the HHR would struggle to form and cleave the RNA. Therefore, an intermediate design would give the best chances for a functional ON switch.

To test the modeling and predicted outcomes, 46 of the designs that ranged in predicted structure formation were then cloned into the 3' UTR of a GFP gene after the stop codon and before the poly-A tail. Additionally, the RBP BIV Tat was linked to a larger protein, maltose binding protein (MBP), using a G4SG4 linker (SEQ ID NO: 395) where MBP was on the N terminus. This was to provide the system with more steric hindrance. They were then tested in HEK293T cells using transient DNA plasmid transfection. A second plasmid containing the corresponding RBP was co-transfected with the ARES designs to evaluate the ON signal from the designs. To evaluate the OFF signal the second plasmid only contained the MBP. The fluorescents expression was analyzed using flow cytometry and a third plasmid containing mCherry was used as a transfection and normalizing marker.

Figure 5A:
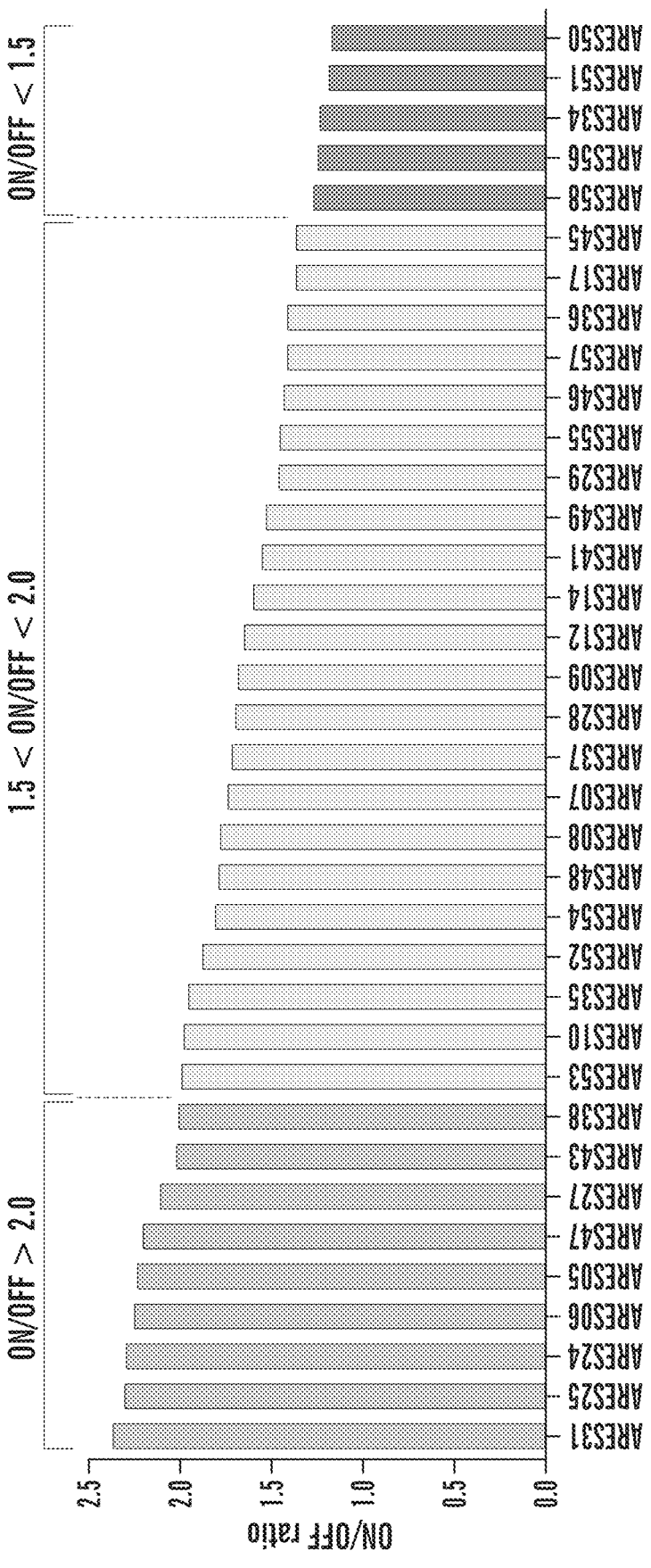
FIG. 5A-5D: Resulting output of 46 ARES ON switches with BIV Tat aptamer and peptide.
Figure 5B:
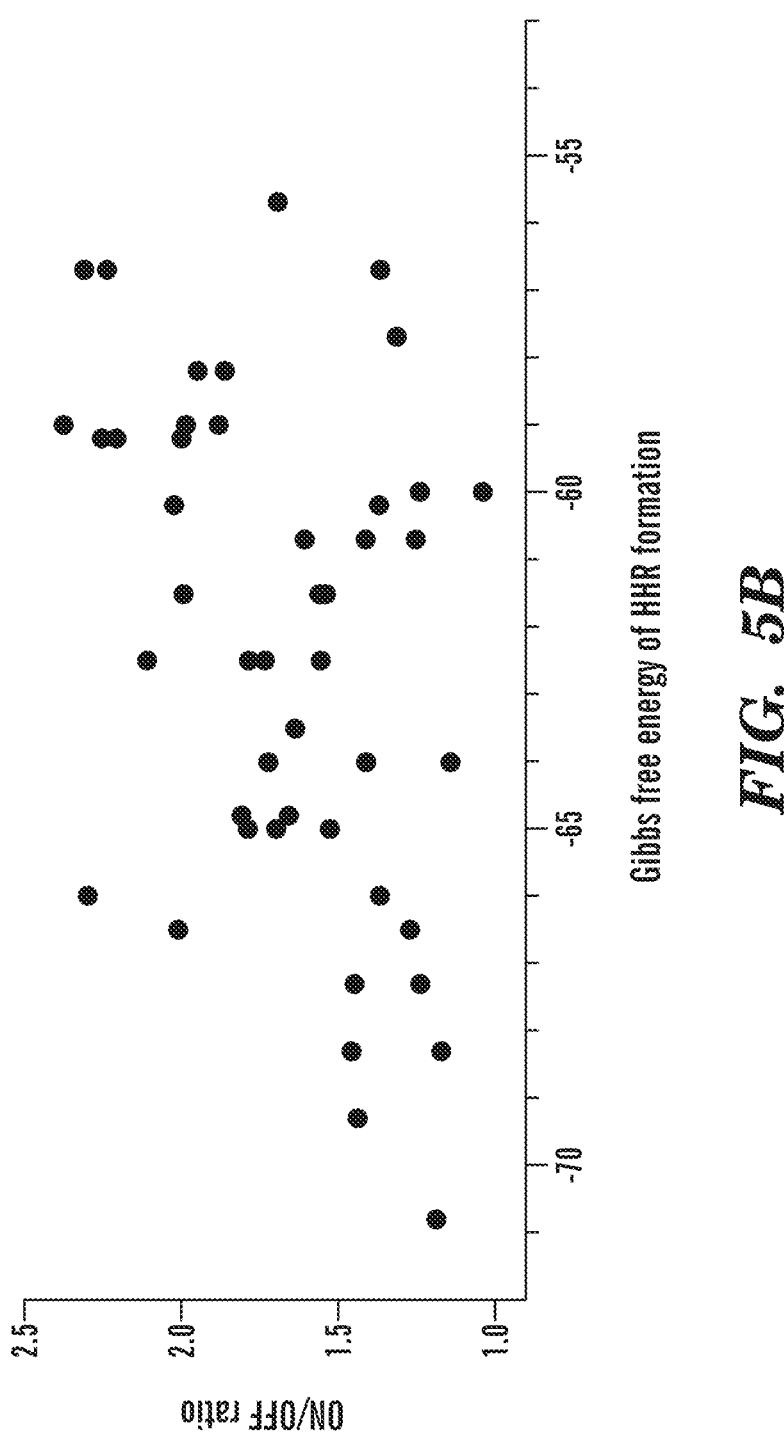
Figure 5C:
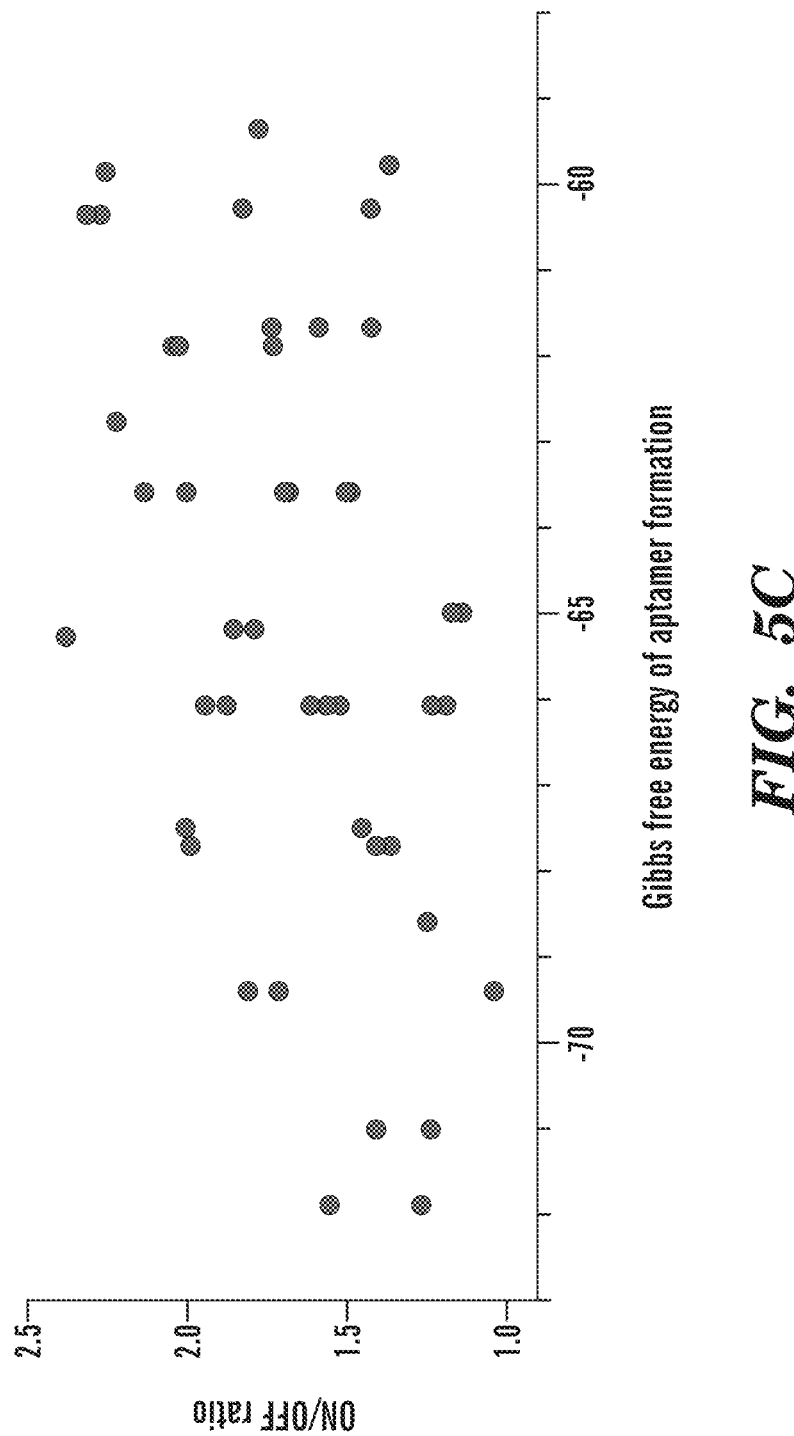
Figure 5D:
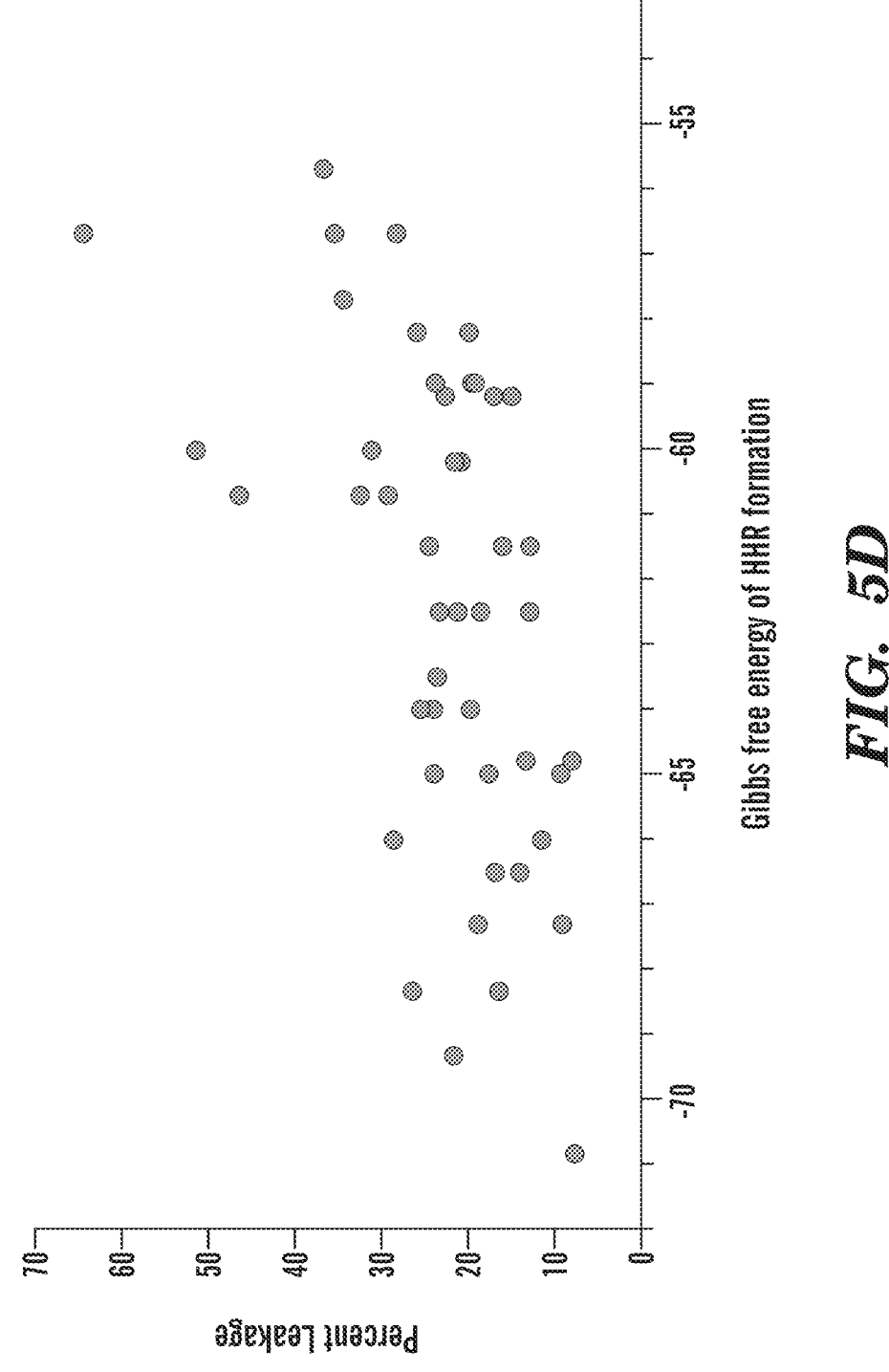

The results showed ON/OFF ratios between 1.04 and 2.38 (FIG. 5A). When comparing the ON/OFF ratios to the model two statistics were used, the Gibbs free energy of the HHR forming and the Gibbs free energy of the aptamer forming. These two statistics describe how likely the RNA is to form the HHR or aptamer structure given that the HHR or aptamer structure is the target structure. The correlation between the two statistics and the ON/OFF ratio was not very strong, but a general trend can still be observed showing that as the probability of the HHR forming increases the ON/OFF ratio decreases (FIG. 5B, 5C). This general trend was expected as well as another trend between the percent leakage of each switch and the Gibbs free energy of the HHR forming. Here 100% leakage represents the full MFI GFP signal and 0% represents no GFP signal, with no RBP present. This correlation showed that as the likelihood of the HHR forming decreases, the leakage of the circuit increases (FIG. 5D). This makes sense as the HHR needs to form and cleave before the ribosome starts translation, but if the HHR formation is hindered by a stronger aptamer formation there will be some translational leakage.

Figure 6A:
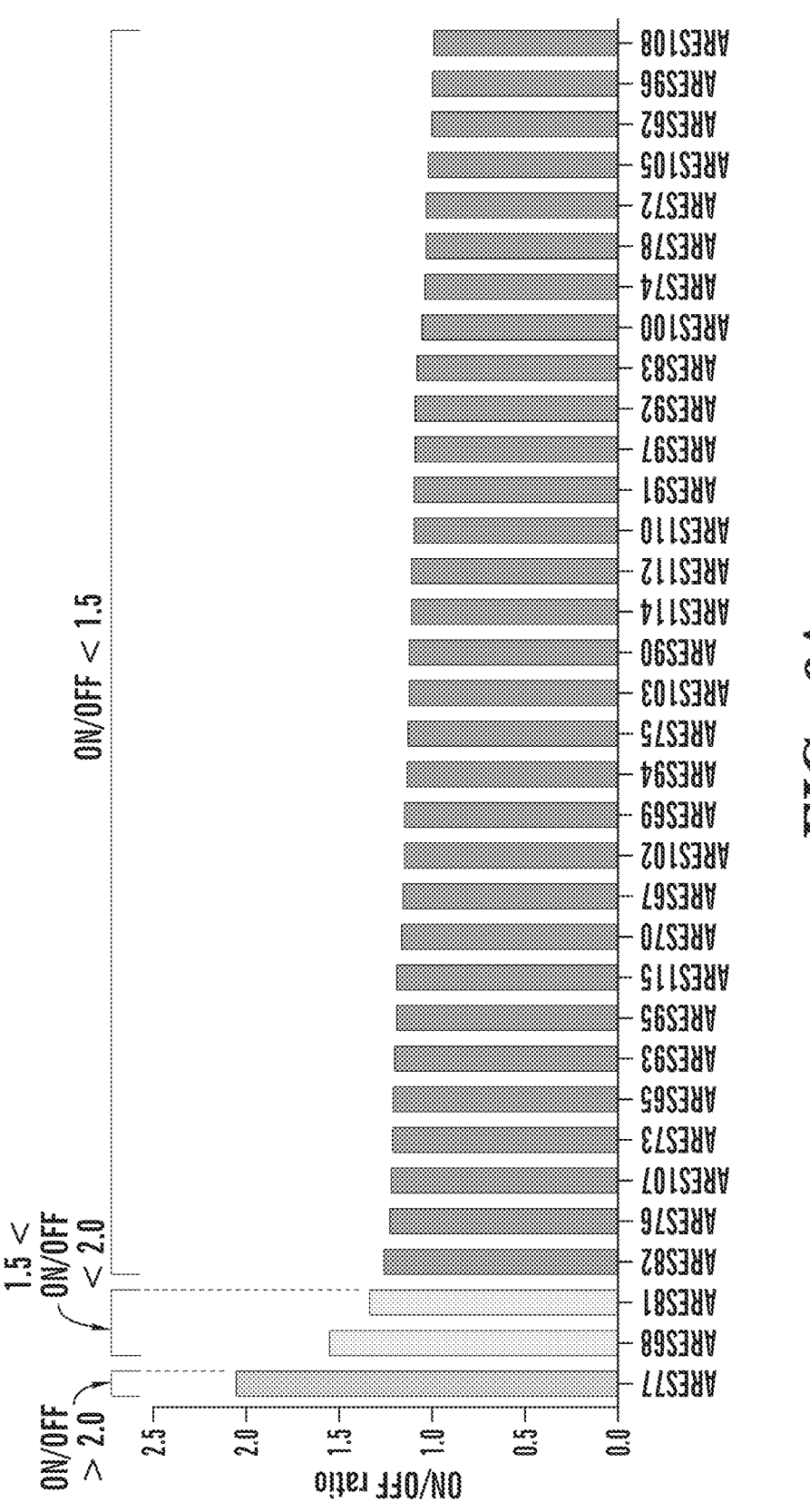
FIG. 6A-6B: Expanding ARES ON switch library to P22N and MCP.
Figure 6B:
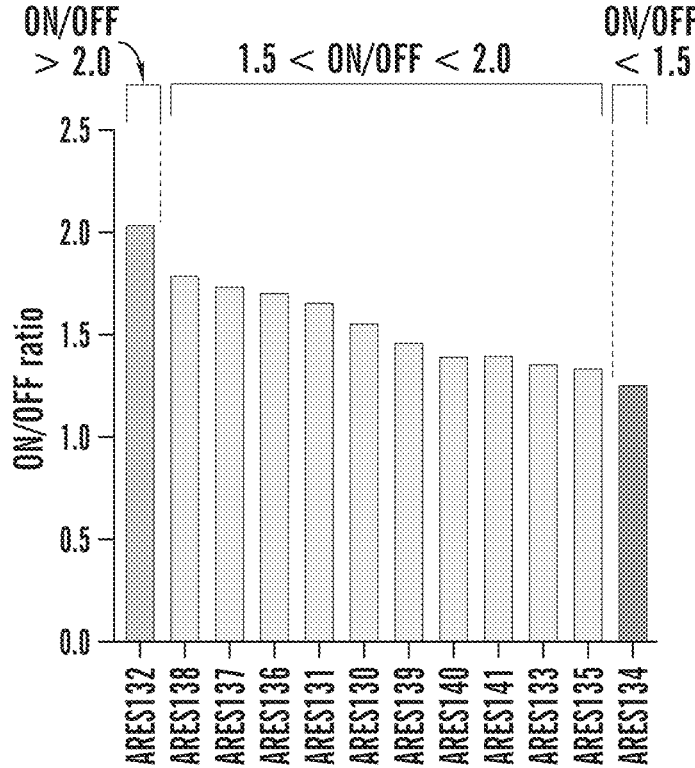

The library of RBPs was expanded to include P22N and MCP with their corresponding aptamers P22 boxB and MS2. The design of these switches considered the trends found with the BT switches. 48 switches were cloned into the 3' UTR of the GFP gene for P22N and 12 for MCP. They were then tested in the same manner as the BT switches including the linkage of MBP to P22N. These switches showed similar ON/OFF ratios as the BT switches with P22N ranging from 0.96 to 2.06 and MCP ranging from 1.26 to 2.04 (FIG. 6A, 6B). The amount of successful P22N designs was significantly less than the BT designs likely owing to P22N's increased Kd value (230 pM) compared to BT (60 pM).[7]

Figure 7A:
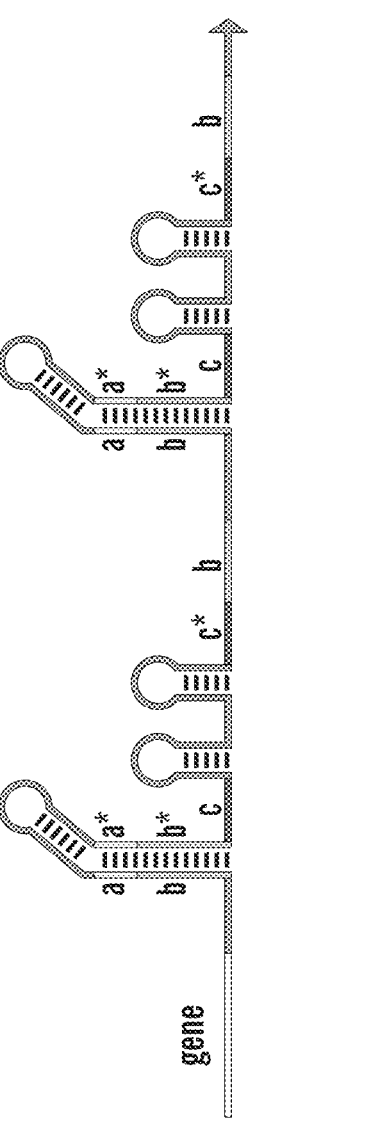
FIG. 7A-7B: Lowering leakage of ARES ON switch.
Figure 7B:
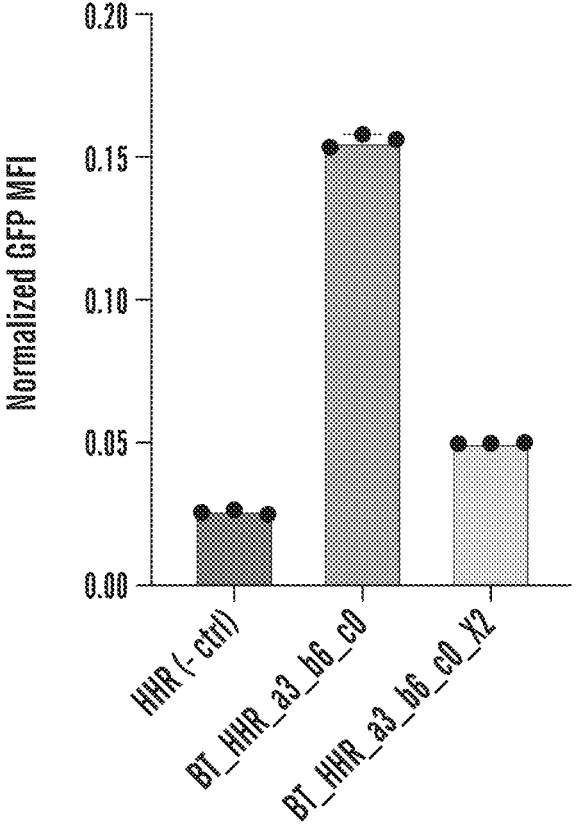

After finding successful switches for all three RBPs, the next focus went to optimizing the triggers. The largest concern with the switches at this point is the amount of leakage when there are no RBPs present. For most applications of the ON switches very minimal to no leakage is required. In these ON switches the leakage amount is consistently higher than 6% with some leaking as much as 20%. One way to minimize the leakage in these designs would be to add more opportunities for the HHR to form and cleave the mRNA. To do this in a way that does not compromise the RBP's ability to prevent cleavage and allow translation is to concatenate several of the ARES switches together in the 3' UTR (FIG. 7A). By doing this concatenation just once (meaning there are two ARES switch units in the same 3' UTR), leakage was minimized by 110% while maintaining a similar ON/OFF ratio for one of the BT switches (FIG. 7B). Similar results were seen with P22N and MCP switches. The decrease in leakage was highly dependent on the switch itself with some showing no change in leakage level after concatenation. By concatenating 3 or more switches together, the leakage level will likely drop even further.

Figure 8:
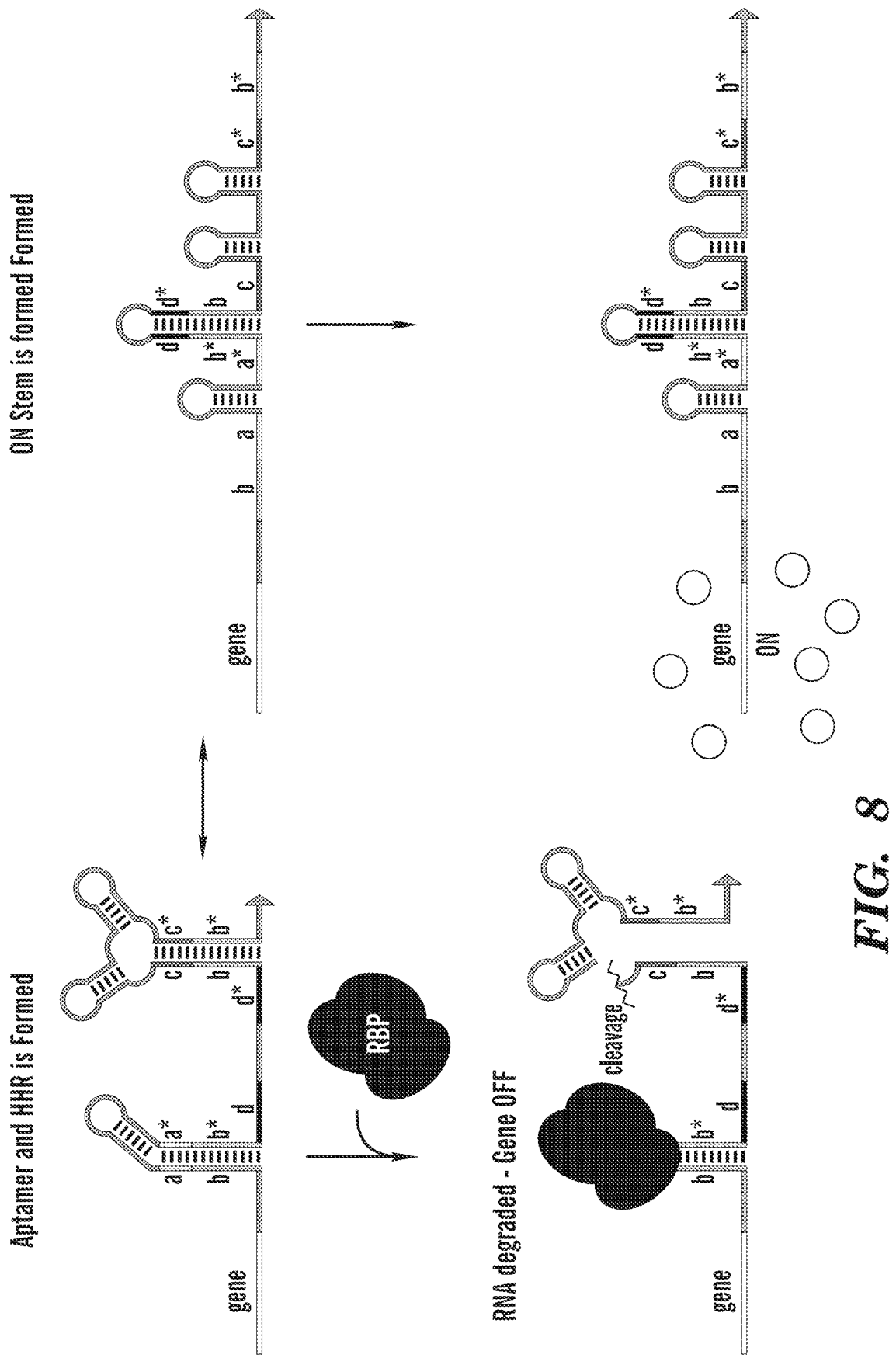
FIG. 8: Schematic representing general ARES OFF switch. At one time both the aptamer and HHR can be fully formed or a middle stem loop structure ("ON stem") due to the shared "b" domain. Domains "a", "c", and "d" change the thermodynamic likelihood that the aptamer/HHR configuration is formed, or the middle stem loop is formed. When the aptamer/HHR is formed and the RBP present, the RBP will bind, stabilizing the HHR leading to a self-cleavage reaction and degradation of the mRNA. Without the RBP the HHR will not be stably formed for long enough to cleave.

An ARES OFF switch was also produced (FIG. 8). This switch is also placed in the 3' UTR after the stop codon and before the poly-A tail. When the RBP of interest is present it causes the mRNA to be degraded, preventing further translation. This OFF switch is another form of the ARES design, but unlike the ON switch, there is an additional stem loop structure involved. For these designs, the aptamer is still furthest upstream followed by the new step loop structure and lastly by the HHR. The base of the stem loop structure is made up of domain "b". This domain is also shared with the base stem of the aptamer and the HHR. Domain "b" is what will allow either both the aptamer and the HHR to be fully formed at one time or the middle stem loop structure will be fully formed. There is still domain "a" at the top of the base stem structure for the aptamer and domain "c" at the top of the base stem structure for the HHR. The stem loop also has a domain "d" at the top of its stem to provide a toehold and to shift the likelihood of the stem forming versus the aptamer and HHR. When there is no RBP present both the stem loop structure and the aptamer and HHR structures can be formed however there will be constant equilibrium shifts between these two phases that will prevent the HHR from being formed long enough to have a self-cleavage reaction, meaning translation can occur normally. When the RBP of interest is introduced then it can bind the aptamer structure making it more difficult for the stem loop structure to pull on the aptamer and HHR structures. This will allow enough time for the HHR to form and cleave the poly-A tail off. Once the mRNA strand is without the poly-A tail it will be degraded, and no more translation will occur.

Figure 9A:
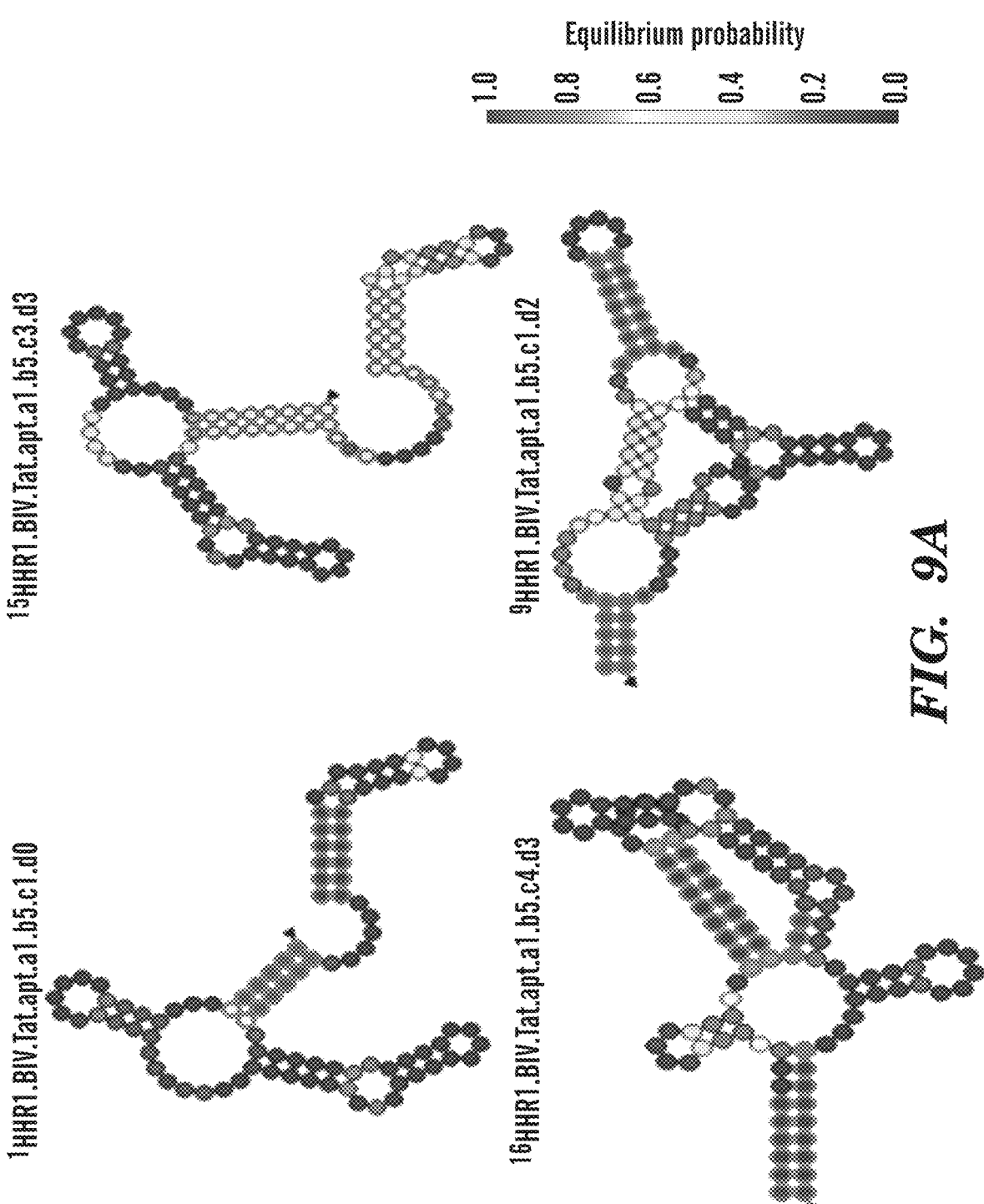
FIG. 9A-9C: Overview of ARES OFF switch.
Figure 9B:
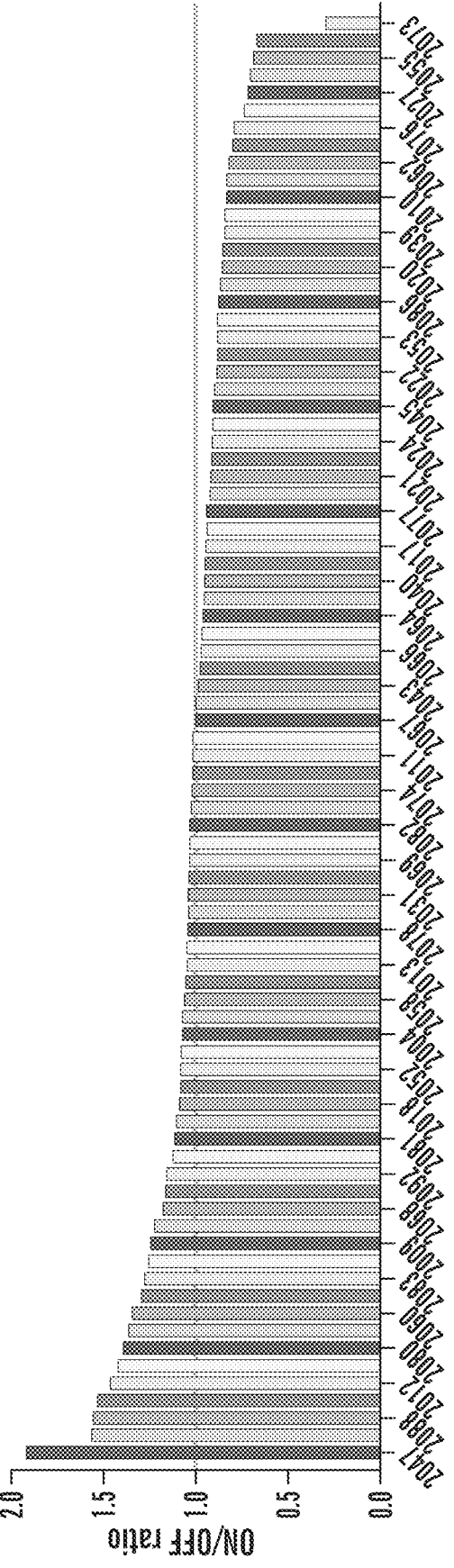
Figure 9C:
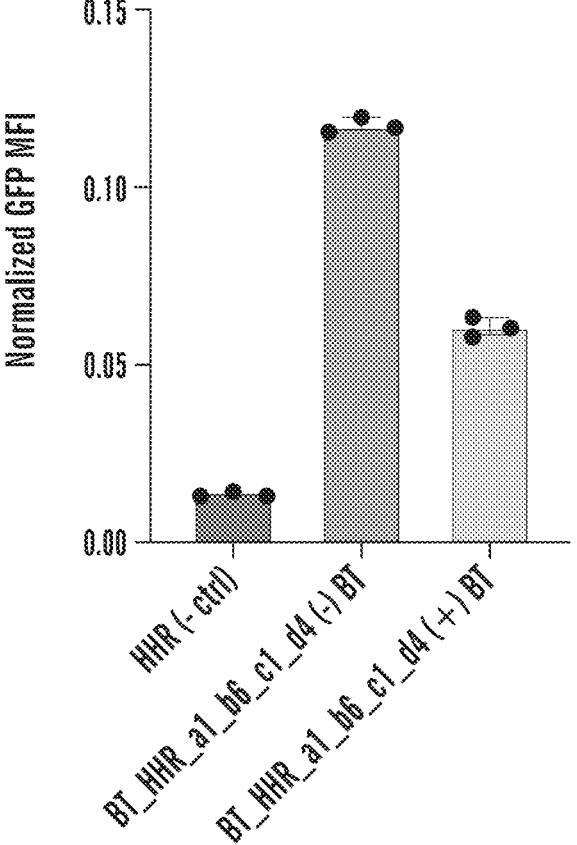

To determine the most optimal lengths for domains "a", "b", "c", and "d" designs were first modeled in MATLAB with NUPACK using the BT aptamer. This time domains "a", "c", and "d" ranged from 0-4 nt and domain "b" varied from 5-7 nt. The results of the model included designs that favored the stem loop structure, the aptamer and HHR structures, and intermediates (FIG. 9A). 83 of these designs were cloned into the 3' UTR of GFP and then the DNA was transiently transfected into HEK293T cells. They were co-transfected with a second plasmid containing either BT linked to the MBP or just the MBP as well as a third plasmid containing mCherry for a transfection marker. The fluorescent expression was analyzed using flow cytometry. The ON/OFF ratios ranged from 0.29 TO 1.93 with most worked as poor ON switches (FIG. 9B, 9C). Here ON represents the GFP signal when no RBP is present. However, 7 designs showed an ON/OFF ratio above 1.40. Because only a small number of designs showed a good ON/OFF ratio it was difficult to determine any trends that would help predict good OFF stitch designs.

Section 1: Attain Cell-Specific and Temporal Control of Translation Through mRNA Stabilizing Switch Triggered by RBPs.

This section will deliver an optimized translational ON switch. These switches will control the translation by stabilizing mRNA when a certain RBP of interest is present but destabilizing the mRNA when it is not. Thus far, the ARES ON switches have been successfully developed with three RBP triggers. To complete this section further optimization of the switches is required. Furthermore, the switches will be tested for cell-specific translation and temporal control. Additionally, an ARES ON switch will be developed with aptamers that are specific to proteins upregulated in pancreatic cancer cells.

Section 1.1—Develop Translational ON Switch with Exogenous RBPs.

Preliminary results have achieved several working translational ON switches that can be triggered by three different RBPs, BT, P22N, and MCP. The final task for this sub section is to optimize the switches for real-world applications meaning the leakage level needs to be reduced. Work has been done to decrease the level of leakage in the switches by concatenating two switches together. To continue to build off this initial optimization, different combinations of switches, all triggered by the same RBP, will be tried and additional concatenations will also be tested. A threshold of 2% leak is ideal as this is a benchmark set in previous works that use the HHR.[6]

Section 1.2—Demonstrate Cell-Specific Translation.

Figure 10:
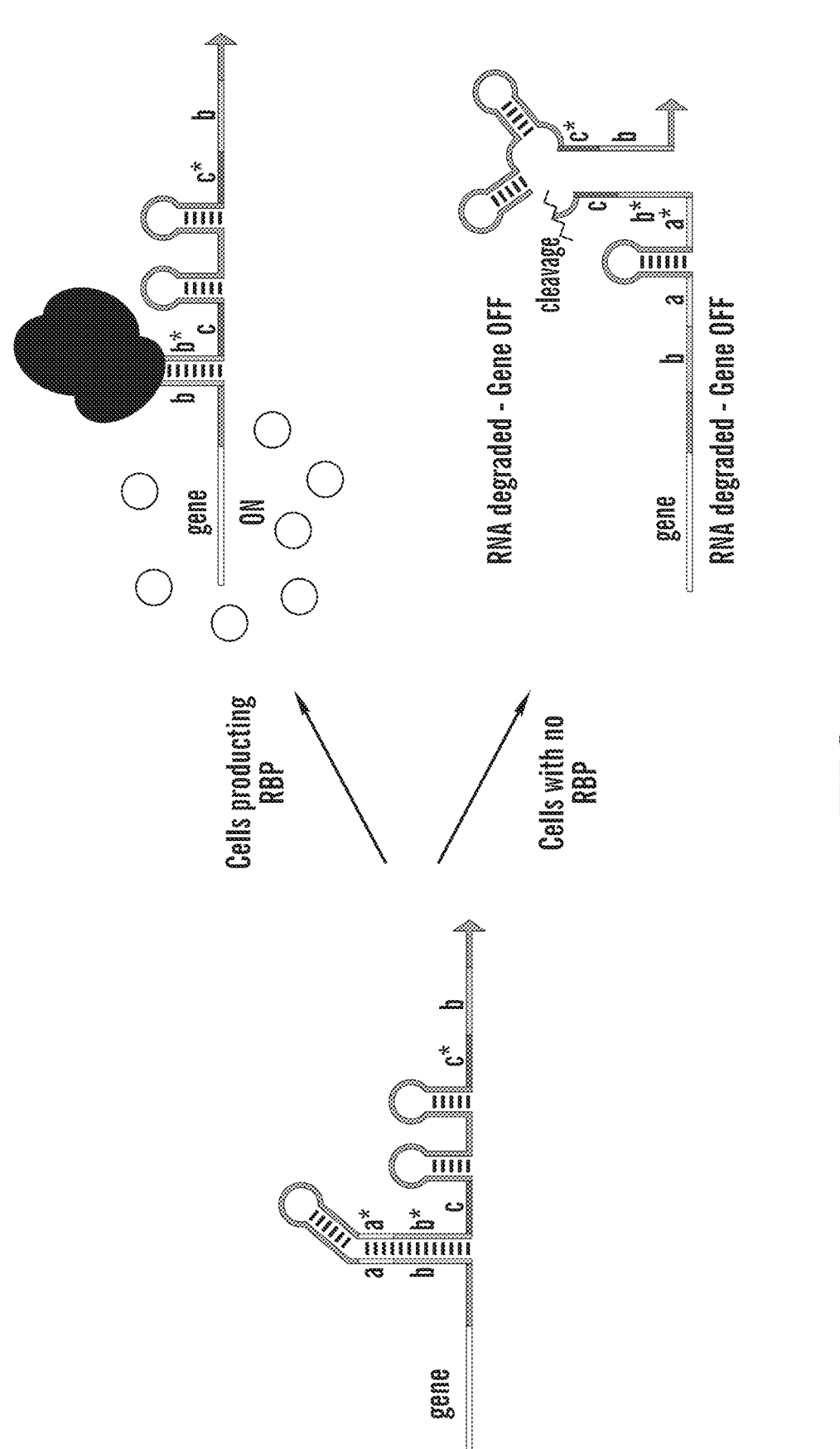
FIG. 10: Schematical representation of cell-specific activation of ARES ON switch. Adding an ARES ON switch to a stable cell line producing the corresponding RBP results in gene expression. Adding the ARES ON switch to cells that do not produce the RBP results in mRNA degradation and no gene expression.

To show cell-specific translation by the ON switch stable cell lines using HEK293T cells will be made to express BT-MBP or MCP-MBP. These cell lines will be made with Lentivirus and correct integration selected for puromycin resistance. Then using DNA transient transfection switches containing the BT aptamer will be transfected into HEK293T cells and HEK293T cells expressing BT. The same will be repeated with MCP-expressing cells and MS2 aptamer switches. A successful cell-specificity test will show a higher fluorescence signal in cells expressing the RBP compared to cells without the RBP (FIG. 10). If this trend is not seen it could be due to a low expression of the RBPs or not enough switch was transfected. Solutions to these pitfalls can include changing the promoter on the RBP to increase production in the cells and to increase the amount of switch transfected into the cells.

Section 1.3—Demonstrate Temporal Control.

Figure 11:
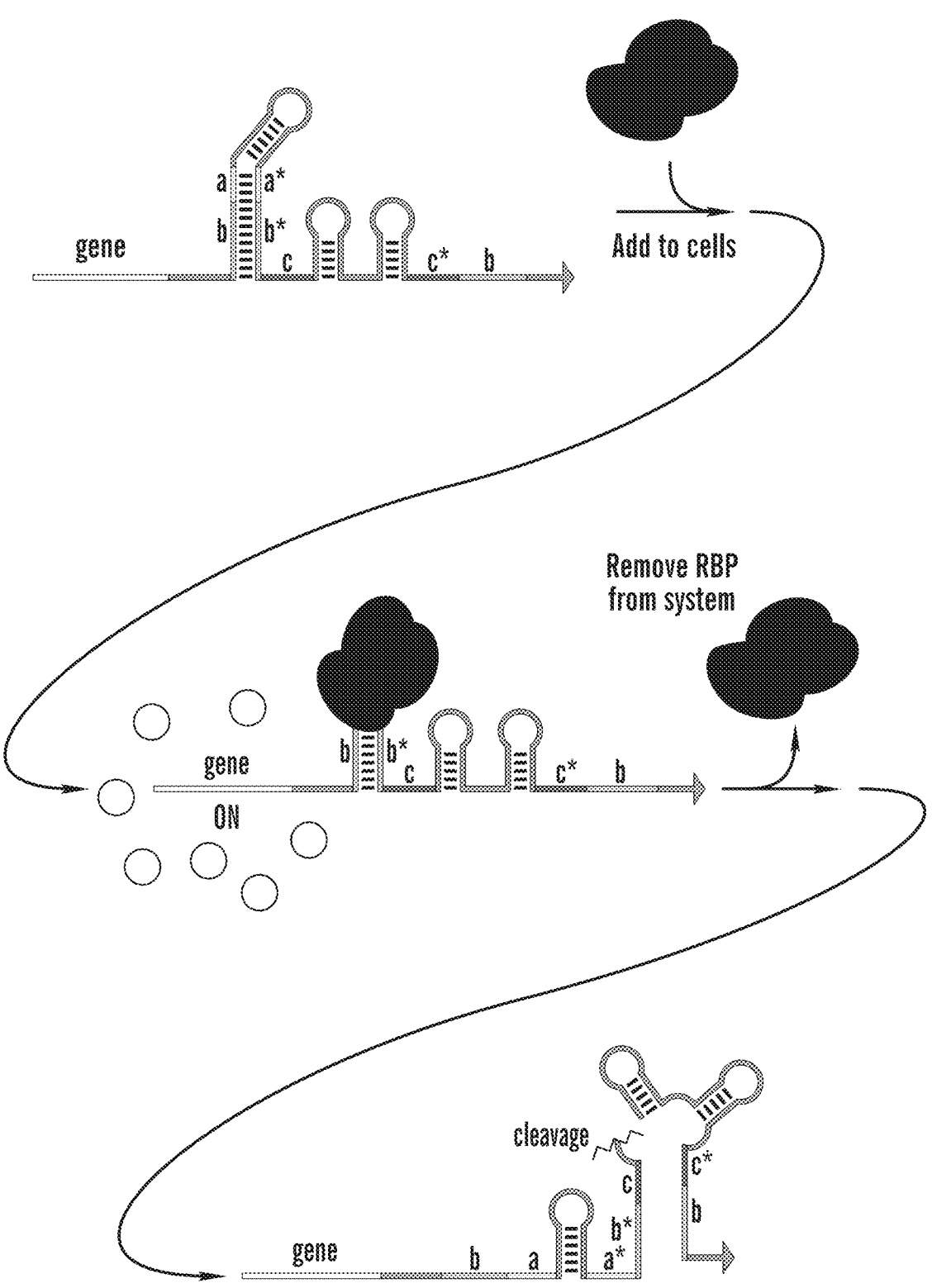
FIG. 11: Schematical representation of temporal control with ARES ON switch. When adding the ARES ON switch along with the corresponding RBP to cells the mRNA is stable and translation can occur. However, once the RBP is removed from cells the mRNA destabilizes and translation stops.

Temporal control will be demonstrated using inducible expression of the RBP. A stable cell line that expresses BT-MBP or MCP-MBP upon tetracycline induction will be developed with lentivirus and correct integration selected for puromycin resistance. Then, using DNA transient transfection switches will be transfected into HEK293T cells and HEK293T cells that express the corresponding RBP under tetracycline induction. A group of the cells will be induced with tetracycline and after some time cells will be tested for fluorescence. Once fluorescence is higher in cells with tetracycline induction, the tetracycline will be removed from the system and the RBP will stop being produced by the cell. When this occurs, the mRNA will destabilize again, and translation will turn ON. This section will be successful if there is an increased fluorescent signal in cells induced to produce the RBP and then a decrease in fluorescence after the removal of tetracycline (FIG. 11). For this to work a degradation tag will also have to be introduced on GFP and the RBP. Potential pitfalls include low expression of the RBPs and not enough of the switch being transfected. To solve these problems the RBPs can be transiently transfected with an inducible promoter to increase the amount produced. Furthermore, the amount of switch DNA being transfected can be optimized.

1.4—Develop Pancreatic Cancer-Specific ARES ON Switch.

An ARES ON switch will be developed with aptamers that are specific to proteins upregulated in pancreatic cancer cells. There are several candidates from previous works to choose from.[26,27,28,29] These will go through the same process as the existing ON switches where they will first be modeled in MATLAB and NUPACK. These switches will then be tested against pancreatic cancer cell lines with DNA transient transfection to show that they can provide cell-specific translation. This section will be established once the ON shows a higher fluorescent signal in pancreatic cancer cells than in normal pancreatic cells. The largest pitfall facing this section is if the ON switch is still turned on in regular pancreatic cells meaning before upregulation in cancer cells, the targeted protein was in a high enough concentration to stabilize the ON switch. To address this, multiple RBPs with known aptamers specific to pancreatic cancer will be tested.

As a non-limiting example, the Iron responsive protein (IRP) and its aptamer the Iron responsive element (IRE) will be tested in a pancreatic cancer-specific ARES ON switch. The IRP responds to iron levels in the cell. This pair is specific to pancreatic cancer because iron is at a higher concentration in pancreatic cancer cells than healthy pancreatic cell. The IRE/IRP pair for ARES can also be used in other diseases that have an increase in iron concentration, including but not limited to ovarian cancer, lung cancer, or Chronic Obstructive Pulmonary Disease (COPD).

Section 2: Achieve Cell-Specific and Temporal Control of Translation by Utilizing an mRNA Destabilizing Switch Triggered by RBPs.

This section will deliver a translational OFF switch by destabilizing the mRNA that has the switch with a specific RBP. To date a translational OFF switch that uses BT as the trigger RBP has been successfully developed. To complete this section the library of switches will be expanded to encompass more RBPs including MCP. Furthermore, cell-specific translation and temporal control will also be demonstrated.

Section 2.1—Develop Translational OFF Switch.

With only a single translational OFF switch developed, at least one more will be produced to complete this sub-section. To accomplish this MATLAB and NUPACK will be used to model an ARES OFF switch that utilizes the MS2 aptamer. A selection of these designs will be cloned into the 3' UTR of the GFP gene and tested with DNA transient transfection in HEK293T cells. Functional switches will show a decreased GFP signal in cells transfected with the MCP compared to cells with only the switch. As no trends were seen with the functional BT switches tested a large range of designs will be tested here. If no successful designs are found a second round of modeling will be done with different domain lengths for domains "a", "b", "c", and "d" and then tested. If there are still no successful designs other aptamers and RBPs can be tried including P22N.

Section 2.2—Demonstrate Cell-Specific Translation.

Figure 12:
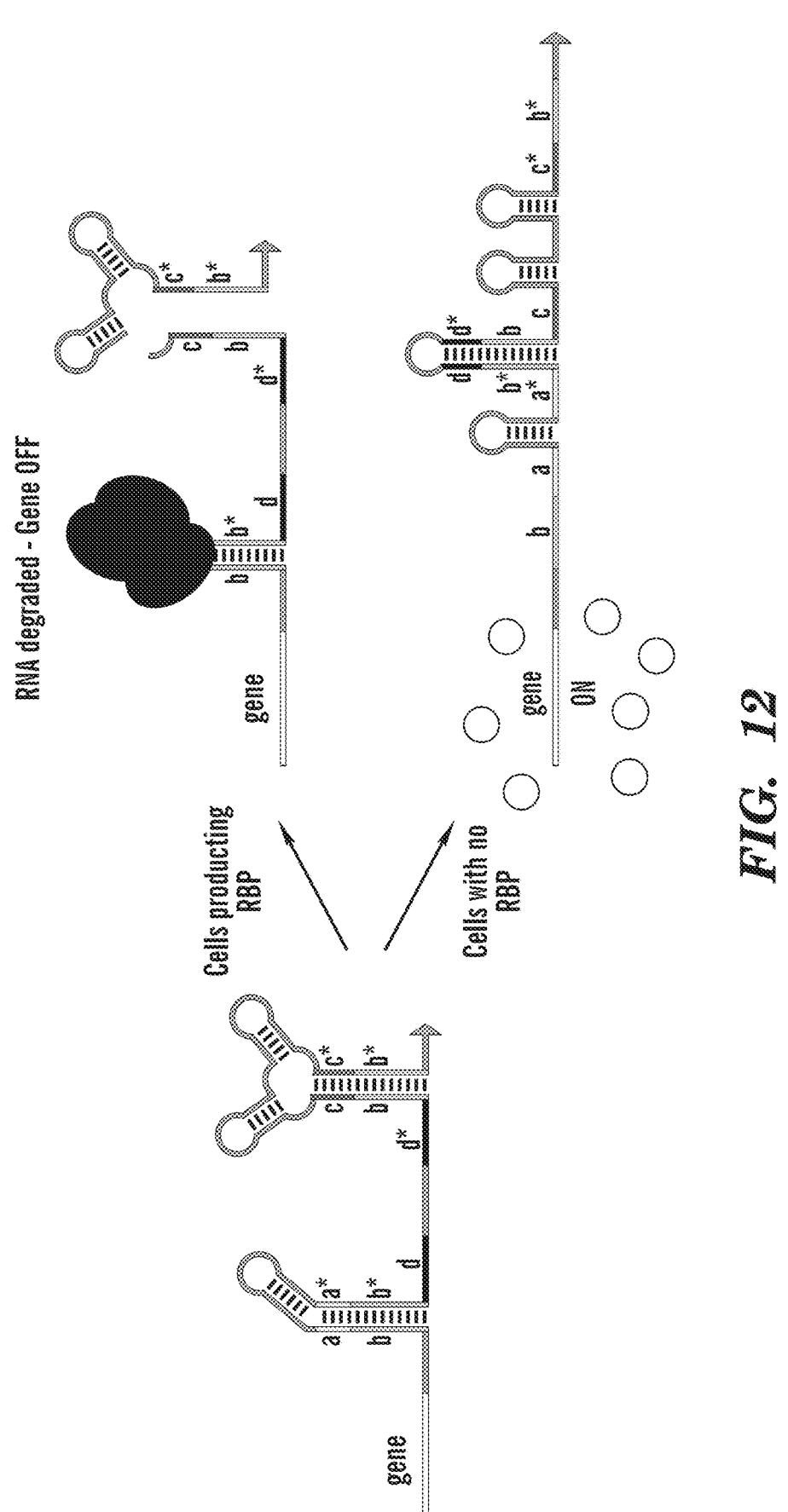
FIG. 12: Schematical representation of cell-specific activation of ARES OFF switch. Adding an ARES OFF switch to a stable cell line producing the corresponding RBP results in mRNA degradation and no translation. Adding the ARES OFF switch to cells that do not produce the RBP results in translation.

Cell-specific translation will be demonstrated with HEK293T cells that stably express BT. The BT translational OFF switch will be transfected into cells that produce BT and cells that do not. A successful experiment will show a higher fluorescent signal in cells without BT compared to cells that produce BT (FIG. 12). If this trend is not seen it could be due to a low expression of the RBPs. Solutions to these pitfalls can include changing the promoter on the RBP to increase production in the cells and to increase the amount of switch transfected into the cells.

Section 2.3—Demonstrate Temporal Control.

Figure 13:
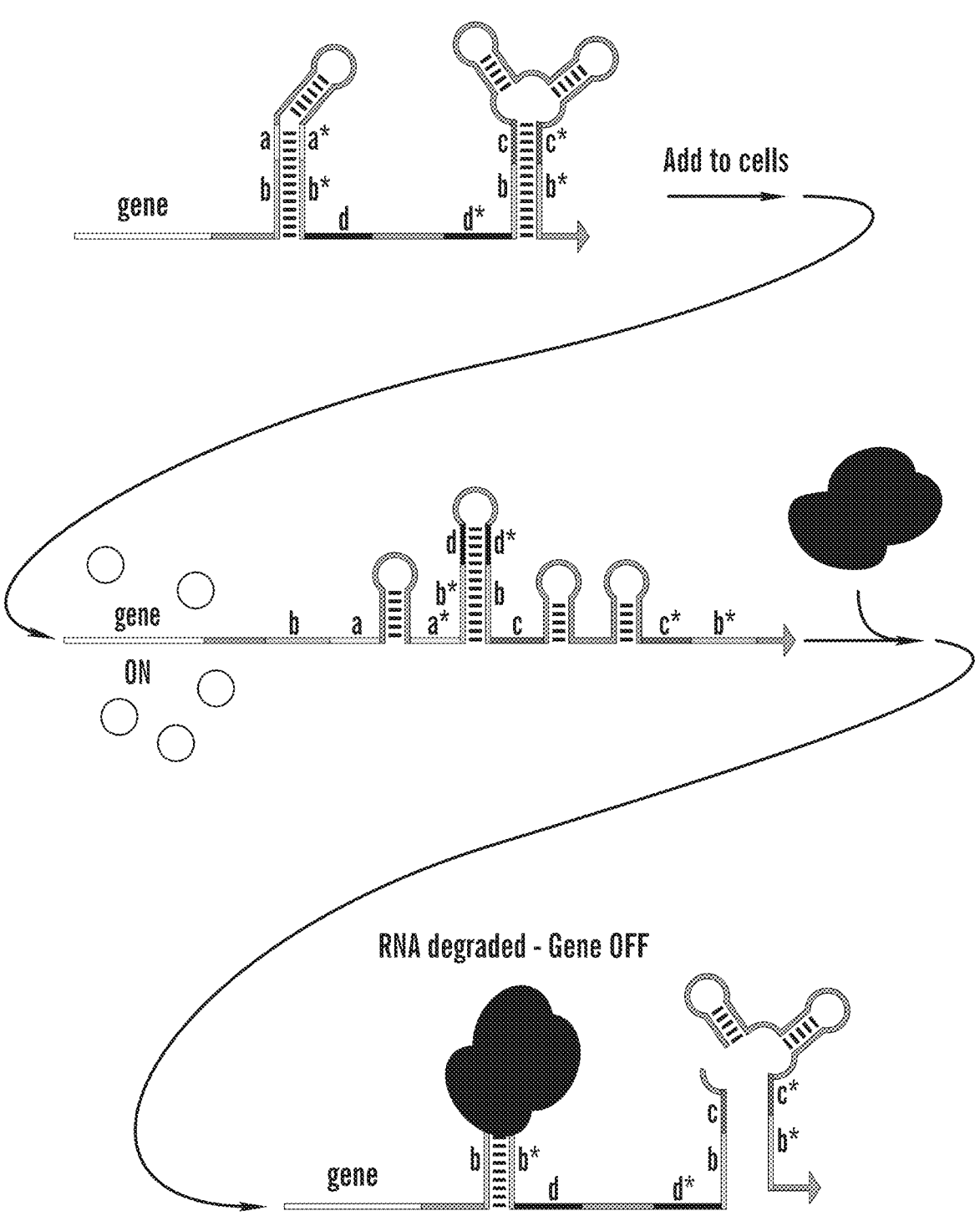
FIG. 13: Schematic representation of temporal control with ARES OFF switch. When the ARES OFF switch is added to cells the mRNA remains stable and translation occurs until the corresponding RBP is added. Once the RBP is added the mRNA is destabilized, degraded, and translation turns off.

Temporal control will be demonstrated with HEK293T cells that produce BT when induced with tetracycline. The developed BT OFF switch will be transfected into these cells then select groups of cells will then be induced with tetracycline to produce BT. A successful result will show that cells before being induced show a fluorescent signal. After being induced, the fluorescent signal will decrease (FIG. 13). To see this decrease in fluorescence the GFP protein being expressed will also be linked to a degradation tag so a better signal corresponding to mRNA stability can be observed. Potential pitfalls include low expression of the RBPs and not enough of the switch being transfected. To solve these problems the RBPs can be transiently transfected with an inducible promoter to increase the amount produced.

Section 3: Demonstrate Increased Control of Translation Using Stabilizing and Destabilizing Switches with Logic Gates.

Section Three will show the plug-and-play options of the ARES ON and OFF switches by developing logic gates to gain further control over mRNA stability. These gates will consist of AND, OR, and A AND NOT B and will be developed using previously established stabilizing and destabilizing switches.

Section 3.1—Increase Switch Complexity with AND Logic Gate.

Figure 14:
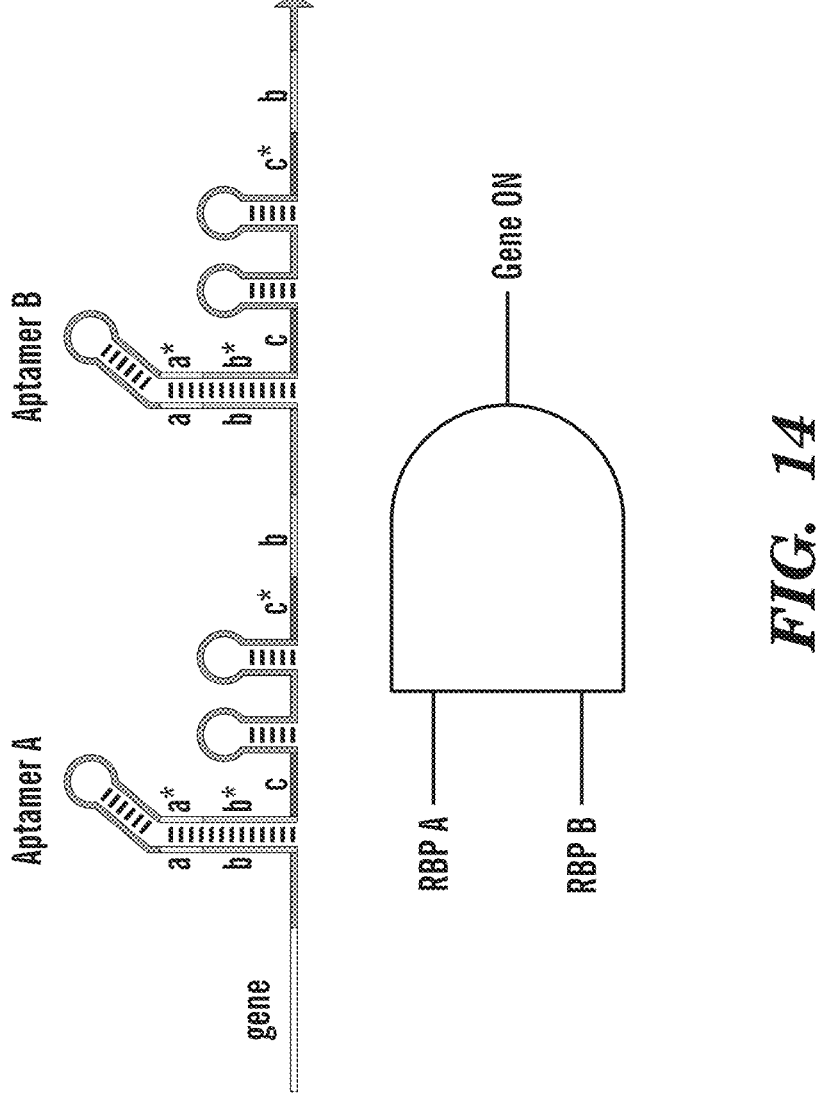
FIG. 14: Diagram showing AND logic gate with ARES system. Two ARES ON switches are concatenated together in the 3' UTR to create an AND gate where both RBPs are required to stabilize the mRNA and allow translation to occur.

To increase the amount of control over translation AND gates will be developed. These gates will require two or more RBPs to be present to turn translation ON. This will be accomplished by concatenating ARES switches together that have aptamers corresponding to different trigger RBPs (FIG. 14). These AND gate switches will then be transfected into HEK293T cells along with no RBPs, one of the RBPs, or both RBPs. A successful AND switch will only show increased fluorescence in cells that have both RBPs. The largest challenge will be to find the best switch combinations so multiple BT, P22N, and MCP switches will be tested.

Section 3.2—Increase Switch Complexity with NOR Logic Gate.

Figure 15:
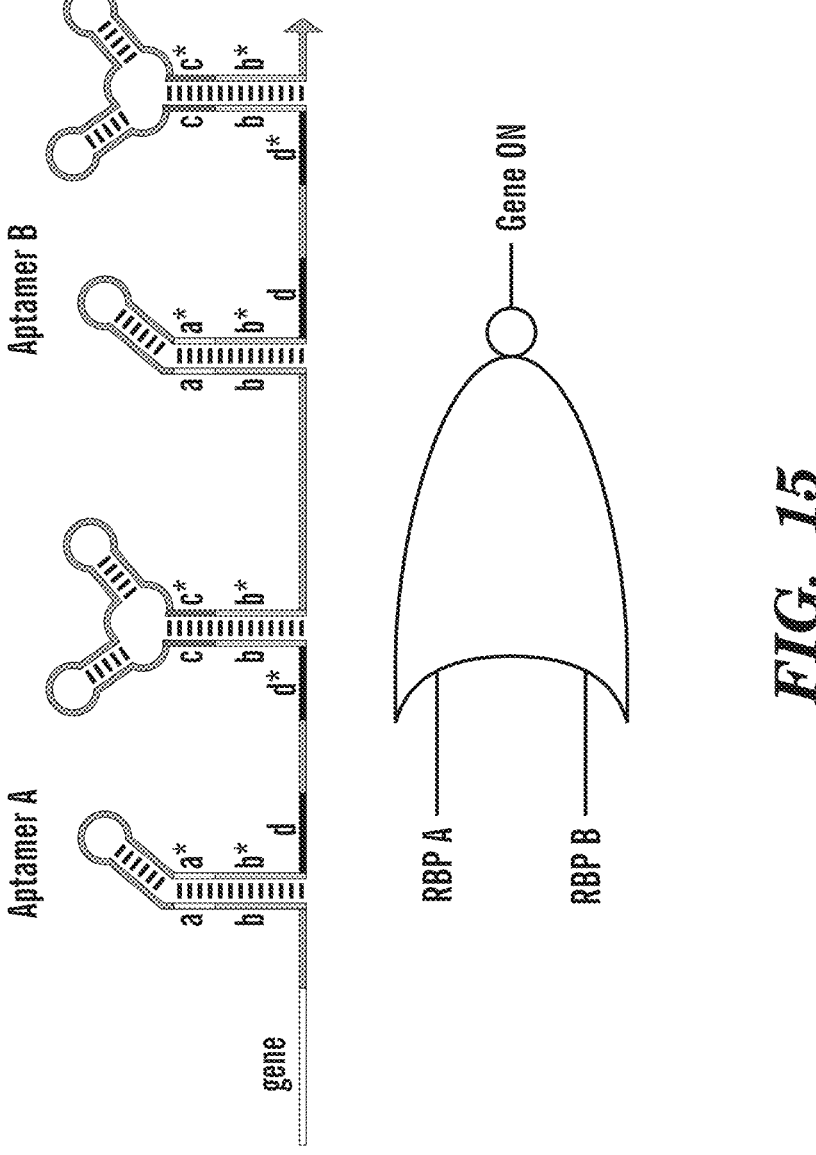
FIG. 15: Diagram showing NOR logic gate with ARES system. Two ARES OFF switches are concatenated together in the 3' UTR to create a NOR gate where at least one RBP is required to destabilize the mRNA, preventing further translation.

To increase the user's ability to turn OFF translation a NOR logic gate will be developed with the ARES OFF switches. This will be done in the same fashion as the AND logic gate where two or more ARES OFF stitches corresponding to different RBPs will be concatenated together (FIG. 15). Then only one of the RBPs needs to be present to destabilize the mRNA, stopping translation. This will be tested by transfecting the NOR gates into HEK293T cells along with no RBPs, one of the RBPs, or both RBPs. A successful NOR switch will show lower fluorescence in cells that have one or both RBPs. The largest challenge will be to find the best switch combinations so multiple BT and MCP switches will be tried and in multiple orders of concatenation.

Section 3.3—Increase Switch Complexity with A AND NOT B Logic Gate.

Figure 16:
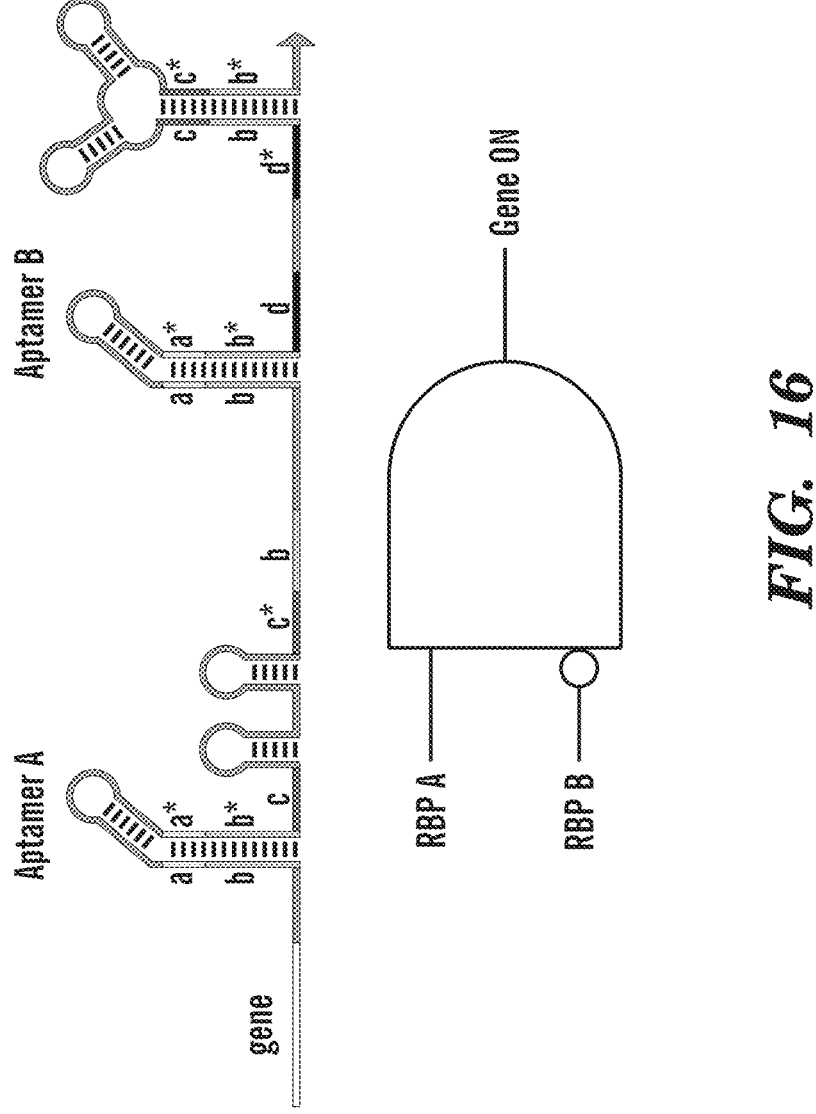
FIG. 16: Diagram showing A AND NOT B logic gate with ARES system. One ARES ON switch and one OFF switch are concatenated together in the 3' UTR to create an A AND NOT B gate. If RBP A is present translation occurs, but if RBP B is present at all, translation is turned off.

Another layer of control can be developed with an A AND NOT B gate. This will be done by concatenating an ARES ON switch with an ARES OFF switch (FIG. 16). Once these gates are developed, they will be transfected into HEK293T cells along with no RBP, one of the RBPs, or both RBPs. The fluorescence signal will be high when only the RBP corresponding to the ARES ON switch is present. If neither RBP is present or the RBP corresponding to the ARES OFF switch is present, then there will be no fluorescence. Just with the OR and AND gates, the largest challenge will be to find the best switch combinations so multiple ARES ON and OFF switches will be tried. Both orders of ARES ON and ARES OFF switches will be tested as well.

REFERENCES

1. Qin, S., Tang, X., Chen, Y. et al. mRNA-based therapeutics: powerful and versatile tools to combat diseases. Sig Transduct Target Ther 7, 166 (2022).
2. Chehelgerdi, M., Chehelgerdi, M. The use of RNA-based treatments in the field of cancer immunotherapy. Mol Cancer 22, 106 (2023).

3. Fenton, Owen S et al. "Synthesis and Biological Evaluation of Ionizable Lipid Materials for the In Vivo Delivery of Messenger RNA to B Lymphocytes." Advanced materials (Deerfield Beach, Fla.) vol. 29,33 (2017): 10.1002/adma.201606944.

4. Geall, Andrew J et al. "Nonviral delivery of self-amplifying RNA vaccines." Proceedings of the National Academy of Sciences of the United States of America vol. 109,36 (2012): 14604-9.

5. Wiedermannová, Jana et al. "The expanding field of non-canonical RNA capping: new enzymes and mechanisms." Royal Society open science vol. 8,5 201979. 19 May. 2021.

6. Zhong, G., Wang, H., He, W. et al. A reversible RNA on-switch that controls gene expression of AAV-delivered therapeutics in vivo. Nat Biotechnol 38, 169-175 (2020).

7. Bayer, Travis S et al. "Arginine-rich motifs present multiple interfaces for specific binding by RNA." RNA (New York, N. Y.) vol. 11,12 (2005): 1848-57.

8. Hinçer, Ahmet et al. "Making the Next Generation of Therapeutics: mRNA Meets Synthetic Biology." ACS synthetic biology vol. 12,9 (2023): 2505-2515.

9. Wroblewska, L., Kitada, T., Endo, K. et al. Mammalian synthetic circuits with RNA binding proteins for RNA-only delivery. Nat Biotechnol 33, 839-841 (2015).

10. Wang, Y S., Kumari, M., Chen, G H. et al. mRNA-based vaccines and therapeutics: an in-depth survey of current and upcoming clinical applications. J Biomed Sci 30, 84 (2023).

11. Rossignoli, Filippo et al. "Developing and characterizing a two-layered safety switch for cell therapies." Cancer biology & therapy vol. 24,1 (2023): 2232146.

12. Bashor, C., Hilton, I. B., Bandukwala, H. et al. Engineering the next generation of cell-based therapeutics. Nat Rev Drug Discov 21, 655-675 (2022).

13. Kim, Yelee et al. "The Potential of Cell-Penetrating Peptides for mRNA Delivery to Cancer Cells." Pharmaceutics vol. 14,6 1271. 15 Jun. 2022.

14. Van Hoecke, L., Roose, K. How mRNA therapeutics are entering the monoclonal antibody field. J Transl Med 17, 54 (2019).

15. Li, Y., TAM, W. W., Yu, Y. et al. The application of Aptamer in biomarker discovery. Biomark Res 11, 70 (2023).

16. Jiang, L., Lin, X., Chen, F. et al. Current research status of tumor cell biomarker detection. Microsyst Nanoeng 9, 123 (2023).

17. Scott, William G et al. "The hammerhead ribozyme: structure, catalysis, and gene regulation." Progress in molecular biology and translational science vol. 120 (2013): 1-23.

18. Xiang, J. S., Kaplan, M., Dykstra, P. et al. Massively parallel RNA device engineering in mammalian cells with RNA-Seq. Nat Commun 10, 4327 (2019).

19. Jacobs, J., Ciccaglione, K., Tournier, V. et al. Implementation of the CRISPR-Cas9 system in fission yeast. *Nat Commun* 5, 5344 (2014).

20. Athanassiou, Zafiria et al. "Structural mimicry of retroviral tat proteins by constrained beta-hairpin peptidomimetics: ligands with high affinity and selectivity for viral TAR RNA regulatory elements." Journal of the American Chemical Society vol. 126,22 (2004): 6906-13.

21. Cocozaki, Alexis I et al. "The RNA-binding domain of bacteriophage P22 N protein is highly mutable, and a single mutation relaxes specificity toward lambda." Journal of bacteriology vol. 190,23 (2008): 7699-708.

22. Johansson, H E et al. "A thermodynamic analysis of the sequence-specific binding of RNA by bacteriophage MS2 coat protein." Proceedings of the National Academy of Sciences of the United States of America vol. 95,16 (1998): 9244-9.

23. Sachdeva, Gairik et al. "In vivo co-localization of enzymes on RNA scaffolds increases metabolic production in a geometrically dependent manner." Nucleic acids research vol. 42,14 (2014): 9493-503.

24. Chai, Chenglin et al. "SELEX (Systematic Evolution of Ligands by EXponential Enrichment), as a powerful tool for deciphering the protein-DNA interaction space." Methods in molecular biology (Clifton, N. J.) vol. 754 (2011): 249-58.

25. Zadeh, J. N., Steenberg, C. D et al. "NUPACK: Analysis and design of nucleic acid systems." J. Comput. Chem., 32 (2011): 170-173.

26. Yoon, Sorah et al. "Targeted Delivery of C/EBPα-saRNA by RNA Aptamers Shows Anti-tumor Effects in a Mouse Model of Advanced PDAC." Molecular therapy. Nucleic acids vol. 18 (2019): 142-154.

27. Yoon, Sorah et al. "Blind SELEX Approach Identifies RNA Aptamers That Regulate EMT and Inhibit Metastasis." Molecular cancer research: MCR vol. 15,7 (2017): 811-820.

28. Xiang, Q., Tan, G., Jiang, X. et al. Suppression of FOXM1 Transcriptional Activities via a Single-Stranded DNA Aptamer Generated by SELEX. Sci Rep 7, 45377 (2017).

29. Varshney, Akhil et al. "Identification of an RNA aptamer binding hTERT-derived peptide and inhibiting telomerase activity in MCF7 cells." Molecular and cellular biochemistry vol. 427,1-2 (2017).

Example 2: Aptamer and Ribozyme Equilibrium Shifting (ARES) RNA Circuits for Protein Sensing Smart mRNAs that can sense proteins and respond by translating or inhibiting translation of its payload has transformative potential across medicine, synthetic biology, and biotechnology[1,2]. In therapeutics, such systems permit targeted protein therapy, allowing precise delivery of treatments only when a specific disease-associated protein is present, minimizing off-target effects. In engineered immune cells for cancer therapy, mRNA circuits can enhance T-cell responses by activating only in the presence of tumor markers.[3,4] Personalized medicine benefits from these responsive mRNA systems by tailoring treatments to an individual's protein expression profile.[5] Additionally, conditional expression systems allow for temporal control, such as a safety switch that prevents unintended persistence of delivered mRNA, improving safety in clinical applications.[6]

In synthetic biology, protein-sensing mRNAs serve as key components of cellular logic systems, permitting complex decision-making within cells based on protein levels. Metabolic engineering applications leverage these systems to fine-tune enzyme production for optimized biosynthesis pathways[7,8]. Diagnostics and biosensors use protein-responsive mRNAs to detect disease markers, offering real-time monitoring of health conditions both in vitro and in vivo.[9] In vaccines, mRNA-based strategies that sense immune signals can optimize antigen expression dynamically.[1] Moreover, these tools enhance the ability to study gene function by controlling protein expression in response to cellular conditions.[10] Altogether, protein-sensing mRNA expands the frontiers of biotechnology, improving therapeutic precision, research capabilities, and bioengineering strategies.

Proteins offer several advantages over RNA or small molecule sensing for controlling gene expression in therapeutic and synthetic biology applications. One key benefit is their higher specificity[11]. Proteins have well-defined three-dimensional structures and distinct binding sites that permit precise molecular recognition. This allows engineered mRNA circuits to distinguish between closely related molecules, reducing off-target effects compared to small molecules, which often interact with multiple cellular pathways. Additionally, proteins can serve as highly selective biomarkers for diseases, making them ideal for targeted therapies, diagnostics, and biosensors.[12,13] Unlike RNA sensing, which may be confounded by sequence similarities, proteins provide a broader range of structural and functional diversity for designing responsive systems.

A particularly powerful advantage of protein-based sensing is the ability to detect single point mutations. By engineering RNA aptamers that specifically recognize mutated proteins of interest but ignore wild-type proteins, mRNA circuits can selectively respond to disease-associated mutations.[13] By targeting mutated proteins, rather than mutated transcripts, such systems can take advantage of the increased copy numbers of proteins in the cell and do not need to compete for target binding with ribosomes, RNA polymerases, and other RNA-binding proteins. This is especially useful in cancer therapy, genetic disorders, and personalized medicine, where distinguishing between normal and aberrant proteins is crucial. Such precision permits highly selective therapies that activate only in the presence of pathogenic mutations, minimizing damage to healthy tissues. Compared to other gene expression control methods including transcriptional regulation or chemically inducible promoters, protein-sensing mRNA provides a rapid, tunable, and mutation-sensitive approach, making it an invaluable tool for dynamic and context-dependent cellular control.[14]

To develop an mRNA sensor capable of responding to proteins, or their absence, a mechanism for modulating mRNA stability was first established. Hammerhead ribozymes (HHR) provide a valuable tool for this purpose. HHR are RNA sequences that can fold into distinct secondary and tertiary structures, which, in the presence of appropriate magnesium levels, trigger a self-cleavage reaction.[15, 16] While various types of self-cleaving ribozymes exist, previous research has optimized type III HHR for rapid cleavage kinetics.[17]

Figure 17A:
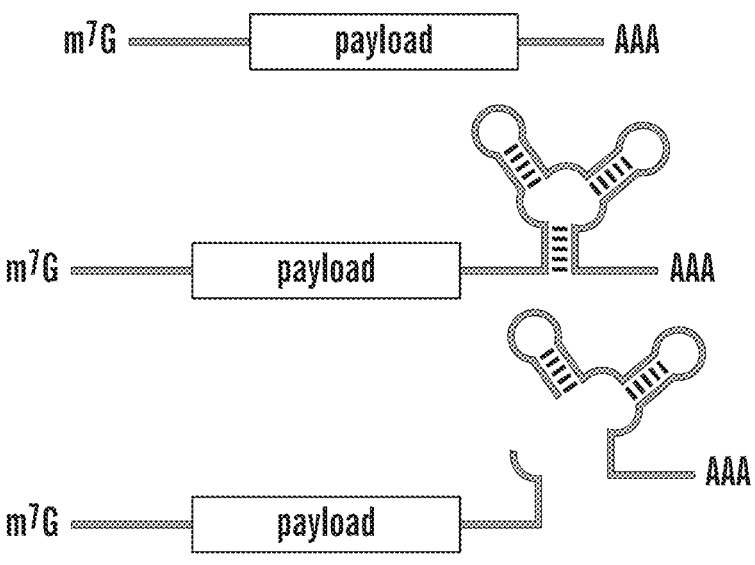
FIG. 17A-17C: Hammerhead Ribozyme (HHR) and Aptamer Structures and Functions.
Figure 17B:
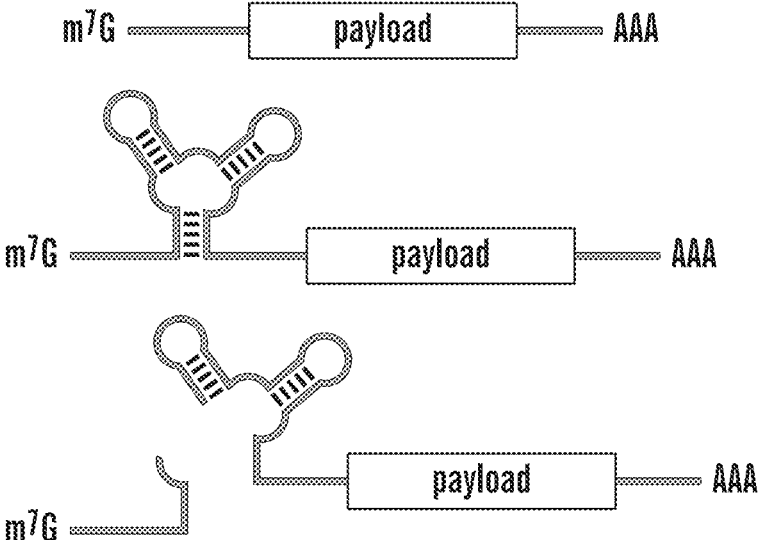

A typical mRNA strand contains several key features, including a 3' polyadenylate (poly-A) tail, which protects it from cytoplasmic degradation. By positioning an HHR downstream of the encoded gene but upstream of the poly-A tail, the ribozyme can cleave the tail from the mRNA strand, initiating degradation before translation occurs. Similarly, HHR-mediated destabilization can also be achieved in the 5' untranslated region (5' UTR) by placing the HHR between the protective 5' cap and the start codon. In both cases, HHR cleavage disrupts mRNA stability, effectively preventing translation (FIG. 17A, 17B).[17]

Figure 17C:
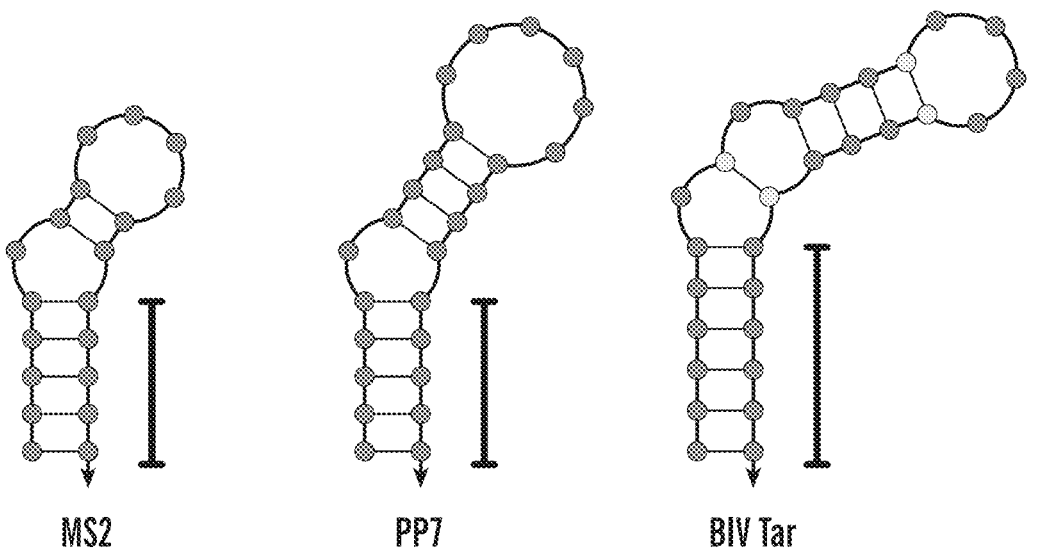

For mRNA to sense proteins, a connection between them is essential, a role fulfilled by RNA binding proteins (RBPs). RBPs are proteins or peptides capable of binding to specific RNA structures known as aptamers. RBPs can occur naturally, exemplified by viral peptides like BIV Tat, MCP, and PCP that bind specifically to their aptamers BIV Tar, MS2, and PP7 (FIG. 17C).[18,19,20] Alternatively, RNA aptamers can be selected for particular proteins using techniques like Systematic Evolution of Ligands by EXponential enrichment (SELEX). This versatility allows RBPs involved in mRNA stability regulation to be either exogenous or biomarker proteins specific to diseases or cell types.[21] Depending on the placement of aptamers within mRNA strands, RBPs can also disrupt nearby RNA structures.[22]

In this technology, Hammerhead ribozymes (HHR) and RNA aptamers were strategically positioned in the 3' UTR of mRNA strands to regulate mRNA stability and, consequently, translation in response to proteins. This approach, referred to herein as Aptamer Ribozyme Equilibrium Shifting (ARES) RNA circuits, is highly generalizable and can be applied across various protein-sensing contexts. It was also demonstrated that ARES elements can be inserted in the 5' UTR mRNA region for protein sensing.

Results

Figure 18A:
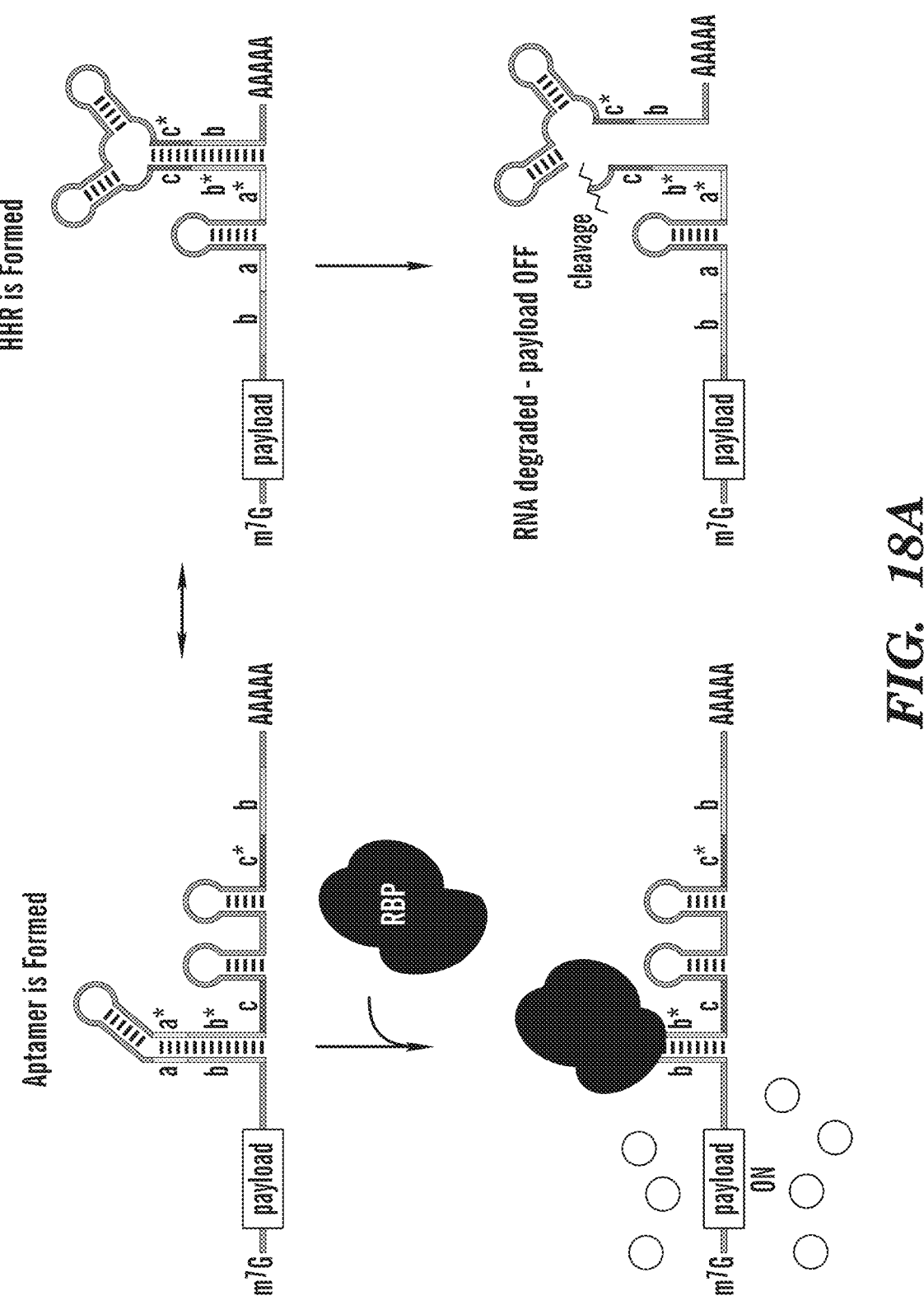
FIG. 18A-18D: The ARES ON Switch in the 3' UTR.

To develop the ARES switch, previously identified and well-characterized aptamer structures and their corresponding RNA-binding proteins (RBPs), including BIV Tat (BT), MCP, and PP7, were selected. In the mRNA strand, the aptamer is positioned upstream of a Hammerhead ribozyme (HHR), with both structures sharing a common nucleotide sequence at their base stems, referred to as domain "b". This is the 3' end for the aptamer and the 5' end for the HHR. Due to this shared domain, only one structure can be fully formed at a given time (FIG. 18A).

Additional domains fine-tune this equilibrium. Domain "a", at the top of the aptamer base stem, is a toehold for the aptamer and can be adjusted in length to favor aptamer formation. Conversely, domain "c", at the top of the HHR base stem, is a toehold for the HHR and influences the stability of the HHR structure. When the corresponding RBP binds the aptamer, it shifts the equilibrium away from the HHR, preventing self-cleavage and stabilizing the mRNA. In the absence of the RBP, the HHR forms and undergoes self-cleavage, removing the poly-A tail (if in the 3' UTR) or 5' cap (if in the 5' UTR), leading to mRNA degradation.

In developing the ARES switches, the optimal domain lengths for effective switching was first determined. Using NUPACK, ARES switch sequences were generated with varying lengths of domain "a" and domain "c", 0 to 4 nucleotides, and domain "b", 5 to 7 nucleotides, for aptamers corresponding to the RBPs BT, PCP, and MCP.[23] Although these ARES switches featured "a" and "c" domain lengths of 0 to 4 nucleotides, the lengths of these domains could range from 0 to 8 nucleotides in general. Additionally, the "b" domain lengths could range from 2 to 12 nucleotides in general. To evaluate functionality, mCherry reporters were constructed containing a library of switches in the 3' UTR, and they were transiently transfected into HEK293T cells alongside a separate plasmid expressing either the inert Maltose Binding Peptide (MBP) or the corresponding RBP.

Initial screening revealed minimal expression changes upon RBP co-transfection. To enhance activation, the RBPs were fused to MBP using a GS linker, increasing steric hindrance to better inhibit HHR self-cleavage. With this modification, the ARES switches demonstrated a broad range of functionality across all three RBPs, indicating improved responsiveness and tunability.

Figure 18B:
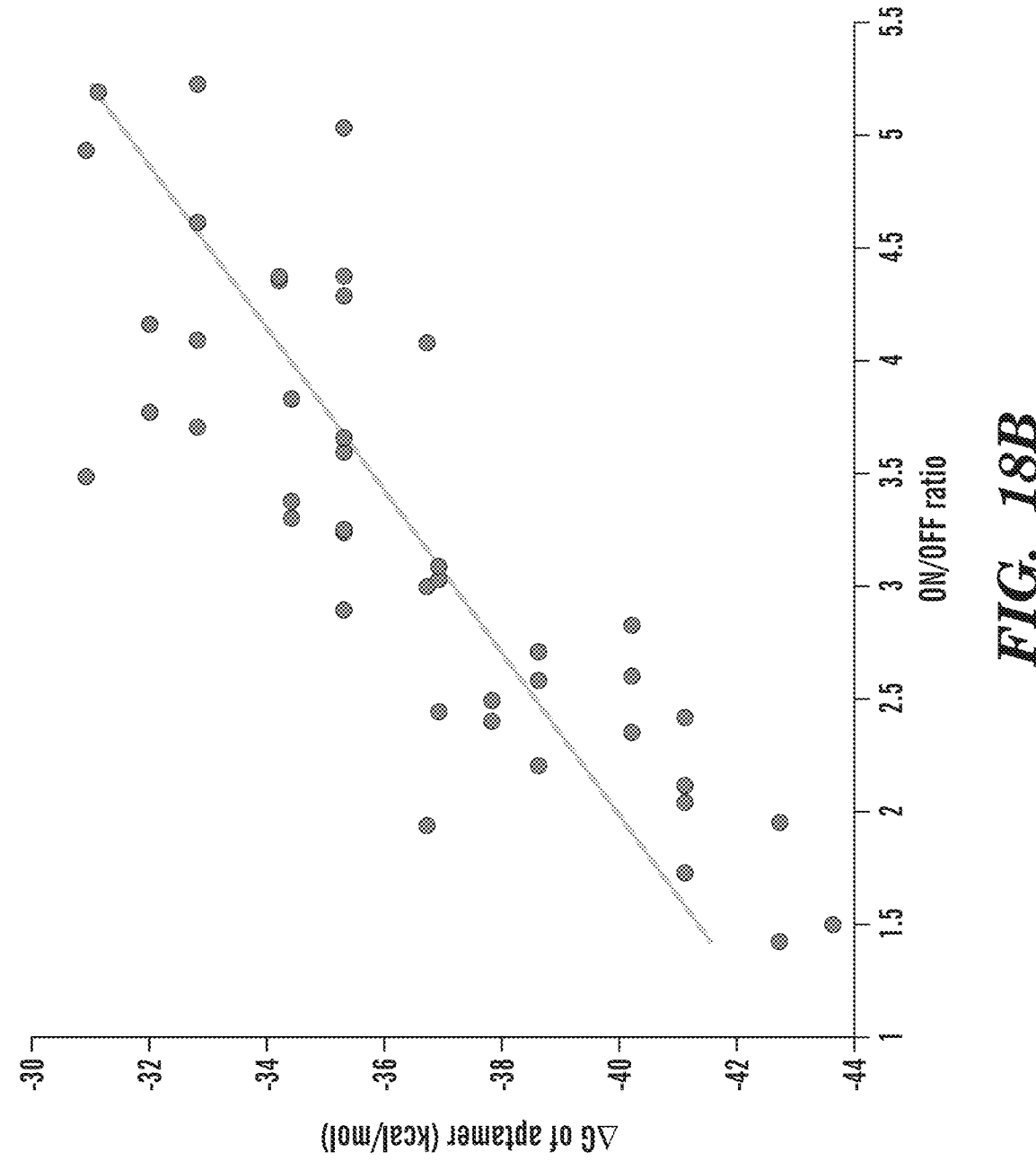
Figure 18C:
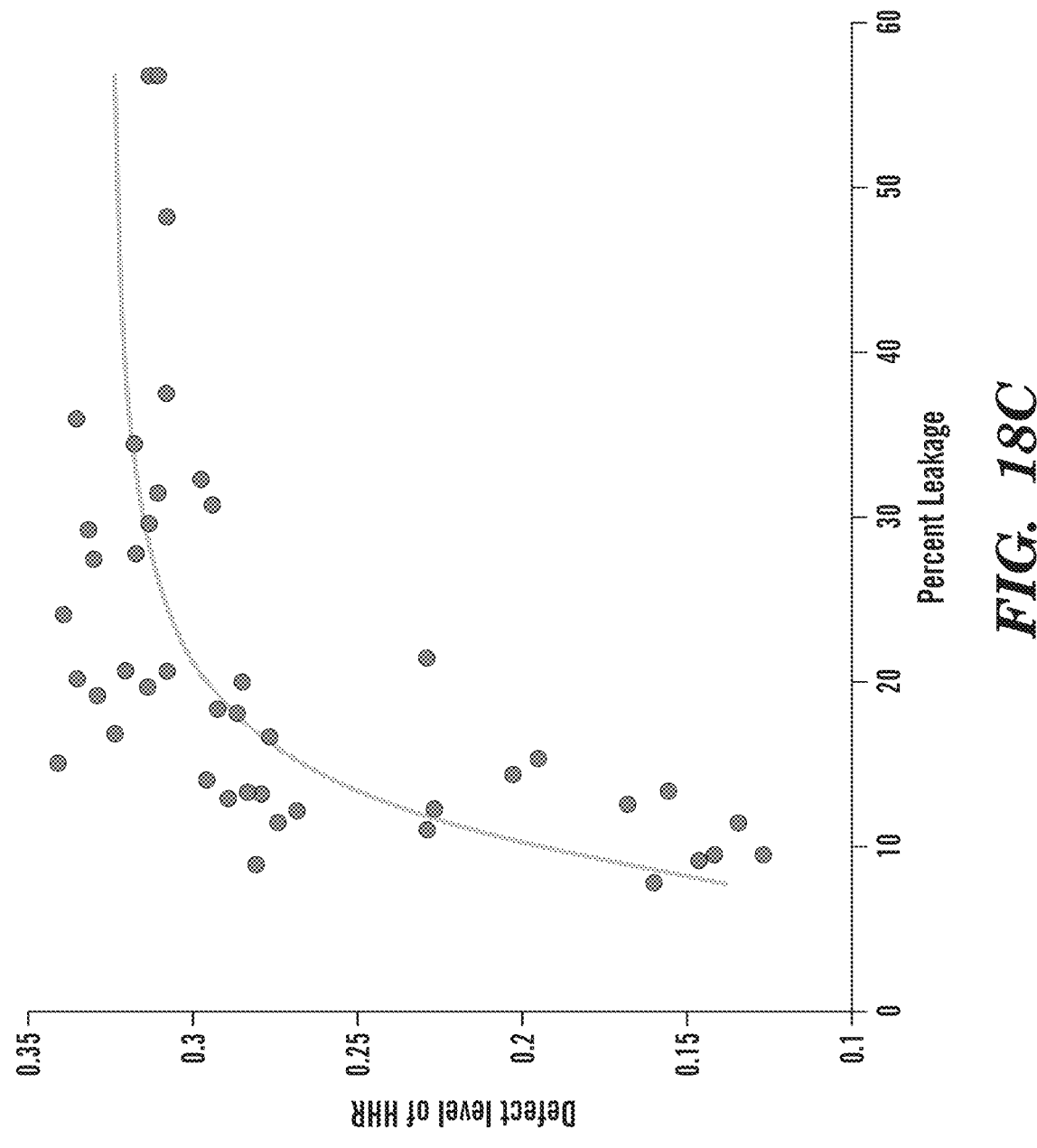

To determine the key factors contributing to optimal switch function, the defect levels and Gibbs free energy of both HHR and aptamer formation were analyzed for each switch. These metrics showed varying degrees of correlation with switch leakage levels and ON/OFF ratios (Table 3). Examining the PP7 aptamer ARES library, trends were identified that can guide the design of ARES switches with different aptamers. Notably, the Gibbs free energy of aptamer formation exhibited a strong linear correlation with the ON/OFF ratio, with an R-squared value of 0.72 (FIG. 18B). Additionally, the defect level of the HHR correlated with switch leakage, following a hill function trend, with an R-squared value of 0.56 (FIG. 18C).

TABLE 3

| Spearman correlation values | | | | |
|---|---|---|---|---|
| Correlation variable 1 | Correlation variable 2 | $MS2_{(n=15)}$ | $PP7_{(n=46)}$ | $BT_{(n=54)}$ |
| ON/OFF ratio | $\Delta G_{APT}$ | 0.5018 | 0.7874 | 0.5073 |
| ON/OFF ratio | $\Delta G_{HHR}$ | 0.2532 | −0.2101 | −0.3470 |
| ON/OFF ratio | Defect level APT | 0.3701 | 0.5291 | 0.6504 |
| ON/OFF ratio | Defect level HHR | −0.1537 | −0.6932 | −0.6318 |
| Percent Leakage | $\Delta G_{APT}$ | −0.3477 | −0.6305 | −0.5264 |
| Percent Leakage | $\Delta G_{HHR}$ | −0.2604 | 0.3937 | 0.3624 |
| Percent Leakage | Defect level APT | −0.4357 | −0.5128 | −0.6144 |
| Percent Leakage | Defect level HHR | −0.1591 | 0.6732 | 0.7159 |

Figure 18D:
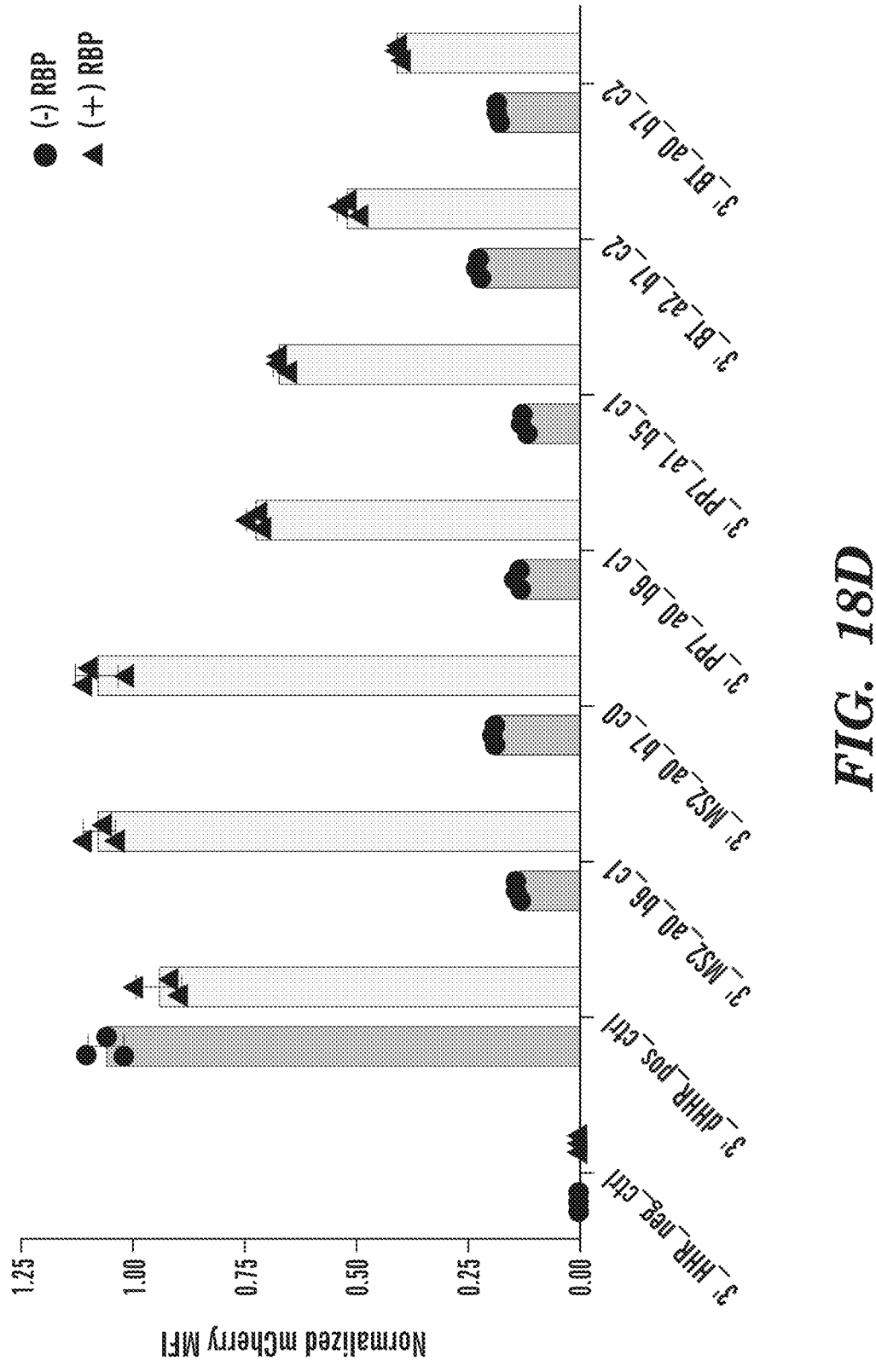

These findings indicate that to develop a strong switch, it is crucial to maximize the Gibbs free energy of the aptamer (reducing its likelihood of forming) while minimizing the defect level of the HHR (increasing its stability). The best-performing switches for BT, PP7, and MS2 aptamers achieved ON/OFF ratios of 2.42, 5.10, and 8.39 in the 3′ UTR, with MS2 aptamers demonstrating the highest dynamic range (FIG. 18D). Furthermore, when MCP protein was expressed in HEK293T cells alongside the ARES switch, expression levels closely matched those of positive controls, confirming effective switch activation.

Figure 19A:
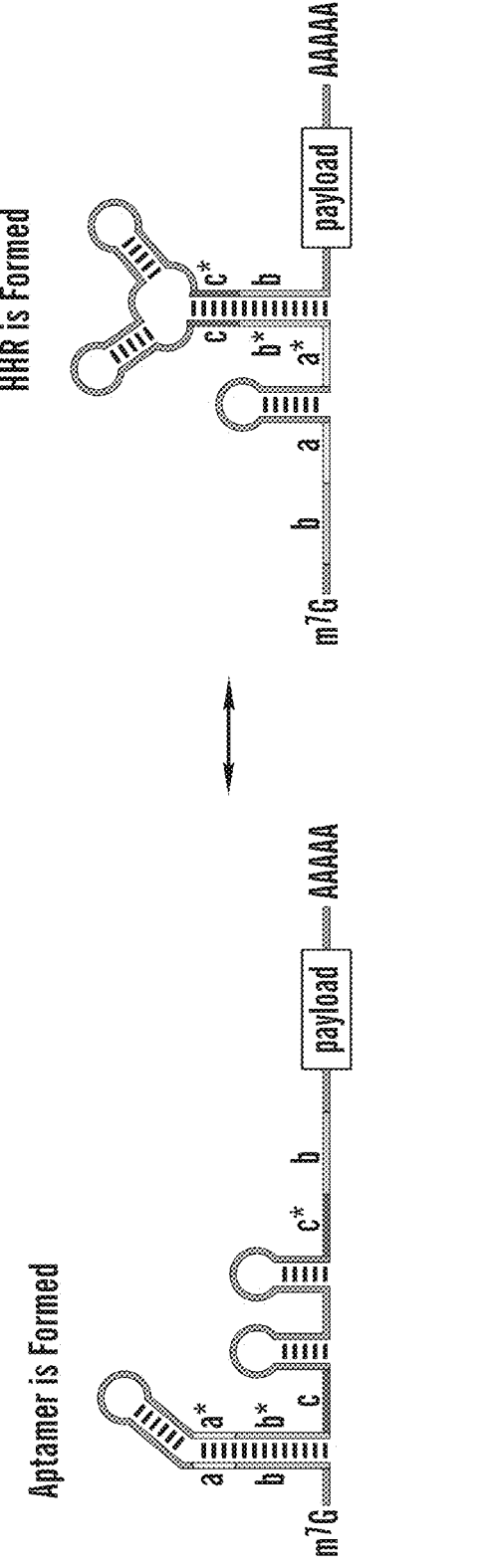
FIG. 19A-19D: Variations of the ARES ON Switch.
Figure 19B:
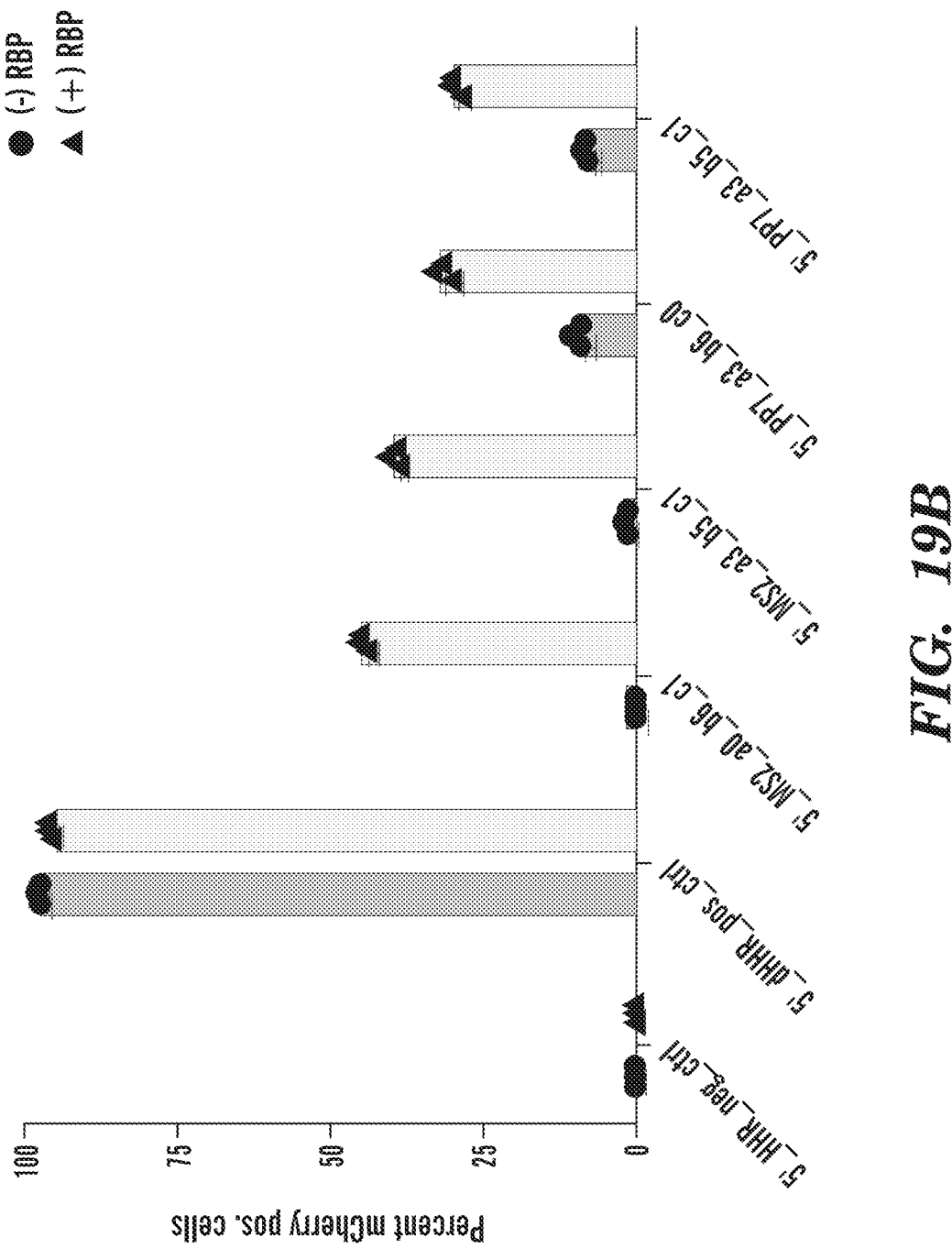

These switches were also evaluated in the 5′ UTR, where placing the HHR upstream leads to stronger suppression of unwanted translation (FIG. 19A). When HHR cleavage removes the 5′ cap, the translation initiation complex cannot form, completely blocking translation. In contrast, in the 3′ UTR, translation can continue until the mRNA is degraded after cleavage. Multiple MS2 and PP7 ARES switches were tested in the 5′ UTR, demonstrating that in the absence of the corresponding RBP, very few cells exhibited mCherry reporter signal. However, when the RBP was introduced, a marked increase in fluorescence was observed, confirming switch activation and robust control over translation (FIG. 19B).

Figure 19C:
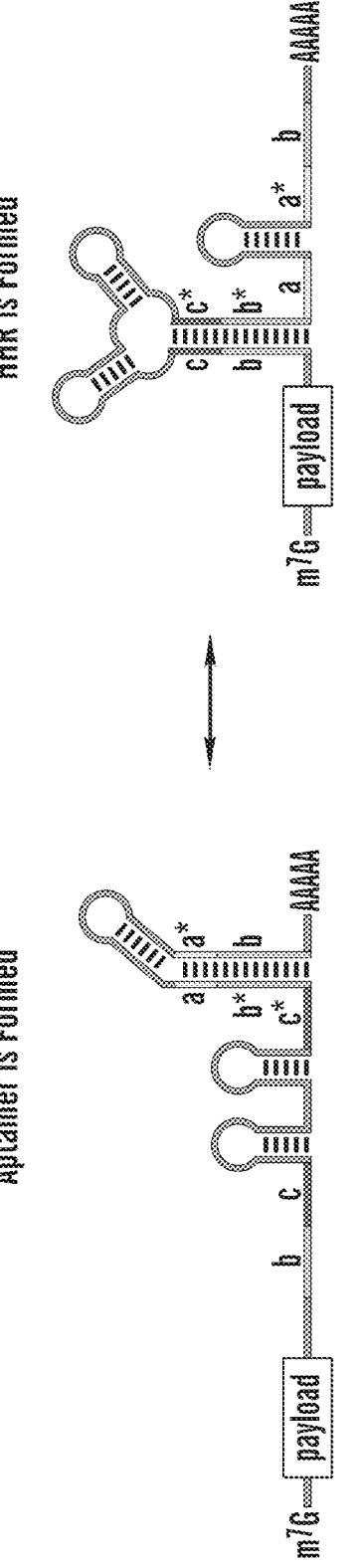
Figure 19D:
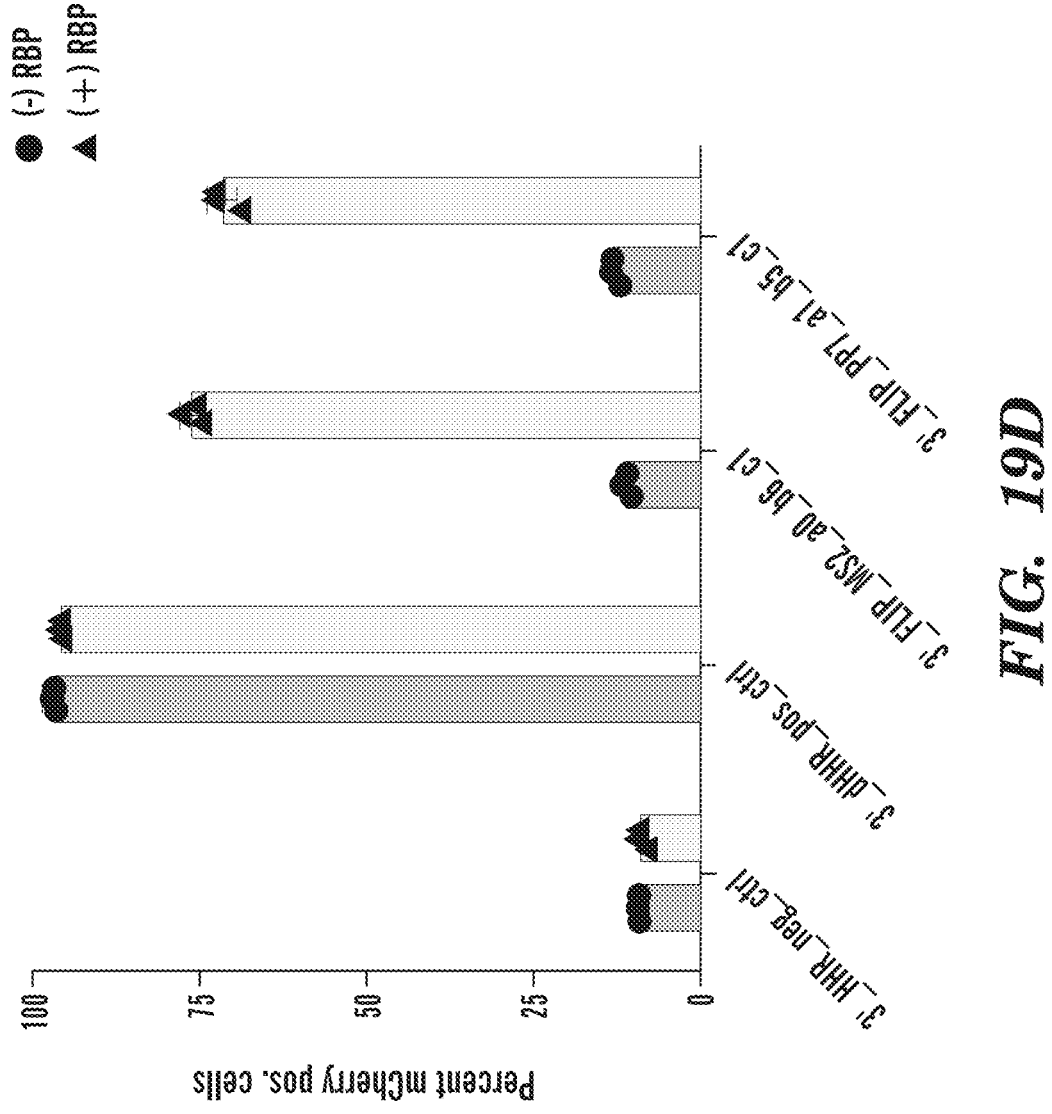

In addition to the original ARES switch design, a flipped design was tested for the MS2 and PP7 aptamer switches, where the HHR was placed upstream of the aptamer while still sharing domain "b" (FIG. 19C). In this configuration, the HHR forms first during transcription, increasing the likelihood of cleavage before the aptamer can fold and establish equilibrium between the two structures. This design resulted in significantly lower leakage levels when the RBP was absent, improving baseline suppression. When the RBP was present, the flipped switches still demonstrated an increase in mCherry expression, confirming they retained functionality (FIG. 19D). However, the maximum signal output was noticeably lower compared to the original designs, indicating that while the flipped design enhances repression, it may reduce overall dynamic range.

Figure 20A:
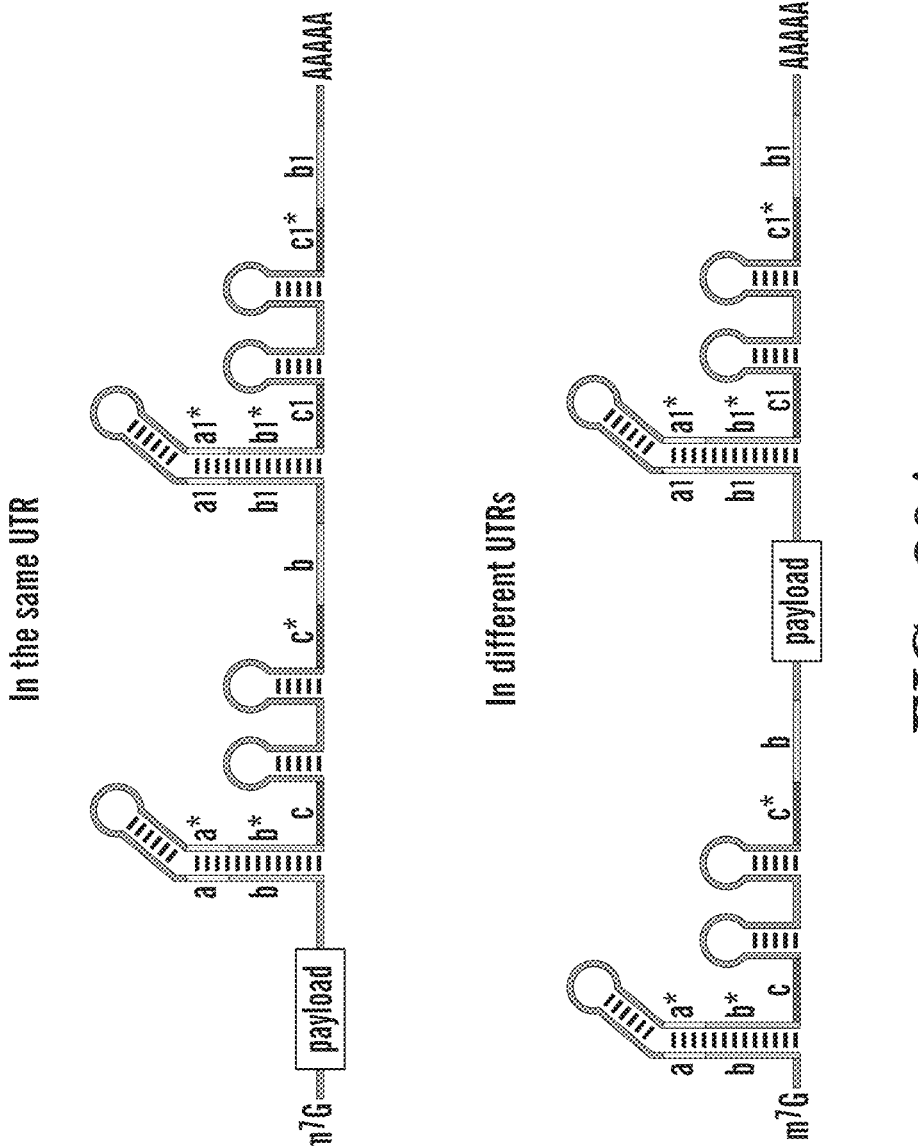
FIG. 20A-20E: Utilizing Multiple ARES Switches to Reduce Leakage and Produce a Digital-to-Analog Effect.
Figure 20B:
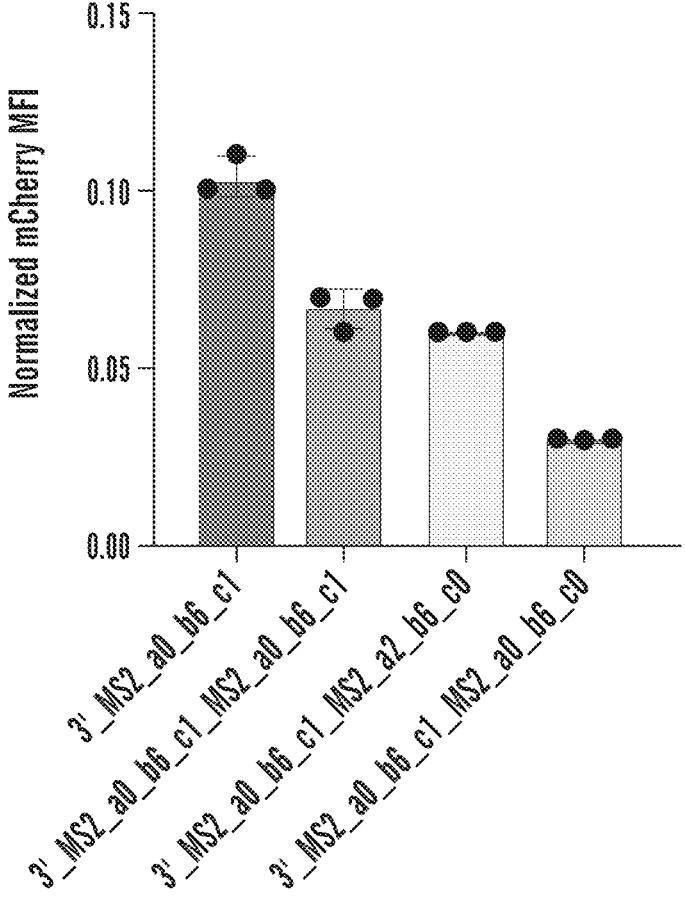
Figure 20C:
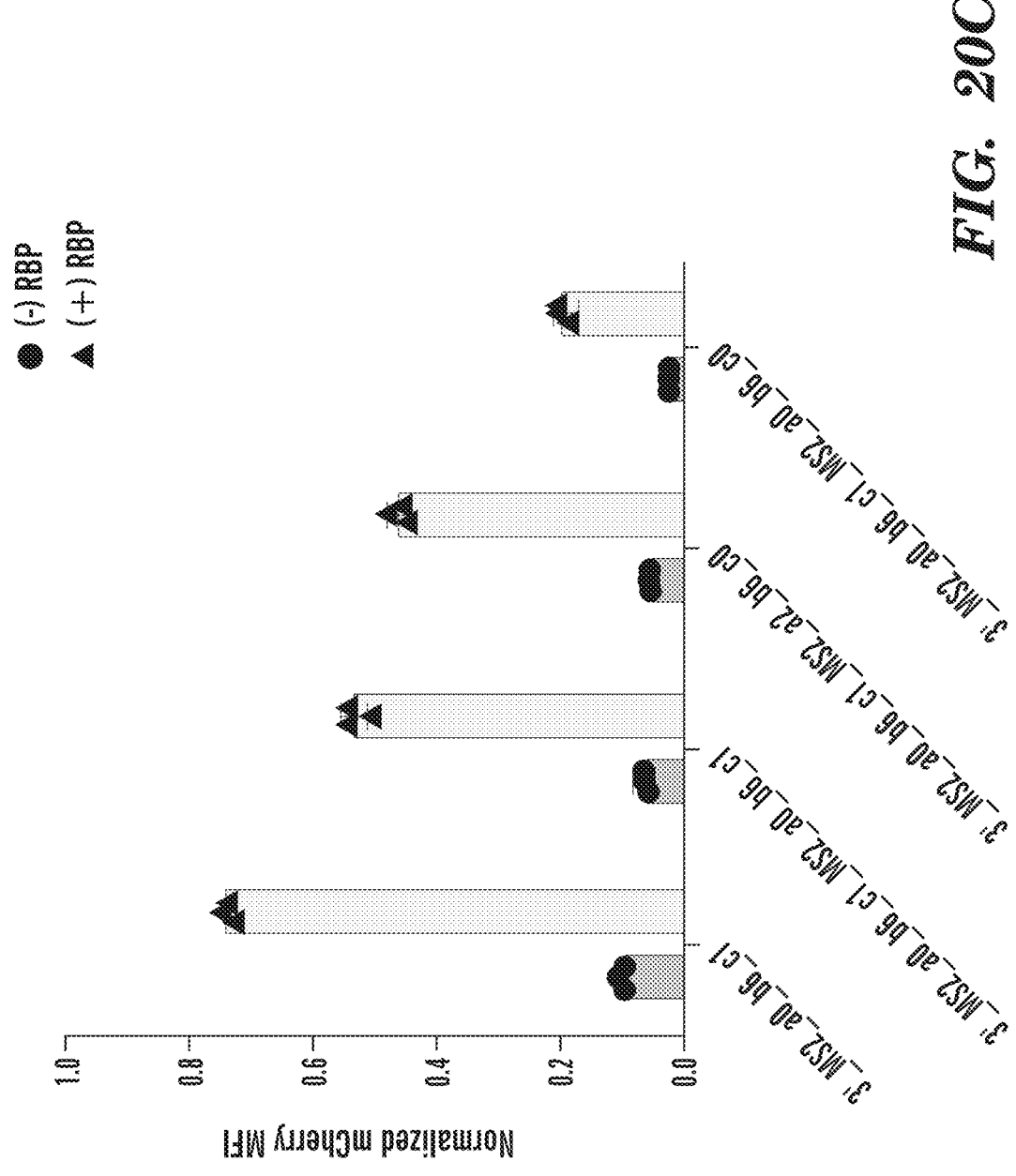
Figure 20D:
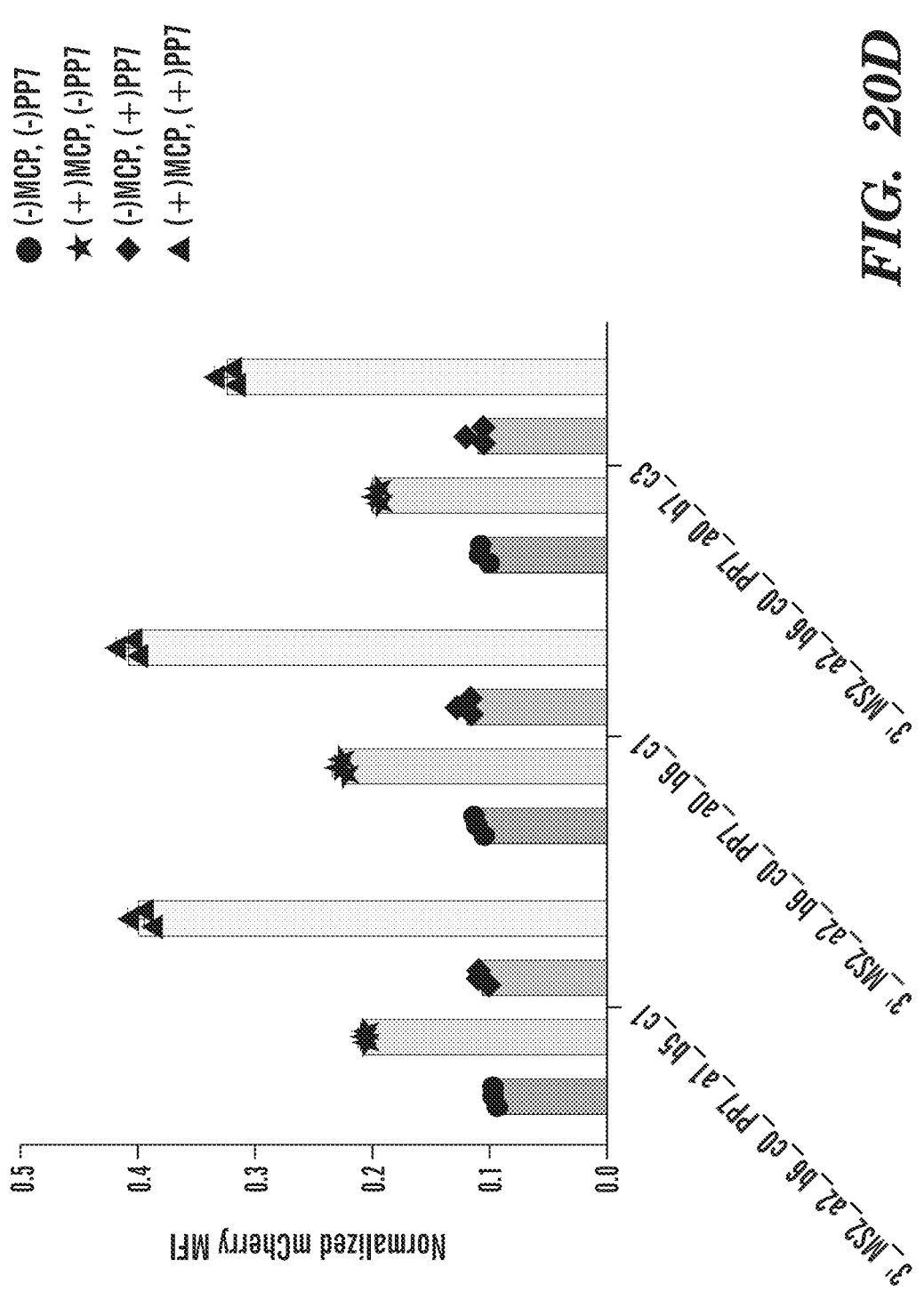

An additional approach to reducing ARES switch leakage in the 3′ UTR is by concatenating multiple ARES switches within the region (FIG. 20A). This can involve placing multiple switches with the same aptamer in the 3′ UTR, which reduces leakage compared to a single ARES switch, while still allowing for activation when the RBP is present (FIG. 20B, 20C). Additionally, concatenating ARES switches with different aptamers in the 3′ UTR can produce a digital-to-analog effect, where discrete input levels generate a range of output payload expression (FIG. 20d). When both RBPs are present, the maximum expression of the payload is achieved, but if only the RBP corresponding to the upstream ARES switch is present, only about half the maximum signal is observed.

Figure 20E:
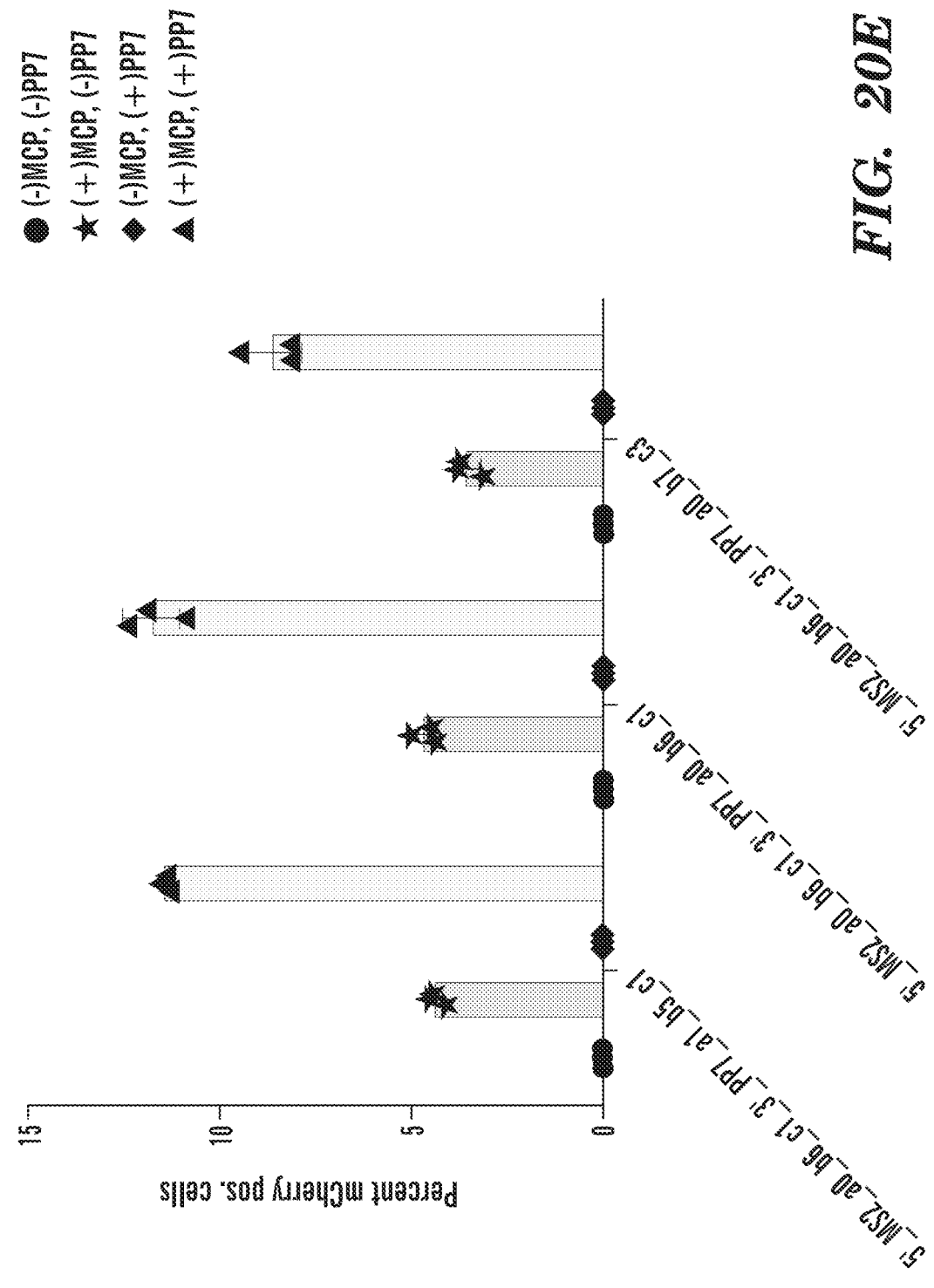

This analog-to-digital effect can also be seen when one ARES switch is placed in the 3′ UTR and another in the 5′ UTR (FIG. 20E). In this case, when only the RBP for the 5′ UTR switch is present, approximately half the maximum signal is observed, demonstrating the versatility of concatenated ARES switches for tuning gene expression in a controlled, modular manner.

Figure 21A:
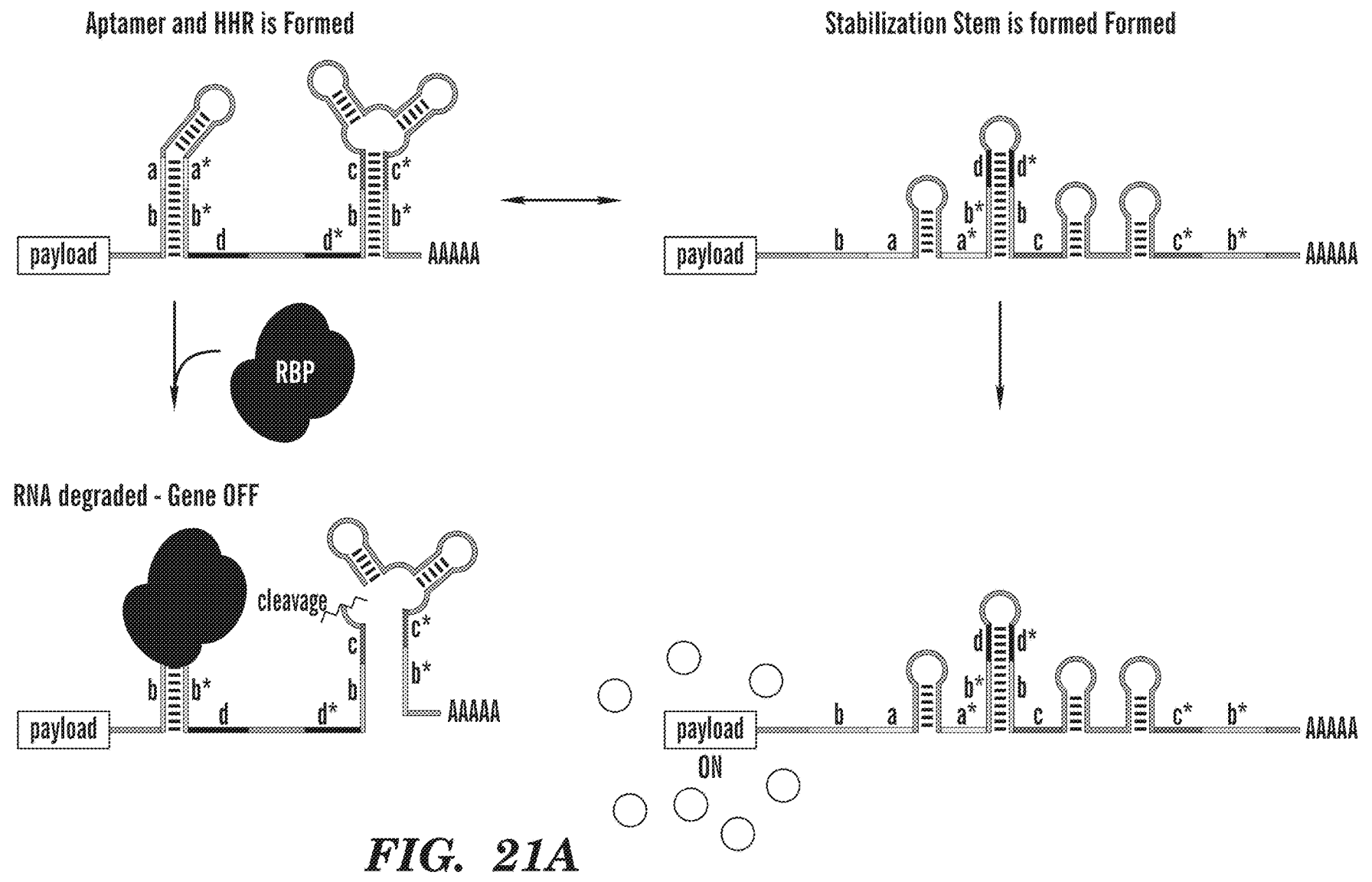
Figure 21B:
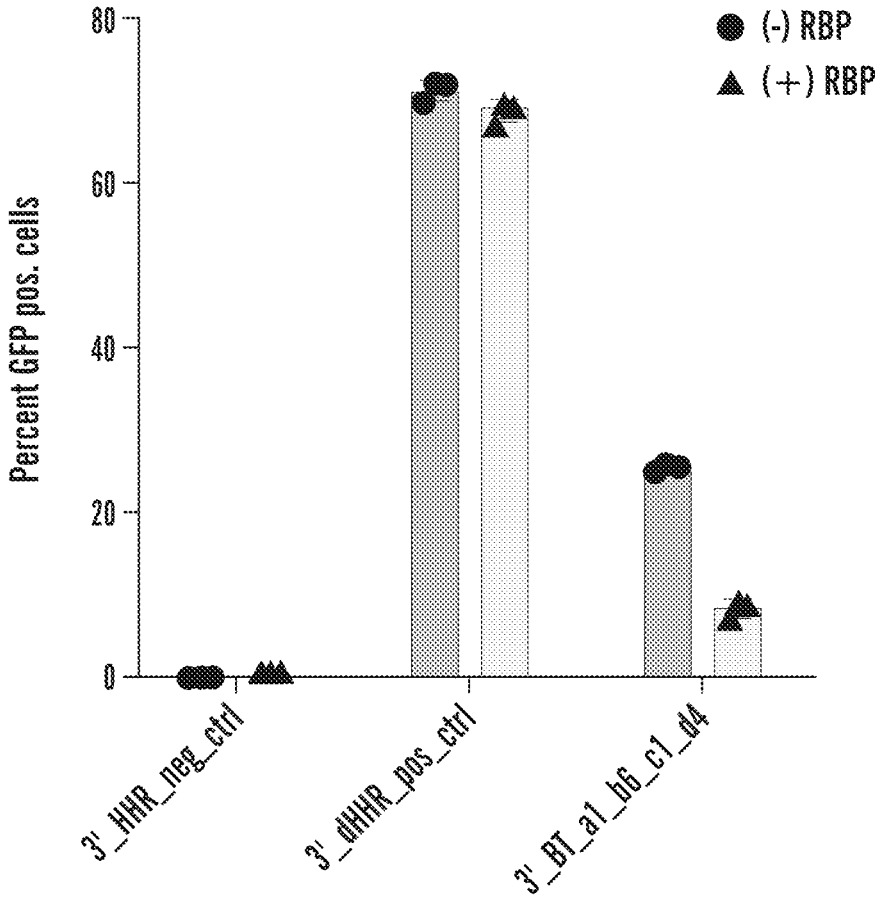

In addition to the ARES ON switch, two variations of an ARES OFF switch were developed. The first OFF switch design closely resembles the ON switch but includes an additional middle stem-loop structure, referred to as the stabilization stem, composed of domains "d" and "b", positioned between an upstream aptamer and a downstream HHR (FIG. 21A). The upstream "b" domain is shared with the aptamer, while the downstream "b" domain is shared with the HHR, creating an equilibrium-shifting effect where either the aptamer and HHR forms or the stabilization stem. To optimize function, domain lengths for "a", "b", and "c" were kept consistent with the ON switch, while domain "d" was varied from 0 to 4 nt. Using the BT aptamer, the best-performing switch showed that 25% of cells expressed GFP (the reporter) in the absence of BT, while only 8.3% expressed GFP when BT was present, confirming functional repression (FIG. 21B).

Figure 21C:
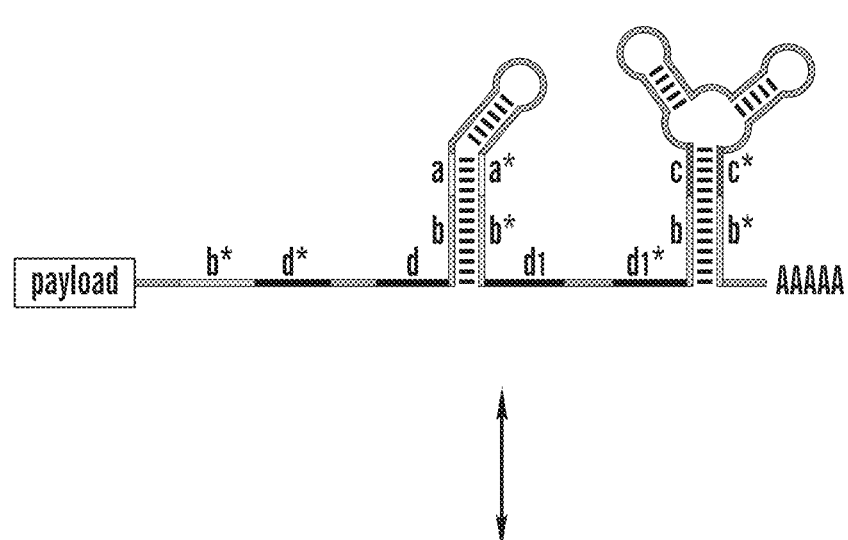
Figure 21C:
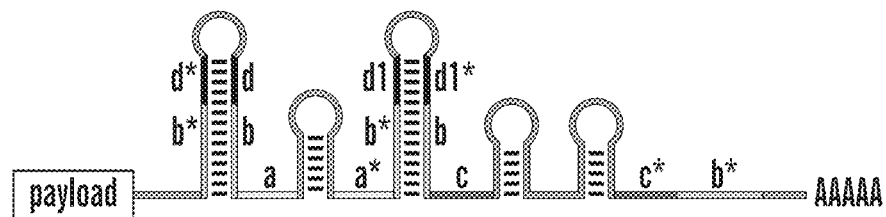
Figure 21D:
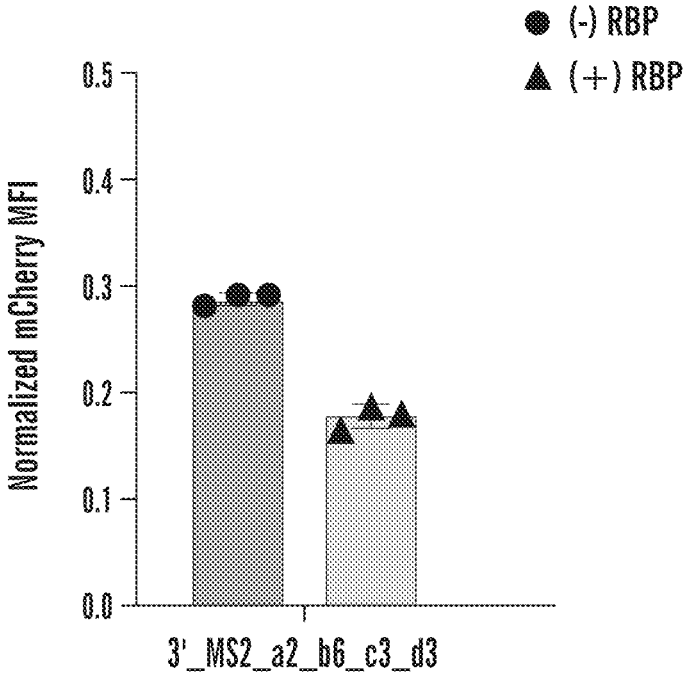

The second OFF switch design introduced an additional upstream stabilization stem, creating a more balanced structure (FIG. 21C). This upstream stabilization stem was formed by domains "d" and "b", while the middle ON stem consisted of a separate "di" domain and the same "b" domain as the upstream stem. This design used the MS2 aptamer, with domain lengths optimized similarly to the first OFF switch. The best-performing switch showed a 12% decrease in mCherry expression when MCP was present (FIG. 21D).

While the OFF switches did not perform as strongly as the ON switches, further domain length optimization can improve their function. Similarly to the ON switches the lengths of the "a" and "c" domains could range from 0 to 8 nucleotides, the "b" domain lengths could range from 2 to 12 nucleotides, and the "d" domain could range from 0 to 12 nucleotides in general.

Additionally, these tests were performed using transient DNA transfection, meaning mRNA was continuously transcribed. Testing the OFF switches as direct mRNA or self-amplifying RNA (saRNA) could enhance performance, as mRNA destabilization upon RBP binding would lead to a more immediate reduction in translation, potentially yielding more pronounced repression effects.

Discussion and Conclusions

This study presents the development and characterization of Aptamer Ribozyme Equilibrium Shifting (ARES) RNA circuits as a novel mechanism for protein-responsive mRNA translation control. These findings demonstrate that ARES switches effectively regulate mRNA stability and translation through the interplay of RNA-binding proteins (RBPs), RNA aptamers, and Hammerhead ribozymes (HHR). The ability of these circuits to modulate gene expression dynamically in response to specific proteins has broad implications for therapeutic applications, synthetic biology, and biotechnology.

Through systematic variation of domain lengths and computational modeling, key parameters were identified influencing ARES switch performance. The Gibbs free energy of aptamer formation strongly correlated with the ON/OFF ratio, indicating that increasing aptamer stability reduces background leakage and enhances switch activation. Similarly, minimizing the defect level of the HHR structure improved switch repression, highlighting the importance of ribozyme stability in achieving robust control over mRNA degradation.

Multiple variations of the ARES switch were tested. First, placing the HHR in the 5' UTR significantly reduced background expression, as cleavage of the 5' cap completely blocked translation initiation. Second, a flipped switch configuration was investigated where the HHR was positioned upstream of the aptamer. This arrangement lowered leakage by promoting HHR cleavage early in transcription, though at the cost of reduced maximum activation. Finally, concatenating multiple ARES switches within the 3' UTR decreased leakage while retaining activation in response to RBP binding, providing a modular approach for tuning gene expression.

In addition to ON switches, two ARES OFF switch designs were developed that repress translation in response to RBPs. The first OFF switch featured an equilibrium-shifting on stem between the aptamer and HHR, reducing translation upon RBP binding. The second design incorporated an additional upstream on stem, creating a more balanced structural equilibrium. Further optimization of domain lengths and testing in direct mRNA or self-amplifying RNA (saRNA) contexts could enhance repression efficiency.

The modular and programmable nature of ARES switches opens new avenues for applications in medicine and synthetic biology. In therapeutics, ARES circuits permit targeted mRNA therapies that activate only in the presence of disease-specific proteins, reducing off-target effects. Engineered immune cells could leverage these switches for precise activation in response to tumor markers, enhancing cancer immunotherapy. Additionally, ARES switches could be integrated into biosensors for real-time monitoring of protein biomarkers, improving diagnostic capabilities.

In summary, ARES RNA circuits provide a versatile and efficient approach to protein-responsive gene regulation. By leveraging aptamer-ribozyme interactions, these switches offer precise, tunable, and programmable control over mRNA translation, with significant potential for advancing biomedical and biotechnological applications.

ARES OFF Switch: Version 3

Figure 22:
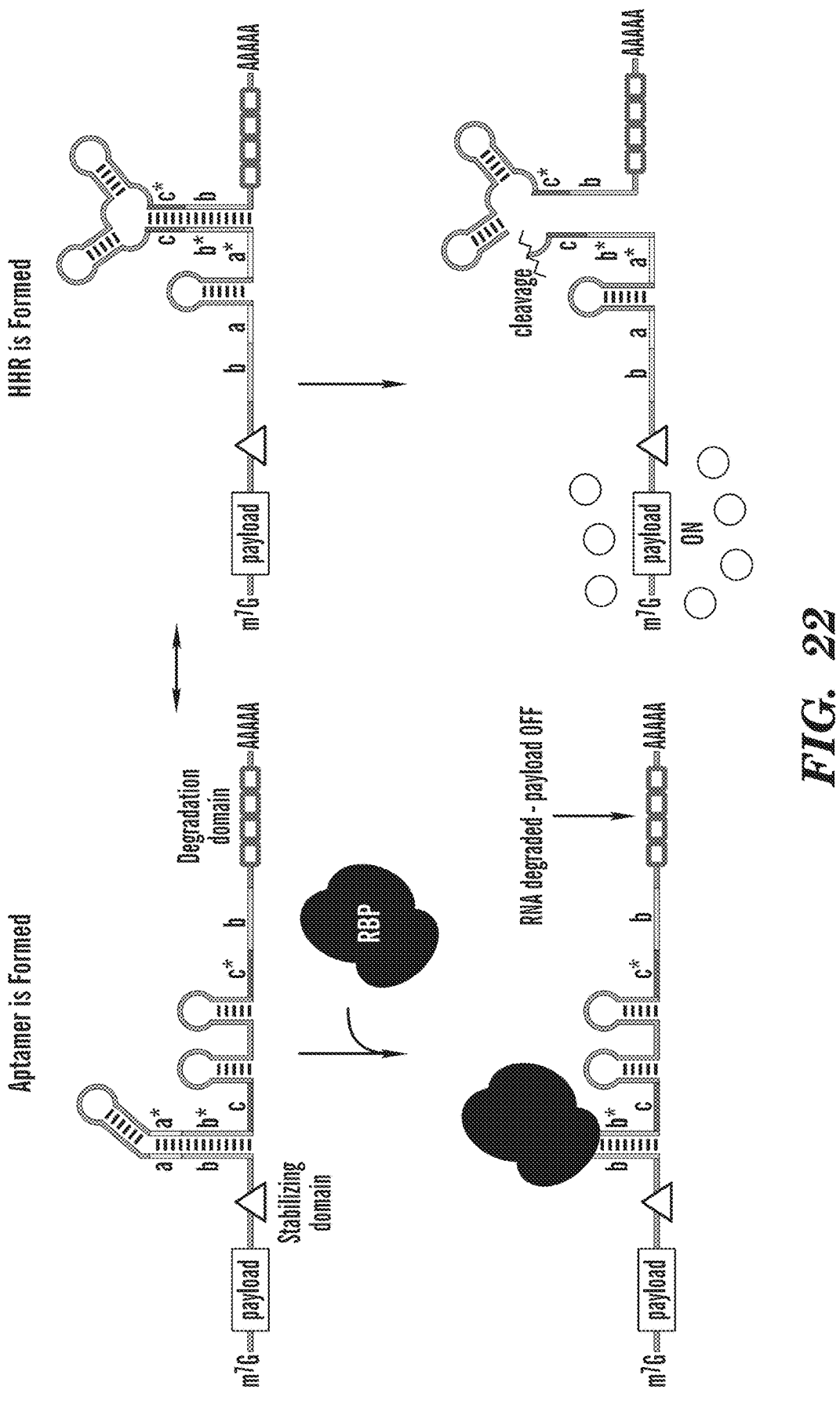
FIG. 22: Additional ARES OFF Switch Design in the 3' UTR. Schematic representation of the third ARES OFF switch design in the 3' UTR. An ARES ON switch is positioned between an upstream stabilizing domain (triangle) and a downstream degradation domain (four box repeat). When the RBP is present, it binds the aptamer and prevents HHR cleavage, keeping the degradation domain attached to the mRNA and leading to its degradation. In the absence of RBP, the HHR cleaves the degradation domain, allowing the stabilizing domain to protect the mRNA from degradation.

To enhance the functionality of the ARES OFF switch, described herein is a third variation that leverages ARES ON switches in combination with 3' UTR stabilizing and destabilizing domains.[24] In this design, a stabilizing domain is placed immediately after the stop codon of the payload, followed by the ARES ON switch, and then a destabilizing domain positioned before the poly-A tail (FIG. 22).

Under normal conditions, the presence of the destabilizing domain signals the transcript for degradation before translation can occur. When the RBP is present, it prevents HHR cleavage, ensuring that the degradation domain remains attached to the transcript, thereby maintaining its instability and preventing translation. Conversely, in the absence of the RBP, the HHR cleaves the degradation domain off the transcript. In this scenario, the stabilizing domain compensates for the loss of the poly-A tail, preventing further degradation and allowing translation of the payload to proceed.

This design aims to improve the effectiveness of the ARES OFF switch by introducing a more precise mechanism for regulating mRNA stability and translation in response to protein signals.

Self-Amplifying RNA (saRNA)

Figure 23A:
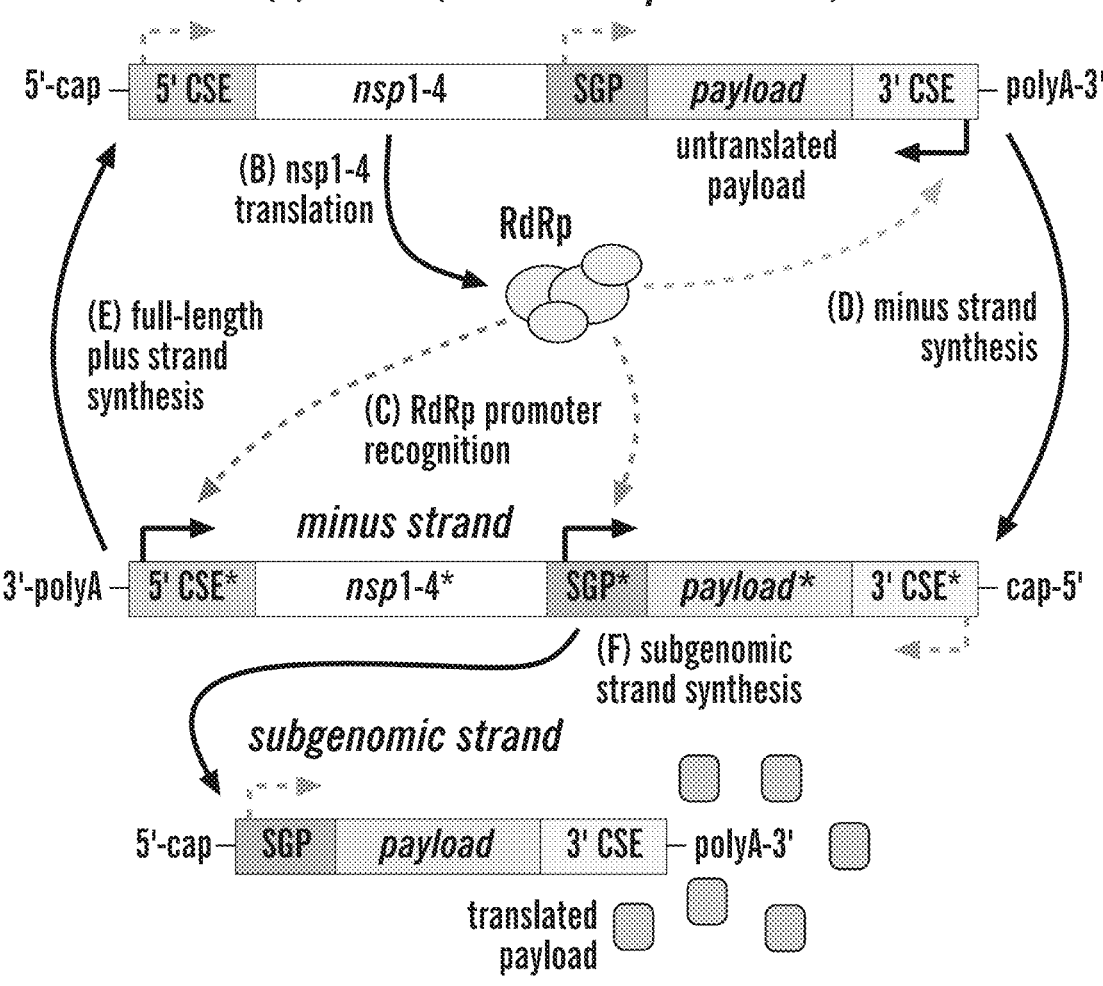
FIG. 23A-23B: Life Cycle of Self-Amplifying RNA (saRNA) and Integration of ARES Switch.

To further expand the functionality of ARES technology, the switches are tested in self-amplifying RNA (saRNA). saRNA presents a promising application for ARES due to its potential to reduce dosage requirements and minimize the need for multiple injections in mRNA-based therapies.[25] Additionally, a key limitation of current ARES technology is the challenge of preventing HHR cleavage before the RNA reaches its intended sensing location. The unique replication cycle of saRNA offers an advantageous mechanism for delivering ARES switches (FIG. 23A).

In the saRNA replication cycle, non-structural proteins (nsPs) are first translated to produce the RNA-dependent RNA polymerase (RdRp). The RdRp synthesizes a complementary negative-sense strand from the delivered saRNA. From this negative-sense strand, the RdRp generates both a full-length positive-sense saRNA strand and a positive-sense subgenomic strand. Translation of the payload occurs only from the subgenomic strand.[25,26] By integrating the ARES switch into the negative-sense strand, precise control can be gained over the timing and localization of payload expression while hindering the HHR activity during delivery.

For example, in the case of an ARES ON switch, the presence of the corresponding RBP would stabilize the negative-sense strand, allowing for the replication of the positive-sense strand and subsequent payload expression. Conversely, in the absence of the RBP, the HHR would cleave the negative strand, preventing the transcription of the positive strand and effectively blocking payload translation.

Figure 23B:
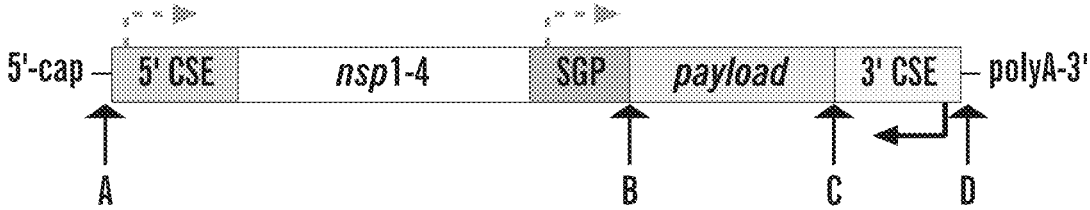

To implement this approach, the optimal placement of the HHR within the saRNA system is first determined. Four locations are being evaluated: (1) within the 5' UTR before the 5' conserved sequence element (CSE), (2) between the sub-genomic promoter and the payload, (3) between the payload and the 3' (CSE), and (4) between the 3' CSE and the poly-A tail (FIG. 23B). Once the most effective location is identified, the top-performing ARES ON switches will be tested in this context to assess their functionality and regulatory efficiency.

Modified NTPs and/or proteins can be utilized in the initial in vitro transcription reaction to create the saRNA strand to prevent ribozyme cleavage until delivery to a cell. Chemical modifications (e.g., modified bases) can be introduced into the saRNA containing the ARES region(s) (e.g., in the sense direction) such that the modification disrupts the function of the ribozyme and ensures the complete saRNA is delivered into the cell without any ribozyme cleavage. As the saRNA is replicated in the cell, the RdRp will eventually synthesize positive sense saRNA copies that do not comprise chemical modifications (e.g., modified bases) and contain an active ribozyme so that the ARES regulatory functions are activated. Non-limiting examples of such modified bases include 5-hydroxymethylcytidine, 5-methylcytidine, and/or 5-methyluridine. Without wishing to be bound by theory, it is expected that at least the cytidine modifications (e.g.,5-hydroxymethylcytidine and/or 5-methylcytidine) can disrupt function since the ribozyme self-cleavage site is immediately 3' of a cytosine.

REFERENCES

1. Qin, S., Tang, X., Chen, Y., Chen, K., Fan, N., Xiao, W., Zheng, Q., Li, G., Teng, Y., Wu, M., & Song, X. (2022).

mRNA-based therapeutics: powerful and versatile tools to combat diseases. *Signal transduction and targeted therapy,* 7(1), 166.

2. Ohner, E., Yang, R., Foo, K. S., Goedel, A., Chien, K. R. (2022). Unlocking the promise of mRNA therapeutics. *Nat Biotechnol* 40, 1586-1600.

3. Wroblewska, L., Kitada, T., Endo, K. et al. Mammalian synthetic circuits with RNA binding proteins for RNA-only delivery. Nat Biotechnol 33, 839-841 (2015). DOI: 10.1038/nbt.3301

4. Fesnak, A. D., June, C. H., & Levine, B. L. (2016). Engineered T cells: the promise and challenges of cancer immunotherapy. Nature reviews. Cancer, 16(9), 566-581.

5. Molla, G., & Bitew, M. (2024). Revolutionizing Personalized Medicine: Synergy with Multi-Omics Data Generation, Main Hurdles, and Future Perspectives. Biomedicines, 12(12), 2750.

6. Saw, P. E., & Song, E. (2024). Advancements in clinical RNA therapeutics: Present developments and prospective outlooks. Cell reports. Medicine, 5(5), 101555.

7. Tinafar, A., Jaenes, K., & Pardee, K. (2019). Synthetic Biology Goes Cell-Free. BMC biology, 17(1), 64.

8. Ono, H., & Saito, H. (2023). Sensing intracellular signatures with synthetic mRNAs. RNA biology, 20(1), 588-602.

9. Flynn, C. D., Chang, D., Mahmud, A., Yousefi, H., Das, J., Riordan, K. T., Sargent, E. H., & Kelley, S. O. (2023). Biomolecular sensors for advanced physiological monitoring. Nature reviews bioengineering, 1-16. Advance online publication.

10. Karagyaur, M., Primak, A., Efimenko, A., Skryabina, M., & Tkachuk, V. (2022). The Power of Gene Technologies: 1001 Ways to Create a Cell Model. Cells, 11(20), 3235.

11. Dykstra, P. B., Kaplan, M., & Smolke, C. D. (2022). Engineering synthetic RNA devices for cell control. Nature reviews. Genetics, 23(4), 215-228.

12. Zhu, W. S., Wheeler, B. D., & Ansel, K. M. (2023). RNA circuits and RNA-binding proteins in T cells. Trends in immunology, 44(10), 792-806.

13. Jiang, H., Xi, H., Juhas, M., & Zhang, Y. (2021). Biosensors for Point Mutation Detection. Frontiers in bioengineering and biotechnology, 9, 797831.

14. Self, W. K., Schoch, K. M., Alex, J., Barth6lemy, N., Bollinger, J. G., Sato, C., Cole, T., Kordasiewicz, H. B., Swayze, E., Bateman, R. J., & Miller, T. M. (2018). Protein production is an early biomarker for RNA-targeted therapies. Annals of clinical and translational neurology, 5(12), 1492-1504.

15. Bashor, C. J., Hilton, I. B., Bandukwala, H., Smith, D. M., & Veiseh, O. (2022). Engineering the next generation of cell-based therapeutics. Nature reviews. *Drug discovery,* 21(9), 655-675.

16. Vlatkovic I. (2021). Non-Immunotherapy Application of LNP-mRNA: Maximizing Efficacy and Safety. *Biomedicines,* 9(5), 530.

17. Bayer, T. S., Booth, L. N., Knudsen, S. M., & Ellington, A. D. (2005). Arginine-rich motifs present multiple interfaces for specific binding by RNA. *RNA (New York, N. Y.),* 11(12), 1848-1857.

18. Johansson, H. E., Dertinger, D., LeCuyer, K. A., Behlen, L. S., Greef, C. H., & Uhlenbeck, O. C. (1998). A thermodynamic analysis of the sequence-specific binding of RNA by bacteriophage MS2 coat protein. *Proceedings of the National Academy of Sciences of the United States of America,* 95(16), 9244-9249.

19. Sachdeva, G., Garg, A., Godding, D., Way, J. C., & Silver, P. A. (2014). In vivo co-localization of enzymes on RNA scaffolds increases metabolic production in a geometrically dependent manner. *Nucleic acids research,* 42(14), 9493-9503.

20. Athanassiou, Z., Dias, R. L., Moehle, K., Dobson, N., Varani, G., & Robinson, J. A. (2004). Structural mimicry of retroviral tat proteins by constrained beta-hairpin peptidomimetics: ligands with high affinity and selectivity for viral TAR RNA regulatory elements. *Journal of the American Chemical Society,* 126(22), 6906-6913.

21. Chai, C., Xie, Z., & Grotewold, E. (2011). SELEX (Systematic Evolution of Ligands by EXponential Enrichment), as a powerful tool for deciphering the protein-DNA interaction space. *Methods in molecular biology (Clifton, N. J.),* 754, 249-258.

22. Wroblewska, L., Kitada, T., Endo, K. et al. Mammalian synthetic circuits with RNA binding proteins for RNA-only delivery. Nat Biotechnol 33, 839-841 (2015).

23. Zadeh, J. N., Steenberg, C. D., Bois, J. S., Wolfe, B. R., Pierce, M. B., Khan, A. R., Dirks, R. M., & Pierce, N. A. (2011). NUPACK: Analysis and design of nucleic acid systems. *Journal of computational chemistry,* 32(1), 170-173.

24. Wroblewska, L., Kitada, T., Endo, K., Siciliano, V., Stillo, B., Saito, H., & Weiss, R. (2015). Mammalian synthetic circuits with RNA binding proteins for RNA-only delivery. Nature biotechnology, 33(8), 839-841.

25. Silva-Pilipich, N., Beloki, U., Salaberry, L., & Smerdou, C. (2024). Self-Amplifying RNA: A Second Revolution of mRNA Vaccines against COVID-19. Vaccines, 12(3), 318.

26. Bloom, K., van den Berg, F., & Arbuthnot, P. (2021). Self-amplifying RNA vaccines for infectious diseases. Gene therapy, 28(3-4), 117-129.

Example 3: Exemplary Sequences

Tables 4-11 below contain exemplary ARES region sequences.

TABLE 4

| Exemplary MS2 ON switches | | |
|---|---|---|
| SEQ ID NO: | Name | Sequence |
| 9 | MS2_a2_b7_c0 | ACGCGCACGagcaucagcCGUGCGCGUCCUGGAUUCGCGGA AACGCGUACAUCCAGCUGACGAGUCCCAAAUAGGACGA AACGCGCA |
| 10 | MS2_a3_b5_c1 | CGCGCACGagcaucagcCGUGCGCGUCCUGGAUUCGCGGAA ACGCGUACAUCCAGCUGACGAGUCCCAAAUAGGACGAA ACGCGC |

TABLE 4-continued

Exemplary MS2 ON switches

| SEQ ID NO: | Name | Sequence |
|---|---|---|
| 11 | MS2_a3_b6_c0 | ACGCGCACGagcaucagcCGUGCGCGUCCUGGAUUCGCGGA<br>AACGCGUACAUCCAGCUGACGAGUCCCAAAUAGGACGA<br>AACGCGC |
| 12 | MS2_a0_b6_c1 | CGCACGagcaucagcCGUGCGUCCUGGAUUCGCGGAAACGC<br>GUACAUCCAGCUGACGAGUCCCAAAUAGGACGAAACGC<br>ACG |
| 13 | MS2_a4_b5_c1 | CGCGGCACGagcaucagcCGUGCCGCGUCCUGGAUUCGCGG<br>AAACGCGUACAUCCAGCUGACGAGUCCCAAAUAGGACG<br>AAACGCGG |
| 14 | MS2_a4_b6_c0 | ACGCGGCACGagcaucagcCGUGCCGCGUCCUGGAUUCGCG<br>GAAACGCGUACAUCCAGCUGACGAGUCCCAAAUAGGAC<br>GAAACGCGG |
| 15 | MS2_a1_b5_c1 | CGCACGagcaucagcCGUGCGUCCUGGAUUCGCGGAAACGC<br>GUACAUCCAGCUGACGAGUCCCAAAUAGGACGAAACGC<br>AC |
| 16 | MS2_a1_b6_c0 | ACGCACGagcaucagcCGUGCGUCCUGGAUUCGCGGAAACG<br>CGUACAUCCAGCUGACGAGUCCCAAAUAGGACGAAACG<br>CAC |
| 17 | MS2_a2_b5_c1 | CGGCACGagcaucagcCGUGCCGUCCUGGAUUCGCGGAAAC<br>GCGUACAUCCAGCUGACGAGUCCCAAAUAGGACGAAAC<br>GGCA |
| 18 | MS2_a2_b6_c0 | ACGGCACGagcaucagcCGUGCCGUCCUGGAUUCGCGGAAA<br>CGCGUACAUCCAGCUGACGAGUCCCAAAUAGGACGAAA<br>CGGCA |
| 19 | MS2_a0_b6_c0 | AGCACGagcaucagcCGUGCUCCUGGAUUCGCGGAAACGCG<br>UACAUCCAGCUGACGAGUCCCAAAUAGGACGAAAGCAC<br>G |
| 20 | MS2_a0_b7_c4 | GCGCACGagcaucagcCGUGCGCGCGUCCUGGAUUCGCGGA<br>AACGCGUACAUCCAGCUGACGAGUCCCAAAUAGGACGA<br>AACGCGCGCACG |
| 21 | MS2_a1_b5_c3 | CGCACGagcaucagcCGUGCGCGUCCUGGAUUCGCGGAAAC<br>GCGUACAUCCAGCUGACGAGUCCCAAAUAGGACGAAAC<br>GCGCAC |
| 22 | MS2_a0_b7_c0 | ACGCACGagcaucagcCGUGCGUCCUGGAUUCGCGGAAACG<br>CGUACAUCCAGCUGACGAGUCCCAAAUAGGACGAAACG<br>CACG |
| 23 | MS2_a1_b7_c1 | CGCGCACGagcaucagcCGUGCGCGUCCUGGAUUCGCGGAA<br>ACGCGUACAUCCAGCUGACGAGUCCCAAAUAGGACGAA<br>ACGCGCAC |
| 24 | FLIPPED_MS2_<br>a0_b6_c1 | CGCACGUCCUGGAUUCGCGGAAACGCGUACAUCCAGCU<br>GACGAGUCCCAAAUAGGACGAAACGUGCGAGCAUCAGC<br>CGCACG |
| 25 | FLIPPED_MS2_<br>a2_b5_c1 | CGGCAUCCUGGAUUCGCGGAAACGCGUACAUCCAGCUG<br>ACGAGUCCCAAAUAGGACGAAAUGCCGCGAGCAUCAGC<br>CGCGGCA |
| 26 | FLIPPED_MS2_<br>a2_b6_c0 | ACGGCACCUGGAUUCGCGGAAACGCGUACAUCCAGCUG<br>ACGAGUCCCAAAUAGGACGAAAUGCCGUCGAGCAUCAGC<br>CGACGGCA |

TABLE 5

Exemplary MS2 OFF switches (with 2 stabilization stems)

| SEQ ID NO: | Name | Sequence |
|---|---|---|
| 27 | MS2_a4_b6_c1_d0 | CCGCGCGAUAAGGCGCGGCACGAGCAUCAGCCGUGC<br>CGCGCGAUAAGGCGCGGUCCUGGAUUCGCGGAAACG |

TABLE 5-continued

| SEQ ID NO: | Name | Sequence |
|---|---|---|
| | | Exemplary MS2 OFF switches (with 2 stabilization stems) |
| | | CGUACAUCCAGCUGACGAGUCCCAAAUAGGACGAAA<br>CCGCGC |
| 28 | MS2_a4_b6_c1_d1 | CCGCGCGGAUAAGCGCGCGGCACGAGCAUCAGCCGU<br>GCCGCGCCGAUAAGGGCGCGGUCCUGGAUUCGCGGA<br>AACGCGUACAUCCAGCUGACGAGUCCCAAAUAGGAC<br>GAAACCGCGC |
| 29 | MS2_a4_b6_c1_d4 | CCGCGCUCCGGAUAAGCGGAGCGCGGCACGAGCAUC<br>AGCCGUGCCGCGCCGGAGAUAAGUCCGGCGCGGUCC<br>UGGAUUCGCGGAAACGCGUACAUCCAGCUGACGAGU<br>CCCAAAUAGGACGAAACCGCGC |
| 30 | MS2_a3_b6_c2_d0 | GCGCGCGAUAAGGCGCGCACGAGCAUCAGCCGUGCG<br>CGCGAUAAGGCGCGCGUCCUGGAUUCGCGGAAACGC<br>GUACAUCCAGCUGACGAGUCCCAAAUAGGACGAAAC<br>GCGCGC |
| 31 | MS2_a4_b6_c1_d3 | CCGCGCCCGGAUAAGCGGGCGCGGCACGAGCAUCAG<br>CCGUGCCGCGCCGGGAUAAGCCGGCGCGGUCCUGGA<br>UUCGCGGAAACGCGUACAUCCAGCUGACGAGUCCCA<br>AAUAGGACGAAACCGCGC |
| 32 | MS2_a4_b6_c1_d2 | CCGCGCCGGAUAAGCGGCGCGGCACGAGCAUCAGCC<br>GUGCCGCGCCGGAUAAGCGGCGCGGUCCUGGAUUCG<br>CGGAAACGCGUACAUCCAGCUGACGAGUCCCAAAUA<br>GGACGAAACCGCGC |
| 33 | MS2_a3_b6_c2_d1 | GCGCGCGGAUAAGCGCGCGCACGAGCAUCAGCCGUG<br>CGCGCCGAUAAGGGCGCGCGUCCUGGAUUCGCGGAA<br>ACGCGUACAUCCAGCUGACGAGUCCCAAAUAGGACG<br>AAACGCGCGC |
| 34 | MS2_a3_b6_c2_d4 | GCGCGCUCCGGAUAAGCGGAGCGCGCACGAGCAUCA<br>GCCGUGCGCGCCGGAGAUAAGUCCGGCGCGCGUCCU<br>GGAUUCGCGGAAACGCGUACAUCCAGCUGACGAGUC<br>CCAAAUAGGACGAAACGCGCGC |
| 35 | MS2_a2_b6_c3_d0 | UGCCGCGAUAAGGCGGCACGAGCAUCAGCCGUGCCG<br>CGAUAAGGCGGCACGUCCUGGAUUCGCGGAAACGCG<br>UACAUCCAGCUGACGAGUCCCAAAUAGGACGAAACG<br>UGCCGC |
| 36 | MS2_a3_b6_c2_d3 | GCGCGCCCGGAUAAGCGGGCGCGCACGAGCAUCAGC<br>CGUGCGCGCCGGGAUAAGCCGGCGCGCGUCCUGGAU<br>UCGCGGAAACGCGUACAUCCAGCUGACGAGUCCCAA<br>AUAGGACGAAACGCGCGC |
| 37 | MS2_a3_b6_c2_d2 | GCGCGCCGGAUAAGCGGCGCGCACGAGCAUCAGCCG<br>UGCGCGCCGGAUAAGCGGCGCGCGUCCUGGAUUCGC<br>GGAAACGCGUACAUCCAGCUGACGAGUCCCAAAUAG<br>GACGAAACGCGCGC |
| 38 | MS2_a2_b6_c3_d1 | UGCCGCGGAUAAGCGCGGCACGAGCAUCAGCCGUGC<br>CGCCGAUAAGGGCGGCACGUCCUGGAUUCGCGGAAA<br>CGCGUACAUCCAGCUGACGAGUCCCAAAUAGGACGA<br>AACGUGCCGC |
| 39 | MS2_a2_b6_c3_d4 | UGCCGCUCCGGAUAAGCGGAGCGGCACGAGCAUCAG<br>CCGUGCCGCCGGAGAUAAGUCCGGCGGCACGUCCUG<br>GAUUCGCGGAAACGCGUACAUCCAGCUGACGAGUCC<br>CAAAUAGGACGAAACGUGCCGC |
| 40 | MS2_a1_b6_c4_d0 | GUGCGCGAUAAGGCGCACGAGCAUCAGCCGUGCGCG<br>AUAAGGCGCACGCGUCCUGGAUUCGCGGAAACGCGU<br>ACAUCCAGCUGACGAGUCCCAAAUAGGACGAAACGC<br>GUGCGC |
| 41 | MS2_a2_b6_c3_d3 | UGCCGCCCGGAUAAGCGGGCGGCACGAGCAUCAGCC<br>GUGCCGCCGGGAUAAGCCGGCGGCACGUCCUGGAUU<br>CGCGGAAACGCGUACAUCCAGCUGACGAGUCCCAAA<br>UAGGACGAAACGUGCCGC |

TABLE 5-continued

Exemplary MS2 OFF switches (with 2 stabilization stems)

| SEQ ID NO: | Name | Sequence |
|---|---|---|
| 42 | MS2_a2_b6_c3_d2 | UGCCGCCGGAUAAGCGGCGGCACGAGCAUCAGCCGU GCCGCCGGAUAAGCGGCGGCACGUCCUGGAUUCGCG GAAACGCGUACAUCCAGCUGACGAGUCCCAAAUAGG ACGAAACGUGCCGC |
| 43 | MS2_a1_b6_c4_d1 | GUGCGCGGAUAAGCGCGCACGAGCAUCAGCCGUGCG CCGAUAAGGGCGCACGCGUCCUGGAUUCGCGGAAAC GCGUACAUCCAGCUGACGAGUCCCAAAUAGGACGAA ACGCGUGCGC |
| 44 | MS2_a1_b6_c4_d4 | GUGCGCUCCGGAUAAGCGGAGCGCACGAGCAUCAGC CGUGCGCCGGAGAUAAGUCCGGCGCACGCGUCCUGG AUUCGCGGAAACGCGUACAUCCAGCUGACGAGUCCC AAAUAGGACGAAACGCGUGCGC |
| 45 | MS2_a1_b6_c4_d3 | GUGCGCCCGGAUAAGCGGGCGCACGAGCAUCAGCCG UGCGCCGGGAUAAGCCGGCGCACGCGUCCUGGAUUC GCGGAAACGCGUACAUCCAGCUGACGAGUCCCAAAU AGGACGAAACGCGUGCGC |
| 46 | MS2_a1_b6_c4_d2 | GUGCGCCGGAUAAGCGGCGCACGAGCAUCAGCCGUG CGCCGGAUAAGCGGCGCACGCGUCCUGGAUUCGCGG AAACGCGUACAUCCAGCUGACGAGUCCCAAAUAGGA CGAAACGCGUGCGC |
| 47 | MS2_a3_b6_c1_d0 | GCCGCGGAUAAGCGCGGCACGAGCAUCAGCCGUGCC GCGGAUAAGCGCGGCUCCUGGAUUCGCGGAAACGCG UACAUCCAGCUGACGAGUCCCAAAUAGGACGAAAGC CGCG |
| 48 | MS2_a3_b6_c1_d4 | GCCGCGUCCGGAUAAGCGGACGCGGCACGAGCAUCA GCCGUGCCGCGCGGAGAUAAGUCCGCGCGGCUCCUG GAUUCGCGGAAACGCGUACAUCCAGCUGACGAGUCC CAAAUAGGACGAAAGCCGCG |
| 49 | MS2_a3_b6_c1_d1 | GCCGCGGGAUAAGCCGCGGCACGAGCAUCAGCCGUG CCGCGCGAUAAGGCGCGGCUCCUGGAUUCGCGGAAA CGCGUACAUCCAGCUGACGAGUCCCAAAUAGGACGA AAGCCGCG |
| 50 | MS2_a3_b6_c1_d3 | GCCGCGCCGGAUAAGCGGCGCGGCACGAGCAUCAGC CGUGCCGCGCGGGAUAAGCCGCGCGGCUCCUGGAUU CGCGGAAACGCGUACAUCCAGCUGACGAGUCCCAAA UAGGACGAAAGCCGCG |
| 51 | MS2_a3_b6_c1_d2 | GCCGCGCGGAUAAGCGCGCGGCACGAGCAUCAGCCG UGCCGCGCGGAUAAGCGCGCGGCUCCUGGAUUCGCG GAAACGCGUACAUCCAGCUGACGAGUCCCAAAUAGG ACGAAAGCCGCG |
| 52 | MS2_a1_b6_c3_d0 | GUGCCGGAUAAGCGGCACGAGCAUCAGCCGUGCCGG AUAAGCGGCACCGUCCUGGAUUCGCGGAAACGCGUA CAUCCAGCUGACGAGUCCCAAAUAGGACGAAACGGU GCCG |
| 53 | MS2_a1_b6_c3_d4 | GUGCCGUCCGGAUAAGCGGACGGCACGAGCAUCAGC CGUGCCGCGGAGAUAAGUCCGCGGCACCGUCCUGGA UUCGCGGAAACGCGUACAUCCAGCUGACGAGUCCCA AAUAGGACGAAACGGUGCCG |
| 54 | MS2_a2_b6_c2_d0 | UGCGCGGAUAAGCGCGCACGAGCAUCAGCCGUGCGC GGAUAAGCGCGCAGUCCUGGAUUCGCGGAAACGCGU ACAUCCAGCUGACGAGUCCCAAAUAGGACGAAACUG CGCG |
| 55 | MS2_a0_b6_c4_d0 | CGUGCGGAUAAGCGCACGAGCAUCAGCCGUGCGGAU AAGCGCACGGCGUCCUGGAUUCGCGGAAACGCGUAC AUCCAGCUGACGAGUCCCAAAUAGGACGAAACGCCG UGCG |
| 56 | MS2_a1_b6_c3_d1 | GUGCCGGGAUAAGCCGGCACGAGCAUCAGCCGUGCC GCGAUAAGGCGGCACCGUCCUGGAUUCGCGGAAACG CGUACAUCCAGCUGACGAGUCCCAAAUAGGACGAAA CGGUGCCG |

TABLE 5-continued

| SEQ ID NO: | Name | Sequence |
|---|---|---|

Exemplary MS2 OFF switches (with 2 stabilization stems)

| SEQ ID NO: | Name | Sequence |
|---|---|---|
| 57 | MS2_a1_b6_c3_d3 | GUGCCGCCGGAUAAGCGGCGGCACGAGCAUCAGCCG UGCCGCGGGAUAAGCCGCGGCACCGUCCUGGAUUCG CGGAAACGCGUACAUCCAGCUGACGAGUCCCAAAUA GGACGAAACGGUGCCG |
| 58 | MS2_a1_b6_c3_d2 | GUGCCGCGGAUAAGCGCGGCACGAGCAUCAGCCGUG CCGCGGAUAAGCGCGGCACCGUCCUGGAUUCGCGGA AACGCGUACAUCCAGCUGACGAGUCCCAAAUAGGAC GAAACGGUGCCG |
| 59 | MS2_a4_b6_c0_d0 | CACGCGGAUAAGCGCGUGCACGAGCAUCAGCCGUGC ACGCGGAUAAGCGCGUGCCUGGAUUCGCGGAAACGC GUACAUCCAGCUGACGAGUCCCAAAUAGGACGAACA CGCG |
| 60 | MS2_a2_b6_c2_d4 | UGCGCGUCCGGAUAAGCGGACGCGCACGAGCAUCAG CCGUGCGCGCGGAGAUAAGUCCGCGCGCAGUCCUGG AUUCGCGGAAACGCGUACAUCCAGCUGACGAGUCCC AAAUAGGACGAAACUGCGCG |
| 61 | MS2_a0_b6_c4_d4 | CGUGCGUCCGGAUAAGCGGACGCGCACGAGCAUCAGCC GUGCGCGGAGAUAAGUCCGCGCACGGCGUCCUGGAU UCGCGGAAACGCGUACAUCCAGCUGACGAGUCCCAA AUAGGACGAAACGCCGUGCG |
| 62 | MS2_a2_b6_c2_d1 | UGCGCGGGAUAAGCCGCGCACGAGCAUCAGCCGUGC GCGCGAUAAGGCGCGCAGUCCUGGAUUCGCGGAAAC GCGUACAUCCAGCUGACGAGUCCCAAAUAGGACGAA ACUGCGCG |
| 63 | MS2_a0_b6_c4_d1 | CGUGCGGGAUAAGCCGCACGAGCAUCAGCCGUGCGC GAUAAGGCGCACGGCGUCCUGGAUUCGCGGAAACGC GUACAUCCAGCUGACGAGUCCCAAAUAGGACGAAAC GCCGUGCG |
| 64 | MS2_a2_b6_c2_d3 | UGCGCGCCGGAUAAGCGGCGCGCACGAGCAUCAGCC GUGCGCGCGGGAUAAGCCGCGCGCAGUCCUGGAUUC GCGGAAACGCGUACAUCCAGCUGACGAGUCCCAAAU AGGACGAAACUGCGCG |
| 65 | MS2_a0_b6_c4_d3 | CGUGCGCCGGAUAAGCGGCGCACGAGCAUCAGCCGU GCGCGGGAUAAGCCGCGCACGGCGUCCUGGAUUCGC GGAAACGCGUACAUCCAGCUGACGAGUCCCAAAUAG GACGAAACGCCGUGCG |
| 66 | MS2_a2_b6_c2_d2 | UGCGCGCGGAUAAGCGCGCGCACGAGCAUCAGCCGU GCGCGCGGAUAAGCGCGCGCAGUCCUGGAUUCGCGG AAACGCGUACAUCCAGCUGACGAGUCCCAAAUAGGA CGAAACUGCGCG |
| 67 | MS2_a0_b6_c4_d2 | CGUGCGCGGAUAAGCGCGCACGAGCAUCAGCCGUGC GCGGAUAAGCGCGCACGGCGUCCUGGAUUCGCGGAA ACGCGUACAUCCAGCUGACGAGUCCCAAAUAGGACG AAACGCCGUGCG |
| 68 | MS2_a4_b6_c0_d4 | CACGCGUCCGGAUAAGCGGACGCGUGCACGAGCAUC AGCCGUGCACGCGCGGAGAUAAGUCCGCGCGUGCCU GGAUUCGCGGAAACGCGUACAUCCAGCUGACGAGUC CCAAAUAGGACGAACACGCG |
| 69 | MS2_a4_b6_c0_d1 | CACGCGGGAUAAGCCGCGUGCACGAGCAUCAGCCGU GCACGCGCGAUAAGGCGCGUGCCUGGAUUCGCGGAA ACGCGUACAUCCAGCUGACGAGUCCCAAAUAGGACG AACACGCG |
| 70 | MS2_a4_b6_c0_d3 | CACGCGCCGGAUAAGCGGCGCGUGCACGAGCAUCAG CCGUGCACGCGCGGGAUAAGCCGCGCGUGCCUGGAU UCGCGGAAACGCGUACAUCCAGCUGACGAGUCCCAA AUAGGACGAACACGCG |
| 71 | MS2_a4_b6_c0_d2 | CACGCGCGGAUAAGCGCGCGUGCACGAGCAUCAGCC GUGCACGCGCGGAUAAGCGCGCGUGCCUGGAUUCGC GGAAACGCGUACAUCCAGCUGACGAGUCCCAAAUAG GACGAACACGCG |

TABLE 5-continued

| Exemplary MS2 OFF switches (with 2 stabilization stems) | | |
|---|---|---|
| SEQ ID NO: | Name | Sequence |
| 72 | MS2_a2_b6_c1_d0 | UGCCGCGAUAAGGCGGCACGAGCAUCAGCCGUGCCG<br>CGAUAAGGCGGCAUCCUGGAUUCGCGGAAACGCGUA<br>CAUCCAGCUGACGAGUCCCAAAUAGGACGAAAUGCC<br>GC |
| 73 | MS2_a0_b6_c3_d0 | CGUGCCGAUAAGGGCACGAGCAUCAGCCGUGCCGAU<br>AAGGGCACGCGUCCUGGAUUCGCGGAAACGCGUACA<br>UCCAGCUGACGAGUCCCAAAUAGGACGAAACGCGUG<br>CC |
| 74 | MS2_a3_b6_c0_d0 | GCACGCGAUAAGGCGUGCACGAGCAUCAGCCGUGCA<br>CGCGAUAAGGCGUGCCCUGGAUUCGCGGAAACGCGU<br>ACAUCCAGCUGACGAGUCCCAAAUAGGACGAAGCAC<br>GC |
| 75 | MS2_a2_b6_c1_d1 | UGCCGCGGAUAAGCGCGGCACGAGCAUCAGCCGUGC<br>CGCCGAUAAGGGCGGCAUCCUGGAUUCGCGGAAACG<br>CGUACAUCCAGCUGACGAGUCCCAAAUAGGACGAAA<br>UGCCGC |
| 76 | MS2_a2_b6_c1_d4 | UGCCGCUCCGGAUAAGCGGAGCGGCACGAGCAUCAG<br>CCGUGCCGCCGGAGAUAAGUCCGGCGGCAUCCUGGA<br>UUCGCGGAAACGCGUACAUCCAGCUGACGAGUCCCA<br>AAUAGGACGAAAUGCCGC |
| 77 | MS2_a0_b6_c3_d1 | CGUGCCGGAUAAGCGGCACGAGCAUCAGCCGUGCCC<br>GAUAAGGGGCACGCGUCCUGGAUUCGCGGAAACGCG<br>UACAUCCAGCUGACGAGUCCCAAAUAGGACGAAACG<br>CGUGCC |
| 78 | MS2_a0_b6_c3_d4 | CGUGCCUCCGGAUAAGCGGAGGCACGAGCAUCAGCC<br>GUGCCCGGAGAUAAGUCCGGGCACGCGUCCUGGAUU<br>CGCGGAAACGCGUACAUCCAGCUGACGAGUCCCAAA<br>UAGGACGAAACGCGUGCC |
| 79 | MS2_a2_b6_c1_d3 | UGCCGCCCGGAUAAGCGGGCGGCACGAGCAUCAGCC<br>GUGCCGCCGGGAUAAGCCGGCGGCAUCCUGGAUUCG<br>CGGAAACGCGUACAUCCAGCUGACGAGUCCCAAAUA<br>GGACGAAAUGCCGC |
| 80 | MS2_a2_b6_c1_d2 | UGCCGCCGGAUAAGCGGCGGCACGAGCAUCAGCCGU<br>GCCGCCGGAUAAGCGGCGGCAUCCUGGAUUCGCGGA<br>AACGCGUACAUCCAGCUGACGAGUCCCAAAUAGGAC<br>GAAAUGCCGC |
| 81 | MS2_a3_b6_c0_d1 | GCACGCGGAUAAGCGCGUGCACGAGCAUCAGCCGUG<br>CACGCCGAUAAGGGCGUGCCCUGGAUUCGCGGAAAC<br>GCGUACAUCCAGCUGACGAGUCCCAAAUAGGACGAA<br>GCACGC |
| 82 | MS2_a1_b6_c2_d0 | GUGCGCGAUAAGGCGCACGAGCAUCAGCCGUGCGCG<br>AUAAGGCGCACGUCCUGGAUUCGCGGAAACGCGUAC<br>AUCCAGCUGACGAGUCCCAAAUAGGACGAAACGUGC<br>GC |
| 83 | MS2_a3_b6_c0_d4 | GCACGCUCCGGAUAAGCGGAGCGUGCACGAGCAUCA<br>GCCGUGCACGCCGGAGAUAAGUCCGGCGUGCCCUGG<br>AUUCGCGGAAACGCGUACAUCCAGCUGACGAGUCCC<br>AAAUAGGACGAAGCACGC |
| 84 | MS2_a0_b6_c3_d3 | CGUGCCCCGGAUAAGCGGGGCACGAGCAUCAGCCGU<br>GCCCGGGAUAAGCCGGGCACGCGUCCUGGAUUCGCG<br>GAAACGCGUACAUCCAGCUGACGAGUCCCAAAUAGG<br>ACGAAACGCGUGCC |
| 85 | MS2_a0_b6_c3_d2 | CGUGCCCGGAUAAGCGGGCACGAGCAUCAGCCGUGC<br>CCGGAUAAGCGGGCACGCGUCCUGGAUUCGCGGAAA<br>CGCGUACAUCCAGCUGACGAGUCCCAAAUAGGACGA<br>AACGCGUGCC |
| 86 | MS2_a3_b6_c0_d3 | GCACGCCCGGAUAAGCGGGCGUGCACGAGCAUCAGC<br>CGUGCACGCCGGGAUAAGCCGGCGUGCCCUGGAUUC<br>GCGGAAACGCGUACAUCCAGCUGACGAGUCCCAAAU<br>AGGACGAAGCACGC |

TABLE 5-continued

| Exemplary MS2 OFF switches (with 2 stabilization stems) | | |
| --- | --- | --- |
| SEQ ID NO: | Name | Sequence |
| 87 | MS2_a3_b6_c0_d2 | GCACGCCGGAUAAGCGGCGUGCACGAGCAUCAGCCG UGCACGCCGGAUAAGCGGCGUGCCCUGGAUUCGCGG AAACGCGUACAUCCAGCUGACGAGUCCCAAAUAGGA CGAAGCACGC |
| 88 | MS2_a1_b6_c2_d1 | GUGCGCGGAUAAGCGCGCACGAGCAUCAGCCGUGCG CCGAUAAGGGCGCACGUCCUGGAUUCGCGGAAACGC GUACAUCCAGCUGACGAGUCCCAAAUAGGACGAAAC GUGCGC |
| 89 | MS2_a1_b6_c2_d4 | GUGCGCUCCGGAUAAGCGGAGCGCACGAGCAUCAGC CGUGCGCCGGAGAUAAGUCCGGCGCACGUCCUGGAU UCGCGGAAACGCGUACAUCCAGCUGACGAGUCCCAA AUAGGACGAAACGUGCGC |
| 90 | MS2_a1_b6_c2_d3 | GUGCGCCCGGAUAAGCGGGCGCACGAGCAUCAGCCG UGCGCCGGGAUAAGCCGGCGCACGUCCUGGAUUCGC GGAAACGCGUACAUCCAGCUGACGAGUCCCAAAUAG GACGAAACGUGCGC |
| 91 | MS2_a1_b6_c2_d2 | GUGCGCCGGAUAAGCGGCGCACGAGCAUCAGCCGUG CGCCGGAUAAGCGGCGCACGUCCUGGAUUCGCGGAA ACGCGUACAUCCAGCUGACGAGUCCCAAAUAGGACG AAACGUGCGC |
| 92 | MS2_a1_b6_c1_d0 | GUGCCGGAUAAGCGGCACGAGCAUCAGCCGUGCCGG AUAAGCGGCACUCCUGGAUUCGCGGAAACGCGUACA UCCAGCUGACGAGUCCCAAAUAGGACGAAAGUGCCG |
| 93 | MS2_a1_b6_c1_d4 | GUGCCGUCCGGAUAAGCGGACGGCACGAGCAUCAGC CGUGCCGCGGAGAUAAGUCCGCGGCACUCCUGGAUU CGCGGAAACGCGUACAUCCAGCUGACGAGUCCCAAA UAGGACGAAAGUGCCG |
| 94 | MS2_a0_b6_c2_d0 | CGUGCGGAUAAGCGCACGAGCAUCAGCCGUGCGGAU AAGCGCACGGUCCUGGAUUCGCGGAAACGCGUACAU CCAGCUGACGAGUCCCAAAUAGGACGAAACCGUGCG |
| 95 | MS2_a1_b6_c1_d1 | GUGCCGGGAUAAGCGGCACGAGCAUCAGCCGUGCC GCGAUAAGGCGGCACUCCUGGAUUCGCGGAAACGCG UACAUCCAGCUGACGAGUCCCAAAUAGGACGAAAGU GCCG |
| 96 | MS2_a1_b6_c1_d3 | GUGCCGCCGGAUAAGCGGCGGCACGAGCAUCAGCCG UGCCGCGGGAUAAGCCGCGGCACUCCUGGAUUCGCG GAAACGCGUACAUCCAGCUGACGAGUCCCAAAUAGG ACGAAAGUGCCG |
| 97 | MS2_a1_b6_c1_d2 | GUGCCGCGGAUAAGCGCGGCACGAGCAUCAGCCGUG CCGCGGAUAAGCGCGGCACUCCUGGAUUCGCGGAAA CGCGUACAUCCAGCUGACGAGUCCCAAAUAGGACGA AAGUGCCG |
| 98 | MS2_a0_b6_c2_d4 | CGUGCGUCCGGAUAAGCGGACGCACGAGCAUCAGCC GUGCGCGGAGAUAAGUCCGCGCACGGUCCUGGAUUC GCGGAAACGCGUACAUCCAGCUGACGAGUCCCAAAU AGGACGAAACCGUGCG |
| 99 | MS2_a0_b6_c2_d1 | CGUGCGGGAUAAGCCGCACGAGCAUCAGCCGUGCGC GAUAAGGCGCACGGUCCUGGAUUCGCGGAAACGCGU ACAUCCAGCUGACGAGUCCCAAAUAGGACGAAACCG UGCG |
| 100 | MS2_a0_b6_c2_d3 | CGUGCGCCGGAUAAGCGGCGCACGAGCAUCAGCCGU GCGCGGGAUAAGCCGCGCACGGUCCUGGAUUCGCGG AAACGCGUACAUCCAGCUGACGAGUCCCAAAUAGGA CGAAACCGUGCG |
| 101 | MS2_a0_b6_c2_d2 | CGUGCGCGGAUAAGCGCGCACGAGCAUCAGCCGUGC GCGGAUAAGCGCGCACGGUCCUGGAUUCGCGGAAAC GCGUACAUCCAGCUGACGAGUCCCAAAUAGGACGAA ACCGUGCG |
| 102 | MS2_a2_b6_c0_d0 | UGCACGGAUAAGCGUGCACGAGCAUCAGCCGUGCAC GGAUAAGCGUGCACCUGGAUUCGCGGAAACGCGUAC AUCCAGCUGACGAGUCCCAAAUAGGACGAAUGCACG |

TABLE 5-continued

| SEQ ID NO: | Name | Sequence |
|---|---|---|
| | Exemplary MS2 OFF switches (with 2 stabilization stems) | |
| 103 | MS2_a0_b6_c1_d0 | CGUGCCGAUAAGGGCACGAGCAUCAGCCGUGCCGAU AAGGGCACGUCCUGGAUUCGCGGAAACGCGUACAUC CAGCUGACGAGUCCCAAAUAGGACGAAACGUGCC |
| 104 | MS2_a2_b6_c0_d4 | UGCACGUCCGGAUAAGCGGACGUGCACGAGCAUCAG CCGUGCACGCGGAGAUAAGUCCGCGUGCACCUGGAU UCGCGGAAACGCGUACAUCCAGCUGACGAGUCCCAA AUAGGACGAAUGCACG |
| 105 | MS2_a2_b6_c0_d1 | UGCACGGGAUAAGCCGUGCACGAGCAUCAGCCGUGC ACGCGAUAAGGCGUGCACCUGGAUUCGCGGAAACGC GUACAUCCAGCUGACGAGUCCCAAAUAGGACGAAUG CACG |
| 106 | MS2_a0_b6_c1_d1 | CGUGCCGGAUAAGCGGCACGAGCAUCAGCCGUGCCC GAUAAGGGGCACGUCCUGGAUUCGCGGAAACGCGUA CAUCCAGCUGACGAGUCCCAAAUAGGACGAAACGUG CC |
| 107 | MS2_a0_b6_c1_d4 | CGUGCCUCCGGAUAAGCGGAGGCACGAGCAUCAGCC GUGCCCGGAGAUAAGUCCGGGCACGUCCUGGAUUCG CGGAAACGCGUACAUCCAGCUGACGAGUCCCAAAUA GGACGAAACGUGCC |
| 108 | MS2_a2_b6_c0_d3 | UGCACGCCGGAUAAGCGGCGUGCACGAGCAUCAGCC GUGCACGCGGGAUAAGCCGCGUGCACCUGGAUUCGC GGAAACGCGUACAUCCAGCUGACGAGUCCCAAAUAG GACGAAUGCACG |
| 109 | MS2_a2_b6_c0_d2 | UGCACGCGGAUAAGCGCGUGCACGAGCAUCAGCCGU GCACGCGGAUAAGCGCGUGCACCUGGAUUCGCGGAA ACGCGUACAUCCAGCUGACGAGUCCCAAAUAGGACG AAUGCACG |
| 110 | MS2_a0_b6_c1_d3 | CGUGCCCCGGAUAAGCGGGGCACGAGCAUCAGCCGU GCCCGGGAUAAGCCGGGCACGUCCUGGAUUCGCGGA AACGCGUACAUCCAGCUGACGAGUCCCAAAUAGGAC GAAACGUGCC |
| 111 | MS2_a0_b6_c1_d2 | CGUGCCCGGAUAAGCGGGCACGAGCAUCAGCCGUGC CCGGAUAAGCGGGCACGUCCUGGAUUCGCGGAAACG CGUACAUCCAGCUGACGAGUCCCAAAUAGGACGAAA CGUGCC |
| 112 | MS2_a1_b6_c0_d0 | GUGCACGAUAAGGUGCACGAGCAUCAGCCGUGCACG AUAAGGUGCACCCUGGAUUCGCGGAAACGCGUACAU CCAGCUGACGAGUCCCAAAUAGGACGAAGUGCAC |
| 113 | MS2_a1_b6_c0_d1 | GUGCACGGAUAAGCGUGCACGAGCAUCAGCCGUGCA CCGAUAAGGGUGCACCCUGGAUUCGCGGAAACGCGU ACAUCCAGCUGACGAGUCCCAAAUAGGACGAAGUGC AC |
| 114 | MS2_a1_b6_c0_d4 | GUGCACUCCGGAUAAGCGGAGUGCACGAGCAUCAGC CGUGCACCGGAGAUAAGUCCGGUGCACCCUGGAUUC GCGGAAACGCGUACAUCCAGCUGACGAGUCCCAAAU AGGACGAAGUGCAC |
| 115 | MS2_a1_b6_c0_d3 | GUGCACCCGGAUAAGCGGGUGCACGAGCAUCAGCCG UGCACCGGGAUAAGCCGGUGCACCCUGGAUUCGCGG AAACGCGUACAUCCAGCUGACGAGUCCCAAAUAGGA CGAAGUGCAC |
| 116 | MS2_a1_b6_c0_d2 | GUGCACCGGAUAAGCGGUGCACGAGCAUCAGCCGUG CACCGGAUAAGCGGUGCACCCUGGAUUCGCGGAAAC GCGUACAUCCAGCUGACGAGUCCCAAAUAGGACGAA GUGCAC |
| 117 | MS2_a0_b6_c0_d0 | CGUGCAGAUAAGUGCACGAGCAUCAGCCGUGCAGAU AAGUGCACGCCUGGAUUCGCGGAAACGCGUACAUCC AGCUGACGAGUCCCAAAUAGGACGAACGUGCA |

TABLE 5-continued

| | Exemplary MS2 OFF switches (with 2 stabilization stems) | |
| --- | --- | --- |
| SEQ ID NO: | Name | Sequence |
| 118 | MS2_a0_b6_c0_d4 | CGUGCAUCCGGAUAAGCGGAUGCACGAGCAUCAGCC GUGCACGGAGAUAAGUCCGUGCACGCCUGGAUUCGC GGAAACGCGUACAUCCAGCUGACGAGUCCCAAAUAG GACGAACGUGCA |
| 119 | MS2_a0_b6_c0_d3 | CGUGCACCGGAUAAGCGGUGCACGAGCAUCAGCCGU GCACGGGAUAAGCCGUGCACGCCUGGAUUCGCGGAA ACGCGUACAUCCAGCUGACGAGUCCCAAAUAGGACG AACGUGCA |
| 120 | MS2_a0_b6_c0_d2 | CGUGCACGGAUAAGCGUGCACGAGCAUCAGCCGUGC ACGGAUAAGCGUGCACGCCUGGAUUCGCGGAAACGC GUACAUCCAGCUGACGAGUCCCAAAUAGGACGAACG UGCA |
| 121 | MS2_a0_b6_c0_d1 | CGUGCAGGAUAAGCUGCACGAGCAUCAGCCGUGCAC GAUAAGGUGCACGCCUGGAUUCGCGGAAACGCGUAC AUCCAGCUGACGAGUCCCAAAUAGGACGAACGUGCA |

TABLE 6

| | Exemplary PP7 ON switches | |
| --- | --- | --- |
| SEQ ID NO: | Name | Sequence |
| 122 | PP7_a1_b5_c1 | CGGCACAGAAGAUAUGGCUUCGUGCCGUCCUGGAUUCGC GGAAACGCGUACAUCCAGCUGACGAGUCCCAAAUAGGAC GAAACGGCA |
| 123 | PP7_a1_b5_c2 | GGGCACAGAAGAUAUGGCUUCGUGCCCGUCCUGGAUUCG CGGAAACGCGUACAUCCAGCUGACGAGUCCCAAAUAGGA CGAAACGGGCA |
| 124 | PP7_a1_b5_c3 | CGGCACAGAAGAUAUGGCUUCGUGCCGCGUCCUGGAUUC GCGGAAACGCGUACAUCCAGCUGACGAGUCCCAAAUAGG ACGAAACGCGGCA |
| 125 | PP7_a1_b5_c4 | GGGCACAGAAGAUAUGGCUUCGUGCCCGCGUCCUGGAUU CGCGGAAACGCGUACAUCCAGCUGACGAGUCCCAAAUAG GACGAAACGCGGGCA |
| 126 | PP7_a2_b5_c1 | CGGGCACAGAAGAUAUGGCUUCGUGCCCGUCCUGGAUUC GCGGAAACGCGUACAUCCAGCUGACGAGUCCCAAAUAGG ACGAAACGGGC |
| 127 | PP7_a2_b5_c2 | GCGGCACAGAAGAUAUGGCUUCGUGCCGCGUCCUGGAUU CGCGGAAACGCGUACAUCCAGCUGACGAGUCCCAAAUAG GACGAAACGCGGC |
| 128 | PP7_a2_b5_c3 | CGGGCACAGAAGAUAUGGCUUCGUGCCCGCGUCCUGGAU UCGCGGAAACGCGUACAUCCAGCUGACGAGUCCCAAAUA GGACGAAACGCGGGC |
| 129 | PP7_a2_b5_c4 | GCGGCACAGAAGAUAUGGCUUCGUGCCGCGCGUCCUGGA UUCGCGGAAACGCGUACAUCCAGCUGACGAGUCCCAAAU AGGACGAAACGCGCGGC |
| 130 | PP7_a3_b5_c1 | CGCGGCACAGAAGAUAUGGCUUCGUGCCGCGUCCUGGAU UCGCGGAAACGCGUACAUCCAGCUGACGAGUCCCAAAUA GGACGAAACGCGG |
| 131 | PP7_a3_b5_c2 | GCGGGCACAGAAGAUAUGGCUUCGUGCCCGCGUCCUGGA UUCGCGGAAACGCGUACAUCCAGCUGACGAGUCCCAAAU AGGACGAAACGCGGG |
| 132 | PP7_a3_b5_c3 | CGCGGCACAGAAGAUAUGGCUUCGUGCCGCGCGUCCUGG AUUCGCGGAAACGCGUACAUCCAGCUGACGAGUCCCAAA UAGGACGAAACGCGCGG |
| 133 | PP7_a4_b5_c1 | CGCGGGCACAGAAGAUAUGGCUUCGUGCCCGCGUCCUGG AUUCGCGGAAACGCGUACAUCCAGCUGACGAGUCCCAAA UAGGACGAAACGCGGG |

TABLE 6-continued

Exemplary PP7 ON switches

| SEQ ID NO: | Name | Sequence |
|---|---|---|
| 134 | PP7_a4_b5_c2 | GCGCGGCACAGAAGAUAUGGCUUCGUGCCGCGCGUCCUG GAUUCGCGGAAACGCGUACAUCCAGCUGACGAGUCCCAA AUAGGACGAAACGCGCG |
| 135 | PP7_a0_b6_c0 | AGGCACAGAAGAUAUGGCUUCGUGCCUCCUGGAUUCGCG GAAACGCGUACAUCCAGCUGACGAGUCCCAAAUAGGACG AAAGGCAC |
| 136 | PP7_a0_b6_c1 | CGGCACAGAAGAUAUGGCUUCGUGCCGUCCUGGAUUCGC GGAAACGCGUACAUCCAGCUGACGAGUCCCAAAUAGGAC GAAACGGCAC |
| 137 | PP7_a0_b6_c2 | GGGCACAGAAGAUAUGGCUUCGUGCCCGUCCUGGAUUCG CGGAAACGCGUACAUCCAGCUGACGAGUCCCAAAUAGGA CGAAACGGGCAC |
| 138 | PP7_a0_b6_c3 | CGGCACAGAAGAUAUGGCUUCGUGCCGCGUCCUGGAUUC GCGGAAACGCGUACAUCCAGCUGACGAGUCCCAAAUAGG ACGAAACGCGGCAC |
| 139 | PP7_a0_b6_c4 | GGGCACAGAAGAUAUGGCUUCGUGCCCGCGUCCUGGAUU CGCGGAAACGCGUACAUCCAGCUGACGAGUCCCAAAUAG GACGAAACGCGGGCAC |
| 140 | PP7_a1_b6_c0 | ACGGCACAGAAGAUAUGGCUUCGUGCCGUCCUGGAUUCG CGGAAACGCGUACAUCCAGCUGACGAGUCCCAAAUAGGA CGAAACGGCA |
| 141 | PP7_a1_b6_c1 | CGGGCACAGAAGAUAUGGCUUCGUGCCCGUCCUGGAUUC GCGGAAACGCGUACAUCCAGCUGACGAGUCCCAAAUAGG ACGAAACGGGCA |
| 142 | PP7_a1_b6_c2 | GCGGCACAGAAGAUAUGGCUUCGUGCCGCGUCCUGGAUU CGCGGAAACGCGUACAUCCAGCUGACGAGUCCCAAAUAG GACGAAACGCGGCA |
| 143 | PP7_a1_b6_c3 | CGGGCACAGAAGAUAUGGCUUCGUGCCCGCGUCCUGGAU UCGCGGAAACGCGUACAUCCAGCUGACGAGUCCCAAAUA GGACGAAACGCGGGCA |
| 144 | PP7_a1_b6_c4 | GCGGCACAGAAGAUAUGGCUUCGUGCCGCGCGUCCUGGA UUCGCGGAAACGCGUACAUCCAGCUGACGAGUCCCAAAU AGGACGAAACGCGCGGCA |
| 145 | PP7_a2_b6_c0 | ACGGGCACAGAAGAUAUGGCUUCGUGCCCGUCCUGGAUU CGCGGAAACGCGUACAUCCAGCUGACGAGUCCCAAAUAG GACGAAACGGGC |
| 146 | PP7_a2_b6_c1 | CGCGGCACAGAAGAUAUGGCUUCGUGCCGCGUCCUGGAU UCGCGGAAACGCGUACAUCCAGCUGACGAGUCCCAAAUA GGACGAAACGCGGC |
| 147 | PP7_a2_b6_c2 | GCGGGCACAGAAGAUAUGGCUUCGUGCCCGCGUCCUGGA UUCGCGGAAACGCGUACAUCCAGCUGACGAGUCCCAAAU AGGACGAAACGCGGGC |
| 148 | PP7_a2_b6_c3 | CGCGGCACAGAAGAUAUGGCUUCGUGCCGCGCGUCCUGG AUUCGCGGAAACGCGUACAUCCAGCUGACGAGUCCCAAA UAGGACGAAACGCGCGGC |
| 149 | PP7_a3_b6_c0 | ACGCGGCACAGAAGAUAUGGCUUCGUGCCGCGUCCUGGA UUCGCGGAAACGCGUACAUCCAGCUGACGAGUCCCAAAU AGGACGAAACGCGG |
| 150 | PP7_a3_b6_c1 | CGCGGGCACAGAAGAUAUGGCUUCGUGCCCGCGUCCUGG AUUCGCGGAAACGCGUACAUCCAGCUGACGAGUCCCAAA UAGGACGAAACGCGGG |
| 151 | PP7_a3_b6_c2 | GCGCGGCACAGAAGAUAUGGCUUCGUGCCGCGCGUCCUG GAUUCGCGGAAACGCGUACAUCCAGCUGACGAGUCCCAA AUAGGACGAAACGCGCGG |
| 152 | PP7_a4_b6_c0 | ACGCGGGCACAGAAGAUAUGGCUUCGUGCCCGCGUCCUG GAUUCGCGGAAACGCGUACAUCCAGCUGACGAGUCCCAA AUAGGACGAAACGCGCG |

TABLE 6-continued

Exemplary PP7 ON switches

| SEQ ID NO: | Name | Sequence |
|---|---|---|
| 153 | PP7_a4_b6_c1 | CGCGCGGCACAGAAGAUAUGGCUUCGUGCCGCGCGUCCU<br>GGAUUCGCGGAAACGCGUACAUCCAGCUGACGAGUCCCA<br>AAUAGGACGAAACGCGCG |
| 154 | PP7_a0_b7_c0 | ACGGCACAGAAGAUAUGGCUUCGUGCCGUCCUGGAUUCG<br>CGGAAACGCGUACAUCCAGCUGACGAGUCCCAAAUAGGA<br>CGAAACGGCAC |
| 155 | PP7_a0_b7_c1 | CGGGCACAGAAGAUAUGGCUUCGUGCCCGUCCUGGAUUC<br>GCGGAAACGCGUACAUCCAGCUGACGAGUCCCAAAUAGG<br>ACGAAACGGGCAC |
| 156 | PP7_a0_b7_c2 | GCGGCACAGAAGAUAUGGCUUCGUGCCGCGUCCUGGAUU<br>CGCGGAAACGCGUACAUCCAGCUGACGAGUCCCAAAUAG<br>GACGAAACGCGGCAC |
| 157 | PP7_a0_b7_c3 | CGGGCACAGAAGAUAUGGCUUCGUGCCCGCGUCCUGGAU<br>UCGCGGAAACGCGUACAUCCAGCUGACGAGUCCCAAAUA<br>GGACGAAACGCGGGCAC |
| 158 | PP7_a0_b7_c4 | GCGGCACAGAAGAUAUGGCUUCGUGCCGCGCGUCCUGGA<br>UUCGCGGAAACGCGUACAUCCAGCUGACGAGUCCCAAAU<br>AGGACGAAACGCGCGGCAC |
| 159 | PP7_a1_b7_c0 | ACGGGCACAGAAGAUAUGGCUUCGUGCCCGUCCUGGAUU<br>CGCGGAAACGCGUACAUCCAGCUGACGAGUCCCAAAUAG<br>GACGAAACGGGCA |
| 160 | PP7_a1_b7_c1 | CGCGGCACAGAAGAUAUGGCUUCGUGCCGCGUCCUGGAU<br>UCGCGGAAACGCGUACAUCCAGCUGACGAGUCCCAAAUA<br>GGACGAAACGCGGCA |
| 161 | PP7_a1_b7_c2 | GCGGGCACAGAAGAUAUGGCUUCGUGCCCGCGUCCUGGA<br>UUCGCGGAAACGCGUACAUCCAGCUGACGAGUCCCAAAU<br>AGGACGAAACGCGGGCA |
| 162 | PP7_a1_b7_c3 | CGCGGCACAGAAGAUAUGGCUUCGUGCCGCGCGUCCUGG<br>AUUCGCGGAAACGCGUACAUCCAGCUGACGAGUCCCAAA<br>UAGGACGAAACGCGCGGCA |
| 163 | PP7_a2_b7_c0 | ACGCGGCACAGAAGAUAUGGCUUCGUGCCGCGUCCUGGA<br>UUCGCGGAAACGCGUACAUCCAGCUGACGAGUCCCAAAU<br>AGGACGAAACGCGGC |
| 164 | PP7_a2_b7_c1 | CGCGGGCACAGAAGAUAUGGCUUCGUGCCCGCGUCCUGG<br>AUUCGCGGAAACGCGUACAUCCAGCUGACGAGUCCCAAA<br>UAGGACGAAACGCGGGC |
| 165 | PP7_a2_b7_c2 | GCGCGGCACAGAAGAUAUGGCUUCGUGCCGCGCGUCCUG<br>GAUUCGCGGAAACGCGUACAUCCAGCUGACGAGUCCCAA<br>AUAGGACGAAACGCGCGGC |
| 166 | PP7_a3_b7_c0 | ACGCGGGCACAGAAGAUAUGGCUUCGUGCCCGCGUCCUG<br>GAUUCGCGGAAACGCGUACAUCCAGCUGACGAGUCCCAA<br>AUAGGACGAAACGCGGG |
| 167 | PP7_a3_b7_c1 | CGCGCGGCACAGAAGAUAUGGCUUCGUGCCGCGCGUCCU<br>GGAUUCGCGGAAACGCGUACAUCCAGCUGACGAGUCCCA<br>AAUAGGACGAAACGCGCGG |
| 168 | PP7_a4_b7_c0 | ACGCGCGGCACAGAAGAUAUGGCUUCGUGCCGCGCGUCC<br>UGGAUUCGCGGAAACGCGUACAUCCAGCUGACGAGUCCC<br>AAAUAGGACGAAACGCGCG |
| 169 | FLIPPED_PP7_<br>a1_b5_c1 | CGGCAUCCUGGAUUCGCGGAAACGCGUACAUCCAGCUGA<br>CGAGUCCCAAAUAGGACGAAAUGCCGCAGAAGAUAUGG<br>CUUCGCGGCA |
| 170 | FLIPPED_PP7_<br>a0_b6_c1 | CGGCACUCCUGGAUUCGCGGAAACGCGUACAUCCAGCUG<br>ACGAGUCCCAAAUAGGACGAAAGUGCCGAGAAGAUAUG<br>GCUUCCGGCAC |
| 171 | FLIPPED_PP7_<br>a0_b6_c3 | CGGCACCGUCCUGGAUUCGCGGAAACGCGUACAUCCAGC<br>UGACGAGUCCCAAAUAGGACGAAACGGUGCCGAGAAGA<br>UAUGGCUUCCGGCAC |

TABLE 6-continued

Exemplary PP7 ON switches

| SEQ ID NO: | Name | Sequence |
|---|---|---|
| 172 | FLIPPED_PP7_ a0_b7_c3 | CGGGCACCGUCCUGGAUUCGCGGAAACGCGUACAUCCAG CUGACGAGUCCCAAAUAGGACGAAACGGUGCCCGAGAAG AUAUGGCUUCCGGGCAC |

TABLE 7

Exemplary BIV Tar ON switches

| SEQ ID NO: | Name | Sequence |
|---|---|---|
| 173 | BT_a1_b5_c1 | GGCUCGUGUAGCUCAUUAGCUCCGAGCCUCCUGGAUUCG CGGAAACGCGUACAUCCAGCUGACGAGUCCCAAAUAGGA CGAAAGGCUC |
| 174 | BT_a1_b5_c2 | GGCUCGUGUAGCUCAUUAGCUCCGAGCCGUCCUGGAUUC GCGGAAACGCGUACAUCCAGCUGACGAGUCCCAAAUAGG ACGAAACGGCUC |
| 175 | BT_a1_b5_c3 | GGCUCGUGUAGCUCAUUAGCUCCGAGCCCGUCCUGGAUU CGCGGAAACGCGUACAUCCAGCUGACGAGUCCCAAAUAG GACGAAACGGGCUC |
| 176 | BT_a1_b5_c4 | GGCUCGUGUAGCUCAUUAGCUCCGAGCCGCGUCCUGGAU UCGCGGAAACGCGUACAUCCAGCUGACGAGUCCCAAAUA GGACGAAACGCGGCUC |
| 177 | BT_a2_b5_c1 | CGGCUCGUGUAGCUCAUUAGCUCCGAGCCGUCCUGGAUU CGCGGAAACGCGUACAUCCAGCUGACGAGUCCCAAAUAG GACGAAACGGCU |
| 178 | BT_a2_b5_c2 | GGGCUCGUGUAGCUCAUUAGCUCCGAGCCCGUCCUGGAU UCGCGGAAACGCGUACAUCCAGCUGACGAGUCCCAAAUA GGACGAAACGGGCU |
| 179 | BT_a2_b5_c3 | CGGCUCGUGUAGCUCAUUAGCUCCGAGCCGCGUCCUGGA UUCGCGGAAACGCGUACAUCCAGCUGACGAGUCCCAAAU AGGACGAAACGCGGCU |
| 180 | BT_a2_b5_c4 | GGGCUCGUGUAGCUCAUUAGCUCCGAGCCCGCGUCCUGG AUUCGCGGAAACGCGUACAUCCAGCUGACGAGUCCCAAA UAGGACGAAACGCGGGCU |
| 181 | BT_a3_b5_c1 | CGGGCUCGUGUAGCUCAUUAGCUCCGAGCCCGUCCUGGA UUCGCGGAAACGCGUACAUCCAGCUGACGAGUCCCAAAU AGGACGAAACGGGC |
| 182 | BT_a3_b5_c2 | GCGGCUCGUGUAGCUCAUUAGCUCCGAGCCGCGUCCUGG AUUCGCGGAAACGCGUACAUCCAGCUGACGAGUCCCAAA UAGGACGAAACGCGGC |
| 183 | BT_a3_b5_c3 | CGGGCUCGUGUAGCUCAUUAGCUCCGAGCCCGCGUCCUG GAUUCGCGGAAACGCGUACAUCCAGCUGACGAGUCCCAA AUAGGACGAAACGCGGGC |
| 184 | BT_a4_b5_c1 | CGCGGCUCGUGUAGCUCAUUAGCUCCGAGCCGCGUCCUG GAUUCGCGGAAACGCGUACAUCCAGCUGACGAGUCCCAA AUAGGACGAAACGCGG |
| 185 | BT_a4_b5_c2 | GCGGGCUCGUGUAGCUCAUUAGCUCCGAGCCCGCGUCCU GGAUUCGCGGAAACGCGUACAUCCAGCUGACGAGUCCCA AAUAGGACGAAACGCGGG |
| 186 | BT_a0_b6_c1 | GGCUCGUGUAGCUCAUUAGCUCCGAGCCUCCUGGAUUCG CGGAAACGCGUACAUCCAGCUGACGAGUCCCAAAUAGGA CGAAAGGCUCG |
| 187 | BT_a0_b6_c2 | GGCUCGUGUAGCUCAUUAGCUCCGAGCCGUCCUGGAUUC GCGGAAACGCGUACAUCCAGCUGACGAGUCCCAAAUAGG ACGAAACGGCUCG |

TABLE 7-continued

Exemplary BIV Tar ON switches

| SEQ ID NO: | Name | Sequence |
|---|---|---|
| 188 | BT_a0_b6_c4 | GGCUCGUGUAGCUCAUUAGCUCCGAGCCGCGUCCUGGAU UCGCGGAAACGCGUACAUCCAGCUGACGAGUCCCAAAUA GGACGAAACGCGGCUCG |
| 189 | BT_a1_b6_c0 | AGGCUCGUGUAGCUCAUUAGCUCCGAGCCUCCUGGAUUC GCGGAAACGCGUACAUCCAGCUGACGAGUCCCAAAUAGG ACGAAAGGCUC |
| 190 | BT_a1_b6_c1 | CGGCUCGUGUAGCUCAUUAGCUCCGAGCCGUCCUGGAUU CGCGGAAACGCGUACAUCCAGCUGACGAGUCCCAAAUAG GACGAAACGGCUC |
| 191 | BT_a1_b6_c2 | GGGCUCGUGUAGCUCAUUAGCUCCGAGCCCGUCCUGGAU UCGCGGAAACGCGUACAUCCAGCUGACGAGUCCCAAAUA GGACGAAACGGGCUC |
| 192 | BT_a1_b6_c3 | CGGCUCGUGUAGCUCAUUAGCUCCGAGCCGCGUCCUGGA UUCGCGGAAACGCGUACAUCCAGCUGACGAGUCCCAAAU AGGACGAAACGCGGCUC |
| 193 | BT_a1_b6_c4 | GGGCUCGUGUAGCUCAUUAGCUCCGAGCCCGCGUCCUGG AUUCGCGGAAACGCGUACAUCCAGCUGACGAGUCCCAAA UAGGACGAAACGCGGGCUC |
| 194 | BT_a2_b6_c1 | CGGGCUCGUGUAGCUCAUUAGCUCCGAGCCCGUCCUGGA UUCGCGGAAACGCGUACAUCCAGCUGACGAGUCCCAAAU AGGACGAAACGGGCU |
| 195 | BT_a2_b6_c2 | GCGGCUCGUGUAGCUCAUUAGCUCCGAGCCGCGUCCUGG AUUCGCGGAAACGCGUACAUCCAGCUGACGAGUCCCAAA UAGGACGAAACGCGGCU |
| 196 | BT_a2_b6_c4 | GCGGCUCGUGUAGCUCAUUAGCUCCGAGCCGCGCGUCCU GGAUUCGCGGAAACGCGUACAUCCAGCUGACGAGUCCCA AAUAGGACGAAACGCGCGGCU |
| 197 | BT_a3_b6_c0 | ACGGGCUCGUGUAGCUCAUUAGCUCCGAGCCCGUCCUGG AUUCGCGGAAACGCGUACAUCCAGCUGACGAGUCCCAAA UAGGACGAAACGGGC |
| 198 | BT_a3_b6_c1 | CGCGGCUCGUGUAGCUCAUUAGCUCCGAGCCGCGUCCUG GAUUCGCGGAAACGCGUACAUCCAGCUGACGAGUCCCAA AUAGGACGAAACGCGGC |
| 199 | BT_a3_b6_c2 | GCGGGCUCGUGUAGCUCAUUAGCUCCGAGCCCGCGUCCU GGAUUCGCGGAAACGCGUACAUCCAGCUGACGAGUCCCA AAUAGGACGAAACGCGGGC |
| 200 | BT_a3_b6_c3 | CGCGGCUCGUGUAGCUCAUUAGCUCCGAGCCGCGCGUCC UGGAUUCGCGGAAACGCGUACAUCCAGCUGACGAGUCCC AAAUAGGACGAAACGCGCGGC |
| 201 | BT_a4_b6_c1 | CGCGGGCUCGUGUAGCUCAUUAGCUCCGAGCCCGCGUCC UGGAUUCGCGGAAACGCGUACAUCCAGCUGACGAGUCCC AAAUAGGACGAAACGCGGG |
| 202 | BT_a4_b6_c2 | GCGCGGCUCGUGUAGCUCAUUAGCUCCGAGCCGCGCGUC CUGGAUUCGCGGAAACGCGUACAUCCAGCUGACGAGUCC CAAAUAGGACGAAACGCGCGG |
| 203 | BT_a0_b7_c1 | CGGCUCGUGUAGCUCAUUAGCUCCGAGCCGUCCUGGAUU CGCGGAAACGCGUACAUCCAGCUGACGAGUCCCAAAUAG GACGAAACGGCUCG |
| 204 | BT_a0_b7_c2 | GGGCUCGUGUAGCUCAUUAGCUCCGAGCCCGUCCUGGAU UCGCGGAAACGCGUACAUCCAGCUGACGAGUCCCAAAUA GGACGAAACGGGCUCG |
| 205 | BT_a0_b7_c3 | CGGCUCGUGUAGCUCAUUAGCUCCGAGCCGCGUCCUGGA UUCGCGGAAACGCGUACAUCCAGCUGACGAGUCCCAAAU AGGACGAAACGCGGCUCG |
| 206 | BT_a0_b7_c4 | GGGCUCGUGUAGCUCAUUAGCUCCGAGCCCGCGUCCUGG AUUCGCGGAAACGCGUACAUCCAGCUGACGAGUCCCAAA UAGGACGAAACGCGGGCUCG |

TABLE 7-continued

Exemplary BIV Tar ON switches

| SEQ ID NO: | Name | Sequence |
|---|---|---|
| 207 | BT_a1_b7_c0 | ACGGCUCGUGUAGCUCAUUAGCUCCGAGCCGUCCUGGAU UCGCGGAAACGCGUACAUCCAGCUGACGAGUCCCAAAUA GGACGAAACGGCUC |
| 208 | BT_a1_b7_c1 | CGGGCUCGUGUAGCUCAUUAGCUCCGAGCCCGUCCUGGA UUCGCGGAAACGCGUACAUCCAGCUGACGAGUCCCAAAU AGGACGAAACGGGCUC |
| 209 | BT_a1_b7_c2 | GCGGCUCGUGUAGCUCAUUAGCUCCGAGCCGCGUCCUGG AUUCGCGGAAACGCGUACAUCCAGCUGACGAGUCCCAAA UAGGACGAAACGCGGCUC |
| 210 | BT_a1_b7_c3 | CGGGCUCGUGUAGCUCAUUAGCUCCGAGCCCGCGUCCUG GAUUCGCGGAAACGCGUACAUCCAGCUGACGAGUCCCAA AUAGGACGAAACGCGGGCUC |
| 211 | BT_a1_b7_c4 | GCGGCUCGUGUAGCUCAUUAGCUCCGAGCCGCGCGUCCU GGAUUCGCGGAAACGCGUACAUCCAGCUGACGAGUCCCA AAUAGGACGAAACGCGCGGCUC |
| 212 | BT_a2_b7_c0 | ACGGGCUCGUGUAGCUCAUUAGCUCCGAGCCCGUCCUGG AUUCGCGGAAACGCGUACAUCCAGCUGACGAGUCCCAAA UAGGACGAAACGGGCU |
| 213 | BT_a2_b7_c1 | CGCGGCUCGUGUAGCUCAUUAGCUCCGAGCCGCGUCCUG GAUUCGCGGAAACGCGUACAUCCAGCUGACGAGUCCCAA AUAGGACGAAACGCGGCU |
| 214 | BT_a2_b7_c2 | GCGGGCUCGUGUAGCUCAUUAGCUCCGAGCCCGCGUCCU GGAUUCGCGGAAACGCGUACAUCCAGCUGACGAGUCCCA AAUAGGACGAAACGCGGGCU |
| 215 | BT_a2_b7_c3 | CGCGGCUCGUGUAGCUCAUUAGCUCCGAGCCGCGCGUCC UGGAUUCGCGGAAACGCGUACAUCCAGCUGACGAGUCCC AAAUAGGACGAAACGCGCGGCU |
| 216 | BT_a3_b7_c0 | ACGCGGCUCGUGUAGCUCAUUAGCUCCGAGCCGCGUCCU GGAUUCGCGGAAACGCGUACAUCCAGCUGACGAGUCCCA AAUAGGACGAAACGCGGC |
| 217 | BT_a3_b7_c1 | CGCGGGCUCGUGUAGCUCAUUAGCUCCGAGCCCGCGUCC UGGAUUCGCGGAAACGCGUACAUCCAGCUGACGAGUCCC AAAUAGGACGAAACGCGGGC |
| 218 | BT_a3_b7_c2 | GCGCGGCUCGUGUAGCUCAUUAGCUCCGAGCCGCGCGUC CUGGAUUCGCGGAAACGCGUACAUCCAGCUGACGAGUCC CAAAUAGGACGAAACGCGCGGC |

TABLE 8

Exemplary BIV Tar OFF switches (with 1 stabilization stem)

| SEQ ID NO: | Name | Sequence |
|---|---|---|
| 219 | BT_a1_b5_c1_d0 | GGCUCGUGUAGCUCAUUAGCUCCGAGCCGAUAAGGGC UCUCCUGGAUUCGCGGAAACGCGUACAUCCAGCUGAC GAGUCCCAAAUAGGACGAAAGAGCC |
| 220 | BT_a1_b5_c4_d0 | GGCUCGUGUAGCUCAUUAGCUCCGAGCCGAUAAGGGC UCGCGUCCUGGAUUCGCGGAAACGCGUACAUCCAGCU GACGAGUCCCAAAUAGGACGAAACGCGAGCC |
| 221 | BT_a1_b5_c2_d1 | GGCUCGUGUAGCUCAUUAGCUCCGAGCCCGAUAAGGG GCUCGUCCUGGAUUCGCGGAAACGCGUACAUCCAGCU GACGAGUCCCAAAUAGGACGAAACGAGCC |
| 222 | BT_a1_b5_c3_d1 | GGCUCGUGUAGCUCAUUAGCUCCGAGCCCGAUAAGGG GCUCCGUCCUGGAUUCGCGGAAACGCGUACAUCCAGC UGACGAGUCCCAAAUAGGACGAAACGGAGCC |

TABLE 8-continued

Exemplary BIV Tar OFF switches (with 1 stabilization stem)

| SEQ ID NO: | Name | Sequence |
|---|---|---|
| 223 | BT_a1_b5_c4_d1 | GGCUCGUGUAGCUCAUUAGCUCCGAGCCCGAUAAGGG<br>GCUCGCGUCCUGGAUUCGCGGAAACGCGUACAUCCAG<br>CUGACGAGUCCCAAAUAGGACGAAACGCGAGCC |
| 224 | BT_a1_b5_c1_d2 | GGCUCGUGUAGCUCAUUAGCUCCGAGCCCGGAUAAGC<br>GGGCUCUCCUGGAUUCGCGGAAACGCGUACAUCCAGC<br>UGACGAGUCCCAAAUAGGACGAAAGAGCC |
| 225 | BT_a1_b5_c4_d2 | GGCUCGUGUAGCUCAUUAGCUCCGAGCCCGGAUAAGC<br>GGGCUCGCGUCCUGGAUUCGCGGAAACGCGUACAUCC<br>AGCUGACGAGUCCCAAAUAGGACGAAACGCGAGCC |
| 226 | BT_a1_b5_c1_d3 | GGCUCGUGUAGCUCAUUAGCUCCGAGCCCGAGAUAAG<br>UCGGGCUCUCCUGGAUUCGCGGAAACGCGUACAUCCA<br>GCUGACGAGUCCCAAAUAGGACGAAAGAGCC |
| 227 | BT_a1_b5_c4_d3 | GGCUCGUGUAGCUCAUUAGCUCCGAGCCCGAGAUAAG<br>UCGGGCUCGCGUCCUGGAUUCGCGGAAACGCGUACAU<br>CCAGCUGACGAGUCCCAAAUAGGACGAAACGCGAGCC |
| 228 | BT_a1_b5_c3_d4 | GGCUCGUGUAGCUCAUUAGCUCCGAGCCCGACGAUAA<br>GGUCGGGCUCCGUCCUGGAUUCGCGGAAACGCGUACA<br>UCCAGCUGACGAGUCCCAAAUAGGACGAAACGGAGCC |
| 229 | BT_a2_b5_c3_d0 | GGGCUCGUGUAGCUCAUUAGCUCCGAGCCCGAUAAGG<br>GGCUCGUCCUGGAUUCGCGGAAACGCGUACAUCCAGC<br>UGACGAGUCCCAAAUAGGACGAAACGAGCCC |
| 230 | BT_a2_b5_c1_d1 | GGGCUCGUGUAGCUCAUUAGCUCCGAGCCCCGAUAAG<br>GGGGCUUCCUGGAUUCGCGGAAACGCGUACAUCCAGC<br>UGACGAGUCCCAAAUAGGACGAAAAGCCC |
| 231 | BT_a2_b5_c3_d1 | GGGCUCGUGUAGCUCAUUAGCUCCGAGCCCCGAUAAG<br>GGGGCUCGUCCUGGAUUCGCGGAAACGCGUACAUCCA<br>GCUGACGAGUCCCAAAUAGGACGAAACGAGCCC |
| 232 | BT_a2_b5_c1_d2 | GGGCUCGUGUAGCUCAUUAGCUCCGAGCCCCGGAUAA<br>GCGGGGCUUCCUGGAUUCGCGGAAACGCGUACAUCCA<br>GCUGACGAGUCCCAAAUAGGACGAAAAGCCC |
| 233 | BT_a2_b5_c2_d2 | CGGCUCGUGUAGCUCAUUAGCUCCGAGCCGCGGAUAA<br>GCGCGGCUGUCCUGGAUUCGCGGAAACGCGUACAUCC<br>AGCUGACGAGUCCCAAAUAGGACGAAACAGCCG |
| 234 | BT_a2_b5_c3_d2 | GGGCUCGUGUAGCUCAUUAGCUCCGAGCCCCGGAUAA<br>GCGGGGCUCGUCCUGGAUUCGCGGAAACGCGUACAUC<br>CAGCUGACGAGUCCCAAAUAGGACGAAACGAGCCC |
| 235 | BT_a2_b5_c4_d2 | CGGCUCGUGUAGCUCAUUAGCUCCGAGCCGCGGAUAA<br>GCGCGGCUGCGUCCUGGAUUCGCGGAAACGCGUACAU<br>CCAGCUGACGAGUCCCAAAUAGGACGAAACGCAGCCG |
| 236 | BT_a2_b5_c1_d3 | GGGCUCGUGUAGCUCAUUAGCUCCGAGCCCCGAGAUA<br>AGUCGGGGCUUCCUGGAUUCGCGGAAACGCGUACAUC<br>CAGCUGACGAGUCCCAAAUAGGACGAAAAGCCC |
| 237 | BT_a3_b5_c2_d1 | GCGGCUCGUGUAGCUCAUUAGCUCCGAGCCGCCGAUA<br>AGGGCGGCGUCCUGGAUUCGCGGAAACGCGUACAUCC<br>AGCUGACGAGUCCCAAAUAGGACGAAACGCCGC |
| 238 | BT_a3_b5_c4_d1 | GCGGCUCGUGUAGCUCAUUAGCUCCGAGCCGCCGAUA<br>AGGGCGGCGCGUCCUGGAUUCGCGGAAACGCGUACAU<br>CCAGCUGACGAGUCCCAAAUAGGACGAAACGCGCCGC |
| 239 | BT_a3_b5_c1_d3 | CGGGCUCGUGUAGCUCAUUAGCUCCGAGCCCGCGAGA<br>UAAGUCGCGGGCUCCUGGAUUCGCGGAAACGCGUACA<br>UCCAGCUGACGAGUCCCAAAUAGGACGAAAGCCCG |
| 240 | BT_a3_b5_c4_d3 | GCGGCUCGUGUAGCUCAUUAGCUCCGAGCCGCCGAGA<br>UAAGUCGGCGGCGCGUCCUGGAUUCGCGGAAACGCGU<br>ACAUCCAGCUGACGAGUCCCAAAUAGGACGAAACGCG<br>CCGC |
| 241 | BT_a3_b5_c2_d4 | GCGGCUCGUGUAGCUCAUUAGCUCCGAGCCGCCGACG<br>AUAAGGUCGGCGGCGUCCUGGAUUCGCGGAAACGCGU |

TABLE 8-continued

Exemplary BIV Tar OFF switches (with 1 stabilization stem)

| SEQ ID NO: | Name | Sequence |
|---|---|---|
| | | ACAUCCAGCUGACGAGUCCCAAAUAGGACGAAACGCC GC |
| 242 | BT_a4_b5_c1_d0 | GCGGGCUCGUGUAGCUCAUUAGCUCCGAGCCCGCGAU AAGGCGGGUCCUGGAUUCGCGGAAACGCGUACAUCCA GCUGACGAGUCCCAAAUAGGACGAAACCCGC |
| 243 | BT_a4_b5_c3_d0 | GCGGGCUCGUGUAGCUCAUUAGCUCCGAGCCCGCGAU AAGGCGGGCGUCCUGGAUUCGCGGAAACGCGUACAUC CAGCUGACGAGUCCCAAAUAGGACGAAACGCCCGC |
| 244 | BT_a4_b5_c3_d1 | GCGGGCUCGUGUAGCUCAUUAGCUCCGAGCCCGCCGA UAAGGGCGGGCGUCCUGGAUUCGCGGAAACGCGUACA UCCAGCUGACGAGUCCCAAAUAGGACGAAACGCCCGC |
| 245 | BT_a4_b5_c3_d3 | GCGGGCUCGUGUAGCUCAUUAGCUCCGAGCCCGCCGA GAUAAGUCGGCGGGCGUCCUGGAUUCGCGGAAACGCG UACAUCCAGCUGACGAGUCCCAAAUAGGACGAAACGC CCGC |
| 246 | BT_a4_b5_c2_d4 | CGCGGCUCGUGUAGCUCAUUAGCUCCGAGCCGCGCGA CGAUAAGGUCGCGCGGGUCCUGGAUUCGCGGAAACGC GUACAUCCAGCUGACGAGUCCCAAAUAGGACGAAACC CGCG |
| 247 | BT_a0_b6_c1_d0 | GGCUCGUGUAGCUCAUUAGCUCCGAGCCGAUAAGGGC UCGUCCUGGAUUCGCGGAAACGCGUACAUCCAGCUGA CGAGUCCCAAAUAGGACGAAACGAGCC |
| 248 | BT_a0_b6_c0_d2 | GGCUCGUGUAGCUCAUUAGCUCCGAGCCCGGAUAAGC GGGCUCGCCUGGAUUCGCGGAAACGCGUACAUCCAGC UGACGAGUCCCAAAUAGGACGAACGAGCC |
| 249 | BT_a0_b6_c2_d2 | GGCUCGUGUAGCUCAUUAGCUCCGAGCCCGGAUAAGC GGGCUCGGUCCUGGAUUCGCGGAAACGCGUACAUCCA GCUGACGAGUCCCAAAUAGGACGAAACCGAGCC |
| 250 | BT_a0_b6_c3_d2 | GGCUCGUGUAGCUCAUUAGCUCCGAGCCCGGAUAAGC GGGCUCGCGUCCUGGAUUCGCGGAAACGCGUACAUCC AGCUGACGAGUCCCAAAUAGGACGAAACGCGAGCC |
| 251 | BT_a0_b6_c4_d2 | GGCUCGUGUAGCUCAUUAGCUCCGAGCCCGGAUAAGC GGGCUCGGCGUCCUGGAUUCGCGGAAACGCGUACAUC CAGCUGACGAGUCCCAAAUAGGACGAAACGCCGAGCC |
| 252 | BT_a0_b6_c3_d3 | GGCUCGUGUAGCUCAUUAGCUCCGAGCCCGAGAUAAG UCGGGCUCGCGUCCUGGAUUCGCGGAAACGCGUACAU CCAGCUGACGAGUCCCAAAUAGGACGAAACGCGAGCC |
| 253 | BT_a0_b6_c0_d4 | GGCUCGUGUAGCUCAUUAGCUCCGAGCCCGACGAUAA GGUCGGGCUCGCCUGGAUUCGCGGAAACGCGUACAUC CAGCUGACGAGUCCCAAAUAGGACGAACGAGCC |
| 254 | BT_a0_b6_c4_d4 | GGCUCGUGUAGCUCAUUAGCUCCGAGCCCGACGAUAA GGUCGGGCUCGGCGUCCUGGAUUCGCGGAAACGCGUA CAUCCAGCUGACGAGUCCCAAAUAGGACGAAACGCCG AGCC |
| 255 | BT_a1_b6_c1_d0 | GGGCUCGUGUAGCUCAUUAGCUCCGAGCCCGAUAAGG GGCUCUCCUGGAUUCGCGGAAACGCGUACAUCCAGCU GACGAGUCCCAAAUAGGACGAAAGAGCCC |
| 256 | BT_a1_b6_c4_d1 | CGGCUCGUGUAGCUCAUUAGCUCCGAGCCGCGAUAAG GCGGCUCGCGUCCUGGAUUCGCGGAAACGCGUACAUC CAGCUGACGAGUCCCAAAUAGGACGAAACGCGAGCCG |
| 257 | BT_a1_b6_c0_d2 | UGGCUCGUGUAGCUCAUUAGCUCCGAGCCACGGAUAA GCGUGGCUCCCUGGAUUCGCGGAAACGCGUACAUCCA GCUGACGAGUCCCAAAUAGGACGAAGAGCCA |
| 258 | BT_a1_b6_c3_d2 | GGGCUCGUGUAGCUCAUUAGCUCCGAGCCCCGGAUAA GCGGGGCUCCGUCCUGGAUUCGCGGAAACGCGUACAU CCAGCUGACGAGUCCCAAAUAGGACGAAACGGAGCCC |

TABLE 8-continued

Exemplary BIV Tar OFF switches (with 1 stabilization stem)

| SEQ ID NO: | Name | Sequence |
|---|---|---|
| 259 | BT_a1_b6_c0_d3 | UGGCUCGUGUAGCUCAUUAGCUCCGAGCCACGAGAUA<br>AGUCGUGGCUCCCUGGAUUCGCGGAAACGCGUACAUC<br>CAGCUGACGAGUCCCAAAUAGGACGAAGAGCCA |
| 260 | BT_a1_b6_c2_d3 | CGGCUCGUGUAGCUCAUUAGCUCCGAGCCGCGAGAUA<br>AGUCGCGGCUCGUCCUGGAUUCGCGGAAACGCGUACA<br>UCCAGCUGACGAGUCCCAAAUAGGACGAAACGAGCCG |
| 261 | BT_a1_b6_c4_d3 | CGGCUCGUGUAGCUCAUUAGCUCCGAGCCGCGAGAUA<br>AGUCGCGGCUCGCGUCCUGGAUUCGCGGAAACGCGUA<br>CAUCCAGCUGACGAGUCCCAAAUAGGACGAAACGCGA<br>GCCG |
| 262 | BT_a1_b6_c0_d4 | UGGCUCGUGUAGCUCAUUAGCUCCGAGCCACGACGAU<br>AAGGUCGUGGCUCCCUGGAUUCGCGGAAACGCGUACA<br>UCCAGCUGACGAGUCCCAAAUAGGACGAAGAGCCA |
| 263 | BT_a1_b6_c1_d4 | GGGCUCGUGUAGCUCAUUAGCUCCGAGCCCCGACGAU<br>AAGGUCGGGGCUCUCCUGGAUUCGCGGAAACGCGUAC<br>AUCCAGCUGACGAGUCCCAAAUAGGACGAAAGAGCCC |
| 264 | BT_a1_b6_c2_d4 | CGGCUCGUGUAGCUCAUUAGCUCCGAGCCGCGACGAU<br>AAGGUCGCGGCUCGUCCUGGAUUCGCGGAAACGCGUA<br>CAUCCAGCUGACGAGUCCCAAAUAGGACGAAACGAGC<br>CG |
| 265 | BT_a1_b6_c3_d4 | GGGCUCGUGUAGCUCAUUAGCUCCGAGCCCCGACGAU<br>AAGGUCGGGGCUCCGUCCUGGAUUCGCGGAAACGCGU<br>ACAUCCAGCUGACGAGUCCCAAAUAGGACGAAACGGA<br>GCCC |
| 266 | BT_a2_b6_c0_d1 | GUGGCUCGUGUAGCUCAUUAGCUCCGAGCCACCGAUA<br>AGGGUGGCUCCUGGAUUCGCGGAAACGCGUACAUCCA<br>GCUGACGAGUCCCAAAUAGGACGAAAGCCAC |
| 267 | BT_a2_b6_c2_d1 | GCGGCUCGUGUAGCUCAUUAGCUCCGAGCCGCCGAUA<br>AGGGCGGCUCGUCCUGGAUUCGCGGAAACGCGUACAUC<br>CAGCUGACGAGUCCCAAAUAGGACGAAACAGCCGC |
| 268 | BT_a2_b6_c3_d2 | CGGGCUCGUGUAGCUCAUUAGCUCCGAGCCCGCGGAU<br>AAGCGCGGGCUCGUCCUGGAUUCGCGGAAACGCGUAC<br>AUCCAGCUGACGAGUCCCAAAUAGGACGAAACGAGCC<br>CG |
| 269 | BT_a2_b6_c4_d3 | GCGGCUCGUGUAGCUCAUUAGCUCCGAGCCGCCGAGA<br>UAAGUCGGCGGCUGCGUCCUGGAUUCGCGGAAACGCG<br>UACAUCCAGCUGACGAGUCCCAAAUAGGACGAAACGC<br>AGCCGC |
| 270 | BT_a3_b6_c2_d0 | CGCGGCUCGUGUAGCUCAUUAGCUCCGAGCCGCGGAU<br>AAGCGCGGCGUCCUGGAUUCGCGGAAACGCGUACAUC<br>CAGCUGACGAGUCCCAAAUAGGACGAAACGCCGCG |
| 271 | BT_a3_b6_c3_d0 | GCGGGCUCGUGUAGCUCAUUAGCUCCGAGCCCGCGAU<br>AAGGCGGGCCGUCCUGGAUUCGCGGAAACGCGUACAU<br>CCAGCUGACGAGUCCCAAAUAGGACGAAACGGCCCGC |
| 272 | BT_a3_b6_c2_d2 | CGCGGCUCGUGUAGCUCAUUAGCUCCGAGCCGCGCGG<br>AUAAGCGCGCGGCGUCCUGGAUUCGCGGAAACGCGUA<br>CAUCCAGCUGACGAGUCCCAAAUAGGACGAAACGCCG<br>CG |
| 273 | BT_a3_b6_c3_d2 | GCGGGCUCGUGUAGCUCAUUAGCUCCGAGCCCGCCGG<br>AUAAGCGGCGGGCCGUCCUGGAUUCGCGGAAACGCGU<br>ACAUCCAGCUGACGAGUCCCAAAUAGGACGAAACGGC<br>CCGC |
| 274 | BT_a3_b6_c0_d3 | CGUGGCUCGUGUAGCUCAUUAGCUCCGAGCCACGCGA<br>GAUAAGUCGCGUGGCCCUGGAUUCGCGGAAACGCGUA<br>CAUCCAGCUGACGAGUCCCAAAUAGGACGAAGCCACG |
| 275 | BT_a3_b6_c2_d4 | CGCGGCUCGUGUAGCUCAUUAGCUCCGAGCCGCGCGA<br>CGAUAAGGUCGCGCGGCGUCCUGGAUUCGCGGAAACG<br>CGUACAUCCAGCUGACGAGUCCCAAAUAGGACGAAAC<br>GCCGCG |

TABLE 8-continued

Exemplary BIV Tar OFF switches (with 1 stabilization stem)

| SEQ ID NO: | Name | Sequence |
|---|---|---|
| 276 | BT_a3_b6_c3_d4 | GCGGGCUCGUGUAGCUCAUUAGCUCCGAGCCCGCCGA<br>CGAUAAGGUCGGCGGGCCGUCCUGGAUUCGCGGGAAAC<br>GCGUACAUCCAGCUGACGAGUCCCAAAUAGGACGAAA<br>CGGCCCGC |
| 277 | BT_a4_b6_c0_d1 | GCGUGGCUCGUGUAGCUCAUUAGCUCCGAGCCACGCC<br>GAUAAGGGCGUGGCCUGGAUUCGCGGGAAACGCGUACA<br>UCCAGCUGACGAGUCCCAAAUAGGACGAACCACGC |
| 278 | BT_a4_b6_c1_d1 | CGCGGGCUCGUGUAGCUCAUUAGCUCCGAGCCCGCGC<br>GAUAAGGCGCGGGUCCUGGAUUCGCGGGAAACGCGUAC<br>AUCCAGCUGACGAGUCCCAAAUAGGACGAAACCCGCG |
| 279 | BT_a4_b6_c2_d1 | GCGCGGCUCGUGUAGCUCAUUAGCUCCGAGCCGCGCC<br>GAUAAGGGCGCGGGUCCUGGAUUCGCGGGAAACGCGUA<br>CAUCCAGCUGACGAGUCCCAAAUAGGACGAAACCCGC<br>GC |
| 280 | BT_a4_b6_c1_d2 | CGCGGGCUCGUGUAGCUCAUUAGCUCCGAGCCCGCGC<br>GGAUAAGCGCGCGGGUCCUGGAUUCGCGGGAAACGCGU<br>ACAUCCAGCUGACGAGUCCCAAAUAGGACGAAACCCG<br>CG |
| 281 | BT_a0_b7_c1_d0 | GGGCUCGUGUAGCUCAUUAGCUCCGAGCCCGAUAAGG<br>GGCUCGUCCUGGAUUCGCGGGAAACGCGUACAUCCAGC<br>UGACGAGUCCCAAAUAGGACGAAACGAGCCC |
| 282 | BT_a0_b7_c2_d0 | CGGCUCGUGUAGCUCAUUAGCUCCGAGCCGGAUAAGC<br>GGCUCGGUCCUGGAUUCGCGGGAAACGCGUACAUCCAG<br>CUGACGAGUCCCAAAUAGGACGAAACCGAGCCG |
| 283 | BT_a0_b7_c4_d0 | CGGCUCGUGUAGCUCAUUAGCUCCGAGCCGGAUAAGC<br>GGCUCGGCGUCCUGGAUUCGCGGGAAACGCGUACAUCC<br>AGCUGACGAGUCCCAAAUAGGACGAAACGCCGAGCCG |
| 284 | BT_a0_b7_c2_d1 | CGGCUCGUGUAGCUCAUUAGCUCCGAGCCGCGAUAAG<br>GCGGCUCGGUCCUGGAUUCGCGGGAAACGCGUACAUCC<br>AGCUGACGAGUCCCAAAUAGGACGAAACCGAGCCG |
| 285 | BT_a0_b7_c4_d2 | CGGCUCGUGUAGCUCAUUAGCUCCGAGCCGCGGAUAA<br>GCGCGGCUCGGCGUCCUGGAUUCGCGGGAAACGCGUAC<br>AUCCAGCUGACGAGUCCCAAAUAGGACGAAACGCCGA<br>GCCG |
| 286 | BT_a0_b7_c1_d3 | GGGCUCGUGUAGCUCAUUAGCUCCGAGCCCCGAGAUA<br>AGUCGGGGCUCGUCCUGGAUUCGCGGGAAACGCGUACA<br>UCCAGCUGACGAGUCCCAAAUAGGACGAAACGAGCCC |
| 287 | BT_a0_b7_c3_d3 | GGGCUCGUGUAGCUCAUUAGCUCCGAGCCCCGAGAUA<br>AGUCGGGGCUCGCGUCCUGGAUUCGCGGGAAACGCGUA<br>CAUCCAGCUGACGAGUCCCAAAUAGGACGAAACGCGA<br>GCCC |
| 288 | BT_a0_b7_c4_d4 | CGGCUCGUGUAGCUCAUUAGCUCCGAGCCGCGACGAU<br>AAGGUCGCGGCUCGGCGUCCUGGAUUCGCGGGAAACGC<br>GUACAUCCAGCUGACGAGUCCCAAAUAGGACGAAACG<br>CCGAGCCG |
| 289 | BT_a1_b7_c3_d0 | CGGGCUCGUGUAGCUCAUUAGCUCCGAGCCCGGAUAA<br>GCGGGCUCCGUCCUGGAUUCGCGGGAAACGCGUACAUC<br>CAGCUGACGAGUCCCAAAUAGGACGAAACGGAGCCCG |
| 290 | BT_a1_b7_c4_d0 | GCGGCUCGUGUAGCUCAUUAGCUCCGAGCCGCGAUAA<br>GGCGGCUCGCGUCCUGGAUUCGCGGGAAACGCGUACAU<br>CCAGCUGACGAGUCCCAAAUAGGACGAAACGCGAGCC<br>GC |
| 291 | BT_a1_b7_c0_d1 | GUGGCUCGUGUAGCUCAUUAGCUCCGAGCCACCGAUA<br>AGGGUGGCUCCCUGGAUUCGCGGGAAACGCGUACAUCC<br>AGCUGACGAGUCCCAAAUAGGACGAAGAGCCAC |
| 292 | BT_a1_b7_c1_d1 | CGGGCUCGUGUAGCUCAUUAGCUCCGAGCCCGCGAUA<br>AGGCGGGCUCUCCUGGAUUCGCGGGAAACGCGUACAUC<br>CAGCUGACGAGUCCCAAAUAGGACGAAAGAGCCCG |

TABLE 8-continued

Exemplary BIV Tar OFF switches (with 1 stabilization stem)

| SEQ ID NO: | Name | Sequence |
|---|---|---|
| 293 | BT_a1_b7_c3_d1 | CGGGCUCGUGUAGCUCAUUAGCUCCGAGCCCGCGAUA AGGCGGGCUCCGUCCUGGAUUCGCGGAAACGCGUACA UCCAGCUGACGAGUCCCAAAUAGGACGAAACGGAGCC CG |
| 294 | BT_a1_b7_c0_d2 | GUGGCUCGUGUAGCUCAUUAGCUCCGAGCCACCGGAU AAGCGGUGGCUCCCUGGAUUCGCGGAAACGCGUACAU CCAGCUGACGAGUCCCAAAUAGGACGAAGAGCCAC |
| 295 | BT_a1_b7_c1_d2 | CGGGCUCGUGUAGCUCAUUAGCUCCGAGCCCGCGGAU AAGCGCGGGCUCUCCUGGAUUCGCGGAAACGCGUACA UCCAGCUGACGAGUCCCAAAUAGGACGAAAGAGCCCG |
| 296 | BT_a1_b7_c4_d2 | GCGGCUCGUGUAGCUCAUUAGCUCCGAGCCGCCGGAU AAGCGGCGGCUCGCGUCCUGGAUUCGCGGAAACGCGU ACAUCCAGCUGACGAGUCCCAAAUAGGACGAAACGCG AGCCGC |
| 297 | BT_a1_b7_c0_d3 | GUGGCUCGUGUAGCUCAUUAGCUCCGAGCCACCGAGA UAAGUCGGUGGCUCCCUGGAUUCGCGGAAACGCGUAC AUCCAGCUGACGAGUCCCAAAUAGGACGAAGAGCCAC |
| 298 | BT_a1_b7_c3_d3 | CGGGCUCGUGUAGCUCAUUAGCUCCGAGCCCGCGAGA UAAGUCGCGGGCUCCGUCCUGGAUUCGCGGAAACGCG UACAUCCAGCUGACGAGUCCCAAAUAGGACGAAACGG AGCCCG |
| 299 | BT_a1_b7_c4_d3 | GCGGCUCGUGUAGCUCAUUAGCUCCGAGCCGCCGAGA UAAGUCGGCGGCUCGCGUCCUGGAUUCGCGGAAACGC GUACAUCCAGCUGACGAGUCCCAAAUAGGACGAAACG CGAGCCGC |
| 300 | BT_a1_b7_c3_d4 | CGGGCUCGUGUAGCUCAUUAGCUCCGAGCCCGCGACG AUAAGGUCGCGGGCUCCGUCCUGGAUUCGCGGAAACG CGUACAUCCAGCUGACGAGUCCCAAAUAGGACGAAAC GGAGCCCG |
| 301 | BT_a1_b7_c4_d4 | GCGGCUCGUGUAGCUCAUUAGCUCCGAGCCGCCGACG AUAAGGUCGGCGGCUCGCGUCCUGGAUUCGCGGAAAC GCGUACAUCCAGCUGACGAGUCCCAAAUAGGACGAAA CGCGAGCCGC |
| 302 | BT_a2_b7_c2_d0 | CGCGGCUCGUGUAGCUCAUUAGCUCCGAGCCGCGGAU AAGCGCGGCUGUCCUGGAUUCGCGGAAACGCGUACAU CCAGCUGACGAGUCCCAAAUAGGACGAAACAGCCGCG |
| 303 | BT_a2_b7_c3_d3 | GCGGGCUCGUGUAGCUCAUUAGCUCCGAGCCCGCCGA GAUAAGUCGGCGGGCUCGUCCUGGAUUCGCGGAAACG CGUACAUCCAGCUGACGAGUCCCAAAUAGGACGAAAC GAGCCCGC |
| 304 | BT_a2_b7_c0_d4 | CGUGGCUCGUGUAGCUCAUUAGCUCCGAGCCACGCGA CGAUAAGGUCGCGUGGCUCCUGGAUUCGCGGAAACGC GUACAUCCAGCUGACGAGUCCCAAAUAGGACGAAAGC CACG |
| 305 | BT_a3_b7_c1_d2 | CGCGGGCUCGUGUAGCUCAUUAGCUCCGAGCCCGCGC GGAUAAGCGCGCGGGCUCCUGGAUUCGCGGAAACGCG UACAUCCAGCUGACGAGUCCCAAAUAGGACGAAAGCC CGCG |
| 306 | BT_a3_b7_c2_d2 | GCGCGGCUCGUGUAGCUCAUUAGCUCCGAGCCGCGCC GGAUAAGCGGCGCGGCGUCCUGGAUUCGCGGAAACGC GUACAUCCAGCUGACGAGUCCCAAAUAGGACGAAACG CCGCGC |
| 307 | BT_a3_b7_c0_d3 | GCGUGGCUCGUGUAGCUCAUUAGCUCCGAGCCACGCC GAGAUAAGUCGGCGUGGCCCUGGAUUCGCGGAAACGC GUACAUCCAGCUGACGAGUCCCAAAUAGGACGAAGCC ACGC |
| 308 | BT_a3_b7_c2_d4 | GCGCGGCUCGUGUAGCUCAUUAGCUCCGAGCCGCGCC GACGAUAAGGUCGGCGCGGCGUCCUGGAUUCGCGGAA ACGCGUACAUCCAGCUGACGAGUCCCAAAUAGGACGA AACGCCGCGC |

TABLE 8-continued

| Exemplary BIV Tar OFF switches (with 1 stabilization stem) | | |
| --- | --- | --- |
| SEQ ID NO: | Name | Sequence |
| 309 | BT_a4_b7_c1_d1 | GCGCGGGCUCGUGUAGCUCAUUAGCUCCGAGCCCGCG CCGAUAAGGGCGCGGGUCCUGGAUUCGCGGAAACGCG UACAUCCAGCUGACGAGUCCCAAAUAGGACGAAACCC GCGC |
| 310 | BT_a4_b7_c1_d2 | GCGCGGGCUCGUGUAGCUCAUUAGCUCCGAGCCCGCG CCGGAUAAGCGGCGCGGGUCCUGGAUUCGCGGAAACG CGUACAUCCAGCUGACGAGUCCCAAAUAGGACGAAAC CCGCGC |
| 311 | BT_a4_b7_c0_d4 | CGCGUGGCUCGUGUAGCUCAUUAGCUCCGAGCCACGC GCGACGAUAAGGUCGCGCGUGGCCUGGAUUCGCGGAA ACGCGUACAUCCAGCUGACGAGUCCCAAAUAGGACGA ACCACGCG |
| 312 | BT_a4_b7_c1_d4 | GCGCGGGCUCGUGUAGCUCAUUAGCUCCGAGCCCGCG CCGACGAUAAGGUCGGCGCGGGUCCUGGAUUCGCGGA AACGCGUACAUCCAGCUGACGAGUCCCAAAUAGGACG AAACCCGCGC |

TABLE 9

| Exemplary P22N ON switches | | |
| --- | --- | --- |
| SEQ ID NO: | Name | Sequence |
| 313 | P22N_a1_b5_c1 | GUGCGCGACAAGCGCACCCCUGGAUUCGCGGAAACGCG UACAUCCAGCUGACGAGUCCCAAAUAGGACGAAGGUGC G |
| 314 | P22N_a1_b5_c2 | UGCGCUGACAAAGCGCACCCCUGGAUUCGCGGAAACGC GUACAUCCAGCUGACGAGUCCCAAAUAGGACGAAGGUG CGC |
| 315 | P22N_a1_b5_c3 | UGCGCUGACAAAGCGCACCUCCUGGAUUCGCGGAAACG CGUACAUCCAGCUGACGAGUCCCAAAUAGGACGAAAGG UGCGC |
| 316 | P22N_a1_b5_c4 | UGCGCUGACAAAGCGCACCGUCCUGGAUUCGCGGAAAC GCGUACAUCCAGCUGACGAGUCCCAAAUAGGACGAAAC GGUGCGC |
| 317 | P22N_a2_b5_c1 | GUGCGCUGACAAAGCGCACCCCUGGAUUCGCGGAAACG CGUACAUCCAGCUGACGAGUCCCAAAUAGGACGAAGGU GCG |
| 318 | P22N_a2_b5_c2 | GUGCGCUGACAAAGCGCACCUCCUGGAUUCGCGGAAAC GCGUACAUCCAGCUGACGAGUCCCAAAUAGGACGAAAG GUGCG |
| 319 | P22N_a2_b5_c3 | GUGCGCUGACAAAGCGCACCGUCCUGGAUUCGCGGAAA CGCGUACAUCCAGCUGACGAGUCCCAAAUAGGACGAAA CGGUGCG |
| 320 | P22N_a2_b5_c4 | GUGCGCUGACAAAGCGCACCCGUCCUGGAUUCGCGGAA ACGCGUACAUCCAGCUGACGAGUCCCAAAUAGGACGAA ACGGGUGCG |
| 321 | P22N_a3_b5_c1 | GGUGCGCUGACAAAGCGCACCUCCUGGAUUCGCGGAAA CGCGUACAUCCAGCUGACGAGUCCCAAAUAGGACGAAA GGUGC |
| 322 | P22N_a3_b5_c2 | GGUGCGCUGACAAAGCGCACCGUCCUGGAUUCGCGGAA ACGCGUACAUCCAGCUGACGAGUCCCAAAUAGGACGAA ACGGUGC |
| 323 | P22N_a3_b5_c3 | GGUGCGCUGACAAAGCGCACCCGUCCUGGAUUCGCGGA AACGCGUACAUCCAGCUGACGAGUCCCAAAUAGGACGA AACGGGUGC |

TABLE 9-continued

Exemplary P22N ON switches

| SEQ ID NO: | Name | Sequence |
|---|---|---|
| 324 | P22N_a3_b5_c4 | GGUGCGCUGACAAAGCGCACCGCGUCCUGGAUUCGCGG<br>AAACGCGUACAUCCAGCUGACGAGUCCCAAAUAGGACG<br>AAACGCGGUGC |
| 325 | P22N_a4_b5_c1 | CGGUGCGCUGACAAAGCGCACCGUCCUGGAUUCGCGGA<br>AACGCGUACAUCCAGCUGACGAGUCCCAAAUAGGACGA<br>AACGGUG |
| 326 | P22N_a4_b5_c2 | GGGUGCGCUGACAAAGCGCACCCGUCCUGGAUUCGCGG<br>AAACGCGUACAUCCAGCUGACGAGUCCCAAAUAGGACG<br>AAACGGGUG |
| 327 | P22N_a4_b5_c3 | CGGUGCGCUGACAAAGCGCACCGCGUCCUGGAUUCGCG<br>GAAACGCGUACAUCCAGCUGACGAGUCCCAAAUAGGAC<br>GAAACGCGGUG |
| 328 | P22N_a4_b5_c4 | GGGUGCGCUGACAAAGCGCACCCGCGUCCUGGAUUCGC<br>GGAAACGCGUACAUCCAGCUGACGAGUCCCAAAUAGGA<br>CGAAACGCGGGUG |
| 329 | P22N_a0_b6_c0 | GGUGCGGACAACGCACCCCUGGAUUCGCGGAAACGCGU<br>ACAUCCAGCUGACGAGUCCCAAAUAGGACGAAGGUGCG |
| 330 | P22N_a0_b6_c1 | GUGCGCGACAAGCGCACCCCUGGAUUCGCGGAAACGCG<br>UACAUCCAGCUGACGAGUCCCAAAUAGGACGAAGGUGC<br>GC |
| 331 | P22N_a0_b6_c2 | UGCGCUGACAAAGCGCACCCCUGGAUUCGCGGAAACGC<br>GUACAUCCAGCUGACGAGUCCCAAAUAGGACGAAGGUG<br>CGCU |
| 332 | P22N_a0_b6_c3 | UGCGCUGACAAAGCGCACCUCCUGGAUUCGCGGAAACG<br>CGUACAUCCAGCUGACGAGUCCCAAAUAGGACGAAAGG<br>UGCGCU |
| 333 | P22N_a0_b6_c4 | UGCGCUGACAAAGCGCACCGUCCUGGAUUCGCGGAAAC<br>GCGUACAUCCAGCUGACGAGUCCCAAAUAGGACGAAAC<br>GGUGCGCU |
| 334 | P22N_a1_b6_c0 | GGUGCGCGACAAGCGCACCCCUGGAUUCGCGGAAACGC<br>GUACAUCCAGCUGACGAGUCCCAAAUAGGACGAAGGUG<br>CG |
| 335 | P22N_a1_b6_c1 | GUGCGCUGACAAAGCGCACCCCUGGAUUCGCGGAAACG<br>CGUACAUCCAGCUGACGAGUCCCAAAUAGGACGAAGGU<br>GCGC |
| 336 | P22N_a1_b6_c3 | GUGCGCUGACAAAGCGCACCGUCCUGGAUUCGCGGAAA<br>CGCGUACAUCCAGCUGACGAGUCCCAAAUAGGACGAAA<br>CGGUGCGC |
| 337 | P22N_a1_b6_c4 | GUGCGCUGACAAAGCGCACCGUCCUGGAUUCGCGGAA<br>ACGCGUACAUCCAGCUGACGAGUCCCAAAUAGGACGAA<br>ACGGGUGCGC |
| 338 | P22N_a2_b6_c0 | GGUGCGCUGACAAAGCGCACCCCUGGAUUCGCGGAAAC<br>GCGUACAUCCAGCUGACGAGUCCCAAAUAGGACGAAGG<br>UGCG |
| 339 | P22N_a2_b6_c2 | GGUGCGCUGACAAAGCGCACCGUCCUGGAUUCGCGGAA<br>ACGCGUACAUCCAGCUGACGAGUCCCAAAUAGGACGAA<br>ACGGUGCG |
| 340 | P22N_a2_b6_c3 | GGUGCGCUGACAAAGCGCACCCGUCCUGGAUUCGCGGA<br>AACGCGUACAUCCAGCUGACGAGUCCCAAAUAGGACGA<br>AACGGGUGCG |
| 341 | P22N_a2_b6_c4 | GGUGCGCUGACAAAGCGCACCGCGUCCUGGAUUCGCGG<br>AAACGCGUACAUCCAGCUGACGAGUCCCAAAUAGGACG<br>AAACGCGGUGCG |
| 342 | P22N_a3_b6_c0 | AGGUGCGCUGACAAAGCGCACCUCCUGGAUUCGCGGAA<br>ACGCGUACAUCCAGCUGACGAGUCCCAAAUAGGACGAA<br>AGGUGC |

TABLE 9-continued

| | Exemplary P22N ON switches | |
| --- | --- | --- |
| SEQ ID NO: | Name | Sequence |
| 343 | P22N_a3_b6_c1 | CGGUGCGCUGACAAAGCGCACCGUCCUGGAUUCGCGGA AACGCGUACAUCCAGCUGACGAGUCCCAAAUAGGACGA AACGGUGC |
| 344 | P22N_a3_b6_c2 | GGGUGCGCUGACAAAGCGCACCCGUCCUGGAUUCGCGG AAACGCGUACAUCCAGCUGACGAGUCCCAAAUAGGACG AAACGGGUGC |
| 345 | P22N_a3_b6_c3 | CGGUGCGCUGACAAAGCGCACCGCGUCCUGGAUUCGCG GAAACGCGUACAUCCAGCUGACGAGUCCCAAAUAGGAC GAAACGCGGUGC |
| 346 | P22N_a3_b6_c4 | GGGUGCGCUGACAAAGCGCACCCGCGUCCUGGAUUCGC GGAAACGCGUACAUCCAGCUGACGAGUCCCAAAUAGGA CGAAACGCGGGUGC |
| 347 | P22N_a4_b6_c0 | ACGGUGCGCUGACAAAGCGCACCGUCCUGGAUUCGCGG AAACGCGUACAUCCAGCUGACGAGUCCCAAAUAGGACG AAACGGUG |
| 348 | P22N_a4_b6_c1 | CGGGUGCGCUGACAAAGCGCACCCGUCCUGGAUUCGCG GAAACGCGUACAUCCAGCUGACGAGUCCCAAAUAGGAC GAAACGGGUG |
| 349 | P22N_a4_b6_c2 | GCGGUGCGCUGACAAAGCGCACCGCGUCCUGGAUUCGC GGAAACGCGUACAUCCAGCUGACGAGUCCCAAAUAGGA CGAAACGCGGUG |
| 350 | P22N_a4_b6_c3 | CGGGUGCGCUGACAAAGCGCACCCGCGUCCUGGAUUCG CGGAAACGCGUACAUCCAGCUGACGAGUCCCAAAUAGG ACGAAACGCGGGUG |
| 351 | P22N_a4_b6_c4 | GCGGUGCGCUGACAAAGCGCACCGCGCGUCCUGGAUUC GCGGAAACGCGUACAUCCAGCUGACGAGUCCCAAAUAG GACGAAACGCGCGGUG |
| 352 | P22N_a0_b7_c0 | GGUGCGCGACAAGCGCACCCCUGGAUUCGCGGAAACGC GUACAUCCAGCUGACGAGUCCCAAAUAGGACGAAGGUG CGC |
| 353 | P22N_a0_b7_c2 | GUGCGCUGACAAAGCGCACCUCCUGGAUUCGCGGAAAC GCGUACAUCCAGCUGACGAGUCCCAAAUAGGACGAAAG GUGCGCU |
| 354 | P22N_a0_b7_c3 | GUGCGCUGACAAAGCGCACCGUCCUGGAUUCGCGGAAA CGCGUACAUCCAGCUGACGAGUCCCAAAUAGGACGAAA CGGUGCGCU |
| 355 | P22N_a0_b7_c4 | GUGCGCUGACAAAGCGCACCCGUCCUGGAUUCGCGGAA ACGCGUACAUCCAGCUGACGAGUCCCAAAUAGGACGAA ACGGGUGCGCU |
| 356 | P22N_a1_b7_c0 | GGUGCGCUGACAAAGCGCACCCCUGGAUUCGCGGAAAC GCGUACAUCCAGCUGACGAGUCCCAAAUAGGACGAAGG UGCGC |
| 357 | P22N_a1_b7_c2 | GGUGCGCUGACAAAGCGCACCGUCCUGGAUUCGCGGAA ACGCGUACAUCCAGCUGACGAGUCCCAAAUAGGACGAA ACGGUGCGC |
| 358 | P22N_a1_b7_c3 | GGUGCGCUGACAAAGCGCACCCGUCCUGGAUUCGCGGA AACGCGUACAUCCAGCUGACGAGUCCCAAAUAGGACGA AACGGGUGCGC |
| 359 | P22N_a1_b7_c4 | GGUGCGCUGACAAAGCGCACCGCGUCCUGGAUUCGCGG AAACGCGUACAUCCAGCUGACGAGUCCCAAAUAGGACG AAACGCGGUGCGC |
| 360 | P22N_a2_b7_c1 | CGGUGCGCUGACAAAGCGCACCGUCCUGGAUUCGCGGA AACGCGUACAUCCAGCUGACGAGUCCCAAAUAGGACGA AACGGUGCG |
| 361 | P22N_a2_b7_c2 | GGGUGCGCUGACAAAGCGCACCCGUCCUGGAUUCGCGG AAACGCGUACAUCCAGCUGACGAGUCCCAAAUAGGACG AAACGGGUGCG |

TABLE 9-continued

Exemplary P22N ON switches

| SEQ ID NO: | Name | Sequence |
|---|---|---|
| 362 | P22N_a2_b7_c3 | CGGUGCGCUGACAAAGCGCACCGCGUCCUGGAUUCGCG GAAACGCGUACAUCCAGCUGACGAGUCCCAAAUAGGAC GAAACGCGGUGCG |
| 363 | P22N_a2_b7_c4 | GGGUGCGCUGACAAAGCGCACCCGCGUCCUGGAUUCGC GGAAACGCGUACAUCCAGCUGACGAGUCCCAAAUAGGA CGAAACGCGGGUGCG |
| 364 | P22N_a3_b7_c0 | ACGGUGCGCUGACAAAGCGCACCGUCCUGGAUUCGCGG AAACGCGUACAUCCAGCUGACGAGUCCCAAAUAGGACG AAACGGUGC |
| 365 | P22N_a3_b7_c3 | CGGGUGCGCUGACAAAGCGCACCCGCGUCCUGGAUUCG CGGAAACGCGUACAUCCAGCUGACGAGUCCCAAAUAGG ACGAAACGCGGGUGC |
| 366 | P22N_a3_b7_c4 | GCGGUGCGCUGACAAAGCGCACCGCGCGUCCUGGAUUC GCGGAAACGCGUACAUCCAGCUGACGAGUCCCAAAUAG GACGAAACGCGCGGUGC |
| 367 | P22N_a4_b7_c0 | ACGGGUGCGCUGACAAAGCGCACCCGUCCUGGAUUCGC GGAAACGCGUACAUCCAGCUGACGAGUCCCAAAUAGGA CGAAACGGGUG |
| 368 | P22N_a4_b7_c1 | CGCGGUGCGCUGACAAAGCGCACCGCGUCCUGGAUUCG CGGAAACGCGUACAUCCAGCUGACGAGUCCCAAAUAGG ACGAAACGCGGUG |
| 369 | P22N_a4_b7_c3 | CGCGGUGCGCUGACAAAGCGCACCGCGCGUCCUGGAUU CGCGGAAACGCGUACAUCCAGCUGACGAGUCCCAAAUA GGACGAAACGCGCGGUG |

TABLE 10

Exemplary High-Performing ON and OFF switches

| SEQ ID NO: | Name | Sequence |
|---|---|---|
| | | ON Switches |
| 10 | MS2_a3_b5_c1 | CGCGCACGagcaucagcCGUGCGCGUCCUGGAUUCGCGGAAA CGCGUACAUCCAGCUGACGAGUCCCAAAUAGGACGAAAC GCGC |
| 12 | MS2_a0_b6_c1 | CGCACGagcaucagcCGUGCGUCCUGGAUUCGCGGAAACGCG UACAUCCAGCUGACGAGUCCCAAAUAGGACGAAACGCAC G |
| 18 | MS2_a2_b6_c0 | ACGGCACGagcaucagcCGUGCCGUCCUGGAUUCGCGGAAAC GCGUACAUCCAGCUGACGAGUCCCAAAUAGGACGAAACG GCA |
| 22 | MS2_a0_b7_c0 | ACGCACGagcaucagcCGUGCGUCCUGGAUUCGCGGAAACGC GUACAUCCAGCUGACGAGUCCCAAAUAGGACGAAACGCA CG |
| 24 | FLIPPED_HHR_ MS2_a0_b6_ c1 | CGCACGUCCUGGAUUCGCGGAAACGCGUACAUCCAGCUG ACGAGUCCCAAAUAGGACGAAACGUGCGAGCAUCAGCCG CACG |
| 122 | PP7_a1_b5_c1 | CGGCACAGAAGAUAUGGCUUCGUGCCGUCCUGGAUUCGC GGAAACGCGUACAUCCAGCUGACGAGUCCCAAAUAGGAC GAAACGGCA |
| 130 | PP7_a3_b5_c1 | CGCGGCACAGAAGAUAUGGCUUCGUGCCGCGUCCUGGAU UCGCGGAAACGCGUACAUCCAGCUGACGAGUCCCAAAUA GGACGAAACGCGG |
| 136 | PP7_a0_b6_c1 | CGGCACAGAAGAUAUGGCUUCGUGCCGUCCUGGAUUCGC GGAAACGCGUACAUCCAGCUGACGAGUCCCAAAUAGGAC GAAACGGCAC |

TABLE 10-continued

Exemplary High-Performing ON and OFF switches

| SEQ ID NO: | Name | Sequence |
|---|---|---|
| 149 | PP7_a3_b6_c0 | ACGCGGCACAGAAGAUAUGGCUUCGUGCCGCGUCCUGGA UUCGCGGAAACGCGUACAUCCAGCUGACGAGUCCCAAAU AGGACGAAACGCGG |
| 157 | PP7_a0_b7_c3 | CGGGCACAGAAGAUAUGGCUUCGUGCCCGCGUCCUGGAU UCGCGGAAACGCGUACAUCCAGCUGACGAGUCCCAAAUA GGACGAAACGCGGGCAC |
| 169 | FLIPPED_HHR_ PP7_a1_b5_ c1 | CGGCAUCCUGGAUUCGCGGAAACGCGUACAUCCAGCUGA CGAGUCCCAAAUAGGACGAAAUGCCGCAGAAGAUAUGGC UUCGCGGCA |
| 394 | BT_a0_b7_c2 | GCGCUCGUGUAGCUCAUUAGCUCCGAGCGCGUCCUGGAU UCGCGGAAACGCGUACAUCCAGCUGACGAGUCCCAAAUA GGACGAAACGCGCUCG |
| 214 | BT_a2_b7_c2 | GCGGGCUCGUGUAGCUCAUUAGCUCCGAGCCCGCGUCCU GGAUUCGCGGAAACGCGUACAUCCAGCUGACGAGUCCCA AAUAGGACGAAACGCGGGCU |

OFF Switches

| 263 | BT_a1_b6_c1_ d4 | GGGCUCGUGUAGCUCAUUAGCUCCGAGCCCCGACGAUAA GGUCGGGGCUCUCCUGGAUUCGCGGAAACGCGUACAUCC AGCUGACGAGUCCCAAAUAGGACGAAAGAGCCC |
| 41 | MS2_a2_b6_c3_ d3 | UGCCGCCCGGAUAAGCGGGCGGCACAGAGCAUCAGCCGUG CCGCCGGGAUAAGCCGGCGGCACGUCCUGGAUUCGCGGA AACGCGUACAUCCAGCUGACGAGUCCCAAAUAGGACGAA ACGUGCCGC |

TABLE 11

Exemplary saRNA sequences

| SEQ ID NO | Name | Sequence |
|---|---|---|
| 377 | saRNA_17_5'UTR_ NSP_SGP_ 5'UTR_mCherry_ 3'UTR_CSE Bolded text marks 5 exemplary insertion sites for ARES and controls sequences | ggg_INSERT_SITE_1_cggcgcatgagagaagcccagaccaattacctacccaaaa tggagaaagttcacgttgacatcgaggaagacagcccattcctcagagctttgcagcggagcttc ccgcagtttgaggtagaagccaagcaggtcactgataatgaccatgctaatgccagagcgttttc gcatctggcttcaaaactgatcgaaacggaggtggacccatccgacacgatccttgacattggaa gtgcgcccgcccgcagaatgtattctaagcacaagtatcattgtatctgtccgatgagatgtgcgg aagatccggacagattgtataagtatgcaactaagctgaagaaaaactgtaaggaaataactgat aaggaattggacaagaaaatgaaggagctggccgccgtcatgagcgaccctgacctggaaact gagactatgtgcctccacgacgacgagtcgtgtcgctacgaagggcaagtcgctgtttaccagg atgtatacgcggttgacggaccgacaagtctctatcaccaagccaataagggagttagagtcgc ctactggataggctttgacaccaccccttttatgtttaagaacttggctggagcatatccatcatact ctaccaactgggccgacgaaaccgtgttaacggctcgtaacataggcctatgcagctctgacgtt atggagcggtcacgtagagggatgtccattcttagaaagaagtatttgaaaccatccaacaatgtt ctattctctgttggctcgaccatctaccacgagaagagggacttactgaggagctggcacctgcc gtctgtatttcacttacgtggcaagcaaaattacacatgtcggtgtgagactatagttagttgcgac gggtacgtcgttaaaagaatagctatcagtccaggcctgtatgggaagccttcaggctatgctgct acgatgcaccgcgagggattcttgtgctgcaaagtgacagacacattgaacggggagagggtc tcttttcccgtgtgcacgtatgtgccagctacattgtgtgaccaaatgactggcatactggcaacag atgtcagtgcggacgacgcgcaaaaactgctggttgggctcaaccagcgtatagtcgtcaacgg tcgcacccagagaaacaccaataccatgaaaaattaccttttgcccgtagtggcccaggcatttg ctaggtgggcaaaggaatataaggaagatcaagaagatgaaaggccactaggactacgagata gacagttagtcatggggtgttgttgggcttttagaaggcacaagataacatctatttataagcgccc ggatacccaaaccatcatcaaagtgaacagcgatttccactcattcgtgctgcccaggataggca gtaacacattggagatcgggctgagaacaagaatcaggaaaatgttagaggagcacaaggagc cgtcacctctcattaccgccgaggacgtacaagaagctaagtgcgcagccgatgaggctaagg aggtgcgtgaagccgaggagttgcgcgcagctctaccaccctttggcagctgatgttgaggagcc cactctggaggcagacgtcgacttgatgttacaagaggctggggccggctcagtggagacacc tcgtggcttgataaaggttaccagctacgatggcgaggacaagatcggctcttacgctgtgctttc tccgcaggctgtactcaagagtgaaaaattatcttgcatccaccctctcgctgaacaagtcatagt gataacacactctggccgaaaagggcgttatgccgtggaaccataccatggtaaagtagtggtg ccagagggacatgcaatacccgtccaggactttcaagctctgagtgaaagtgccaccattgtgta caacgaacgtgagttcgtaaacaggtacctgcaccatattgccacacatggaggagcgctgaac actgatgaagaatattacaaaactgtcaagcccagcgagcacgacggcgaatacctgtacgaca tcgacaggaaacagtgcgtcaagaaagaactagtcactgggctagggctcacaggcgagctg |

TABLE 11-continued

Exemplary saRNA sequences

| SEQ ID NO | Name | Sequence |
|---|---|---| gtggatcctcccttccatgaattcgcctacgagagtctgagaacacgaccagccgctccttacca
agtaccaaccatagggtgtatggcgtgccaggatcaggcaagtctggcatcattaaaagcgca
gtcaccaaaaaagatctagtggtgagcgccaagagaaaactgtgcagaaattataagggac
gtcaagaaaatgaaagggctggacgtcaatgccagaactgtggactcagtgctcttgaatggat
gcaaacaccccgtagagaccctgtatattgacgaagcttttgcttgtcatgcaggtactctcagag
cgctcatagccattataagacctaaaaaggcagtgctctgcggggatcccaaacagtgcggttttt
ttaacatgatgtgcctgaaagtgcattttaaccacgagatttgcacacaagtcttccacaaaagcat
ctctcgccgttgcactaaatctgtgacttcggtcgtctcaaccttgtttttacgacaaaaaaatgagaa
cgacgaatccgaaagagactaagattgtgattgacactaccggcagtaccaaacctaagcagga
cgatctcattctcacttgtttcagagggtgggtgaagcagttgcaaatagattacaaaggcaacga
aataatgacggcagctgcctctcaagggctgacccgtaaaggtgtgtatgccgttcggtacaag
gtgaatgaaaatcctctgtacgcacccacctcagaacatgtgaacgtcctactacccgcacgga
ggaccgcatcgtgtggaaaacactagccggcgacccatggataaaaacactgactgccaagta
ccctgggaatttcactgccacgatagaggagtggcaagcagagcatgatgccatcatgaggca
catcttggagagaccggaccctaccgacgtcttccagaataaggcaaacgtgtgttgggccaag
gctttagtgccggtgctgaagaccgctggcatagacatgaccactgaacaatggaacactgtgg
attattttgaaacggacaaagctcactcagcagagatagtattgaaccaactatgcgtgaggttctt
tggactcgatctggactccggtctattttctgcacccactgttccgttatccattaggaataatcact
gggataactccccgtcgcctaacatgtacgggctgaataaagaagtggtccgtcagctctctcgca
ggtacccacaactgcctcgggcagttgccactggaagagtctatgacatgaacactggtacact
gcgcaattatgatccgcgcataaacctagtacctgtaaacagaagactgcctcatgctttagtcctc
caccataatgaacacccacagagtgacttttcttcattcgtcagcaaattgaagggcagaactgtc
ctggtggtcggggaaaagttgtccgtcccaggcaaaatggttgactggttgtcagaccggcctg
aggctaccttcagagctcggctggattttaggcatcccaggtgatgtgcccaaatatgacataatat
ttgttaatgtgaggaccccatataaataccatcactatcagcagtgtgaagaccatgccattaagct
tagcatgttgaccaagaaagcttgtctgcatctgaatcccggcggaacctgtgtcagcataggtta
tggttacgctgacagggccagcgaaagcatcattggtgctatagcgcggcagttcaagttttccc
gggtatgcaaaccgaaatcctcacttgaagagacggaagttctgtttgtattcattgggtacgatcg
caaggcccgtacgcacaattcttacaagctttcatcaaccttgaccaacatttatacaggttccaga
ctccacgaagccggatgtgcaccctcatatcatgtggtgcgaggggatattgccacggccaccg
aaggagtgattatataatgctgctaacagcaaaggacaacctggcggagggggtgtgcggagcgc
tgtataagaaattcccgggaaagcttcgatttacagccgatcgaagtaggaaaagcgcgactggtc
aaaggtgcagctaaacatatcattcatgccgtaggaccaaaacttcaacaaagtttcggaggttgaa
ggtgacaaacagttggcagaggcttatgagtccatcgctaagattgtcaacgataacaattacaa
gtcagtagcgattccactgttgtccaccggcatctttccgggaacaaagatcgactaacccaatc
attgaaccatttgctgacagctttagacaccactgatgcagatgtagccatatactgcagggacaa
gaaatgggaaatgactctcaaggaagcagtggctaggagagaagcagtggaggagatatgcat
atccgacgactcttcagtgacagaacctgatgcagagctggtgagggtgcatccgaagagttctt
tggctggaaggaagggctacagcacaagcgatggcaaaactttctcatatttggaagggaccaa
gtttcaccaggcggccaaggatatagcagaaattaatgccatgtggcccgttgcaacggaggcc
aatgagcaggtatgcatgtatatcctcggagaaagcatgagcagtattaggtcgaaatgccccgt
cgaagagtcggaagcctccacaccacctagcacgctgccttgcttgtgcatccatgccatgactc
cagaaagagtacagcgcctaaaagcctcacgtccagaacaaattactgtgtgctcatcctttccat
tgccgaagtatagaatcactggtgtgcagaagatccaatgctcccagcctatattgttctcaccga
aagtgcctgcgtatattcatccaaggaagtatctcgtgggaaacaccaccggtagacgagactccg
gagccatcggcagagaaccaatccacagaggggacacctgaacaaccaccacttataaccga
ggatgagaccaggactagaacgcctgagccgatcatcatcgaagaggaagaagaggatagca
taagtttgctgtcagatggcccgacccaccaggtgctgcaagtcgaggcagacattcacgggcc
gccctctgtatctagctcatcctggtccattcctcatgcatccgactttgatgtggacagtttatcc
atacttgacaccctggagggagctagcgtgaccagcggggcaacgtcagccgagactaactctta
cttcgcaaagagtatggagtttctggcgcgaccggtgcctgcgcctcgaacagtattcaggaacc
ctccacatcccgctccgcgcacaagaacaccgtcacttgcacccagcagggcctgctcgagaa
ccagcctagtttccaccccgccaggcgtgaatagggtgatcactagagaggagctcgaggcgc
ttacccgtcacgcactcctagcaggtcggtctcgagaaccagcctggtctccaacccgccagg
cgtaaataggtgattacaagagaggagtttgaggcgttcgtagcacaacaacaatgacggtttg
atgcgggtgcatacatcttttcctccgacaccggtcaagggcatttacaacaaaaatcagtaaggc
aaacggtgctatccgaagtggtgttggagaggaccgaattggagatttcgtatgccccgcggcctc
gaccaagaaaaagaagaattactacgcaagaaattacagttaaatcccacacctgctaacagaa
gcagataccagtccaggaaggtggagaacatgaaagccataacagctagacgtattctgcaag
gcctagggcattatttgaaggcagaaggaaaagtggagtgctaccgaaccctgcatcctgttcct
ttgtattcatctagtgtgaacgtgcctttcaccagccaaggtcgcagtggaagcctgtaacgcc
atgttgaaagagaacttttccgactgtggcttcttactgtattattccagagtacgatgcctatttgg
acatggttgacggagcttcatgctgcttagcactgccagttttttgccctgcaaagctcgcgcagctt
tccaaagaaacactcctatttggaacccacaatacgatcggcagtgccttcagcgatccagaacac
gctccagaacgtcctggcagctgccacaaaaagaaattgcaatgtcacgcaaatgagagaattg
cccgtattggattcggcggccttttaatgtggaatgcttcaagaaatatgcgtgtaataatgaatatt
gggaaacgtttaaagaaaaccccatcaggcttactgaagaaaacgtggtaaattacattaccaaatt
aaaaggaccaaaagctgctgctcttttttgcgaagacacataatttgaatatgttgcaggacatacc
aatggacaggtttgtaatggacttaaagaagacgtgaaagtgactccaggaacaaaacatact
gaagaacggcccaaggtacaggtgatccaggctgccgatccgctagcaacagcgtatctgtgc
ggaatccaccgagagctggttaggagattaaatgcggtcctgcttccgaacattcatacactgttt
gatatgtcggctgaagactttgacgcgtattatagccgagcacttccagcctgggggattgtgttctgg
aaactgacatcgcgtcgtttgataaaagtgaggacgacgccatggctctgaccgcgttaatgattc
tggaagacttaggtgtggacgcagagctgttgacgctgattgaggcggcctttcggcgaaatttcat TABLE 11-continued Exemplary saRNA sequences

| SEQ ID NO | Name | Sequence |
|---|---|---|
| | | caatacatttgcccactaaaactaaatttaaattcggagccatgatgaaatctggaatgttcctcac actgtttgtgaacacagtcattaacattgtaatcgcaagcagagtgttgagagaacggctaaccgga tcaccatgtgcagcattcattggagatgacaatatcgtgaaaggagtcaaatcggacaaattaatg gcagacaggtgcgccacctggttgaatatggaagtcaagattatagatgctgtggtgggcgaga aagcgccttatttctgtggagggtttattttgtgtgactccgtgaccggcacagcgtgccgtgtggc agacccctaaaaaggctgtttaagcttggcaaacctctggcagcagacgatgaacatgatgatg acaggagaagggcattgcatgaagagtcaacacgctggaaccgagtgggtattctttcagagct gtgcaaggcagtagaatcaaggtatgaaaccgtaggaacttccatcatagttatggccatgacta ctctagctagcagtgttaaatcattcagctacctgagaggggcccctataactctctacggctaac ctgaatggactacgacatagtctagtccgccaag_INSERT_SITE_2_tctagcaGG AGAgtcccgacctcca_INSERT_SITE_3_ggagagaccagggccaccCTTA AG_INSERT_SITE_4_GCCGCCACCATGGTTAGCAAAGGCG AGGAAGACAACATGGCTATTATTAAAGAGTTCATGCGCTTC AAGGTGCACATGGAGGGCTCCGTGAACGGCCACGAGTTCG AGATCGAGGGCGAGGGCGAGGGCCGCCCCTACGAGGGCA CCCAGACCGCCAAGCTGAAGGTGACCAAGGGTGGCCCCCT GCCCTTCGCCTGGGACATCCTGTCCCCTCAGTTCATGTACG GCTCCAAGGCCTACGTGAAGCACCCCGCCGACATCCCCGA CTACTTGAAGCTGTCCTTCCCCGAGGGCTTCAAGTGGGAG CGCGTGATGAACTTCGAGGACGGCGGCGTGGTGACCGTGA CCCAGGACTCCTCCCTGCAGGACGGCGAGTTCATCTACAA GGTGAAGCTGCGCGGCACCAACTTCCCCTCCGACGGCCCC GTAATGCAGAAGAAGACCATGGGCTGGGAGGCCTCCTCCG AGCGGATGTACCCCGAGGACGGCGCCCTGAAGGGCGAGAT CAAGCAGAGGCTGAAGCTGAAGGACGGCGGCCACTACGA CGCTGAGGTCAAGACCACCTACAAGGCCAAGAAGCCCGT GCAGCTGCCCGGCGCCTACAACGTCAACATCAAGTTGGAC ATCACCTCCCACAACGAGGACTACACCATCGTGGAACAGT ACGAACGCGCCGAGGGCCGCCACTCCACCGGCGGCATGG ACGAGCTGTACAAGAGATCTCGAGCTCAAGCTTCGAATTC TGCAGTCGACGGTACCGCGGGCCCGGGATCCACCGGATCT AGATAATAACAT_INSERT_SITE_5_ATGgaattggcaagctgcttacata gaactcgcggcgattgGcatgccgccttaaaattttatttattttttctttttctttttccgaatc ggattttgttttaatatttc |
| 378 | saRNA_18_5'UTR_ HHR_NSP_SGP_5'UTR_ mCherry_3'UTR_CSE E.g., Insert site: 1 | TACACTTACCATACCCCGCGCGTCCTGGATTCGCGGAAACG CGTACATCCAGCTGACGAGTCCCAAATAGGACGAAACGCG CCCCCACAATTTCAACAA |
| 379 | saRNA_19_5'UTR_ dHHR_NSP_SGP_5'UTR_ mCherry_3'UTR_CSE E.g., Insert site: 1 | TACACTTACCATACCCCGCGCGTCTGGATTCGCGGAAACGC GTACATCCAGGTCCCAAATAGGACACGCGCCCCCACAATTT CAACAA |
| 380 | saRNA_20_5'UTR_ RCHHR_NSP_SGP_ 5'UTR_mCherry_ 3'UTR_CSE E.g., Insert site: 1 | TACACTTACCATACCCCGCGCGTTTCGTCCTATTTGGGACTC GTCAGCTGGATGTACGCGTTTCCGCGAATCCAGGACGCGC CCCCACAATTTCAACAA |
| 381 | saRNA_27_5'UTR_ NSP_SGP_HHR_5'UTR_ mCherry_3'UTR_CSE E.g., Insert site: 4 | TACACTTACCATACCCCGCGCGTCCTGGATTCGCGGAAACG CGTACATCCAGCTGACGAGTCCCAAATAGGACGAAACGCG CCCCCACAATTTCAACAA |
| 382 | saRNA_28_5'UTR_ NSP_SGP_dHHR_5'UTR_ mCherry_3'UTR_CSE E.g., Insert site: 4 | TACACTTACCATACCCCGCGCGTCTGGATTCGCGGAAACGC GTACATCCAGGTCCCAAATAGGACACGCGCCCCCACAATTT CAACAA |
| 383 | saRNA_29_5'UTR_ NSP_SGP_RCHHR_ 5'UTR_mCherry_ 3'UTR_CSE E.g., Insert site: 4 | TACACTTACCATACCCCGCGCGTTTCGTCCTATTTGGGACTC GTCAGCTGGATGTACGCGTTTCCGCGAATCCAGGACGCGC CCCCACAATTTCAACAA |
| 384 | saRNA_30_5'UTR_ NSP_SGP_5'UTR_ mCherry_HHR_3'UTR_ CSE E.g., Insert site: 5 | TACACTTACCATACCCCGCGCGTCCTGGATTCGCGGAAACG CGTACATCCAGCTGACGAGTCCCAAATAGGACGAAACGCG CCCCCACAATTTCAACAA |

TABLE 11-continued

| SEQ ID NO | Name | Sequence |
|---|---|---|
| 385 | saRNA_31_5'UTR_ NSP_SGP_5'UTR_ mCherry_dHHR_ 3'UTR_CSE E.g., Insert site: 5 | TACACTTACCATACCCCGCGCGTCTGGATTCGCGGAAACGC GTACATCCAGGTCCCAAATAGGACACGCGCCCCCACAATTT CAACAA |
| 386 | saRNA_32_5'UTR_ NSP_SGP_5'UTR_ mCherry_RCHHR_ 3'UTR_CSE E.g., Insert site: 5 | TACACTTACCATACCCCGCGCGTTTCGTCCTATTTGGGACTC GTCAGCTGGATGTACGCGTTTCCGCGAATCCAGGACGCGC CCCCACAATTTCAACAA |
| 387 | saRNA_33_5'UTR_ NSP_SGP_RC_MS2_ a0_b7_c0_5'UTR_ mCherry_3'UTR_CSE E.g., Insert site: 2 | CACGTGGATCTGAGATCCAATTAGGTCGTGCGTTTCGTCCT ATTTGGGACTCGTCAGCTGGATGTACGCGTTTCCGCGAATC CAGGACGCACGGCTGATGCTCGTGCGTGAGAGGTGGGGA AAAGAG |
| 388 | saRNA_36_5'UTR_ NSP_SGP_RC_PP7_ a0_b6_c1_5'UTR_ mCherry_3'UTR_CSE E.g., Insert site: 2 | CACGTGGATCTGAGATCCAATTAGGTGTGCCGTTTCGTCCT ATTTGGGACTCGTCAGCTGGATGTACGCGTTTCCGCGAATC CAGGACGGCACGAAGCCATATCTTCTGTGCCGGAGAGGTG GGGAAAAGAG |
| 389 | saRNA_41_5'UTR_ NSP_SGP_RC_MS2_ a0_b7_c0_5'UTR_ mCherry_3'UTR_ CSE E.g., Insert site: 4 | CACGTGGATCTGAGATCCAATTAGGTCGTGCGTTTCGTCCT ATTTGGGACTCGTCAGCTGGATGTACGCGTTTCCGCGAATC CAGGACGCACGGCTGATGCTCGTGCGTGAGAGGTGGGGA AAAGAG |
| 390 | saRNA_44_5'UTR_ NSP_SGP_RC_PP7_ a0_b6_c1_5'UTR_ mCherry_3'UTR_CSE E.g., Insert site: 4 | CACGTGGATCTGAGATCCAATTAGGTGTGCCGTTTCGTCCT ATTTGGGACTCGTCAGCTGGATGTACGCGTTTCCGCGAATC CAGGACGGCACGAAGCCATATCTTCTGTGCCGGAGAGGTG GGGAAAAGAG |
| 391 | saRNA_45_5'UTR_ NSP_SGP_5'UTR_ mCherry_RC_MS2_a0_ b7_c0_3'UTR_CSE E.g., Insert site: 5 | CACGTGGATCTGAGATCCAATTAGGTCGTGCGTTTCGTCCT ATTTGGGACTCGTCAGCTGGATGTACGCGTTTCCGCGAATC CAGGACGCACGGCTGATGCTCGTGCGTGAGAGGTGGGGA AAAGAG |
| 392 | saRNA_47_5'UTR_ NSP_SGP_5'UTR_ mCherry_RC_PP7_a1_ b5_c1_3'UTR_CSE E.g., Insert site: 5 | CACGTGGATCTGAGATCCAATTAGGTTGCCGTTTCGTCCTAT TTGGGACTCGTCAGCTGGATGTACGCGTTTCCGCGAATCCA GGACGGCACGAAGCCATATCTTCTGTGCCGGAGAGGTGGG GAAAAGAG |
| 393 | saRNA_48_5'UTR_ NSP_SGP_5'UTR_ mCherry_RC_PP7_a0_ b6_c1_3'UTR_CSE E.g., Insert site: 5 | CACGTGGATCTGAGATCCAATTAGGTGTGCCGTTTCGTCCT ATTTGGGACTCGTCAGCTGGATGTACGCGTTTCCGCGAATC CAGGACGGCACGAAGCCATATCTTCTGTGCCGGAGAGGTG GGGAAAAGAG |

SEQUENCE LISTING

Sequence total quantity: 395
SEQ ID NO: 1                moltype = RNA   length = 19
FEATURE                 Location/Qualifiers
source                   1..19
                         mol_type = other RNA
                         organism = synthetic construct
SEQUENCE: 1
gcacgagcat cagccgtgc                                           19

SEQ ID NO: 2                moltype = RNA   length = 25
FEATURE                 Location/Qualifiers -continued

```
source                  1..25
                        mol_type = other RNA
                        organism = synthetic construct
SEQUENCE: 2
ggcacagaag atatggcttc gtgcc                                        25

SEQ ID NO: 3            moltype = RNA   length = 28
FEATURE                 Location/Qualifiers
source                  1..28
                        mol_type = other RNA
                        organism = synthetic construct
SEQUENCE: 3
ggctcgtgta gctcattagc tccgagcc                                     28

SEQ ID NO: 4            moltype = RNA   length = 21
FEATURE                 Location/Qualifiers
source                  1..21
                        mol_type = other RNA
                        organism = synthetic construct
SEQUENCE: 4
ggtgcgctga caaagcgcgc c                                            21

SEQ ID NO: 5            moltype = AA   length = 117
FEATURE                 Location/Qualifiers
source                  1..117
                        mol_type = protein
                        organism = unidentified
SEQUENCE: 5
MASNFTQFVL VDNGGTGDVT VAPSNFANGI AEWISSNSRS QAYKVTCSVR QSSAQNRKYT   60
IKVEVPKGAW RSYLNMELTI PIFATNSDCE LIVKAMQGLL KDGNPIPSAI AANSGIY      117

SEQ ID NO: 6            moltype = AA   length = 121
FEATURE                 Location/Qualifiers
source                  1..121
                        mol_type = protein
                        organism = unidentified
SEQUENCE: 6
MSKTIVLSVG EATRTLTEIQ STADRQIFEE KVGPLVGRLR LTASLRQNGA KTAYRVNLKL   60
DQADVVDSGL PKVRYTQVWS HDVTIVANST EASRKSLYDL TKSLVATSQV EDLVVNLVPL   120
G                                                                  121

SEQ ID NO: 7            moltype = AA   length = 17
FEATURE                 Location/Qualifiers
source                  1..17
                        mol_type = protein
                        organism = Lentivirus bovimdef
SEQUENCE: 7
SGPRPRGTRG KGRRIRR                                                 17

SEQ ID NO: 8            moltype = AA   length = 17
FEATURE                 Location/Qualifiers
source                  1..17
                        mol_type = protein
                        organism = unidentified
SEQUENCE: 8
NAKTRRHERR RKLAIER                                                 17

SEQ ID NO: 9            moltype = RNA   length = 87
FEATURE                 Location/Qualifiers
source                  1..87
                        mol_type = other RNA
                        organism = synthetic construct
SEQUENCE: 9
acgcgcacga gcatcagccg tgcgcgtcct ggattcgcgg aaacgcgtac atccagctga   60
cgagtcccaa ataggacgaa acgcgca                                      87

SEQ ID NO: 10           moltype = RNA   length = 85
FEATURE                 Location/Qualifiers
source                  1..85
                        mol_type = other RNA
                        organism = synthetic construct
SEQUENCE: 10
cgcgcacgag catcagccgt gcgcgtcctg gattcgcgga aacgcgtaca tccagctgac   60
gagtcccaaa taggacgaaa cgcgc                                        85

SEQ ID NO: 11           moltype = RNA   length = 86
FEATURE                 Location/Qualifiers
source                  1..86
                        mol_type = other RNA
```

-continued

```
                              organism = synthetic construct
SEQUENCE: 11
acgcgcacga gcatcagccg tgcgcgtcct ggattcgcgg aaacgcgtac atccagctga    60
cgagtcccaa ataggacgaa acgcgc                                          86

SEQ ID NO: 12          moltype = RNA   length = 82
FEATURE                Location/Qualifiers
source                 1..82
                       mol_type = other RNA
                       organism = synthetic construct
SEQUENCE: 12
cgcacgagca tcagccgtgc gtcctggatt cgcggaaacg cgtacatcca gctgacgagt    60
cccaaatagg acgaaacgca cg                                             82

SEQ ID NO: 13          moltype = RNA   length = 87
FEATURE                Location/Qualifiers
source                 1..87
                       mol_type = other RNA
                       organism = synthetic construct
SEQUENCE: 13
cgcggcacga gcatcagccg tgccgcgtcc tggattcgcg gaaacgcgta catccagctg    60
acgagtccca aataggacga aacgcgg                                        87

SEQ ID NO: 14          moltype = RNA   length = 88
FEATURE                Location/Qualifiers
source                 1..88
                       mol_type = other RNA
                       organism = synthetic construct
SEQUENCE: 14
acgcggcacg agcatcagcc gtgccgcgtc ctggattcgc ggaaacgcgt acatccagct    60
gacgagtccc aaataggacg aaacgcgg                                       88

SEQ ID NO: 15          moltype = RNA   length = 81
FEATURE                Location/Qualifiers
source                 1..81
                       mol_type = other RNA
                       organism = synthetic construct
SEQUENCE: 15
cgcacgagca tcagccgtgc gtcctggatt cgcggaaacg cgtacatcca gctgacgagt    60
cccaaatagg acgaaacgca c                                             81

SEQ ID NO: 16          moltype = RNA   length = 82
FEATURE                Location/Qualifiers
source                 1..82
                       mol_type = other RNA
                       organism = synthetic construct
SEQUENCE: 16
acgcacgagc atcagccgtg cgtcctggat tcgcggaaac gcgtacatcc agctgacgag    60
tcccaaatag gacgaaacgc ac                                             82

SEQ ID NO: 17          moltype = RNA   length = 83
FEATURE                Location/Qualifiers
source                 1..83
                       mol_type = other RNA
                       organism = synthetic construct
SEQUENCE: 17
cggcacgagc atcagccgtg ccgtcctgga ttcgcggaaa cgcgtacatc cagctgacga    60
gtcccaaata ggacgaaacg gca                                            83

SEQ ID NO: 18          moltype = RNA   length = 84
FEATURE                Location/Qualifiers
source                 1..84
                       mol_type = other RNA
                       organism = synthetic construct
SEQUENCE: 18
acggcacgag catcagccgt gccgtcctgg attcgcggaa acgcgtacat ccagctgacg    60
agtcccaaat aggacgaaac ggca                                           84

SEQ ID NO: 19          moltype = RNA   length = 80
FEATURE                Location/Qualifiers
source                 1..80
                       mol_type = other RNA
                       organism = synthetic construct
SEQUENCE: 19
agcacgagca tcagccgtgc tcctggattc gcggaaacgc gtacatccag ctgacgagtc    60
ccaaatagga cgaaagcacg                                                80

SEQ ID NO: 20          moltype = RNA   length = 91
FEATURE                Location/Qualifiers
```

US 12,674,171 B2

-continued

```
source                  1..91
                        mol_type = other RNA
                        organism = synthetic construct
SEQUENCE: 20
gcgcacgagc atcagccgtg cgcgcgtcct ggattcgcgg aaacgcgtac atccagctga  60
cgagtcccaa ataggacgaa acgcgcgcac g                                  91

SEQ ID NO: 21           moltype = RNA   length = 85
FEATURE                 Location/Qualifiers
source                  1..85
                        mol_type = other RNA
                        organism = synthetic construct
SEQUENCE: 21
cgcacgagca tcagccgtgc gcgtcctgga ttcgcggaaa cgcgtacatc cagctgacga  60
gtcccaaata ggacgaaacg cgcac                                         85

SEQ ID NO: 22           moltype = RNA   length = 83
FEATURE                 Location/Qualifiers
source                  1..83
                        mol_type = other RNA
                        organism = synthetic construct
SEQUENCE: 22
acgcacgagc atcagccgtg cgtcctggat tcgcggaaac gcgtacatcc agctgacgag  60
tcccaaatag gacgaaacgc acg                                           83

SEQ ID NO: 23           moltype = RNA   length = 87
FEATURE                 Location/Qualifiers
source                  1..87
                        mol_type = other RNA
                        organism = synthetic construct
SEQUENCE: 23
cgcgcacgag catcagccgt gcgcgtcctg gattcgcgga aacgcgtaca tccagctgac  60
gagtcccaaa taggacgaaa cgcgcac                                       87

SEQ ID NO: 24           moltype = RNA   length = 82
FEATURE                 Location/Qualifiers
source                  1..82
                        mol_type = other RNA
                        organism = synthetic construct
SEQUENCE: 24
cgcacgtcct ggattcgcgg aaacgcgtac atcagctga cgagtcccaa ataggacgaa   60
acgtgcgagc atcagccgca cg                                            82

SEQ ID NO: 25           moltype = RNA   length = 83
FEATURE                 Location/Qualifiers
source                  1..83
                        mol_type = other RNA
                        organism = synthetic construct
SEQUENCE: 25
cggcatcctg gattcgcgga aacgcgtaca tccagctgac gagtcccaaa taggacgaaa  60
tgccgcgagc atcagccgcg gca                                           83

SEQ ID NO: 26           moltype = RNA   length = 84
FEATURE                 Location/Qualifiers
source                  1..84
                        mol_type = other RNA
                        organism = synthetic construct
SEQUENCE: 26
acggcacctg gattcgcgga aacgcgtaca tccagctgac gagtcccaaa taggacgaat  60
gccgtcgagc atcagccgac ggca                                          84

SEQ ID NO: 27           moltype = RNA   length = 114
FEATURE                 Location/Qualifiers
source                  1..114
                        mol_type = other RNA
                        organism = synthetic construct
SEQUENCE: 27
ccgcgcgata aggcgcggca cgagcatcag ccgtgccgcg cgataaggcg cggtcctgga  60
ttcgcggaaa cgcgtacatc cagctgacga gtcccaaata ggacgaaacc gcgc         114

SEQ ID NO: 28           moltype = RNA   length = 118
FEATURE                 Location/Qualifiers
source                  1..118
                        mol_type = other RNA
                        organism = synthetic construct
SEQUENCE: 28
ccgcgcggat aagcgcgcgg cacgagcatc agccgtgccg cgccgataag ggcgcggtcc  60
tggattcgcg gaaacgcgta catccagctg acgagtccca aataggacga aaccgcgc    118
```

-continued

```
SEQ ID NO: 29          moltype = RNA   length = 130
FEATURE                Location/Qualifiers
source                 1..130
                       mol_type = other RNA
                       organism = synthetic construct
SEQUENCE: 29
ccgcgctccg gataagcgga gcgcggcacg agcatcagcc gtgccgcgcc ggagataagt   60
ccggcgcggt cctggattcg cggaaacgcg tacatccagc tgacgagtcc caaataggac  120
gaaaccgcgc                                                         130

SEQ ID NO: 30          moltype = RNA   length = 114
FEATURE                Location/Qualifiers
source                 1..114
                       mol_type = other RNA
                       organism = synthetic construct
SEQUENCE: 30
gcgcgcgata aggcgcgcac gagcatcagc cgtgcgcgcg ataaggcgcg cgtcctggat   60
tcgcggaaac gcgtacatcc agctgacgag tcccaaatag gacgaaacgc gcgc        114

SEQ ID NO: 31          moltype = RNA   length = 126
FEATURE                Location/Qualifiers
source                 1..126
                       mol_type = other RNA
                       organism = synthetic construct
SEQUENCE: 31
ccgcgcccgg ataagcgggc gcggcacgag catcagccgt gccgcgccgg gataagccgg   60
cgcggtcctg gattcgcgga aacgcgtaca tccagctgac gagtcccaaa taggacgaaa  120
ccgcgc                                                             126

SEQ ID NO: 32          moltype = RNA   length = 122
FEATURE                Location/Qualifiers
source                 1..122
                       mol_type = other RNA
                       organism = synthetic construct
SEQUENCE: 32
ccgcgccgga taagcggcgc ggcacgagca tcagccgtgc cgcgccggat aagcggcgcg   60
gtcctggatt cgcggaaacg cgtacatcca gctgacgagt cccaaatagg acgaaaccgc  120
gc                                                                 122

SEQ ID NO: 33          moltype = RNA   length = 118
FEATURE                Location/Qualifiers
source                 1..118
                       mol_type = other RNA
                       organism = synthetic construct
SEQUENCE: 33
gcgcgcggat aagcgcgcgc acgagcatca gccgtgcgcg ccgataaggg cgcgcgtcct   60
ggattcgcgg aaacgcgtac atccagctga cgagtcccaa ataggacgaa acgcgcgc    118

SEQ ID NO: 34          moltype = RNA   length = 130
FEATURE                Location/Qualifiers
source                 1..130
                       mol_type = other RNA
                       organism = synthetic construct
SEQUENCE: 34
gcgcgctccg gataagcgga gcgcgcacga gcatcagccg tgcgcgccgg agataagtcc   60
ggcgcgcgtc ctggattcgc ggaaacgcgt acatccagct gacgagtccc aaataggacg  120
aaacgcgcgc                                                         130

SEQ ID NO: 35          moltype = RNA   length = 114
FEATURE                Location/Qualifiers
source                 1..114
                       mol_type = other RNA
                       organism = synthetic construct
SEQUENCE: 35
tgccgcgata aggcggcacg agcatcagcc gtgccgcgat aaggcggcac gtcctggatt   60
cgcggaaacg cgtacatcca gctgacgagt cccaaatagg acgaaacgtg ccgc        114

SEQ ID NO: 36          moltype = RNA   length = 126
FEATURE                Location/Qualifiers
source                 1..126
                       mol_type = other RNA
                       organism = synthetic construct
SEQUENCE: 36
gcgcgcccgg ataagcgggc gcgcacgagc atcagccgtg cgcgccggga taagccggcg   60
cgcgtcctgg attcgcggaa acgcgtacat ccagctgacg agtcccaaat aggacgaaac  120
gcgcgc                                                             126

SEQ ID NO: 37          moltype = RNA   length = 122
FEATURE                Location/Qualifiers
```

```
source                    1..122
                          mol_type = other RNA
                          organism = synthetic construct
SEQUENCE: 37
gcgcgccgga taagcggcgc gcacgagcat cagccgtgcg cgccggataa gcggcgcgcg   60
tcctggattc gcggaaacgc gtacatccag ctgacgagtc ccaaatagga cgaaacgcgc  120
gc                                                                 122

SEQ ID NO: 38              moltype = RNA   length = 118
FEATURE                   Location/Qualifiers
source                    1..118
                          mol_type = other RNA
                          organism = synthetic construct
SEQUENCE: 38
tgccgcggat aagcgcggca cgagcatcag ccgtgccgcc gataagggcg gcacgtcctg   60
gattcgcgga aacgcgtaca tccagctgac gagtcccaaa taggacgaaa cgtgccgc    118

SEQ ID NO: 39              moltype = RNA   length = 130
FEATURE                   Location/Qualifiers
source                    1..130
                          mol_type = other RNA
                          organism = synthetic construct
SEQUENCE: 39
tgccgctccg gataagcgga gcggcacgag catcagccgt gccgccggag ataagtccgg   60
cggcacgtcc tggattcgcg gaaacgcgta catccagctg acgagtccca aataggacga  120
aacgtgccgc                                                         130

SEQ ID NO: 40              moltype = RNA   length = 114
FEATURE                   Location/Qualifiers
source                    1..114
                          mol_type = other RNA
                          organism = synthetic construct
SEQUENCE: 40
gtgcgcgata aggcgcacga gcatcagccg tgcgcgataa ggcgcacgcg tcctggattc   60
gcggaaacgc gtacatccag ctgacgagtc ccaaatagga cgaaacgcgt gcgc        114

SEQ ID NO: 41              moltype = RNA   length = 126
FEATURE                   Location/Qualifiers
source                    1..126
                          mol_type = other RNA
                          organism = synthetic construct
SEQUENCE: 41
tgccgccgg ataagcgggc ggcacgagca tcagccgtgc cgccgggata agccggcggc    60
acgtcctgga ttcgcggaaa cgcgtacatc cagctgacga gtcccaaata ggacgaaacg  120
tgccgc                                                             126

SEQ ID NO: 42              moltype = RNA   length = 122
FEATURE                   Location/Qualifiers
source                    1..122
                          mol_type = other RNA
                          organism = synthetic construct
SEQUENCE: 42
tgccgccgga taagcggcgg cacgagcatc agccgtgccg ccggataagc ggcggcacgt   60
cctggattcg cggaaacgcg tacatccagc tgacgagtcc caaataggac gaaacgtgcc  120
gc                                                                 122

SEQ ID NO: 43              moltype = RNA   length = 118
FEATURE                   Location/Qualifiers
source                    1..118
                          mol_type = other RNA
                          organism = synthetic construct
SEQUENCE: 43
gtgcgcggat aagcgcgcac gagcatcagc cgtgcgccga taagggcgca cgcgtcctgg   60
attcgcggaa acgcgtacat ccagctgacg agtcccaaat aggacgaaac gcgtgcgc    118

SEQ ID NO: 44              moltype = RNA   length = 130
FEATURE                   Location/Qualifiers
source                    1..130
                          mol_type = other RNA
                          organism = synthetic construct
SEQUENCE: 44
gtgcgctccg gataagcgga gcgcacgagc atcagccgtg cgccggagat aagtccggcg   60
cacgcgtcct ggattcgcgg aaacgcgtac atccagctga cgagtcccaa ataggacgaa  120
acgcgtgcgc                                                         130

SEQ ID NO: 45              moltype = RNA   length = 126
FEATURE                   Location/Qualifiers
source                    1..126
                          mol_type = other RNA
```

-continued

```
                         organism = synthetic construct
SEQUENCE: 45
gtgcgcccgg ataagcgggc gcacgagcat cagccgtgcg ccgggataag ccggcgcacg    60
cgtcctggat tcgcggaaac gcgtacatcc agctgacgag tcccaaatag gacgaaacgc   120
gtgcgc                                                               126

SEQ ID NO: 46            moltype = RNA   length = 122
FEATURE                  Location/Qualifiers
source                   1..122
                         mol_type = other RNA
                         organism = synthetic construct
SEQUENCE: 46
gtgcgccgga taagcggcgc acgagcatca gccgtgcgcc ggataagcgg cgcacgcgtc    60
ctggattcgc ggaaacgcgt acatccagct gacgagtccc aaataggacg aaacgcgtgc   120
gc                                                                   122

SEQ ID NO: 47            moltype = RNA   length = 112
FEATURE                  Location/Qualifiers
source                   1..112
                         mol_type = other RNA
                         organism = synthetic construct
SEQUENCE: 47
gccgcggata agcgcggcac gagcatcagc cgtgccgcgg ataagcgcgg ctcctggatt    60
cgcggaaacg cgtacatcca gctgacgagt cccaaatagg acgaaagccg cg           112

SEQ ID NO: 48            moltype = RNA   length = 128
FEATURE                  Location/Qualifiers
source                   1..128
                         mol_type = other RNA
                         organism = synthetic construct
SEQUENCE: 48
gccgcgtccg ataagcgga cgcggcacga gcatcagccg tgccgcgcgg agataagtcc     60
gcgcggctcc tggattcgcg gaaacgcgta catccagctg acgagtccca aataggacga   120
aagccgcg                                                             128

SEQ ID NO: 49            moltype = RNA   length = 116
FEATURE                  Location/Qualifiers
source                   1..116
                         mol_type = other RNA
                         organism = synthetic construct
SEQUENCE: 49
gccgcgggat aagccgcggc acgagcatca gccgtgccgc gcgataaggc gcggctcctg    60
gattcgcgga aacgcgtaca tccagctgac gagtcccaaa taggacgaaa gccgcg       116

SEQ ID NO: 50            moltype = RNA   length = 124
FEATURE                  Location/Qualifiers
source                   1..124
                         mol_type = other RNA
                         organism = synthetic construct
SEQUENCE: 50
gccgcgccgg ataagcggcg cggcacgagc atcagccgtg ccgcgcggga taagccgcgc    60
ggctcctgga ttcgcgaaa cgcgtacatc cagctgacga gtcccaaata ggacgaaagc   120
cgcg                                                                 124

SEQ ID NO: 51            moltype = RNA   length = 120
FEATURE                  Location/Qualifiers
source                   1..120
                         mol_type = other RNA
                         organism = synthetic construct
SEQUENCE: 51
gccgcgcgga taagcgcgcg gcacgagcat cagccgtgcc gcgcggataa gcgcgcggct    60
cctggattcg cggaaacgcg tacatccagc tgacgagtcc caaataggac gaaagccgcg   120

SEQ ID NO: 52            moltype = RNA   length = 112
FEATURE                  Location/Qualifiers
source                   1..112
                         mol_type = other RNA
                         organism = synthetic construct
SEQUENCE: 52
gtgccggata agcggcacga gcatcagccg tgccggataa gcggcaccgt cctggattcg    60
cggaaacgcg tacatccagc tgacgagtcc caaataggac gaaacggtgc cg           112

SEQ ID NO: 53            moltype = RNA   length = 128
FEATURE                  Location/Qualifiers
source                   1..128
                         mol_type = other RNA
                         organism = synthetic construct
SEQUENCE: 53
gtgccgtccg ataagcgga cggcacgagc atcagccgtg ccgcggagat aagtccgcgg    60
```

```
caccgtcctg gattcgcgga aacgcgtaca tccagctgac gagtcccaaa taggacgaaa    120
cggtgccg                                                             128

SEQ ID NO: 54           moltype = RNA   length = 112
FEATURE                 Location/Qualifiers
source                  1..112
                        mol_type = other RNA
                        organism = synthetic construct
SEQUENCE: 54
tgcgcggata agcgcgcacg agcatcagcc gtgcgcggat aagcgcgcag tcctggattc    60
gcggaaacgc gtacatccag ctgacgagtc ccaaatagga cgaaactgcg cg            112

SEQ ID NO: 55           moltype = RNA   length = 112
FEATURE                 Location/Qualifiers
source                  1..112
                        mol_type = other RNA
                        organism = synthetic construct
SEQUENCE: 55
cgtgcggata agcgcacgag catcagccgt gcggataagc gcacggcgtc ctggattcgc    60
ggaaacgcgt acatccagct gacgagtccc aaataggacg aaacgccgtg cg            112

SEQ ID NO: 56           moltype = RNA   length = 116
FEATURE                 Location/Qualifiers
source                  1..116
                        mol_type = other RNA
                        organism = synthetic construct
SEQUENCE: 56
gtgccgggat aagccggcac gagcatcagc cgtgccgcga taaggcggca ccgtcctgga    60
ttcgcggaaa cgcgtacatc cagctgacga gtcccaaata ggacgaaacg gtgccg        116

SEQ ID NO: 57           moltype = RNA   length = 124
FEATURE                 Location/Qualifiers
source                  1..124
                        mol_type = other RNA
                        organism = synthetic construct
SEQUENCE: 57
gtgccgccgg ataagcggcg gcacgagcat cagccgtgcc gcgggataag ccgcggcacc    60
gtcctggatt cgcggaaacg cgtacatcca gctgacgagt cccaaatagg acgaaacggt    120
gccg                                                                 124

SEQ ID NO: 58           moltype = RNA   length = 120
FEATURE                 Location/Qualifiers
source                  1..120
                        mol_type = other RNA
                        organism = synthetic construct
SEQUENCE: 58
gtgccgcgga taagcgcggc acgagcatca gccgtgccgc ggataagcgc ggcaccgtcc    60
tggattcgcg gaaacgcgta catccagctg acgagtccca aataggacga aacggtgccg    120

SEQ ID NO: 59           moltype = RNA   length = 112
FEATURE                 Location/Qualifiers
source                  1..112
                        mol_type = other RNA
                        organism = synthetic construct
SEQUENCE: 59
cacgcggata agcgcgtgca cgagcatcag ccgtgcacgc ggataagcgc gtgcctggat    60
tcgcggaaac gcgtacatcc agctgacgag tcccaaatag gacgaacacg cg            112

SEQ ID NO: 60           moltype = RNA   length = 128
FEATURE                 Location/Qualifiers
source                  1..128
                        mol_type = other RNA
                        organism = synthetic construct
SEQUENCE: 60
tgcgcgtccg ataagcggga cgcgcacgag catcagccgt gcgcgcggag ataagtccgc    60
gcgcagtcct ggattcgcgg aaacgcgtac atccagctga cgagtcccaa ataggacgaa    120
actgcgcg                                                             128

SEQ ID NO: 61           moltype = RNA   length = 128
FEATURE                 Location/Qualifiers
source                  1..128
                        mol_type = other RNA
                        organism = synthetic construct
SEQUENCE: 61
cgtgcgtccg ataagcggga cgcacgagca tcagccgtgc gcggagataa gtccgcgcac    60
ggcgtcctgg attcgcggaa acgcgtacat ccagctgacg agtcccaaat aggacgaaac    120
gccgtgcg                                                             128

SEQ ID NO: 62           moltype = RNA   length = 116
```

-continued

```
FEATURE                Location/Qualifiers
source                 1..116
                       mol_type = other RNA
                       organism = synthetic construct
SEQUENCE: 62
tgcgcgggat aagccgcgca cgagcatcag ccgtgcgcgc gataaggcgc gcagtcctgg   60
attcgcggaa acgcgtacat ccagctgacg agtcccaaat aggacgaaac tgcgcg       116

SEQ ID NO: 63          moltype = RNA   length = 116
FEATURE                Location/Qualifiers
source                 1..116
                       mol_type = other RNA
                       organism = synthetic construct
SEQUENCE: 63
cgtgcgggat aagccgcacg agcatcagcc gtgcgcgata aggcgcacgg cgtcctggat   60
tcgcggaaac gcgtacatcc agctgacgag tcccaaatag gacgaaacgc cgtgcg       116

SEQ ID NO: 64          moltype = RNA   length = 124
FEATURE                Location/Qualifiers
source                 1..124
                       mol_type = other RNA
                       organism = synthetic construct
SEQUENCE: 64
tgcgcgccgg ataagcggcg cgcacgagca tcagccgtgc gcgcgggata agccgcgcgc   60
agtcctggat tcgcggaaac gcgtacatcc agctgacgag tcccaaatag gacgaaactg   120
cgcg                                                                124

SEQ ID NO: 65          moltype = RNA   length = 124
FEATURE                Location/Qualifiers
source                 1..124
                       mol_type = other RNA
                       organism = synthetic construct
SEQUENCE: 65
cgtgcgccgg ataagcggcg cacgagcatc agccgtgcgc gggataagcc gcgcacggcg   60
tcctggattc gcggaaacgc gtacatccag ctgacgagtc ccaaatagga cgaaacgccg   120
tgcg                                                                124

SEQ ID NO: 66          moltype = RNA   length = 120
FEATURE                Location/Qualifiers
source                 1..120
                       mol_type = other RNA
                       organism = synthetic construct
SEQUENCE: 66
tgcgcgcgga taagcgcgcg cacgagcatc agccgtgcgc gcggataagc gcgcgcagtc   60
ctggattcgc ggaaacgcgt acatccagct gacgagtccc aaataggacg aaactgcgcg   120

SEQ ID NO: 67          moltype = RNA   length = 120
FEATURE                Location/Qualifiers
source                 1..120
                       mol_type = other RNA
                       organism = synthetic construct
SEQUENCE: 67
cgtgcgcgga taagcgcgca cgagcatcag ccgtgcgcgg ataagcgcgc acggcgtcct   60
ggattcgcgg aaacgcgtac atccagctga cgagtcccaa ataggacgaa acgccgtgcg   120

SEQ ID NO: 68          moltype = RNA   length = 128
FEATURE                Location/Qualifiers
source                 1..128
                       mol_type = other RNA
                       organism = synthetic construct
SEQUENCE: 68
cacgcgtccg gataagcgga cgcgtgcacg agcatcagcc gtgcacgcgc ggagataagt   60
ccgcgcgtgc ctggattcgc ggaaacgcgt acatccagct gacgagtccc aaataggacg   120
aacacgcg                                                            128

SEQ ID NO: 69          moltype = RNA   length = 116
FEATURE                Location/Qualifiers
source                 1..116
                       mol_type = other RNA
                       organism = synthetic construct
SEQUENCE: 69
cacgcgggat aagccgcgtg cacgagcatc agccgtgcac gcgcgataag gcgcgtgcct   60
ggattcgcgg aaacgcgtac atccagctga cgagtcccaa ataggacgaa cacgcg       116

SEQ ID NO: 70          moltype = RNA   length = 124
FEATURE                Location/Qualifiers
source                 1..124
                       mol_type = other RNA
                       organism = synthetic construct
```

```
SEQUENCE: 70
cacgcgccgg ataagcggcg cgtgcacgag catcagccgt gcacgcgcgg gataagccgc      60
gcgtgcctgg attcgcggaa acgcgtacat ccagctgacg agtcccaaat aggacgaaca     120
cgcg                                                                    124

SEQ ID NO: 71             moltype = RNA   length = 120
FEATURE                   Location/Qualifiers
source                    1..120
                          mol_type = other RNA
                          organism = synthetic construct
SEQUENCE: 71
cacgcgcgga taagcgcgcg tgcacgagca tcagccgtgc acgcgcgat aagcgcgcgt       60
gcctggattc gcggaaacgc gtacatccag ctgacgagtc ccaaatagga cgaacacgcg     120

SEQ ID NO: 72             moltype = RNA   length = 110
FEATURE                   Location/Qualifiers
source                    1..110
                          mol_type = other RNA
                          organism = synthetic construct
SEQUENCE: 72
tgccgcgata aggcggcacg agcatcagcc gtgccgcgat aaggcggcat cctggattcg      60
cggaaacgcg tacatccagc tgacgagtcc caaataggac gaaatgccgc               110

SEQ ID NO: 73             moltype = RNA   length = 110
FEATURE                   Location/Qualifiers
source                    1..110
                          mol_type = other RNA
                          organism = synthetic construct
SEQUENCE: 73
cgtgccgata agggcacgag catcagccgt gccgataagg gcacgcgtcc tggattcgcg      60
gaaacgcgta catccagctg acgagtccca aataggacga aacgcgtgcc               110

SEQ ID NO: 74             moltype = RNA   length = 110
FEATURE                   Location/Qualifiers
source                    1..110
                          mol_type = other RNA
                          organism = synthetic construct
SEQUENCE: 74
gcacgcgata aggcgtgcac gagcatcagc cgtgcacgcg ataaggcgtg ccctggattc      60
gcggaaacgc gtacatccag ctgacgagtc ccaaatagga cgaagcacgc               110

SEQ ID NO: 75             moltype = RNA   length = 114
FEATURE                   Location/Qualifiers
source                    1..114
                          mol_type = other RNA
                          organism = synthetic construct
SEQUENCE: 75
tgccgcggat aagcgcggca cgagcatcag ccgtgccgcc gataagggcg gcatcctgga      60
ttcgcggaaa cgcgtacatc cagctgacga gtcccaaata ggacgaaatg ccgc          114

SEQ ID NO: 76             moltype = RNA   length = 126
FEATURE                   Location/Qualifiers
source                    1..126
                          mol_type = other RNA
                          organism = synthetic construct
SEQUENCE: 76
tgccgctccg gataagcgga gcggcacgag catcagccgt gccgccggag ataagtccgg      60
cggcatcctg gattcgcgga aacgcgtaca tccagctgac gagtcccaaa taggacgaaa     120
tgccgc                                                                  126

SEQ ID NO: 77             moltype = RNA   length = 114
FEATURE                   Location/Qualifiers
source                    1..114
                          mol_type = other RNA
                          organism = synthetic construct
SEQUENCE: 77
cgtgccggat aagcggcacg agcatcagcc gtgcccgata aggggcacgc gtcctggatt      60
cgcggaaacg cgtacatcca gctgacgagt cccaaatagg acgaaacgcg tgcc          114

SEQ ID NO: 78             moltype = RNA   length = 126
FEATURE                   Location/Qualifiers
source                    1..126
                          mol_type = other RNA
                          organism = synthetic construct
SEQUENCE: 78
cgtgcctccg gataagcgga ggcacgagca tcagccgtgc ccggagataa gtccgggcac      60
gcgtcctgga ttcgcggaaa cgcgtacatc cagctgacga gtcccaaata ggacgaaacg     120
cgtgcc                                                                  126
```

-continued

```
SEQ ID NO: 79          moltype = RNA   length = 122
FEATURE                Location/Qualifiers
source                 1..122
                       mol_type = other RNA
                       organism = synthetic construct
SEQUENCE: 79
tgccgcccgg ataagcgggc ggcacgagca tcagccgtgc cgccgggata agccggcggc     60
atcctggatt cgcggaaacg cgtacatcca gctgacgagt cccaaatagg acgaaatgcc    120
gc                                                                   122

SEQ ID NO: 80          moltype = RNA   length = 118
FEATURE                Location/Qualifiers
source                 1..118
                       mol_type = other RNA
                       organism = synthetic construct
SEQUENCE: 80
tgccgccgga taagcggcgg cacgagcatc agccgtgccg ccggataagc ggcggcatcc     60
tggattcgcg gaaacgcgta catccagctg acgagtccca aataggacga aatgccgc      118

SEQ ID NO: 81          moltype = RNA   length = 114
FEATURE                Location/Qualifiers
source                 1..114
                       mol_type = other RNA
                       organism = synthetic construct
SEQUENCE: 81
gcacgcggat aagcgcgtgc acgagcatca gccgtgcacg ccgataaggg cgtgccctgg     60
attcgcggaa acgcgtacat ccagctgacg agtcccaaat aggacgaagc acgc          114

SEQ ID NO: 82          moltype = RNA   length = 110
FEATURE                Location/Qualifiers
source                 1..110
                       mol_type = other RNA
                       organism = synthetic construct
SEQUENCE: 82
gtgcgcgata aggcgcacga gcatcagccg tgcgcgataa ggcgcacgtc ctggattcgc     60
ggaaacgcgt acatccagct gacgagtccc aaataggacg aaacgtgcgc               110

SEQ ID NO: 83          moltype = RNA   length = 126
FEATURE                Location/Qualifiers
source                 1..126
                       mol_type = other RNA
                       organism = synthetic construct
SEQUENCE: 83
gcacgctccg gataagcgga gcgtgcacga gcatcagccg tgcacgccgg agataagtcc     60
ggcgtgccct ggattcgcgg aaacgcgtac atccagctga cgagtcccaa ataggacgaa    120
gcacgc                                                               126

SEQ ID NO: 84          moltype = RNA   length = 122
FEATURE                Location/Qualifiers
source                 1..122
                       mol_type = other RNA
                       organism = synthetic construct
SEQUENCE: 84
cgtgccccgg ataagcgggg cacgagcatc agccgtgccc gggataagcc gggcacgcgt     60
cctggattcg cggaaacgcg tacatccagc tgacgagtcc caaataggac gaaacgcgtg    120
cc                                                                   122

SEQ ID NO: 85          moltype = RNA   length = 118
FEATURE                Location/Qualifiers
source                 1..118
                       mol_type = other RNA
                       organism = synthetic construct
SEQUENCE: 85
cgtgcccgga taagcgggca cgagcatcag ccgtgcccgg ataagcgggc acgcgtcctg     60
gattcgcgga aacgcgtaca tccagctgac gagtcccaaa taggacgaaa cgcgtgcc     118

SEQ ID NO: 86          moltype = RNA   length = 122
FEATURE                Location/Qualifiers
source                 1..122
                       mol_type = other RNA
                       organism = synthetic construct
SEQUENCE: 86
gcacgcccga taagcgggc gtgcacgagc atcagccgtg cacgccggga taagccggcg     60
tgccctggat tcgcggaaac gcgtacatcc agctgacgag tcccaaatag gacgaagcac    120
gc                                                                   122

SEQ ID NO: 87          moltype = RNA   length = 118
FEATURE                Location/Qualifiers
source                 1..118
```

-continued

```
                        mol_type = other RNA
                        organism = synthetic construct
SEQUENCE: 87
gcacgccgga taagcggcgt gcacgagcat cagccgtgca cgccggataa gcggcgtgcc   60
ctggattcgc ggaaacgcgt acatccagct gacgagtccc aaataggacg aagcacgc    118

SEQ ID NO: 88          moltype = RNA   length = 114
FEATURE                Location/Qualifiers
source                 1..114
                       mol_type = other RNA
                       organism = synthetic construct
SEQUENCE: 88
gtgcgcggat aagcgcgcac gagcatcagc cgtgcgccga taagggcgca cgtcctggat   60
tcgcggaaac gcgtacatcc agctgacgag tcccaaatag gacgaaacgt gcgc         114

SEQ ID NO: 89          moltype = RNA   length = 126
FEATURE                Location/Qualifiers
source                 1..126
                       mol_type = other RNA
                       organism = synthetic construct
SEQUENCE: 89
gtgcgctccg gataagcgga gcgcacgagc atcagccgtg cgccggagat aagtccggcg   60
cacgtcctgg attcgcggaa acgcgtacat ccagctgacg agtcccaaat aggacgaaac  120
gtgcgc                                                              126

SEQ ID NO: 90          moltype = RNA   length = 122
FEATURE                Location/Qualifiers
source                 1..122
                       mol_type = other RNA
                       organism = synthetic construct
SEQUENCE: 90
gtgcgcccgg ataagcgggc gcacgagcat cagccgtgcg ccgggataag ccggcgcacg   60
tcctggattc gcggaaacgc gtacatccag ctgacgagtc ccaaatagga cgaaacgtgc  120
gc                                                                  122

SEQ ID NO: 91          moltype = RNA   length = 118
FEATURE                Location/Qualifiers
source                 1..118
                       mol_type = other RNA
                       organism = synthetic construct
SEQUENCE: 91
gtgcgccgga taagcggcgc acgagcatca gccgtgcgcc ggataagcgg cgcacgtcct   60
ggattcgcgg aaacgcgtac atccagctga cgagtcccaa ataggacgaa acgtgcgc    118

SEQ ID NO: 92          moltype = RNA   length = 108
FEATURE                Location/Qualifiers
source                 1..108
                       mol_type = other RNA
                       organism = synthetic construct
SEQUENCE: 92
gtgccggata agcggcacga gcatcagccg tgccggataa gcggcactcc tggattcgcg   60
gaaacgcgta catccagctg acgagtccca aataggacga aagtgccg               108

SEQ ID NO: 93          moltype = RNA   length = 124
FEATURE                Location/Qualifiers
source                 1..124
                       mol_type = other RNA
                       organism = synthetic construct
SEQUENCE: 93
gtgccgtccg gataagcgga cggcacgagc atcagccgtg ccgcggagat aagtccgcgg   60
cactcctgga ttcgcggaaa cgcgtacatc cagctgacga gtcccaaata ggacgaaagt  120
gccg                                                                124

SEQ ID NO: 94          moltype = RNA   length = 108
FEATURE                Location/Qualifiers
source                 1..108
                       mol_type = other RNA
                       organism = synthetic construct
SEQUENCE: 94
cgtgcggata agcgcacgag catcagccgt gcggataagc gcacggtcct ggattcgcgg   60
aaacgcgtac atccagctga cgagtcccaa ataggacgaa accgtgcg               108

SEQ ID NO: 95          moltype = RNA   length = 112
FEATURE                Location/Qualifiers
source                 1..112
                       mol_type = other RNA
                       organism = synthetic construct
SEQUENCE: 95
gtgccgggat aagccggcac gagcatcagc cgtgccgcga taaggcggca ctcctggatt   60
```

-continued

```
cgcggaaacg cgtacatcca gctgacgagt cccaaatagg acgaaagtgc cg          112

SEQ ID NO: 96             moltype = RNA   length = 120
FEATURE                   Location/Qualifiers
source                    1..120
                          mol_type = other RNA
                          organism = synthetic construct
SEQUENCE: 96
gtgccgccgg ataagcggcg gcacgagcat cagccgtgcc gcgggataag ccgcggcact   60
cctggattcg cggaaacgcg tacatccagc tgacgagtcc caaataggac gaaagtgccg  120

SEQ ID NO: 97             moltype = RNA   length = 116
FEATURE                   Location/Qualifiers
source                    1..116
                          mol_type = other RNA
                          organism = synthetic construct
SEQUENCE: 97
gtgccgcgga taagcgcggc acgagcatca gccgtgccgc ggataagcgc ggcactcctg   60
gattcgcgga aacgcgtaca tccagctgac gagtcccaaa taggacgaaa gtgccg      116

SEQ ID NO: 98             moltype = RNA   length = 124
FEATURE                   Location/Qualifiers
source                    1..124
                          mol_type = other RNA
                          organism = synthetic construct
SEQUENCE: 98
cgtgcgtccg gataagcgga cgcacgagca tcagccgtgc gcggagataa gtccgcgcac   60
ggtcctggat tcgcggaaac gcgtacatcc agctgacgag tcccaaatag gacgaaaccg  120
tgcg                                                                124

SEQ ID NO: 99             moltype = RNA   length = 112
FEATURE                   Location/Qualifiers
source                    1..112
                          mol_type = other RNA
                          organism = synthetic construct
SEQUENCE: 99
cgtgcgggat aagccgcacg agcatcagcc gtgcgcgata aggcgcacgg tcctggattc   60
gcggaaacgc gtacatccag ctgacgagtc ccaaataggga cgaaaccgtg cg         112

SEQ ID NO: 100            moltype = RNA   length = 120
FEATURE                   Location/Qualifiers
source                    1..120
                          mol_type = other RNA
                          organism = synthetic construct
SEQUENCE: 100
cgtgcgccgg ataagcggcg cacgagcatc agccgtgcgc gggataagcc gcgcacggtc   60
ctggattcgc ggaaacgcgt acatccagct gacgagtccc aaataggacg aaaccgtgcg  120

SEQ ID NO: 101            moltype = RNA   length = 116
FEATURE                   Location/Qualifiers
source                    1..116
                          mol_type = other RNA
                          organism = synthetic construct
SEQUENCE: 101
cgtgcgcgga taagcgcgca cgagcatcag ccgtgcgcgg ataagcgcgc acggtcctgg   60
attcgcggaa acgcgtacat ccagctgacg agtcccaaat aggacgaaac cgtgcg      116

SEQ ID NO: 102            moltype = RNA   length = 108
FEATURE                   Location/Qualifiers
source                    1..108
                          mol_type = other RNA
                          organism = synthetic construct
SEQUENCE: 102
tgcacggata agcgtgcacg agcatcagcc gtgcacggat aagcgtgcac ctggattcgc   60
ggaaacgcgt acatccagct gacgagtccc aaataggacg aatgcacg               108

SEQ ID NO: 103            moltype = RNA   length = 106
FEATURE                   Location/Qualifiers
source                    1..106
                          mol_type = other RNA
                          organism = synthetic construct
SEQUENCE: 103
cgtgccgata aaggcacgag catcagccgt gccgataagg gcacgtcctg gattcgcgga   60
aacgcgtaca tccagctgac gagtcccaaa taggacgaaa cgtgcc                 106

SEQ ID NO: 104            moltype = RNA   length = 124
FEATURE                   Location/Qualifiers
source                    1..124
                          mol_type = other RNA
```

-continued

```
                              organism = synthetic construct
SEQUENCE: 104
tgcacgtccg gataagcgga cgtgcacgag catcagccgt gcacgcggag ataagtccgc   60
gtgcacctgg attcgcggaa acgcgtacat ccagctgacg agtcccaaat aggacgaatg  120
cacg                                                               124

SEQ ID NO: 105           moltype = RNA   length = 112
FEATURE                  Location/Qualifiers
source                   1..112
                         mol_type = other RNA
                         organism = synthetic construct
SEQUENCE: 105
tgcacgggat aagccgtgca cgagcatcag ccgtgcacgc gataaggcgt gcacctggat   60
tcgcggaaac gcgtacatcc agctgacgag tcccaaatag gacgaatgca cg          112

SEQ ID NO: 106           moltype = RNA   length = 110
FEATURE                  Location/Qualifiers
source                   1..110
                         mol_type = other RNA
                         organism = synthetic construct
SEQUENCE: 106
cgtgccggat aagcggcacg agcatcagcc gtgcccgata aggggcacgt cctggattcg   60
cggaaacgcg tacatccagc tgacgagtcc caaataggac gaaacgtgcc             110

SEQ ID NO: 107           moltype = RNA   length = 122
FEATURE                  Location/Qualifiers
source                   1..122
                         mol_type = other RNA
                         organism = synthetic construct
SEQUENCE: 107
cgtgcctccg gataagcgga ggcacgagca tcagccgtgc ccggagataa gtccgggcac   60
gtcctggatt cgcggaaacg cgtacatcca gctgacgagt cccaaatagg acgaaacgtg  120
cc                                                                 122

SEQ ID NO: 108           moltype = RNA   length = 120
FEATURE                  Location/Qualifiers
source                   1..120
                         mol_type = other RNA
                         organism = synthetic construct
SEQUENCE: 108
tgcacgccgg ataagcggcg tgcacgagca tcagccgtgc acgcgggata agccgcgtgc   60
acctggattc gcggaaacgc gtacatccag ctgacgagtc ccaaatagga cgaatgcacg  120

SEQ ID NO: 109           moltype = RNA   length = 116
FEATURE                  Location/Qualifiers
source                   1..116
                         mol_type = other RNA
                         organism = synthetic construct
SEQUENCE: 109
tgcacgcgga taagcgcgtg cacgagcatc agccgtgcac gcggataagc gcgtgcacct   60
ggattcgcgg aaacgcgtac atccagctga cgagtcccaa ataggacgaa tgcacg      116

SEQ ID NO: 110           moltype = RNA   length = 118
FEATURE                  Location/Qualifiers
source                   1..118
                         mol_type = other RNA
                         organism = synthetic construct
SEQUENCE: 110
cgtgccccgg ataagcgggg cacgagcatc agccgtgccc gggataagcc gggcacgtcc   60
tggattcgcg gaaacgcgta catccagctg acgagtccca ataggacga aacgtgcc     118

SEQ ID NO: 111           moltype = RNA   length = 114
FEATURE                  Location/Qualifiers
source                   1..114
                         mol_type = other RNA
                         organism = synthetic construct
SEQUENCE: 111
cgtgcccgga taagcgggca cgagcatcag ccgtgcccgg ataagcgggc acgtcctgga   60
ttcgcggaaa cgcgtacatc cagctgacga gtcccaaata ggacgaaacg tgcc        114

SEQ ID NO: 112           moltype = RNA   length = 106
FEATURE                  Location/Qualifiers
source                   1..106
                         mol_type = other RNA
                         organism = synthetic construct
SEQUENCE: 112
gtgcacgata aggtgcacga gcatcagccg tgcacgataa ggtgcaccct ggattcgcgg   60
aaacgcgtac atccagctga cgagtcccaa ataggacgaa gtgcac                 106
```

-continued

```
SEQ ID NO: 113         moltype = RNA  length = 110
FEATURE                Location/Qualifiers
source                 1..110
                       mol_type = other RNA
                       organism = synthetic construct
SEQUENCE: 113
gtgcacggat aagcgtgcac gagcatcagc cgtgcaccga taagggtgca ccctggattc    60
gcggaaacgc gtacatccag ctgacgagtc ccaaatagga cgaagtgcac               110

SEQ ID NO: 114         moltype = RNA  length = 122
FEATURE                Location/Qualifiers
source                 1..122
                       mol_type = other RNA
                       organism = synthetic construct
SEQUENCE: 114
gtgcactccg ataagcggga gtgcacgagc atcagccgtg caccggagat aagtccggtg    60
caccctggat tcgcggaaac gcgtacatcc agctgacgag tcccaaatag gacgaagtgc   120
ac                                                                  122

SEQ ID NO: 115         moltype = RNA  length = 118
FEATURE                Location/Qualifiers
source                 1..118
                       mol_type = other RNA
                       organism = synthetic construct
SEQUENCE: 115
gtgcaccgg ataagcgggt gcacgagcat cagccgtgca ccgggataag ccggtgcacc     60
ctggattcgc ggaaacgcgt acatccagct gacgagtccc aaataggacg aagtgcac     118

SEQ ID NO: 116         moltype = RNA  length = 114
FEATURE                Location/Qualifiers
source                 1..114
                       mol_type = other RNA
                       organism = synthetic construct
SEQUENCE: 116
gtgcaccgga taagcggtgc acgagcatca gccgtgcacc ggataagcgg tgcaccctgg    60
attcgcggaa acgcgtacat ccagctgacg agtcccaaat aggacgaagt gcac          114

SEQ ID NO: 117         moltype = RNA  length = 104
FEATURE                Location/Qualifiers
source                 1..104
                       mol_type = other RNA
                       organism = synthetic construct
SEQUENCE: 117
cgtgcagata agtgcacgag catcagccgt gcagataagt gcacgcctgg attcgcggaa    60
acgcgtacat ccagctgacg agtcccaaat aggacgaacg tgca                    104

SEQ ID NO: 118         moltype = RNA  length = 120
FEATURE                Location/Qualifiers
source                 1..120
                       mol_type = other RNA
                       organism = synthetic construct
SEQUENCE: 118
cgtgcatccg ataagcgga tgcacgagca tcagccgtgc acggagataa gtccgtgcac     60
gcctggattc gcggaaacgc gtacatccag ctgacgagtc ccaaatagga cgaacgtgca   120

SEQ ID NO: 119         moltype = RNA  length = 116
FEATURE                Location/Qualifiers
source                 1..116
                       mol_type = other RNA
                       organism = synthetic construct
SEQUENCE: 119
cgtgcaccgg ataagcggtg cacgagcatc agccgtgcac gggataagcc gtgcacgcct    60
ggattcgcgg aaacgcgtac atccagctga cgagtcccaa ataggacgaa cgtgca       116

SEQ ID NO: 120         moltype = RNA  length = 112
FEATURE                Location/Qualifiers
source                 1..112
                       mol_type = other RNA
                       organism = synthetic construct
SEQUENCE: 120
cgtgcacgga taagcgtgca cgagcatcag ccgtgcacgg ataagcgtgc acgcctggat    60
tcgcggaaac gcgtacatcc agctgacgag tcccaaatag gacgaacgtg ca           112

SEQ ID NO: 121         moltype = RNA  length = 108
FEATURE                Location/Qualifiers
source                 1..108
                       mol_type = other RNA
                       organism = synthetic construct
SEQUENCE: 121
```

```
cgtgcaggat aagctgcacg agcatcagcc gtgcacgata aggtgcacgc ctggattcgc    60
ggaaacgcgt acatccagct gacgagtccc aaataggacg aacgtgca                108

SEQ ID NO: 122              moltype = RNA   length = 87
FEATURE                     Location/Qualifiers
source                      1..87
                            mol_type = other RNA
                            organism = synthetic construct
SEQUENCE: 122
cggcacagaa gatatggctt cgtgccgtcc tggattcgcg gaaacgcgta catccagctg    60
acgagtccca aataggacga aacggca                                        87

SEQ ID NO: 123              moltype = RNA   length = 89
FEATURE                     Location/Qualifiers
source                      1..89
                            mol_type = other RNA
                            organism = synthetic construct
SEQUENCE: 123
gggcacagaa gatatggctt cgtgcccgtc ctggattcgc ggaaacgcgt acatccagct    60
gacgagtccc aaataggacg aaacgggca                                      89

SEQ ID NO: 124              moltype = RNA   length = 91
FEATURE                     Location/Qualifiers
source                      1..91
                            mol_type = other RNA
                            organism = synthetic construct
SEQUENCE: 124
cggcacagaa gatatggctt cgtgccgcgt cctggattcg cggaaacgcg tacatccagc    60
tgacgagtcc caaataggac gaaacgcggc a                                   91

SEQ ID NO: 125              moltype = RNA   length = 93
FEATURE                     Location/Qualifiers
source                      1..93
                            mol_type = other RNA
                            organism = synthetic construct
SEQUENCE: 125
gggcacagaa gatatggctt cgtgcccgcg tcctggattc gcggaaacgc gtacatccag    60
ctgacgagtc ccaaatagga cgaaacgcgg gca                                 93

SEQ ID NO: 126              moltype = RNA   length = 89
FEATURE                     Location/Qualifiers
source                      1..89
                            mol_type = other RNA
                            organism = synthetic construct
SEQUENCE: 126
cgggcacaga agatatggct tcgtgcccgt cctggattcg cggaaacgcg tacatccagc    60
tgacgagtcc caaataggac gaaacgggc                                      89

SEQ ID NO: 127              moltype = RNA   length = 91
FEATURE                     Location/Qualifiers
source                      1..91
                            mol_type = other RNA
                            organism = synthetic construct
SEQUENCE: 127
gcggcacaga agatatggct tcgtgccgcg tcctggattc gcggaaacgc gtacatccag    60
ctgacgagtc ccaaatagga cgaaacgcgg c                                   91

SEQ ID NO: 128              moltype = RNA   length = 93
FEATURE                     Location/Qualifiers
source                      1..93
                            mol_type = other RNA
                            organism = synthetic construct
SEQUENCE: 128
cgggcacaga agatatggct tcgtgcccgc gtcctggatt cgcggaaacg cgtacatcca    60
gctgacgagt cccaaatagg acgaaacgcg ggc                                 93

SEQ ID NO: 129              moltype = RNA   length = 95
FEATURE                     Location/Qualifiers
source                      1..95
                            mol_type = other RNA
                            organism = synthetic construct
SEQUENCE: 129
gcggcacaga agatatggct tcgtgccgcg cgtcctggat tcgcggaaac gcgtacatcc    60
agctgacgag tcccaaatag gacgaaacgc gcggc                               95

SEQ ID NO: 130              moltype = RNA   length = 91
FEATURE                     Location/Qualifiers
source                      1..91
                            mol_type = other RNA
```

```
                           organism = synthetic construct
SEQUENCE: 130
cgcggcacag aagatatggc ttcgtgccgc gtcctggatt cgcggaaacg cgtacatcca    60
gctgacgagt cccaaatagg acgaaacgcg g                                    91

SEQ ID NO: 131          moltype = RNA  length = 93
FEATURE                 Location/Qualifiers
source                  1..93
                        mol_type = other RNA
                        organism = synthetic construct
SEQUENCE: 131
gcggcacag aagatatggc ttcgtgcccg cgtcctggat tcgcggaaac gcgtacatcc     60
agctgacgag tcccaaatag gacgaaacgc ggg                                  93

SEQ ID NO: 132          moltype = RNA  length = 95
FEATURE                 Location/Qualifiers
source                  1..95
                        mol_type = other RNA
                        organism = synthetic construct
SEQUENCE: 132
cgcggcacag aagatatggc ttcgtgccgc gcgtcctgga ttcgcggaaa cgcgtacatc    60
cagctgacga gtcccaaata ggacgaaacg cgcgg                                95

SEQ ID NO: 133          moltype = RNA  length = 93
FEATURE                 Location/Qualifiers
source                  1..93
                        mol_type = other RNA
                        organism = synthetic construct
SEQUENCE: 133
cgcgggcaca gaagatatgg cttcgtgccc gcgtcctgga ttcgcggaaa cgcgtacatc    60
cagctgacga gtcccaaata ggacgaaacg cgg                                  93

SEQ ID NO: 134          moltype = RNA  length = 95
FEATURE                 Location/Qualifiers
source                  1..95
                        mol_type = other RNA
                        organism = synthetic construct
SEQUENCE: 134
gcgcggcaca gaagatatgg cttcgtgccg cgcgtcctgg attcgcggaa acgcgtacat    60
ccagctgacg agtcccaaat aggacgaaac gcgcg                                95

SEQ ID NO: 135          moltype = RNA  length = 86
FEATURE                 Location/Qualifiers
source                  1..86
                        mol_type = other RNA
                        organism = synthetic construct
SEQUENCE: 135
aggcacagaa gatatggctt cgtgcctcct ggattcgcgg aaacgcgtac atccagctga    60
cgagtcccaa ataggacgaa aggcac                                          86

SEQ ID NO: 136          moltype = RNA  length = 88
FEATURE                 Location/Qualifiers
source                  1..88
                        mol_type = other RNA
                        organism = synthetic construct
SEQUENCE: 136
cggcacagaa gatatggctt cgtgccgtcc tggattcgcg gaaacgcgta catccagctg    60
acgagtccca ataggacga aacggcac                                         88

SEQ ID NO: 137          moltype = RNA  length = 90
FEATURE                 Location/Qualifiers
source                  1..90
                        mol_type = other RNA
                        organism = synthetic construct
SEQUENCE: 137
gggcacagaa gatatggctt cgtgcccgtc ctggattcgc ggaaacgcgt acatccagct    60
gacgagtccc aaataggacg aaacgggcac                                      90

SEQ ID NO: 138          moltype = RNA  length = 92
FEATURE                 Location/Qualifiers
source                  1..92
                        mol_type = other RNA
                        organism = synthetic construct
SEQUENCE: 138
cggcacagaa gatatggctt cgtgccgcgt cctggattcg cggaaacgcg tacatccagc    60
tgacgagtcc caaataggac gaaacgcggc ac                                   92

SEQ ID NO: 139          moltype = RNA  length = 94
FEATURE                 Location/Qualifiers
```

```
source                  1..94
                        mol_type = other RNA
                        organism = synthetic construct
SEQUENCE: 139
gggcacagaa gatatggctt cgtgcccgcg tcctggattc gcggaaacgc gtacatccag  60
ctgacgagtc ccaaatagga cgaaacgcgg gcac                                94

SEQ ID NO: 140          moltype = RNA   length = 88
FEATURE                 Location/Qualifiers
source                  1..88
                        mol_type = other RNA
                        organism = synthetic construct
SEQUENCE: 140
acggcacaga agatatggct tcgtgccgtc ctggattcgc ggaaacgcgt acatccagct  60
gacgagtccc aaataggacg aaacggca                                       88

SEQ ID NO: 141          moltype = RNA   length = 90
FEATURE                 Location/Qualifiers
source                  1..90
                        mol_type = other RNA
                        organism = synthetic construct
SEQUENCE: 141
cgggcacaga agatatggct tcgtgcccgt cctggattcg cggaaacgcg tacatccagc  60
tgacgagtcc caaataggac gaaacgggca                                     90

SEQ ID NO: 142          moltype = RNA   length = 92
FEATURE                 Location/Qualifiers
source                  1..92
                        mol_type = other RNA
                        organism = synthetic construct
SEQUENCE: 142
gcggcacaga agatatggct tcgtgccgcg tcctggattc gcggaaacgc gtacatccag  60
ctgacgagtc ccaaatagga cgaaacgcgg ca                                  92

SEQ ID NO: 143          moltype = RNA   length = 94
FEATURE                 Location/Qualifiers
source                  1..94
                        mol_type = other RNA
                        organism = synthetic construct
SEQUENCE: 143
cgggcacaga agatatggct tcgtgcccgc gtcctggatt cgcggaaacg cgtacatcca  60
gctgacgagt cccaaatagg acgaaacgcg ggca                                94

SEQ ID NO: 144          moltype = RNA   length = 96
FEATURE                 Location/Qualifiers
source                  1..96
                        mol_type = other RNA
                        organism = synthetic construct
SEQUENCE: 144
gcggcacaga agatatggct tcgtgccgcg cgtcctggat tcgcggaaac gcgtacatcc  60
agctgacgag tcccaaatag gacgaaacgc gcggca                              96

SEQ ID NO: 145          moltype = RNA   length = 90
FEATURE                 Location/Qualifiers
source                  1..90
                        mol_type = other RNA
                        organism = synthetic construct
SEQUENCE: 145
acgggcacag aagatatggc ttcgtgcccg tcctggattc gcggaaacgc gtacatccag  60
ctgacgagtc ccaaatagga cgaaacgggc                                     90

SEQ ID NO: 146          moltype = RNA   length = 92
FEATURE                 Location/Qualifiers
source                  1..92
                        mol_type = other RNA
                        organism = synthetic construct
SEQUENCE: 146
cgcggcacag aagatatggc ttcgtgccgc gtcctggatt cgcggaaacg cgtacatcca  60
gctgacgagt cccaaatagg acgaaacgcg gc                                  92

SEQ ID NO: 147          moltype = RNA   length = 94
FEATURE                 Location/Qualifiers
source                  1..94
                        mol_type = other RNA
                        organism = synthetic construct
SEQUENCE: 147
gcgggcacag aagatatggc ttcgtgcccg cgtcctggat tcgcggaaac gcgtacatcc  60
agctgacgag tcccaaatag gacgaaacgc gggc                                94
```

-continued

```
SEQ ID NO: 148          moltype = RNA   length = 96
FEATURE                 Location/Qualifiers
source                  1..96
                        mol_type = other RNA
                        organism = synthetic construct
SEQUENCE: 148
cgcggcacag aagatatggc ttcgtgccgc gcgtcctgga ttcgcggaaa cgcgtacatc   60
cagctgacga gtcccaaata ggacgaaacg cgcggc                             96

SEQ ID NO: 149          moltype = RNA   length = 92
FEATURE                 Location/Qualifiers
source                  1..92
                        mol_type = other RNA
                        organism = synthetic construct
SEQUENCE: 149
acgcggcaca gaagatatgg cttcgtgccg cgtcctggat tcgcggaaac gcgtacatcc   60
agctgacgag tcccaaatag gacgaaacgc gg                                 92

SEQ ID NO: 150          moltype = RNA   length = 94
FEATURE                 Location/Qualifiers
source                  1..94
                        mol_type = other RNA
                        organism = synthetic construct
SEQUENCE: 150
cgcgggcaca gaagatatgg cttcgtgccc gcgtcctgga ttcgcggaaa cgcgtacatc   60
cagctgacga gtcccaaata ggacgaaacg cggg                               94

SEQ ID NO: 151          moltype = RNA   length = 96
FEATURE                 Location/Qualifiers
source                  1..96
                        mol_type = other RNA
                        organism = synthetic construct
SEQUENCE: 151
gcgcggcaca gaagatatgg cttcgtgccg cgcgtcctgg attcgcggaa acgcgtacat   60
ccagctgacg agtcccaaat aggacgaaac gcgcgg                             96

SEQ ID NO: 152          moltype = RNA   length = 94
FEATURE                 Location/Qualifiers
source                  1..94
                        mol_type = other RNA
                        organism = synthetic construct
SEQUENCE: 152
acgcgggcac agaagatatg gcttcgtgcc cgcgtcctgg attcgcggaa acgcgtacat   60
ccagctgacg agtcccaaat aggacgaaac gcgg                               94

SEQ ID NO: 153          moltype = RNA   length = 96
FEATURE                 Location/Qualifiers
source                  1..96
                        mol_type = other RNA
                        organism = synthetic construct
SEQUENCE: 153
cgcgcggcac agaagatatg gcttcgtgcc gcgcgtcctg gattcgcgga aacgcgtaca   60
tccagctgac gagtcccaaa taggacgaaa cgcgcg                             96

SEQ ID NO: 154          moltype = RNA   length = 89
FEATURE                 Location/Qualifiers
source                  1..89
                        mol_type = other RNA
                        organism = synthetic construct
SEQUENCE: 154
acggcacaga agatatggct tcgtgccgtc ctggattcgc ggaaacgcgt acatccagct   60
gacgagtccc aaataggacg aaacggcac                                     89

SEQ ID NO: 155          moltype = RNA   length = 91
FEATURE                 Location/Qualifiers
source                  1..91
                        mol_type = other RNA
                        organism = synthetic construct
SEQUENCE: 155
cgggcacaga agatatggct tcgtgcccgt cctggattcg cggaaacgcg tacatccagc   60
tgacgagtcc caaataggac gaaacgggca c                                  91

SEQ ID NO: 156          moltype = RNA   length = 93
FEATURE                 Location/Qualifiers
source                  1..93
                        mol_type = other RNA
                        organism = synthetic construct
SEQUENCE: 156
gcggcacaga agatatggct tcgtgccgcg tcctggattc gcggaaacgc gtacatccag   60
```

-continued

```
ctgacgagtc ccaaatagga cgaaacgcgg cac                                    93

SEQ ID NO: 157          moltype = RNA   length = 95
FEATURE                 Location/Qualifiers
source                  1..95
                        mol_type = other RNA
                        organism = synthetic construct
SEQUENCE: 157
cgggcacaga agatatggct tcgtgcccgc gtcctggatt cgcggaaacg cgtacatcca      60
gctgacgagt cccaaatagg acgaaacgcg ggcac                                 95

SEQ ID NO: 158          moltype = RNA   length = 97
FEATURE                 Location/Qualifiers
source                  1..97
                        mol_type = other RNA
                        organism = synthetic construct
SEQUENCE: 158
gcggcacaga agatatggct tcgtgccgcg cgtcctggat tcgcggaaac gcgtacatcc      60
agctgacgag tcccaaatag gacgaaacgc gcggcac                               97

SEQ ID NO: 159          moltype = RNA   length = 91
FEATURE                 Location/Qualifiers
source                  1..91
                        mol_type = other RNA
                        organism = synthetic construct
SEQUENCE: 159
acgggcacag aagatatggc ttcgtgcccg tcctggattc gcggaaacgc gtacatccag      60
ctgacgagtc ccaaatagga cgaaacgggc a                                     91

SEQ ID NO: 160          moltype = RNA   length = 93
FEATURE                 Location/Qualifiers
source                  1..93
                        mol_type = other RNA
                        organism = synthetic construct
SEQUENCE: 160
cgcggcacag aagatatggc ttcgtgccgc gtcctggatt cgcggaaacg cgtacatcca      60
gctgacgagt cccaaatagg acgaaacgcg gca                                   93

SEQ ID NO: 161          moltype = RNA   length = 95
FEATURE                 Location/Qualifiers
source                  1..95
                        mol_type = other RNA
                        organism = synthetic construct
SEQUENCE: 161
gcgggcacag aagatatggc ttcgtgcccg cgtcctggat tcgcggaaac gcgtacatcc      60
agctgacgag tcccaaatag gacgaaacgc gggca                                 95

SEQ ID NO: 162          moltype = RNA   length = 97
FEATURE                 Location/Qualifiers
source                  1..97
                        mol_type = other RNA
                        organism = synthetic construct
SEQUENCE: 162
cgcggcacag aagatatggc ttcgtgccgc gcgtcctgga ttcgcggaaa cgcgtacatc      60
cagctgacga gtcccaaata ggacgaaacg cgcggca                               97

SEQ ID NO: 163          moltype = RNA   length = 93
FEATURE                 Location/Qualifiers
source                  1..93
                        mol_type = other RNA
                        organism = synthetic construct
SEQUENCE: 163
acgcggcaca gaagatatgg cttcgtgccg cgtcctggat tcgcggaaac gcgtacatcc      60
agctgacgag tcccaaatag gacgaaacgc ggc                                   93

SEQ ID NO: 164          moltype = RNA   length = 95
FEATURE                 Location/Qualifiers
source                  1..95
                        mol_type = other RNA
                        organism = synthetic construct
SEQUENCE: 164
cgcgggcaca gaagatatgg cttcgtgccc gcgtcctgga ttcgcggaaa cgcgtacatc      60
cagctgacga gtcccaaata ggacgaaacg cgggc                                 95

SEQ ID NO: 165          moltype = RNA   length = 97
FEATURE                 Location/Qualifiers
source                  1..97
                        mol_type = other RNA
                        organism = synthetic construct
```

-continued

```
SEQUENCE: 165
gcgcggcaca gaagatatgg cttcgtgccg cgcgtcctgg attcgcggaa acgcgtacat   60
ccagctgacg agtcccaaat aggacgaaac gcgcggc                            97

SEQ ID NO: 166        moltype = RNA   length = 95
FEATURE               Location/Qualifiers
source                1..95
                      mol_type = other RNA
                      organism = synthetic construct
SEQUENCE: 166
acgcgggcac agaagatatg gcttcgtgcc cgcgtcctgg attcgcggaa acgcgtacat   60
ccagctgacg agtcccaaat aggacgaaac gcggg                              95

SEQ ID NO: 167        moltype = RNA   length = 97
FEATURE               Location/Qualifiers
source                1..97
                      mol_type = other RNA
                      organism = synthetic construct
SEQUENCE: 167
cgcgcggcac agaagatatg gcttcgtgcc gcgcgtcctg gattcgcgga aacgcgtaca   60
tccagctgac gagtcccaaa taggacgaaa cgcgcgg                            97

SEQ ID NO: 168        moltype = RNA   length = 97
FEATURE               Location/Qualifiers
source                1..97
                      mol_type = other RNA
                      organism = synthetic construct
SEQUENCE: 168
acgcgcggca cagaagatat ggcttcgtgc cgcgcgtcct ggattcgcgg aaacgcgtac   60
atccagctga cgagtcccaa ataggacgaa acgcgcg                            97

SEQ ID NO: 169        moltype = RNA   length = 87
FEATURE               Location/Qualifiers
source                1..87
                      mol_type = other RNA
                      organism = synthetic construct
SEQUENCE: 169
cggcatcctg gattcgcgga aacgcgtaca tccagctgac gagtcccaaa taggacgaaa   60
tgccgcagaa gatatggctt cgcggca                                       87

SEQ ID NO: 170        moltype = RNA   length = 88
FEATURE               Location/Qualifiers
source                1..88
                      mol_type = other RNA
                      organism = synthetic construct
SEQUENCE: 170
cggcactcct ggattcgcgg aaacgcgtac atccagctga cgagtcccaa ataggacgaa   60
agtgccgaga agatatggct tccggcac                                      88

SEQ ID NO: 171        moltype = RNA   length = 92
FEATURE               Location/Qualifiers
source                1..92
                      mol_type = other RNA
                      organism = synthetic construct
SEQUENCE: 171
cggcaccgtc ctggattcgc ggaaacgcgt acatccagct gacgagtccc aaataggacg   60
aaacggtgcc gagaagatat ggcttccggc ac                                92

SEQ ID NO: 172        moltype = RNA   length = 95
FEATURE               Location/Qualifiers
source                1..95
                      mol_type = other RNA
                      organism = synthetic construct
SEQUENCE: 172
cgggcaccgt cctggattcg cggaaacgcg tacatccagc tgacgagtcc caaataggac   60
gaaacggtgc cgagaagat atggcttccg ggcac                              95

SEQ ID NO: 173        moltype = RNA   length = 88
FEATURE               Location/Qualifiers
source                1..88
                      mol_type = other RNA
                      organism = synthetic construct
SEQUENCE: 173
ggctcgtgta gctcattagc tccgagcctc ctggattcgc ggaaacgcgt acatccagct   60
gacgagtccc aaataggacg aaaggctc                                      88

SEQ ID NO: 174        moltype = RNA   length = 90
FEATURE               Location/Qualifiers
source                1..90
```

-continued

```
                            mol_type = other RNA
                            organism = synthetic construct
SEQUENCE: 174
ggctcgtgta gctcattagc tccgagccgt cctggattcg cggaaacgcg tacatccagc    60
tgacgagtcc caaataggac gaaacggctc                                     90

SEQ ID NO: 175          moltype = RNA   length = 92
FEATURE                 Location/Qualifiers
source                  1..92
                        mol_type = other RNA
                        organism = synthetic construct
SEQUENCE: 175
ggctcgtgta gctcattagc tccgagcccg tcctggattc gcggaaacgc gtacatccag    60
ctgacgagtc ccaaatagga cgaaacgggc tc                                  92

SEQ ID NO: 176          moltype = RNA   length = 94
FEATURE                 Location/Qualifiers
source                  1..94
                        mol_type = other RNA
                        organism = synthetic construct
SEQUENCE: 176
ggctcgtgta gctcattagc tccgagccgc gtcctggatt cgcggaaacg cgtacatcca    60
gctgacgagt cccaaatagg acgaaacgcg gctc                                94

SEQ ID NO: 177          moltype = RNA   length = 90
FEATURE                 Location/Qualifiers
source                  1..90
                        mol_type = other RNA
                        organism = synthetic construct
SEQUENCE: 177
cggctcgtgt agctcattag ctccgagccg tcctggattc gcggaaacgc gtacatccag    60
ctgacgagtc ccaaatagga cgaaacggct                                     90

SEQ ID NO: 178          moltype = RNA   length = 92
FEATURE                 Location/Qualifiers
source                  1..92
                        mol_type = other RNA
                        organism = synthetic construct
SEQUENCE: 178
gggctcgtgt agctcattag ctccgagccc gtcctggatt cgcggaaacg cgtacatcca    60
gctgacgagt cccaaatagg acgaaacggg ct                                  92

SEQ ID NO: 179          moltype = RNA   length = 94
FEATURE                 Location/Qualifiers
source                  1..94
                        mol_type = other RNA
                        organism = synthetic construct
SEQUENCE: 179
cggctcgtgt agctcattag ctccgagccg cgtcctggat tcgcggaaac gcgtacatcc    60
agctgacgag tcccaaatag gacgaaacgc ggct                                94

SEQ ID NO: 180          moltype = RNA   length = 96
FEATURE                 Location/Qualifiers
source                  1..96
                        mol_type = other RNA
                        organism = synthetic construct
SEQUENCE: 180
gggctcgtgt agctcattag ctccgagccc gcgtcctgga ttcgcggaaa cgcgtacatc    60
cagctgacga gtcccaaata ggacgaaacg cgggct                              96

SEQ ID NO: 181          moltype = RNA   length = 92
FEATURE                 Location/Qualifiers
source                  1..92
                        mol_type = other RNA
                        organism = synthetic construct
SEQUENCE: 181
cgggctcgtg tagctcatta gctccgagcc cgtcctggat tcgcggaaac gcgtacatcc    60
agctgacgag tcccaaatag gacgaaacgg gc                                  92

SEQ ID NO: 182          moltype = RNA   length = 94
FEATURE                 Location/Qualifiers
source                  1..94
                        mol_type = other RNA
                        organism = synthetic construct
SEQUENCE: 182
gcggctcgtg tagctcatta gctccgagcc gcgtcctgga ttcgcggaaa cgcgtacatc    60
cagctgacga gtcccaaata ggacgaaacg cggc                                94

SEQ ID NO: 183          moltype = RNA   length = 96
```

```
FEATURE                  Location/Qualifiers
source                   1..96
                         mol_type = other RNA
                         organism = synthetic construct
SEQUENCE: 183
cgggctcgtg tagctcatta gctccgagcc cgcgtcctgg attcgcggaa acgcgtacat   60
ccagctgacg agtcccaaat aggacgaaac gcgggc                             96

SEQ ID NO: 184           moltype = RNA   length = 94
FEATURE                  Location/Qualifiers
source                   1..94
                         mol_type = other RNA
                         organism = synthetic construct
SEQUENCE: 184
cgcggctcgt gtagctcatt agctccgagc cgcgtcctgg attcgcggaa acgcgtacat   60
ccagctgacg agtcccaaat aggacgaaac gcgg                               94

SEQ ID NO: 185           moltype = RNA   length = 96
FEATURE                  Location/Qualifiers
source                   1..96
                         mol_type = other RNA
                         organism = synthetic construct
SEQUENCE: 185
gcgggctcgt gtagctcatt agctccgagc ccgcgtcctg gattcgcgga aacgcgtaca   60
tccagctgac gagtcccaaa taggacgaaa cgcggg                             96

SEQ ID NO: 186           moltype = RNA   length = 89
FEATURE                  Location/Qualifiers
source                   1..89
                         mol_type = other RNA
                         organism = synthetic construct
SEQUENCE: 186
ggctcgtgta gctcattagc tccgagcctc ctggattcgc ggaaacgcgt acatccagct   60
gacgagtccc aaataggacg aaaggctcg                                     89

SEQ ID NO: 187           moltype = RNA   length = 91
FEATURE                  Location/Qualifiers
source                   1..91
                         mol_type = other RNA
                         organism = synthetic construct
SEQUENCE: 187
ggctcgtgta gctcattagc tccgagccgt cctggattcg cggaaacgcg tacatccagc   60
tgacgagtcc caaataggac gaaacggtc g                                   91

SEQ ID NO: 188           moltype = RNA   length = 95
FEATURE                  Location/Qualifiers
source                   1..95
                         mol_type = other RNA
                         organism = synthetic construct
SEQUENCE: 188
ggctcgtgta gctcattagc tccgagccgc gtcctggatt cgcggaaacg cgtacatcca   60
gctgacgagt cccaaatagg acgaaacgcg gctcg                              95

SEQ ID NO: 189           moltype = RNA   length = 89
FEATURE                  Location/Qualifiers
source                   1..89
                         mol_type = other RNA
                         organism = synthetic construct
SEQUENCE: 189
aggctcgtgt agctcattag ctccgagcct cctggattcg cggaaacgcg tacatccagc   60
tgacgagtcc caaataggac gaaaggctc                                     89

SEQ ID NO: 190           moltype = RNA   length = 91
FEATURE                  Location/Qualifiers
source                   1..91
                         mol_type = other RNA
                         organism = synthetic construct
SEQUENCE: 190
cggctcgtgt agctcattag ctccgagccg tcctggattc gcggaaacgc gtacatccag   60
ctgacgagtc ccaaatagga cgaaacggct c                                  91

SEQ ID NO: 191           moltype = RNA   length = 93
FEATURE                  Location/Qualifiers
source                   1..93
                         mol_type = other RNA
                         organism = synthetic construct
SEQUENCE: 191
gggctcgtgt agctcattag ctccgagccc gtcctggatt cgcggaaacg cgtacatcca   60
gctgacgagt cccaaatagg acgaaacggg ctc                                93
```

```
SEQ ID NO: 192          moltype = RNA  length = 95
FEATURE                 Location/Qualifiers
source                  1..95
                        mol_type = other RNA
                        organism = synthetic construct
SEQUENCE: 192
cggctcgtgt agctcattag ctccgagccg cgtcctggat tcgcggaaac gcgtacatcc   60
agctgacgag tcccaaatag gacgaaacgc ggctc                              95

SEQ ID NO: 193          moltype = RNA  length = 97
FEATURE                 Location/Qualifiers
source                  1..97
                        mol_type = other RNA
                        organism = synthetic construct
SEQUENCE: 193
gggctcgtgt agctcattag ctccgagccc gcgtcctgga ttcgcggaaa cgcgtacatc   60
cagctgacga gtcccaaata ggacgaaacg cgggctc                            97

SEQ ID NO: 194          moltype = RNA  length = 93
FEATURE                 Location/Qualifiers
source                  1..93
                        mol_type = other RNA
                        organism = synthetic construct
SEQUENCE: 194
cgggctcgtg tagctcatta gctccgagcc cgtcctggat tcgcggaaac gcgtacatcc   60
agctgacgag tcccaaatag gacgaaacgg gct                                93

SEQ ID NO: 195          moltype = RNA  length = 95
FEATURE                 Location/Qualifiers
source                  1..95
                        mol_type = other RNA
                        organism = synthetic construct
SEQUENCE: 195
gcggctcgtg tagctcatta gctccgagcc gcgtcctgga ttcgcggaaa cgcgtacatc   60
cagctgacga gtcccaaata ggacgaaacg cggct                              95

SEQ ID NO: 196          moltype = RNA  length = 99
FEATURE                 Location/Qualifiers
source                  1..99
                        mol_type = other RNA
                        organism = synthetic construct
SEQUENCE: 196
gcggctcgtg tagctcatta gctccgagcc gcgcgtcctg gattcgcgga aacgcgtaca   60
tccagctgac gagtcccaaa taggacgaaa cgcgcggct                          99

SEQ ID NO: 197          moltype = RNA  length = 93
FEATURE                 Location/Qualifiers
source                  1..93
                        mol_type = other RNA
                        organism = synthetic construct
SEQUENCE: 197
acgggctcgt gtagctcatt agctccgagc ccgtcctgga ttcgcggaaa cgcgtacatc   60
cagctgacga gtcccaaata ggacgaaacg ggc                                93

SEQ ID NO: 198          moltype = RNA  length = 95
FEATURE                 Location/Qualifiers
source                  1..95
                        mol_type = other RNA
                        organism = synthetic construct
SEQUENCE: 198
cgcggctcgt gtagctcatt agctccgagc cgcgtcctgg attcgcggaa acgcgtacat   60
ccagctgacg agtcccaaat aggacgaaac gcggc                              95

SEQ ID NO: 199          moltype = RNA  length = 97
FEATURE                 Location/Qualifiers
source                  1..97
                        mol_type = other RNA
                        organism = synthetic construct
SEQUENCE: 199
gcgggctcgt gtagctcatt agctccgagc ccgcgtcctg gattcgcgga aacgcgtaca   60
tccagctgac gagtcccaaa taggacgaaa cgcgggc                            97

SEQ ID NO: 200          moltype = RNA  length = 99
FEATURE                 Location/Qualifiers
source                  1..99
                        mol_type = other RNA
                        organism = synthetic construct
SEQUENCE: 200
```

-continued

```
cgcggctcgt gtagctcatt agctccgagc cgcgcgtcct ggattcgcgg aaacgcgtac    60
atccagctga cgagtcccaa ataggacgaa acgcgcggc                            99

SEQ ID NO: 201          moltype = RNA   length = 97
FEATURE                 Location/Qualifiers
source                  1..97
                        mol_type = other RNA
                        organism = synthetic construct
SEQUENCE: 201
cgcgggctcg tgtagctcat tagctccgag cccgcgtcct ggattcgcgg aaacgcgtac    60
atccagctga cgagtcccaa ataggacgaa acgcggg                              97

SEQ ID NO: 202          moltype = RNA   length = 99
FEATURE                 Location/Qualifiers
source                  1..99
                        mol_type = other RNA
                        organism = synthetic construct
SEQUENCE: 202
gcgcggctcg tgtagctcat tagctccgag ccgcgcgtcc tggattcgcg gaaacgcgta    60
catccagctg acgagtccca aataggacga aacgcgcgg                            99

SEQ ID NO: 203          moltype = RNA   length = 92
FEATURE                 Location/Qualifiers
source                  1..92
                        mol_type = other RNA
                        organism = synthetic construct
SEQUENCE: 203
cggctcgtgt agctcattag ctccgagccg tcctggattc gcggaaacgc gtacatccag    60
ctgacgagtc ccaaatagga cgaaacggct cg                                  92

SEQ ID NO: 204          moltype = RNA   length = 94
FEATURE                 Location/Qualifiers
source                  1..94
                        mol_type = other RNA
                        organism = synthetic construct
SEQUENCE: 204
gggctcgtgt agctcattag ctccgagccc gtcctggatt cgcggaaacg cgtacatcca    60
gctgacgagt cccaaatagg acgaaacggg ctcg                                94

SEQ ID NO: 205          moltype = RNA   length = 96
FEATURE                 Location/Qualifiers
source                  1..96
                        mol_type = other RNA
                        organism = synthetic construct
SEQUENCE: 205
cggctcgtgt agctcattag ctccgagccg cgtcctggat tcgcggaaac gcgtacatcc    60
agctgacgag tcccaaatag gacgaaacgc ggctcg                              96

SEQ ID NO: 206          moltype = RNA   length = 98
FEATURE                 Location/Qualifiers
source                  1..98
                        mol_type = other RNA
                        organism = synthetic construct
SEQUENCE: 206
gggctcgtgt agctcattag ctccgagccc gcgtcctgga ttcgcggaaa cgcgtacatc    60
cagctgacga gtcccaaata ggacgaaacg cgggctcg                            98

SEQ ID NO: 207          moltype = RNA   length = 92
FEATURE                 Location/Qualifiers
source                  1..92
                        mol_type = other RNA
                        organism = synthetic construct
SEQUENCE: 207
acggctcgtg tagctcatta gctccgagcc gtcctggatt cgcggaaacg cgtacatcca    60
gctgacgagt cccaaatagg acgaaacggc tc                                  92

SEQ ID NO: 208          moltype = RNA   length = 94
FEATURE                 Location/Qualifiers
source                  1..94
                        mol_type = other RNA
                        organism = synthetic construct
SEQUENCE: 208
cgggctcgtg tagctcatta gctccgagcc cgtcctggat tcgcggaaac gcgtacatcc    60
agctgacgag tcccaaatag gacgaaacgg ctc                                 94

SEQ ID NO: 209          moltype = RNA   length = 96
FEATURE                 Location/Qualifiers
source                  1..96
                        mol_type = other RNA
```

-continued

```
                          organism = synthetic construct
SEQUENCE: 209
gcggctcgtg tagctcatta gctccgagcc gcgtcctgga ttcgcggaaa cgcgtacatc    60
cagctgacga gtcccaaata ggacgaaacg cggctc                              96

SEQ ID NO: 210          moltype = RNA   length = 98
FEATURE                 Location/Qualifiers
source                  1..98
                        mol_type = other RNA
                        organism = synthetic construct
SEQUENCE: 210
cgggctcgtg tagctcatta gctccgagcc cgcgtcctgg attcgcggaa acgcgtacat    60
ccagctgacg agtcccaaat aggacgaaac gcgggctc                            98

SEQ ID NO: 211          moltype = RNA   length = 100
FEATURE                 Location/Qualifiers
source                  1..100
                        mol_type = other RNA
                        organism = synthetic construct
SEQUENCE: 211
gcggctcgtg tagctcatta gctccgagcc gcgcgtcctg gattcgcgga aacgcgtaca    60
tccagctgac gagtcccaaa taggacgaaa cgcgcggctc                          100

SEQ ID NO: 212          moltype = RNA   length = 94
FEATURE                 Location/Qualifiers
source                  1..94
                        mol_type = other RNA
                        organism = synthetic construct
SEQUENCE: 212
acgggctcgt gtagctcatt agctccgagc ccgtcctgga ttcgcggaaa cgcgtacatc    60
cagctgacga gtcccaaata ggacgaaacg ggct                                94

SEQ ID NO: 213          moltype = RNA   length = 96
FEATURE                 Location/Qualifiers
source                  1..96
                        mol_type = other RNA
                        organism = synthetic construct
SEQUENCE: 213
cgcggctcgt gtagctcatt agctccgagc cgcgtcctgg attcgcggaa acgcgtacat    60
ccagctgacg agtcccaaat aggacgaaac gcggct                              96

SEQ ID NO: 214          moltype = RNA   length = 98
FEATURE                 Location/Qualifiers
source                  1..98
                        mol_type = other RNA
                        organism = synthetic construct
SEQUENCE: 214
gcgggctcgt gtagctcatt agctccgagc ccgcgtcctg gattcgcgga aacgcgtaca    60
tccagctgac gagtcccaaa taggacgaaa cgcgggct                            98

SEQ ID NO: 215          moltype = RNA   length = 100
FEATURE                 Location/Qualifiers
source                  1..100
                        mol_type = other RNA
                        organism = synthetic construct
SEQUENCE: 215
cgcggctcgt gtagctcatt agctccgagc cgcgcgtcct ggattcgcgg aaacgcgtac    60
atccagctga cgagtcccaa ataggacgaa acgcgcggct                          100

SEQ ID NO: 216          moltype = RNA   length = 96
FEATURE                 Location/Qualifiers
source                  1..96
                        mol_type = other RNA
                        organism = synthetic construct
SEQUENCE: 216
acgcggctcg tgtagctcat tagctccgag ccgcgtcctg gattcgcgga aacgcgtaca    60
tccagctgac gagtcccaaa taggacgaaa cgcggc                              96

SEQ ID NO: 217          moltype = RNA   length = 98
FEATURE                 Location/Qualifiers
source                  1..98
                        mol_type = other RNA
                        organism = synthetic construct
SEQUENCE: 217
cgcgggctcg tgtagctcat tagctccgag cccgcgtcct ggattcgcgg aaacgcgtac    60
atccagctga cgagtcccaa ataggacgaa acgcgggc                            98

SEQ ID NO: 218          moltype = RNA   length = 100
FEATURE                 Location/Qualifiers
```

-continued

```
source                  1..100
                        mol_type = other RNA
                        organism = synthetic construct
SEQUENCE: 218
gcgcggctcg tgtagctcat tagctccgag ccgcgcgtcc tggattcgcg gaaacgcgta   60
catccagctg acgagtccca aataggacga aacgcgcggc                        100

SEQ ID NO: 219          moltype = RNA   length = 99
FEATURE                 Location/Qualifiers
source                  1..99
                        mol_type = other RNA
                        organism = synthetic construct
SEQUENCE: 219
ggctcgtgta gctcattagc tccgagccga taagggctct cctggattcg cggaaacgcg   60
tacatccagc tgacgagtcc caaataggac gaaagagcc                          99

SEQ ID NO: 220          moltype = RNA   length = 105
FEATURE                 Location/Qualifiers
source                  1..105
                        mol_type = other RNA
                        organism = synthetic construct
SEQUENCE: 220
ggctcgtgta gctcattagc tccgagccga taagggctcg cgtcctggat tcgcggaaac   60
gcgtacatcc agctgacgag tcccaaatag gacgaaacgc gagcc                  105

SEQ ID NO: 221          moltype = RNA   length = 103
FEATURE                 Location/Qualifiers
source                  1..103
                        mol_type = other RNA
                        organism = synthetic construct
SEQUENCE: 221
ggctcgtgta gctcattagc tccgagcccg ataaggggct cgtcctggat tcgcggaaac   60
gcgtacatcc agctgacgag tcccaaatag gacgaaacga gcc                    103

SEQ ID NO: 222          moltype = RNA   length = 105
FEATURE                 Location/Qualifiers
source                  1..105
                        mol_type = other RNA
                        organism = synthetic construct
SEQUENCE: 222
ggctcgtgta gctcattagc tccgagcccg ataaggggct ccgtcctgga ttcgcggaaa   60
cgcgtacatc cagctgacga gtcccaaata ggacgaaacg gagcc                  105

SEQ ID NO: 223          moltype = RNA   length = 107
FEATURE                 Location/Qualifiers
source                  1..107
                        mol_type = other RNA
                        organism = synthetic construct
SEQUENCE: 223
ggctcgtgta gctcattagc tccgagcccg ataaggggct cgcgtcctgg attcgcggaa   60
acgcgtacat ccagctgacg agtcccaaat aggacgaaac gcgagcc                107

SEQ ID NO: 224          moltype = RNA   length = 103
FEATURE                 Location/Qualifiers
source                  1..103
                        mol_type = other RNA
                        organism = synthetic construct
SEQUENCE: 224
ggctcgtgta gctcattagc tccgagcccg gataagcggg ctctcctgga ttcgcggaaa   60
cgcgtacatc cagctgacga gtcccaaata ggacgaaaga gcc                    103

SEQ ID NO: 225          moltype = RNA   length = 109
FEATURE                 Location/Qualifiers
source                  1..109
                        mol_type = other RNA
                        organism = synthetic construct
SEQUENCE: 225
ggctcgtgta gctcattagc tccgagcccg gataagcggg ctcgcgtcct ggattcgcgg   60
aaacgcgtac atccagctga cgagtcccaa ataggacgaa acgcgagcc             109

SEQ ID NO: 226          moltype = RNA   length = 105
FEATURE                 Location/Qualifiers
source                  1..105
                        mol_type = other RNA
                        organism = synthetic construct
SEQUENCE: 226
ggctcgtgta gctcattagc tccgagcccg agataagtcg ggctctcctg gattcgcgga   60
aacgcgtaca tccagctgac gagtcccaaa taggacgaaa gagcc                  105
```

-continued

```
SEQ ID NO: 227          moltype = RNA   length = 111
FEATURE                 Location/Qualifiers
source                  1..111
                        mol_type = other RNA
                        organism = synthetic construct
SEQUENCE: 227
ggctcgtgta gctcattagc tccgagcccg agataagtcg ggctcgcgtc ctggattcgc   60
ggaaacgcgt acatccagct gacgagtccc aaataggacg aaacgcgagc c            111

SEQ ID NO: 228          moltype = RNA   length = 111
FEATURE                 Location/Qualifiers
source                  1..111
                        mol_type = other RNA
                        organism = synthetic construct
SEQUENCE: 228
ggctcgtgta gctcattagc tccgagcccg acgataaggt cgggctccgt cctggattcg   60
cggaaacgcg tacatccagc tgacgagtcc caaataggac gaaacggagc c            111

SEQ ID NO: 229          moltype = RNA   length = 105
FEATURE                 Location/Qualifiers
source                  1..105
                        mol_type = other RNA
                        organism = synthetic construct
SEQUENCE: 229
gggctcgtgt agctcattag ctccgagccc gataaggggc tcgtcctgga ttcgcggaaa   60
cgcgtacatc cagctgacga gtcccaaata ggacgaaacg agccc                   105

SEQ ID NO: 230          moltype = RNA   length = 103
FEATURE                 Location/Qualifiers
source                  1..103
                        mol_type = other RNA
                        organism = synthetic construct
SEQUENCE: 230
gggctcgtgt agctcattag ctccgagccc cgataagggg gcttcctgga ttcgcggaaa   60
cgcgtacatc cagctgacga gtcccaaata ggacgaaaag ccc                     103

SEQ ID NO: 231          moltype = RNA   length = 107
FEATURE                 Location/Qualifiers
source                  1..107
                        mol_type = other RNA
                        organism = synthetic construct
SEQUENCE: 231
gggctcgtgt agctcattag ctccgagccc cgataagggg gctcgtcctg gattcgcgga   60
aacgcgtaca tccagctgac gagtcccaaa taggacgaaa cgagccc                 107

SEQ ID NO: 232          moltype = RNA   length = 105
FEATURE                 Location/Qualifiers
source                  1..105
                        mol_type = other RNA
                        organism = synthetic construct
SEQUENCE: 232
gggctcgtgt agctcattag ctccgagccc cggataagcg gggcttcctg gattcgcgga   60
aacgcgtaca tccagctgac gagtcccaaa taggacgaaa agccc                   105

SEQ ID NO: 233          moltype = RNA   length = 107
FEATURE                 Location/Qualifiers
source                  1..107
                        mol_type = other RNA
                        organism = synthetic construct
SEQUENCE: 233
cggctcgtgt agctcattag ctccgagccg cggataagcg cggctgtcct ggattcgcgg   60
aaacgcgtac atccagctga cgagtcccaa ataggacgaa acagccg                 107

SEQ ID NO: 234          moltype = RNA   length = 109
FEATURE                 Location/Qualifiers
source                  1..109
                        mol_type = other RNA
                        organism = synthetic construct
SEQUENCE: 234
gggctcgtgt agctcattag ctccgagccc cggataagcg gggctcgtcc tggattcgcg   60
gaaacgcgta catccagctg acgagtccca aataggacga aacgagccc               109

SEQ ID NO: 235          moltype = RNA   length = 111
FEATURE                 Location/Qualifiers
source                  1..111
                        mol_type = other RNA
                        organism = synthetic construct
SEQUENCE: 235
cggctcgtgt agctcattag ctccgagccg cggataagcg cggctgcgtc ctggattcgc   60
```

-continued

```
ggaaacgcgt acatccagct gacgagtccc aaataggacg aaacgcagcc g          111

SEQ ID NO: 236        moltype = RNA   length = 107
FEATURE               Location/Qualifiers
source                1..107
                      mol_type = other RNA
                      organism = synthetic construct
SEQUENCE: 236
gggctcgtgt agctcattag ctccgagccc cgagataagt cggggcttcc tggattcgcg   60
gaaacgcgta catccagctg acgagtccca aataggacga aaagccc               107

SEQ ID NO: 237        moltype = RNA   length = 107
FEATURE               Location/Qualifiers
source                1..107
                      mol_type = other RNA
                      organism = synthetic construct
SEQUENCE: 237
gcggctcgtg tagctcatta gctccgagcc gccgataagg gcggcgtcct ggattcgcgg   60
aaacgcgtac atccagctga cgagtcccaa ataggacgaa acgccgc               107

SEQ ID NO: 238        moltype = RNA   length = 111
FEATURE               Location/Qualifiers
source                1..111
                      mol_type = other RNA
                      organism = synthetic construct
SEQUENCE: 238
gcggctcgtg tagctcatta gctccgagcc gccgataagg gcggcgcgtc ctggattcgc   60
ggaaacgcgt acatccagct gacgagtccc aaataggacg aaacgcgccg c           111

SEQ ID NO: 239        moltype = RNA   length = 109
FEATURE               Location/Qualifiers
source                1..109
                      mol_type = other RNA
                      organism = synthetic construct
SEQUENCE: 239
cgggctcgtg tagctcatta gctccgagcc cgcgagataa gtcgcgggct cctggattcg   60
cggaaacgcg tacatccagc tgacgagtcc caaataggac gaaagcccg            109

SEQ ID NO: 240        moltype = RNA   length = 115
FEATURE               Location/Qualifiers
source                1..115
                      mol_type = other RNA
                      organism = synthetic construct
SEQUENCE: 240
gcggctcgtg tagctcatta gctccgagcc gccgagataa gtcggcggcg cgtcctggat   60
tcgcggaaac gcgtacatcc agctgacgag tcccaaatag gacgaaacgc gccgc       115

SEQ ID NO: 241        moltype = RNA   length = 113
FEATURE               Location/Qualifiers
source                1..113
                      mol_type = other RNA
                      organism = synthetic construct
SEQUENCE: 241
gcggctcgtg tagctcatta gctccgagcc gccgacgata aggtcggcgg cgtcctggat   60
tcgcggaaac gcgtacatcc agctgacgag tcccaaatag gacgaaacgc cgc         113

SEQ ID NO: 242        moltype = RNA   length = 105
FEATURE               Location/Qualifiers
source                1..105
                      mol_type = other RNA
                      organism = synthetic construct
SEQUENCE: 242
gcgggctcgt gtagctcatt agctccgagc ccgcgataag gcgggtcctg gattcgcgga   60
aacgcgtaca tccagctgac gagtcccaaa taggacgaaa cccgc                 105

SEQ ID NO: 243        moltype = RNA   length = 109
FEATURE               Location/Qualifiers
source                1..109
                      mol_type = other RNA
                      organism = synthetic construct
SEQUENCE: 243
gcgggctcgt gtagctcatt agctccgagc ccgcgataag gcgggcgtcc tggattcgcg   60
gaaacgcgta catccagctg acgagtccca aataggacga aacgcccgc             109

SEQ ID NO: 244        moltype = RNA   length = 111
FEATURE               Location/Qualifiers
source                1..111
                      mol_type = other RNA
                      organism = synthetic construct
```

-continued

```
SEQUENCE: 244
gcgggctcgt gtagctcatt agctccgagc ccgccgataa gggcgggcgt cctggattcg     60
cggaaacgcg tacatccagc tgacgagtcc caaataggac gaaacgcccg c             111

SEQ ID NO: 245        moltype = RNA   length = 115
FEATURE               Location/Qualifiers
source                1..115
                      mol_type = other RNA
                      organism = synthetic construct
SEQUENCE: 245
gcgggctcgt gtagctcatt agctccgagc ccgccgagat aagtcggcgg gcgtcctgga     60
ttcgcggaaa cgcgtacatc cagctgacga gtcccaaata ggacgaaacg cccgc          115

SEQ ID NO: 246        moltype = RNA   length = 115
FEATURE               Location/Qualifiers
source                1..115
                      mol_type = other RNA
                      organism = synthetic construct
SEQUENCE: 246
cgcggctcgt gtagctcatt agctccgagc cgcgcgacga taaggtcgcg cgggtcctgg     60
attcgcggaa acgcgtacat ccagctgacg agtcccaaat aggacgaaac ccgcg          115

SEQ ID NO: 247        moltype = RNA   length = 101
FEATURE               Location/Qualifiers
source                1..101
                      mol_type = other RNA
                      organism = synthetic construct
SEQUENCE: 247
ggctcgtgta gctcattagc tccgagccga taagggctcg tcctggattc gcggaaacgc     60
gtacatccag ctgacgagtc ccaaatagga cgaaacgagc c                        101

SEQ ID NO: 248        moltype = RNA   length = 103
FEATURE               Location/Qualifiers
source                1..103
                      mol_type = other RNA
                      organism = synthetic construct
SEQUENCE: 248
ggctcgtgta gctcattagc tccgagcccg gataagcggg ctcgcctgga ttcgcggaaa     60
cgcgtacatc cagctgacga gtcccaaata ggacgaacga gcc                      103

SEQ ID NO: 249        moltype = RNA   length = 107
FEATURE               Location/Qualifiers
source                1..107
                      mol_type = other RNA
                      organism = synthetic construct
SEQUENCE: 249
ggctcgtgta gctcattagc tccgagcccg gataagcggg ctcggtcctg gattcgcgga     60
aacgcgtaca tccagctgac gagtcccaaa taggacgaaa ccgagcc                  107

SEQ ID NO: 250        moltype = RNA   length = 109
FEATURE               Location/Qualifiers
source                1..109
                      mol_type = other RNA
                      organism = synthetic construct
SEQUENCE: 250
ggctcgtgta gctcattagc tccgagcccg gataagcggg ctcgcgtcct ggattcgcgg     60
aaacgcgtac atccagctga cgagtcccaa ataggacgaa acgcgagcc               109

SEQ ID NO: 251        moltype = RNA   length = 111
FEATURE               Location/Qualifiers
source                1..111
                      mol_type = other RNA
                      organism = synthetic construct
SEQUENCE: 251
ggctcgtgta gctcattagc tccgagcccg gataagcggg ctcggcgtcc tggattcgcg     60
gaaacgcgta catccagctg acagtcccaa ataggacga aacgccgagc c             111

SEQ ID NO: 252        moltype = RNA   length = 111
FEATURE               Location/Qualifiers
source                1..111
                      mol_type = other RNA
                      organism = synthetic construct
SEQUENCE: 252
ggctcgtgta gctcattagc tccgagcccg agataagtcg ggctcgcgtc ctggattcgc     60
ggaaacgcgt acatccagct gacgagtccc aaataggacg aaacgcgagc c             111

SEQ ID NO: 253        moltype = RNA   length = 107
FEATURE               Location/Qualifiers
source                1..107
```

-continued

```
                          mol_type = other RNA
                          organism = synthetic construct
SEQUENCE: 253
ggctcgtgta gctcattagc tccgagcccg acgataaggt cgggctcgcc tggattcgcg    60
gaaacgcgta catccagctg acgagtccca aataggacga acgagcc                  107

SEQ ID NO: 254         moltype = RNA   length = 115
FEATURE                Location/Qualifiers
source                 1..115
                          mol_type = other RNA
                          organism = synthetic construct
SEQUENCE: 254
ggctcgtgta gctcattagc tccgagcccg acgataaggt cgggctcggc gtcctggatt    60
cgcggaaacg cgtacatcca gctgacgagt cccaaatagg acgaaacgcc gagcc         115

SEQ ID NO: 255         moltype = RNA   length = 103
FEATURE                Location/Qualifiers
source                 1..103
                          mol_type = other RNA
                          organism = synthetic construct
SEQUENCE: 255
gggctcgtgt agctcattag ctccgagccc gataaggggc tctcctggat tcgcggaaac    60
gcgtacatcc agctgacgag tcccaaatag gacgaaagag ccc                     103

SEQ ID NO: 256         moltype = RNA   length = 111
FEATURE                Location/Qualifiers
source                 1..111
                          mol_type = other RNA
                          organism = synthetic construct
SEQUENCE: 256
cggctcgtgt agctcattag ctccgagccg cgataaggcg gctcgcgtcc tggattcgcg    60
gaaacgcgta catccagctg acgagtccca aataggacga aacgcgagcc g            111

SEQ ID NO: 257         moltype = RNA   length = 105
FEATURE                Location/Qualifiers
source                 1..105
                          mol_type = other RNA
                          organism = synthetic construct
SEQUENCE: 257
tggctcgtgt agctcattag ctccgagcca cggataagcg tggctccctg gattcgcgga    60
aacgcgtaca tccagctgac gagtcccaaa taggacgaag agcca                   105

SEQ ID NO: 258         moltype = RNA   length = 111
FEATURE                Location/Qualifiers
source                 1..111
                          mol_type = other RNA
                          organism = synthetic construct
SEQUENCE: 258
gggctcgtgt agctcattag ctccgagccc cggataagcg gggctccgtc ctggattcgc    60
ggaaacgcgt acatccagct gacgagtccc aaataggacg aaacggagcc c            111

SEQ ID NO: 259         moltype = RNA   length = 107
FEATURE                Location/Qualifiers
source                 1..107
                          mol_type = other RNA
                          organism = synthetic construct
SEQUENCE: 259
tggctcgtgt agctcattag ctccgagcca cgagataagt cgtggctccc tggattcgcg    60
gaaacgcgta catccagctg acgagtccca aataggacga agagcca                 107

SEQ ID NO: 260         moltype = RNA   length = 111
FEATURE                Location/Qualifiers
source                 1..111
                          mol_type = other RNA
                          organism = synthetic construct
SEQUENCE: 260
cggctcgtgt agctcattag ctccgagccg cgagataagt cgcggctcgt cctggattcg    60
cggaaacgcg tacatccagc tgacgagtcc caaataggac gaaacgagcc g            111

SEQ ID NO: 261         moltype = RNA   length = 115
FEATURE                Location/Qualifiers
source                 1..115
                          mol_type = other RNA
                          organism = synthetic construct
SEQUENCE: 261
cggctcgtgt agctcattag ctccgagccg cgagataagt cgcggctcgc gtcctggatt    60
cgcggaaacg cgtacatcca gctgacgagt cccaaatagg acgaaacgcg agccg         115

SEQ ID NO: 262         moltype = RNA   length = 109
```

-continued

```
FEATURE               Location/Qualifiers
source                1..109
                      mol_type = other RNA
                      organism = synthetic construct
SEQUENCE: 262
tggctcgtgt agctcattag ctccgagcca cgacgataag gtcgtggctc cctggattcg      60
cggaaacgcg tacatccagc tgacgagtcc caaataggac gaagagcca                  109

SEQ ID NO: 263        moltype = RNA   length = 111
FEATURE               Location/Qualifiers
source                1..111
                      mol_type = other RNA
                      organism = synthetic construct
SEQUENCE: 263
gggctcgtgt agctcattag ctccgagccc cgacgataag gtcggggctc tcctggattc      60
gcggaaacgc gtacatccag ctgacgagtc ccaaatagga cgaaagagcc c              111

SEQ ID NO: 264        moltype = RNA   length = 113
FEATURE               Location/Qualifiers
source                1..113
                      mol_type = other RNA
                      organism = synthetic construct
SEQUENCE: 264
cggctcgtgt agctcattag ctccgagccg cgacgataag gtcgcggctc gtcctggatt      60
cgcggaaacg cgtacatcca gctgacgagt cccaaatagg acgaaacgag ccg            113

SEQ ID NO: 265        moltype = RNA   length = 115
FEATURE               Location/Qualifiers
source                1..115
                      mol_type = other RNA
                      organism = synthetic construct
SEQUENCE: 265
gggctcgtgt agctcattag ctccgagccc cgacgataag gtcggggctc cgtcctggat      60
tcgcggaaac gcgtacatcc agctgacgag tcccaaatag gacgaaacgg agccc          115

SEQ ID NO: 266        moltype = RNA   length = 105
FEATURE               Location/Qualifiers
source                1..105
                      mol_type = other RNA
                      organism = synthetic construct
SEQUENCE: 266
gtggctcgtg tagctcatta gctccgagcc accgataagg gtggctcctg gattcgcgga      60
aacgcgtaca tccagctgac gagtcccaaa taggacgaaa gccac                     105

SEQ ID NO: 267        moltype = RNA   length = 109
FEATURE               Location/Qualifiers
source                1..109
                      mol_type = other RNA
                      organism = synthetic construct
SEQUENCE: 267
gcggctcgtg tagctcatta gctccgagcc gccgataagg gcggctgtcc tggattcgcg      60
gaaacgcgta catccagctg acgagtccca aataggacga aacagccgc                 109

SEQ ID NO: 268        moltype = RNA   length = 113
FEATURE               Location/Qualifiers
source                1..113
                      mol_type = other RNA
                      organism = synthetic construct
SEQUENCE: 268
cgggctcgtg tagctcatta gctccgagcc cgcggataag cgcgggctcg tcctggattc      60
gcggaaacgc gtacatccag ctgacgagtc ccaaatagga cgaaacgagc ccg            113

SEQ ID NO: 269        moltype = RNA   length = 117
FEATURE               Location/Qualifiers
source                1..117
                      mol_type = other RNA
                      organism = synthetic construct
SEQUENCE: 269
gcggctcgtg tagctcatta gctccgagcc gccgagataa gtcggcggct gcgtcctgga      60
ttcgcggaaa cgcgtacatc cagctgacga gtcccaaata ggacgaaacg cagccgc        117

SEQ ID NO: 270        moltype = RNA   length = 109
FEATURE               Location/Qualifiers
source                1..109
                      mol_type = other RNA
                      organism = synthetic construct
SEQUENCE: 270
cgcggctcgt gtagctcatt agctccgagc cgcggataag cgcggcgtcc tggattcgcg      60
gaaacgcgta catccagctg acgagtccca aataggacga aacgccgcg                 109
```

```
SEQ ID NO: 271          moltype = RNA   length = 111
FEATURE                 Location/Qualifiers
source                  1..111
                        mol_type = other RNA
                        organism = synthetic construct
SEQUENCE: 271
gcgggctcgt gtagctcatt agctccgagc ccgcgataag gcgggccgtc ctggattcgc    60
ggaaacgcgt acatccagct gacgagtccc aaataggacg aaacggcccg c            111

SEQ ID NO: 272          moltype = RNA   length = 113
FEATURE                 Location/Qualifiers
source                  1..113
                        mol_type = other RNA
                        organism = synthetic construct
SEQUENCE: 272
cgcggctcgt gtagctcatt agctccgagc cgcgcggata agcgcgcggc gtcctggatt    60
cgcggaaacg cgtacatcca gctgacgagt cccaaatagg acgaaacgcc gcg          113

SEQ ID NO: 273          moltype = RNA   length = 115
FEATURE                 Location/Qualifiers
source                  1..115
                        mol_type = other RNA
                        organism = synthetic construct
SEQUENCE: 273
gcgggctcgt gtagctcatt agctccgagc ccgccggata agcggcgggc cgtcctggat    60
tcgcggaaac gcgtacatcc agctgacgag tcccaaatag gacgaaacgg cccgc        115

SEQ ID NO: 274          moltype = RNA   length = 111
FEATURE                 Location/Qualifiers
source                  1..111
                        mol_type = other RNA
                        organism = synthetic construct
SEQUENCE: 274
cgtggctcgt gtagctcatt agctccgagc cacgcgagat aagtcgcgtg gccctggatt    60
cgcggaaacg cgtacatcca gctgacgagt cccaaatagg acgaagccac g            111

SEQ ID NO: 275          moltype = RNA   length = 117
FEATURE                 Location/Qualifiers
source                  1..117
                        mol_type = other RNA
                        organism = synthetic construct
SEQUENCE: 275
cgcggctcgt gtagctcatt agctccgagc cgcgcgacga taaggtcgcg cggcgtcctg    60
gattcgcgga aacgcgtaca tccagctgac gagtcccaaa taggacgaaa cgccgcg      117

SEQ ID NO: 276          moltype = RNA   length = 119
FEATURE                 Location/Qualifiers
source                  1..119
                        mol_type = other RNA
                        organism = synthetic construct
SEQUENCE: 276
gcgggctcgt gtagctcatt agctccgagc ccgccgacga taaggtcggc gggccgtcct    60
ggattcgcgg aaacgcgtac atccagctga cgagtcccaa ataggacgaa acggcccgc    119

SEQ ID NO: 277          moltype = RNA   length = 109
FEATURE                 Location/Qualifiers
source                  1..109
                        mol_type = other RNA
                        organism = synthetic construct
SEQUENCE: 277
gcgtggctcg tgtagctcat tagctccgag ccacgccgat aagggcgtgg cctggattcg    60
cggaaacgcg tacatccagc tgacgagtcc caaataggac gaaccacgc              109

SEQ ID NO: 278          moltype = RNA   length = 111
FEATURE                 Location/Qualifiers
source                  1..111
                        mol_type = other RNA
                        organism = synthetic construct
SEQUENCE: 278
cgcgggctcg tgtagctcat tagctccgag cccgcgcgat aaggcgcggg tcctggattc    60
gcggaaacgc gtacatccag ctgacgagtc ccaaatagga cgaaacccgc g            111

SEQ ID NO: 279          moltype = RNA   length = 113
FEATURE                 Location/Qualifiers
source                  1..113
                        mol_type = other RNA
                        organism = synthetic construct
SEQUENCE: 279
```

```
gcgcggctcg tgtagctcat tagctccgag ccgcgccgat aagggcgcgg gtcctggatt   60
cgcggaaacg cgtacatcca gctgacgagt cccaaatagg acgaaacccg cgc          113

SEQ ID NO: 280            moltype = RNA   length = 113
FEATURE                   Location/Qualifiers
source                    1..113
                          mol_type = other RNA
                          organism = synthetic construct
SEQUENCE: 280
cgcgggctcg tgtagctcat tagctccgag cccgcgcgga taagcgcgcg ggtcctggat   60
tcgcggaaac gcgtacatcc agctgacgag tcccaaatag gacgaaaccc gcg          113

SEQ ID NO: 281            moltype = RNA   length = 105
FEATURE                   Location/Qualifiers
source                    1..105
                          mol_type = other RNA
                          organism = synthetic construct
SEQUENCE: 281
gggctcgtgt agctcattag ctccgagccc gataaggggc tcgtcctgga ttcgcggaaa   60
cgcgtacatc cagctgacga gtcccaaata ggacgaaacg agccc                  105

SEQ ID NO: 282            moltype = RNA   length = 107
FEATURE                   Location/Qualifiers
source                    1..107
                          mol_type = other RNA
                          organism = synthetic construct
SEQUENCE: 282
cggctcgtgt agctcattag ctccgagccg gataagcggc tcggtcctgg attcgcggaa   60
acgcgtacat ccagctgacg agtcccaaat aggacgaaac cgagccg               107

SEQ ID NO: 283            moltype = RNA   length = 111
FEATURE                   Location/Qualifiers
source                    1..111
                          mol_type = other RNA
                          organism = synthetic construct
SEQUENCE: 283
cggctcgtgt agctcattag ctccgagccg gataagcggc tcggcgtcct ggattcgcgg   60
aaacgcgtac atccagctga cgagtcccaa ataggacgaa acgccgagcc g           111

SEQ ID NO: 284            moltype = RNA   length = 109
FEATURE                   Location/Qualifiers
source                    1..109
                          mol_type = other RNA
                          organism = synthetic construct
SEQUENCE: 284
cggctcgtgt agctcattag ctccgagccg cgataaggcg gctcggtcct ggattcgcgg   60
aaacgcgtac atccagctga cgagtcccaa ataggacgaa accgagccg             109

SEQ ID NO: 285            moltype = RNA   length = 115
FEATURE                   Location/Qualifiers
source                    1..115
                          mol_type = other RNA
                          organism = synthetic construct
SEQUENCE: 285
cggctcgtgt agctcattag ctccgagccg cggataagcg cggctcggcg tcctggattc   60
gcggaaacgc gtacatccag ctgacgagtc ccaaatagga cgaaacgccg agccg       115

SEQ ID NO: 286            moltype = RNA   length = 111
FEATURE                   Location/Qualifiers
source                    1..111
                          mol_type = other RNA
                          organism = synthetic construct
SEQUENCE: 286
gggctcgtgt agctcattag ctccgagccc cgagataagt cggggctcgt cctggattcg   60
cggaaacgcg tacatccagc tgacgagtcc caaataggac gaaacgagcc c           111

SEQ ID NO: 287            moltype = RNA   length = 115
FEATURE                   Location/Qualifiers
source                    1..115
                          mol_type = other RNA
                          organism = synthetic construct
SEQUENCE: 287
gggctcgtgt agctcattag ctccgagccc cgagataagt cggggctcgc gtcctggatt   60
cgcggaaacg cgtacatcca gctgacgagt cccaaatagg acgaaacgcg agccc       115

SEQ ID NO: 288            moltype = RNA   length = 119
FEATURE                   Location/Qualifiers
source                    1..119
                          mol_type = other RNA
```

-continued

```
                            organism = synthetic construct
SEQUENCE: 288
cggctcgtgt agctcattag ctccgagccg cgacgataag gtcgcggctc ggcgtcctgg    60
attcgcggaa acgcgtacat ccagctgacg agtcccaaat aggacgaaac gccgagccg    119

SEQ ID NO: 289          moltype = RNA   length = 111
FEATURE                 Location/Qualifiers
source                  1..111
                        mol_type = other RNA
                        organism = synthetic construct
SEQUENCE: 289
cgggctcgtg tagctcatta gctccgagcc cggataagcg ggctccgtcc tggattcgcg    60
gaaacgcgta catccagctg acgagtccca aataggacga aacggagccc g            111

SEQ ID NO: 290          moltype = RNA   length = 113
FEATURE                 Location/Qualifiers
source                  1..113
                        mol_type = other RNA
                        organism = synthetic construct
SEQUENCE: 290
gcggctcgtt tagctcatta gctccgagcc gcgataaggc ggctcgcgtc ctggattcgc    60
ggaaacgcgt acatccagct gacgagtccc aaataggacg aaacgcgagc cgc          113

SEQ ID NO: 291          moltype = RNA   length = 107
FEATURE                 Location/Qualifiers
source                  1..107
                        mol_type = other RNA
                        organism = synthetic construct
SEQUENCE: 291
gtggctcgtg tagctcatta gctccgagcc accgataagg gtggctccct ggattcgcgg    60
aaacgcgtac atccagctga cgagtcccaa ataggacgaa gagccac                 107

SEQ ID NO: 292          moltype = RNA   length = 109
FEATURE                 Location/Qualifiers
source                  1..109
                        mol_type = other RNA
                        organism = synthetic construct
SEQUENCE: 292
cgggctcgtg tagctcatta gctccgagcc cgcgataagg cgggctctcc tggattcgcg    60
gaaacgcgta catccagctg acgagtccca aataggacga aagagcccg               109

SEQ ID NO: 293          moltype = RNA   length = 113
FEATURE                 Location/Qualifiers
source                  1..113
                        mol_type = other RNA
                        organism = synthetic construct
SEQUENCE: 293
cgggctcgtg tagctcatta gctccgagcc cgcgataagg cgggctccgt cctggattcg    60
cggaaacgcg tacatccagc tgacgagtcc caaataggac gaaacggagc ccg          113

SEQ ID NO: 294          moltype = RNA   length = 109
FEATURE                 Location/Qualifiers
source                  1..109
                        mol_type = other RNA
                        organism = synthetic construct
SEQUENCE: 294
gtggctcgtg tagctcatta gctccgagcc accggataag cggtggctcc ctggattcgc    60
ggaaacgcgt acatccagct gacgagtccc aaataggacg aagagccac               109

SEQ ID NO: 295          moltype = RNA   length = 111
FEATURE                 Location/Qualifiers
source                  1..111
                        mol_type = other RNA
                        organism = synthetic construct
SEQUENCE: 295
cgggctcgtg tagctcatta gctccgagcc cgcggataag cgcgggctct cctggattcg    60
cggaaacgcg tacatccagc tgacgagtcc caaataggac gaaagagccc g            111

SEQ ID NO: 296          moltype = RNA   length = 117
FEATURE                 Location/Qualifiers
source                  1..117
                        mol_type = other RNA
                        organism = synthetic construct
SEQUENCE: 296
gcggctcgtg tagctcatta gctccgagcc gccggataag cggcggctcg cgtcctggat    60
tcgcggaaac gcgtacatcc agctgacgag tcccaaatag gacgaaacgc gagccgc      117

SEQ ID NO: 297          moltype = RNA   length = 111
FEATURE                 Location/Qualifiers
```

-continued

```
source                  1..111
                        mol_type = other RNA
                        organism = synthetic construct
SEQUENCE: 297
gtggctcgtg tagctcatta gctccgagcc accgagataa gtcggtggct ccctggattc   60
gcggaaacgc gtacatccag ctgacgagtc ccaaatagga cgaagagcca c             111

SEQ ID NO: 298          moltype = RNA   length = 117
FEATURE                 Location/Qualifiers
source                  1..117
                        mol_type = other RNA
                        organism = synthetic construct
SEQUENCE: 298
cgggctcgtg tagctcatta gctccgagcc cgcgagataa gtcgcgggct ccgtcctgga   60
ttcgcggaaa cgcgtacatc cagctgacga gtcccaaata ggacgaaacg gagcccg      117

SEQ ID NO: 299          moltype = RNA   length = 119
FEATURE                 Location/Qualifiers
source                  1..119
                        mol_type = other RNA
                        organism = synthetic construct
SEQUENCE: 299
gcggctcgtg tagctcatta gctccgagcc gccgagataa gtcggcggct cgcgtcctgg   60
attcgcggaa acgcgtacat ccagctgacg agtcccaaat aggacgaaac gcgagccgc    119

SEQ ID NO: 300          moltype = RNA   length = 119
FEATURE                 Location/Qualifiers
source                  1..119
                        mol_type = other RNA
                        organism = synthetic construct
SEQUENCE: 300
cgggctcgtg tagctcatta gctccgagcc cgcgacgata aggtcgcggg ctccgtcctg   60
gattcgcgga aacgcgtaca tccagctgac gagtcccaaa taggacgaaa cggagcccg    119

SEQ ID NO: 301          moltype = RNA   length = 121
FEATURE                 Location/Qualifiers
source                  1..121
                        mol_type = other RNA
                        organism = synthetic construct
SEQUENCE: 301
gcggctcgtg tagctcatta gctccgagcc gccgacgata aggtcggcgg ctcgcgtcct   60
ggattcgcgg aaacgcgtac atccagctga cgagtcccaa ataggacgaa acgcgagccg   120
c                                                                    121

SEQ ID NO: 302          moltype = RNA   length = 111
FEATURE                 Location/Qualifiers
source                  1..111
                        mol_type = other RNA
                        organism = synthetic construct
SEQUENCE: 302
cgcggctcgt gtagctcatt agctccgagc cgcggataag cgcggctgtc ctggattcgc   60
ggaaacgcgt acatccagct gacgagtccc aaataggacg aaacagccgc g             111

SEQ ID NO: 303          moltype = RNA   length = 119
FEATURE                 Location/Qualifiers
source                  1..119
                        mol_type = other RNA
                        organism = synthetic construct
SEQUENCE: 303
gcgggctcgt gtagctcatt agctccgagc ccgccgagat aagtcggcgg gctcgtcctg   60
gattcgcgga aacgcgtaca tccagctgac gagtcccaaa taggacgaaa cgagcccgc    119

SEQ ID NO: 304          moltype = RNA   length = 115
FEATURE                 Location/Qualifiers
source                  1..115
                        mol_type = other RNA
                        organism = synthetic construct
SEQUENCE: 304
cgtggctcgt gtagctcatt agctccgagc cacgcgacga taaggtcgcg tggctcctgg   60
attcgcggaa acgcgtacat ccagctgacg agtcccaaat aggacgaaag ccacg        115

SEQ ID NO: 305          moltype = RNA   length = 115
FEATURE                 Location/Qualifiers
source                  1..115
                        mol_type = other RNA
                        organism = synthetic construct
SEQUENCE: 305
cgcgggctcg tgtagctcat tagctccgag cccgcgcgga taagcgcgcg ggctcctgga   60
ttcgcggaaa cgcgtacatc cagctgacga gtcccaaata ggacgaaagc ccgcg        115
```

-continued

```
SEQ ID NO: 306         moltype = RNA   length = 117
FEATURE                Location/Qualifiers
source                 1..117
                       mol_type = other RNA
                       organism = synthetic construct
SEQUENCE: 306
gcgcggctcg tgtagctcat tagctccgag ccgcgccgga taagcggcgc ggcgtcctgg    60
attcgcggaa acgcgtacat ccagctgacg agtcccaaat aggacgaaac gccgcgc      117

SEQ ID NO: 307         moltype = RNA   length = 115
FEATURE                Location/Qualifiers
source                 1..115
                       mol_type = other RNA
                       organism = synthetic construct
SEQUENCE: 307
gcgtggctcg tgtagctcat tagctccgag ccacgccgag ataagtcggc gtggccctgg    60
attcgcggaa acgcgtacat ccagctgacg agtcccaaat aggacgaagc cacgc        115

SEQ ID NO: 308         moltype = RNA   length = 121
FEATURE                Location/Qualifiers
source                 1..121
                       mol_type = other RNA
                       organism = synthetic construct
SEQUENCE: 308
gcgcggctcg tgtagctcat tagctccgag ccgcgccgac gataaggtcg gcgcggcgtc    60
ctggattcgc ggaaacgcgt acatccagct gacgagtccc aaataggacg aaacgccgcg   120
c                                                                   121

SEQ ID NO: 309         moltype = RNA   length = 115
FEATURE                Location/Qualifiers
source                 1..115
                       mol_type = other RNA
                       organism = synthetic construct
SEQUENCE: 309
gcgcgggctc gtgtagctca ttagctccga gcccgcgccg ataagggcgc gggtcctgga    60
ttcgcggaaa cgcgtacatc cagctgacga gtcccaaata ggacgaaacc cgcgc        115

SEQ ID NO: 310         moltype = RNA   length = 117
FEATURE                Location/Qualifiers
source                 1..117
                       mol_type = other RNA
                       organism = synthetic construct
SEQUENCE: 310
gcgcgggctc gtgtagctca ttagctccga gcccgcgccg gataagcggc gcgggtcctg    60
gattcgcgga aacgcgtaca tccagctgac gagtcccaaa taggacgaaa cccgcgc      117

SEQ ID NO: 311         moltype = RNA   length = 119
FEATURE                Location/Qualifiers
source                 1..119
                       mol_type = other RNA
                       organism = synthetic construct
SEQUENCE: 311
cgcgtggctc gtgtagctca ttagctccga gccacgcgcg acgataaggt cgcgcgtggc    60
ctggattcgc ggaaacgcgt acatccagct gacgagtccc aaataggacg aaccacgcg    119

SEQ ID NO: 312         moltype = RNA   length = 121
FEATURE                Location/Qualifiers
source                 1..121
                       mol_type = other RNA
                       organism = synthetic construct
SEQUENCE: 312
gcgcgggctc gtgtagctca ttagctccga gcccgcgccg acgataaggt cggcgcgggt    60
cctggattcg cggaaacgcg tacatccagc tgacgagtcc caaataggac gaaacccgcg   120
c                                                                   121

SEQ ID NO: 313         moltype = RNA   length = 77
FEATURE                Location/Qualifiers
source                 1..77
                       mol_type = other RNA
                       organism = synthetic construct
SEQUENCE: 313
gtgcgcgaca agcgcacccc tggattcgcg gaaacgcgta catccagctg acgagtccca    60
aataggacga aggtgcg                                                   77

SEQ ID NO: 314         moltype = RNA   length = 79
FEATURE                Location/Qualifiers
source                 1..79
                       mol_type = other RNA
```

-continued

```
                              organism = synthetic construct
SEQUENCE: 314
tgcgctgaca aagcgcaccc ctggattcgc ggaaacgcgt acatccagct gacgagtccc    60
aaataggacg aaggtgcgc                                                 79

SEQ ID NO: 315         moltype = RNA   length = 81
FEATURE                Location/Qualifiers
source                 1..81
                       mol_type = other RNA
                       organism = synthetic construct
SEQUENCE: 315
tgcgctgaca aagcgcacct cctggattcg cggaaacgcg tacatccagc tgacgagtcc    60
caaataggac gaaaggtgcg c                                              81

SEQ ID NO: 316         moltype = RNA   length = 83
FEATURE                Location/Qualifiers
source                 1..83
                       mol_type = other RNA
                       organism = synthetic construct
SEQUENCE: 316
tgcgctgaca aagcgcaccg tcctggattc gcggaaacgc gtacatccag ctgacgagtc    60
ccaaatagga cgaaacggtg cgc                                            83

SEQ ID NO: 317         moltype = RNA   length = 79
FEATURE                Location/Qualifiers
source                 1..79
                       mol_type = other RNA
                       organism = synthetic construct
SEQUENCE: 317
gtgcgctgac aaagcgcacc cctggattcg cggaaacgcg tacatccagc tgacgagtcc    60
caaataggac gaaggtgcg                                                 79

SEQ ID NO: 318         moltype = RNA   length = 81
FEATURE                Location/Qualifiers
source                 1..81
                       mol_type = other RNA
                       organism = synthetic construct
SEQUENCE: 318
gtgcgctgac aaagcgcacc tcctggattc gcggaaacgc gtacatccag ctgacgagtc    60
ccaaatagga cgaaaggtgc g                                              81

SEQ ID NO: 319         moltype = RNA   length = 83
FEATURE                Location/Qualifiers
source                 1..83
                       mol_type = other RNA
                       organism = synthetic construct
SEQUENCE: 319
gtgcgctgac aaagcgcacc gtcctggatt cgcggaaacg cgtacatcca gctgacgagt    60
cccaaatagg acgaaacggt gcg                                            83

SEQ ID NO: 320         moltype = RNA   length = 85
FEATURE                Location/Qualifiers
source                 1..85
                       mol_type = other RNA
                       organism = synthetic construct
SEQUENCE: 320
gtgcgctgac aaagcgcacc cgtcctggat tcgcggaaac gcgtacatcc agctgacgag    60
tcccaaatag gacgaaacgg gtgcg                                          85

SEQ ID NO: 321         moltype = RNA   length = 81
FEATURE                Location/Qualifiers
source                 1..81
                       mol_type = other RNA
                       organism = synthetic construct
SEQUENCE: 321
ggtgcgctga caaagcgcac ctcctggatt cgcggaaacg cgtacatcca gctgacgagt    60
cccaaatagg acgaaaggtg c                                              81

SEQ ID NO: 322         moltype = RNA   length = 83
FEATURE                Location/Qualifiers
source                 1..83
                       mol_type = other RNA
                       organism = synthetic construct
SEQUENCE: 322
ggtgcgctga caaagcgcac cgtcctggat tcgcggaaac gcgtacatcc agctgacgag    60
tcccaaatag gacgaaacgg tgc                                            83

SEQ ID NO: 323         moltype = RNA   length = 85
FEATURE                Location/Qualifiers
```

-continued

```
source                  1..85
                        mol_type = other RNA
                        organism = synthetic construct
SEQUENCE: 323
ggtgcgctga caaagcgcac ccgtcctgga ttcgcggaaa cgcgtacatc cagctgacga    60
gtcccaaata ggacgaaacg ggtgc                                          85

SEQ ID NO: 324          moltype = RNA   length = 87
FEATURE                 Location/Qualifiers
source                  1..87
                        mol_type = other RNA
                        organism = synthetic construct
SEQUENCE: 324
ggtgcgctga caaagcgcac cgcgtcctgg attcgcggaa acgcgtacat ccagctgacg    60
agtcccaaat aggacgaaac gcggtgc                                        87

SEQ ID NO: 325          moltype = RNA   length = 83
FEATURE                 Location/Qualifiers
source                  1..83
                        mol_type = other RNA
                        organism = synthetic construct
SEQUENCE: 325
cggtgcgctg acaaagcgca ccgtcctgga ttcgcggaaa cgcgtacatc cagctgacga    60
gtcccaaata ggacgaaacg gtg                                            83

SEQ ID NO: 326          moltype = RNA   length = 85
FEATURE                 Location/Qualifiers
source                  1..85
                        mol_type = other RNA
                        organism = synthetic construct
SEQUENCE: 326
gggtgcgctg acaaagcgca cccgtcctgg attcgcggaa acgcgtacat ccagctgacg    60
agtcccaaat aggacgaaac gggtg                                          85

SEQ ID NO: 327          moltype = RNA   length = 87
FEATURE                 Location/Qualifiers
source                  1..87
                        mol_type = other RNA
                        organism = synthetic construct
SEQUENCE: 327
cggtgcgctg acaaagcgca ccgcgtcctg gattcgcgga aacgcgtaca tccagctgac    60
gagtcccaaa taggacgaaa cgcggtg                                        87

SEQ ID NO: 328          moltype = RNA   length = 89
FEATURE                 Location/Qualifiers
source                  1..89
                        mol_type = other RNA
                        organism = synthetic construct
SEQUENCE: 328
gggtgcgctg acaaagcgca cccgcgtcct ggattcgcgg aaacgcgtac atccagctga    60
cgagtcccaa ataggacgaa acgcgggtg                                      89

SEQ ID NO: 329          moltype = RNA   length = 76
FEATURE                 Location/Qualifiers
source                  1..76
                        mol_type = other RNA
                        organism = synthetic construct
SEQUENCE: 329
ggtgcggaca acgcacccct ggattcgcgg aaacgcgtac atccagctga cgagtcccaa    60
ataggacgaa ggtgcg                                                    76

SEQ ID NO: 330          moltype = RNA   length = 78
FEATURE                 Location/Qualifiers
source                  1..78
                        mol_type = other RNA
                        organism = synthetic construct
SEQUENCE: 330
gtgcgcgaca agcgcacccc tggattcgcg gaaacgcgta catccagctg acgagtccca    60
aataggacga aggtgcgc                                                  78

SEQ ID NO: 331          moltype = RNA   length = 80
FEATURE                 Location/Qualifiers
source                  1..80
                        mol_type = other RNA
                        organism = synthetic construct
SEQUENCE: 331
tgcgctgaca aagcgcaccc ctggattcgc ggaaacgcgt acatccagct gacgagtccc    60
aaataggacg aaggtgcgct                                                80
```

```
SEQ ID NO: 332          moltype = RNA   length = 82
FEATURE                 Location/Qualifiers
source                  1..82
                        mol_type = other RNA
                        organism = synthetic construct
SEQUENCE: 332
tgcgctgaca aagcgcacct cctggattcg cggaaacgcg tacatccagc tgacgagtcc   60
caaataggac gaaaggtgcg ct                                            82

SEQ ID NO: 333          moltype = RNA   length = 84
FEATURE                 Location/Qualifiers
source                  1..84
                        mol_type = other RNA
                        organism = synthetic construct
SEQUENCE: 333
tgcgctgaca aagcgcaccg tcctggattc gcggaaacgc gtacatccag ctgacgagtc   60
ccaaatagga cgaaacggtg cgct                                          84

SEQ ID NO: 334          moltype = RNA   length = 78
FEATURE                 Location/Qualifiers
source                  1..78
                        mol_type = other RNA
                        organism = synthetic construct
SEQUENCE: 334
ggtgcgcgac aagcgcaccc ctggattcgc ggaaacgcgt acatccagct gacgagtccc   60
aaataggacg aaggtgcg                                                 78

SEQ ID NO: 335          moltype = RNA   length = 80
FEATURE                 Location/Qualifiers
source                  1..80
                        mol_type = other RNA
                        organism = synthetic construct
SEQUENCE: 335
gtgcgctgac aaagcgcacc cctggattcg cggaaacgcg tacatccagc tgacgagtcc   60
caaataggac gaaggtgcgc                                               80

SEQ ID NO: 336          moltype = RNA   length = 84
FEATURE                 Location/Qualifiers
source                  1..84
                        mol_type = other RNA
                        organism = synthetic construct
SEQUENCE: 336
gtgcgctgac aaagcgcacc gtcctggatt cgcggaaacg cgtacatcca gctgacgagt   60
cccaaatagg acgaaacggt gcgc                                          84

SEQ ID NO: 337          moltype = RNA   length = 86
FEATURE                 Location/Qualifiers
source                  1..86
                        mol_type = other RNA
                        organism = synthetic construct
SEQUENCE: 337
gtgcgctgac aaagcgcacc cgtcctggat tcgcggaaac gcgtacatcc agctgacgag   60
tcccaaatag gacgaaacgg gtgcgc                                        86

SEQ ID NO: 338          moltype = RNA   length = 80
FEATURE                 Location/Qualifiers
source                  1..80
                        mol_type = other RNA
                        organism = synthetic construct
SEQUENCE: 338
ggtgcgctga caaagcgcac ccctggattc gcggaaacgc gtacatccag ctgacgagtc   60
ccaaatagga cgaaggtgcg                                               80

SEQ ID NO: 339          moltype = RNA   length = 84
FEATURE                 Location/Qualifiers
source                  1..84
                        mol_type = other RNA
                        organism = synthetic construct
SEQUENCE: 339
ggtgcgctga caaagcgcac cgtcctggat tcgcggaaac gcgtacatcc agctgacgag   60
tcccaaatag gacgaaacgg tgcg                                          84

SEQ ID NO: 340          moltype = RNA   length = 86
FEATURE                 Location/Qualifiers
source                  1..86
                        mol_type = other RNA
                        organism = synthetic construct
SEQUENCE: 340
ggtgcgctga caaagcgcac ccgtcctgga ttcgcggaaa cgcgtacatc cagctgacga   60
```

-continued

```
gtcccaaata ggacgaaacg ggtgcg                                              86

SEQ ID NO: 341            moltype = RNA   length = 88
FEATURE                   Location/Qualifiers
source                    1..88
                          mol_type = other RNA
                          organism = synthetic construct
SEQUENCE: 341
ggtgcgctga caaagcgcac cgcgtcctgg attcgcggaa acgcgtacat ccagctgacg    60
agtcccaaat aggacgaaac gcggtgcg                                          88

SEQ ID NO: 342            moltype = RNA   length = 82
FEATURE                   Location/Qualifiers
source                    1..82
                          mol_type = other RNA
                          organism = synthetic construct
SEQUENCE: 342
aggtgcgctg acaaagcgca cctcctggat tcgcggaaac gcgtacatcc agctgacgag    60
tcccaaatag gacgaaaggt gc                                                82

SEQ ID NO: 343            moltype = RNA   length = 84
FEATURE                   Location/Qualifiers
source                    1..84
                          mol_type = other RNA
                          organism = synthetic construct
SEQUENCE: 343
cggtgcgctg acaaagcgca ccgtcctgga ttcgcggaaa cgcgtacatc cagctgacga    60
gtcccaaata ggacgaaacg gtgc                                              84

SEQ ID NO: 344            moltype = RNA   length = 86
FEATURE                   Location/Qualifiers
source                    1..86
                          mol_type = other RNA
                          organism = synthetic construct
SEQUENCE: 344
gggtgcgctg acaaagcgca cccgtcctgg attcgcggaa acgcgtacat ccagctgacg    60
agtcccaaat aggacgaaac gggtgc                                            86

SEQ ID NO: 345            moltype = RNA   length = 88
FEATURE                   Location/Qualifiers
source                    1..88
                          mol_type = other RNA
                          organism = synthetic construct
SEQUENCE: 345
cggtgcgctg acaaagcgca ccgcgtcctg gattcgcgga aacgcgtaca tccagctgac    60
gagtcccaaa taggacgaaa cgcggtgc                                          88

SEQ ID NO: 346            moltype = RNA   length = 90
FEATURE                   Location/Qualifiers
source                    1..90
                          mol_type = other RNA
                          organism = synthetic construct
SEQUENCE: 346
gggtgcgctg acaaagcgca cccgcgtcct ggattcgcgg aaacgcgtac atccagctga    60
cgagtcccaa ataggacgaa acgcgggtgc                                        90

SEQ ID NO: 347            moltype = RNA   length = 84
FEATURE                   Location/Qualifiers
source                    1..84
                          mol_type = other RNA
                          organism = synthetic construct
SEQUENCE: 347
acggtgcgct gacaaagcgc accgtcctgg attcgcggaa acgcgtacat ccagctgacg    60
agtcccaaat aggacgaaac ggtg                                              84

SEQ ID NO: 348            moltype = RNA   length = 86
FEATURE                   Location/Qualifiers
source                    1..86
                          mol_type = other RNA
                          organism = synthetic construct
SEQUENCE: 348
cggggtgcgct gacaaagcgc acccgtcctg gattcgcgga aacgcgtaca tccagctgac    60
gagtcccaaa taggacgaaa cggggtg                                            86

SEQ ID NO: 349            moltype = RNA   length = 88
FEATURE                   Location/Qualifiers
source                    1..88
                          mol_type = other RNA
                          organism = synthetic construct
```

```
SEQUENCE: 349
gcggtgcgct gacaaagcgc accgcgtcct ggattcgcgg aaacgcgtac atccagctga    60
cgagtcccaa ataggacgaa acgcggtg                                        88

SEQ ID NO: 350          moltype = RNA   length = 90
FEATURE                 Location/Qualifiers
source                  1..90
                        mol_type = other RNA
                        organism = synthetic construct
SEQUENCE: 350
cgggtgcgct gacaaagcgc acccgcgtcc tggattcgcg gaaacgcgta catccagctg    60
acgagtccca aataggacga aacgcgggtg                                      90

SEQ ID NO: 351          moltype = RNA   length = 92
FEATURE                 Location/Qualifiers
source                  1..92
                        mol_type = other RNA
                        organism = synthetic construct
SEQUENCE: 351
gcggtgcgct gacaaagcgc accgcgcgtc ctggattcgc ggaaacgcgt acatccagct    60
gacgagtccc aaataggacg aaacgcgcgg tg                                   92

SEQ ID NO: 352          moltype = RNA   length = 79
FEATURE                 Location/Qualifiers
source                  1..79
                        mol_type = other RNA
                        organism = synthetic construct
SEQUENCE: 352
ggtgcgcgac aagcgcaccc ctggattcgc ggaaacgcgt acatccagct gacgagtccc    60
aaataggacg aaggtgcgc                                                  79

SEQ ID NO: 353          moltype = RNA   length = 83
FEATURE                 Location/Qualifiers
source                  1..83
                        mol_type = other RNA
                        organism = synthetic construct
SEQUENCE: 353
gtgcgctgac aaagcgcacc tcctggattc gcggaaacgc gtacatccag ctgacgagtc    60
ccaaatagga cgaaaggtgc gct                                             83

SEQ ID NO: 354          moltype = RNA   length = 85
FEATURE                 Location/Qualifiers
source                  1..85
                        mol_type = other RNA
                        organism = synthetic construct
SEQUENCE: 354
gtgcgctgac aaagcgcacc gtcctggatt cgcggaaacg cgtacatcca gctgacgagt    60
cccaaatagg acgaaacggt gcgct                                           85

SEQ ID NO: 355          moltype = RNA   length = 87
FEATURE                 Location/Qualifiers
source                  1..87
                        mol_type = other RNA
                        organism = synthetic construct
SEQUENCE: 355
gtgcgctgac aaagcgcacc cgtcctggat tcgcggaaac gcgtacatcc agctgacgag    60
tcccaaatag gacgaaacgg gtgcgct                                         87

SEQ ID NO: 356          moltype = RNA   length = 81
FEATURE                 Location/Qualifiers
source                  1..81
                        mol_type = other RNA
                        organism = synthetic construct
SEQUENCE: 356
ggtgcgctga caaagcgcac ccctggattc gcggaaacgc gtacatccag ctgacgagtc    60
ccaaatagga cgaaggtgcg c                                               81

SEQ ID NO: 357          moltype = RNA   length = 85
FEATURE                 Location/Qualifiers
source                  1..85
                        mol_type = other RNA
                        organism = synthetic construct
SEQUENCE: 357
ggtgcgctga caaagcgcac cgtcctggat tcgcggaaac gcgtacatcc agctgacgag    60
tcccaaatag gacgaaacgg tgcgc                                           85

SEQ ID NO: 358          moltype = RNA   length = 87
FEATURE                 Location/Qualifiers
source                  1..87
```

-continued

```
                        mol_type = other RNA
                        organism = synthetic construct
SEQUENCE: 358
ggtgcgctga caaagcgcac ccgtcctgga ttcgcggaaa cgcgtacatc cagctgacga    60
gtcccaaata ggacgaaacg ggtgcgc                                        87

SEQ ID NO: 359           moltype = RNA   length = 89
FEATURE                  Location/Qualifiers
source                   1..89
                         mol_type = other RNA
                         organism = synthetic construct
SEQUENCE: 359
ggtgcgctga caaagcgcac cgcgtcctgg attcgcggaa acgcgtacat ccagctgacg    60
agtcccaaat aggacgaaac gcggtgcgc                                      89

SEQ ID NO: 360           moltype = RNA   length = 85
FEATURE                  Location/Qualifiers
source                   1..85
                         mol_type = other RNA
                         organism = synthetic construct
SEQUENCE: 360
cggtgcgctg acaaagcgca ccgtcctgga ttcgcggaaa cgcgtacatc cagctgacga    60
gtcccaaata ggacgaaacg gtgcg                                          85

SEQ ID NO: 361           moltype = RNA   length = 87
FEATURE                  Location/Qualifiers
source                   1..87
                         mol_type = other RNA
                         organism = synthetic construct
SEQUENCE: 361
gggtgcgctg acaaagcgca cccgtcctgg attcgcggaa acgcgtacat ccagctgacg    60
agtcccaaat aggacgaaac gggtgcg                                        87

SEQ ID NO: 362           moltype = RNA   length = 89
FEATURE                  Location/Qualifiers
source                   1..89
                         mol_type = other RNA
                         organism = synthetic construct
SEQUENCE: 362
cggtgcgctg acaaagcgca ccgcgtcctg gattcgcgga aacgcgtaca tccagctgac    60
gagtcccaaa taggacgaaa cgcggtgcg                                      89

SEQ ID NO: 363           moltype = RNA   length = 91
FEATURE                  Location/Qualifiers
source                   1..91
                         mol_type = other RNA
                         organism = synthetic construct
SEQUENCE: 363
gggtgcgctg acaaagcgca cccgcgtcct ggattcgcgg aaacgcgtac atccagctga    60
cgagtcccaa ataggacgaa acgcgggtgc g                                   91

SEQ ID NO: 364           moltype = RNA   length = 85
FEATURE                  Location/Qualifiers
source                   1..85
                         mol_type = other RNA
                         organism = synthetic construct
SEQUENCE: 364
acggtgcgct gacaaagcgc accgtcctgg attcgcggaa acgcgtacat ccagctgacg    60
agtcccaaat aggacgaaac ggtgc                                          85

SEQ ID NO: 365           moltype = RNA   length = 91
FEATURE                  Location/Qualifiers
source                   1..91
                         mol_type = other RNA
                         organism = synthetic construct
SEQUENCE: 365
cgggtgcgct gacaaagcgc acccgcgtcc tggattcgcg gaaacgcgta catccagctg    60
acgagtccca aataggacga aacgcgggtg c                                   91

SEQ ID NO: 366           moltype = RNA   length = 93
FEATURE                  Location/Qualifiers
source                   1..93
                         mol_type = other RNA
                         organism = synthetic construct
SEQUENCE: 366
gcggtgcgct gacaaagcgc accgcgcgtc ctggattcgc ggaaacgcgt acatccagct    60
gacgagtccc aaataggacg aaacgcgcgg tgc                                 93

SEQ ID NO: 367           moltype = RNA   length = 87
```

```
FEATURE                  Location/Qualifiers
source                   1..87
                         mol_type = other RNA
                         organism = synthetic construct
SEQUENCE: 367
acgggtgcgc tgacaaagcg caccctgtcct ggattcgcgg aaacgcgtac atccagctga   60
cgagtcccaa ataggacgaa acgggtg                                         87

SEQ ID NO: 368           moltype = RNA   length = 89
FEATURE                  Location/Qualifiers
source                   1..89
                         mol_type = other RNA
                         organism = synthetic construct
SEQUENCE: 368
cgcggtgcgc tgacaaagcg caccgcgtcc tggattcgcg gaaacgcgta catccagctg    60
acgagtccca ataggacga aacgcggtg                                        89

SEQ ID NO: 369           moltype = RNA   length = 93
FEATURE                  Location/Qualifiers
source                   1..93
                         mol_type = other RNA
                         organism = synthetic construct
SEQUENCE: 369
cgcggtgcgc tgacaaagcg caccgcgcgt cctggattcg cggaaacgcg tacatccagc    60
tgacgagtcc caaataggac gaaacgcgcg gtg                                  93

SEQ ID NO: 370           moltype = DNA   length = 65
FEATURE                  Location/Qualifiers
source                   1..65
                         mol_type = other DNA
                         organism = synthetic construct
SEQUENCE: 370
gcgcgtcctg gattcgcgga aacgcgtaca tccagctgac gagtcccaaa taggacgaaa    60
cgcgc                                                                 65

SEQ ID NO: 371           moltype = DNA   length = 110
FEATURE                  Location/Qualifiers
source                   1..110
                         mol_type = other DNA
                         organism = synthetic construct
SEQUENCE: 371
gattcgtcag tagggttgta aaggtttttc ttttcctgag aaaacaacct tttgtttttct   60
caggtttttgc tttttggcct ttccctagct ttaaaaaaaa aaaagcaaaa              110

SEQ ID NO: 372           moltype = DNA   length = 240
FEATURE                  Location/Qualifiers
source                   1..240
                         mol_type = other DNA
                         organism = synthetic construct
SEQUENCE: 372
taagttatta agttattaag ttattaagtt attaagttat taagttatta agttattaag   60
ttattaagtt attaagttat taagttatta agttattaag ttattaagtt attaagttat  120
taagttatta agttattaag ttattaagtt attaagttat taagttatta agttattaag  180
ttattaagtt attaagttat taagttatta agttattaag ttattaagtt attaagttat  240

SEQ ID NO: 373           moltype = DNA   length = 351
FEATURE                  Location/Qualifiers
source                   1..351
                         mol_type = unassigned DNA
                         organism = unidentified
SEQUENCE: 373
atggcctcta actttaccca attcgtcctc gtcgataatg gcggcacagg agatgtgaca    60
gtggctccta gtaatttcgc aaatggcatc gctgaatgga tttccagtaa cagccgcagc   120
caggcttata aggtgacctg ttccgttcgg cagtcctcag cacaaaaccg gaaatataca   180
ataaaggtgg aagtacctaa aggcgcttgg cgctcttacc tcaatatgga attaacaatt   240
cccatatttg caacgaattc cgattgcgag ttgatcgtca aggcaatgca ggggctcctg   300
aaagacggga atcccatccc tagtgcaatt gccgctaatt ctggaatcta t            351

SEQ ID NO: 374           moltype = DNA   length = 363
FEATURE                  Location/Qualifiers
source                   1..363
                         mol_type = unassigned DNA
                         organism = unidentified
SEQUENCE: 374
atgtccaaga ctatcgtctt atcagttgga gaggcgaccc gcaccttaac cgagatccaa    60
tccactgccg atagacaaat cttcgaggag aaggtcggcc cactcgtggg tcggttgcgc   120
cttacagcta gtctgcggca gaatggtgcc aagaccgcct acagagtcaa ccttaaactg   180
gatcaagctg atgtggtgga tagcggcctt ccgaaggttc gttatacgca ggtgtggagt   240
catgacgtta caatcgtggc gaactctact gaagcctctc ggaagagctt gtacgacctt   300
```

```
actaagagct tagtggcgac gtcccaggtc gaagacctgg ttgtaaacct ggtacctctg    360
ggc                                                                  363

SEQ ID NO: 375            moltype = DNA   length = 51
FEATURE                   Location/Qualifiers
source                    1..51
                          mol_type = genomic DNA
                          organism = Lentivirus bovimdef
SEQUENCE: 375
agtggaccga gaccaagagg aacacgcgga aagggcaggc ggatccgacg g              51

SEQ ID NO: 376            moltype = DNA   length = 51
FEATURE                   Location/Qualifiers
source                    1..51
                          mol_type = unassigned DNA
                          organism = unidentified
SEQUENCE: 376
aatgccaaga ctcgacggca tgagagaagg cggaaactgg ctatcgaacg g              51

SEQ ID NO: 377            moltype = DNA   length = 9010
FEATURE                   Location/Qualifiers
source                    1..9010
                          mol_type = other DNA
                          organism = synthetic construct
misc_difference           4..102
                          note = This region may encompass one of the following
                            sequences:
                            tacacttaccataccccgcgcgtcctggattcgcggaaacgcgtacatccagctgacga
                            gtcccaaataggacgaaacgcgcccccacaatttcaacaa or
                            tacacttaccataccccgcgcgtctggattcgcggaaacgcgtacatccaggtcccaaa
                            taggacacgcgcccccacaatttcaacaa or
                            tacacttaccataccccgcgcgtttcgtcctatttgggactcgtcagctggatgtacgc
                            gtttccgcgaatccaggacgcgcccccacaatttcaacaa
misc_difference           7659..7790
                          note = This region may encompass one of the following
                            sequences:
                            cacgtggatctgagatccaattaggtcgtgcgtttcgtcctatttgggactcgtcagct
                            ggatgtacgcgtttccgcgaatccaggacgcacggctgatgctcgtgcgtgagaggtgg
                            ggaaaagag or
                            cacgtggatctgagatccaattaggtgtgccgtttcgtcctatttgggactcgtcagct
                            ggatgtacgcgtttccgcgaatccaggacggcacgaagccatatcttctgtgccggaga
                            ggtggggaaaagag
misc_feature              7815..7816
                          note = This region may encompass Insertion Site 3
misc_difference           7840..7971
                          note = This region may encompass one of the following
                            sequences:
                            tacacttaccataccccgcgcgtcctggattcgcggaaacgcgtacatccagctgacga
                            gtcccaaataggacgaaacgcgcccccacaatttcaacaa or
                            tacacttaccataccccgcgcgtctggattcgcggaaacgcgtacatccaggtcccaaa
                            taggacacgcgcccccacaatttcaacaa or
                            tacacttaccataccccgcgcgtttcgtcctatttgggactcgtcagctggatgtacgc
                            gtttccgcgaatccaggacgcgcccccacaatttcaacaa or
                            cacgtggatctgagatccaattaggtcgtgcgtttcgtcctatttgggactcgtcagct
                            ggatgtacgcgtttccgcgaatccaggacgcacggctgatgctcgtgcgtgagaggtgg
                            ggaaaagag or
                            cacgtggatctgagatccaattaggtgtgccgtttcgtcctatttgggactcgtcagct
                            ggatgtacgcgtttccgcgaatccaggacggcacgaagccatatcttctgtgccggaga
                            ggtggggaaaagag
misc_difference           8767..8898
                          note = This region may encompass one of the following
                            sequences:
                            tacacttaccataccccgcgcgtcctggattcgcggaaacgcgtacatccagctgacga
                            gtcccaaataggacgaaacgcgcccccacaatttcaacaa or
                            tacacttaccataccccgcgcgtctggattcgcggaaacgcgtacatccaggtcccaaa
                            taggacacgcgcccccacaatttcaacaa or
                            tacacttaccataccccgcgcgtttcgtcctatttgggactcgtcagctggatgtacgc
                            gtttccgcgaatccaggacgcgcccccacaatttcaacaa or
                            cacgtggatctgagatccaattaggtcgtgcgtttcgtcctatttgggactcgtcagct
                            ggatgtacgcgtttccgcgaatccaggacgcacggctgatgctcgtgcgtgagaggtgg
                            ggaaaagag or
                            cacgtggatctgagatccaattaggttgccgttcgtcctatttgggactcgtcagctg
                            gatgtacgcgtttccgcgaatccaggacggcacgaagccatatcttctgtgccggagag
                            gtggggaaaagag or
                            cacgtggatctgagatccaattaggtgtgccgtttcgtcctatttgggactcgtcagct
                            ggatgtacgcgtttccgcgaatccaggacggcacgaagccatatcttctgtgccggaga
                            ggtggggaaaagag
SEQUENCE: 377
gggnnnnnnn nnnnnnnnnn nnnnnnnnnn nnnnnnnnnn nnnnnnnnnn nnnnnnnnnn    60
```

-continued

```
nnnnnnnnnn nnnnnnnnnn nnnnnnnnnn nnnnnnnnnn nncggcgcat gagagaagcc    120
cagaccaatt acctacccaa aatggagaaa gttcacgttg acatcgagga agacagccca    180
ttcctcagag ctttgcagcg gagcttcccg cagtttgagg tagaagccaa gcaggtcact    240
gataatgacc atgctaatgc cagagcgttt tcgcatctgg cttcaaaact gatcgaaacg    300
gaggtggacc catccgacac gatccttgac atttggaagtg cgcccgcccg cagaatgtat    360
tctaagcaca agtatcattg tatctgtccg atgagatgtg cggaagatcc ggacagattg    420
tataagtatg caactaagct gaagaaaaac tgtaaggaaa taactgataa ggaattggac    480
aagaaaatga aggagctggc cgccgtcatg agcgaccctg acctggaaac tgagactatg    540
tgcctccacg acgacgagtc gtgtcgctac gaagggcaag tcgctgttta ccaggatgta    600
tacgcggttg acggaccgac aagtctctat caccaagcca ataagggagt tagagtcgcc    660
tactggatag gctttgacac caccccttt atgtttaaga acttggctgg agcatatcca    720
tcatactcta ccaactgggc cgacgaaacc gtgttaacgg ctcgtaacat aggcctatgc    780
agctctgacg ttatggagcg gtcacgtaga gggatgtcca ttcttagaaa gaagtatttg    840
aaaccatcca acaatgttct attctctgtt ggctcgacca tctaccacga gaagagggac    900
ttactgagga gctggcacct gccgtctgta tttcacttac gtggcaagca aaattacaca    960
tgtcggtgtg agactatagt tagttgcgac gggtacgtcg ttaaaagaat agctatcagt   1020
ccaggcctgt atgggaagcc ttcaggctat gctgctacga tgcaccgcga gggattcttg   1080
tgctgcaaag tgacagacac attgaacggg gagagggtct cttttcccgt gtgcacgtat   1140
gtgccagcta cattgtgtga ccaaatgact ggcatactgc caacagatgt cagtgcggac   1200
gacgcgcaaa aactgctggt tgggctcaac cagcgtatag tcgtcaacgg tcgcacccag   1260
agaaacacca ataccatgaa aaattacctt ttgcccgtag tggcccaggc atttgctagg   1320
tgggcaaagg aatataagga agatcaagaa gatgaaaggc cactaggact acgagataga   1380
cagttagtca tggggtgttg ttgggctttt agaaggcaca agataacatc tatttataag   1440
cgcccggata cccaaaccat catcaaagtg aacagcgatt tccactcatt cgtgctgccc   1500
aggataggca gtaacacatt ggagatcggg ctgagaacaa gaatcaggaa aatgttagag   1560
gagcacaagg agccgtcacc tctcattacc gccgaggacg tacaagaagc taagtgcgca   1620
gccgatgagg ctaaggaggt gcgtgaagcc gaggagttgc gcgcagctct accacctttg   1680
gcagctgatg ttgaggagcc cactctggag gcagacgtcg acttgatgtt acaagaggct   1740
ggggccggct cagtggagac acctcgtggc ttgataaagg ttaccagcta cgatggcgag   1800
gacaagatcg gctcttacg tgtgctttct ccgcaggctg tactcaagag tgaaaaatta   1860
tcttgcatcc accctctcgc tgaacaagtc atagtgataa cacactctgg ccgaaaaggg   1920
cgttatgccg tggaaccata ccatggtaaa gtagtggtgc cagagggaca tgcaataccc   1980
gtccaggact ttcaagctct gagtgaaagt gccaccattg tgtacaacga acgtgagttc   2040
gtaaacaggt acctgcacca tattgccaca catggaggag cgctgaacac tgatgaagaa   2100
tattacaaaa ctgtcaagcc cagcgagcac gacggcgaat acctgtacga catcgacagg   2160
aaacagtgcg tcaagaaaga actagtcact gggctagggc tcacaggcga gctggtggat   2220
cctccctttcc atgaattcgc ctacgagagt ctgagaacac gaccagccgc tccttaccaa   2280
gtaccaacca taggggtgta tggcgtgcca ggatcaggca agtctggcat cattaaaagc   2340
gcagtcacca aaaaagatct agtggtgagc gccaagaaag aaaactgtgc agaaattata   2400
agggacgtca agaaatgaa agggctggac gtcaatgcca gaactgtgga ctcagtgctc   2460
ttgaatggat gcaaacaccc cgtagagacc ctgtatattg acgaagcttt tgcttgtcat   2520
gcaggtactc tcagagcgct catagccatt ataagaccta aaaaggcagt gctctgcggg   2580
gatcccaaac agtgcggttt ttttaacatg atgtgcctga aagtgcattt taaccacgag   2640
atttgcacac aagtcttcca caaaagcatc tctcgccgtt gcactaaatc tgtgacttcg   2700
gtcgtctcaa ccttgttta cgacaaaaaa atgagaacga cgaatccgaa agagactaag   2760
attgtgattg acactaccgg cagtaccaaa cctaagcagg acgatctcat tctcacttgt   2820
ttcagagggt gggtgaagca gttgcaaata gattacaaag gcaacgaaat aatgacggca   2880
gctgcctctc aagggctgac ccgtaaaggt gtgtatgccg ttcggtacaa ggtgaatgaa   2940
aatcctctgt acgcacccac ctcagaacat gtgaacgtcc tactgacccg cacggaggac   3000
cgcatcgtgt ggaaaacact agccggcgac ccatggataa aaacactgac tgccaagtac   3060
cctgggaatt tcactgccac gatagaggag tggcaagcag agcatgatgc catcatgagg   3120
cacatcttgg agagaccgga ccctaccgac gtcttccaga ataaggcaaa cgtgtgttgg   3180
gccaaggctt tagtgccggt gctgaagacc gctggcatag acatgaccac tgaacaatgg   3240
aacactgtgg attattttga aacggacaaa gctcactcag cagagatagt attgaaccaa   3300
ctatgcgtga ggttctttgg actcgatctg gactccggtc tattttctgc acccactgtt   3360
ccgttatcca ttaggaataa tcactgggat aactccccgt cgcctaacat gtacgggctg   3420
aataaagaag tggtccgtca gctctctcgc aggtacccac aactgcctcg ggcagttgcc   3480
actgaagag tctatgacat gaacactggt acactgcgca attatgatcc gcgcataaac   3540
ctagtacctg taaacagaag actgcctcat gctttagtcc tccaccataa tgaacaccca   3600
cagagtgact tttcttcatt cgtcagcaaa ttgaagggca gaactgtcct ggtggtcggg   3660
gaaaagttgt ccgtcccagg caaaatggtt gactggttgt cagaccggcc tgaggctacc   3720
ttcagagctc ggctggattt aggcatccca ggtgatgtgc ccaaatatga cataatattt   3780
gttaatgtga ggacccccata taaataccat cactatcagc agtgtgaaga ccatgccatt   3840
aagcttagca tgttgaccaa gaaagcttgt ctgcatctga atcccggcag aacctgtgtc   3900
agcataggtt atggttacgc tgacaggggc agcgaaagca tcattggtgc tatagcgcgg   3960
cagttcaagt tttcccgggt atgcaaaccg aaatcctcac ttgaagagac ggaagttctg   4020
tttgtattca ttgggtacga tcgcaaggcc cgtacgcaca attcttacaa gctttcatca   4080
accttgacca acatttatac aggttccaga ctccacgaag ccggatgtgc accctcatat   4140
catgtggtgc gaggggatat tgccacggcc accgaaggag tgattataaa tgctgctaac   4200
agcaaaggac aacctggcgg aggggtgtgc ggagcgctgt ataagaaatt cccggaaagc   4260
ttcgatttac agccgatcga agtaggaaaa gcgcgactgg tcaaaggtgc agctaaacat   4320
atcattcatg ccgtaggacc aaacttcaac aaagtttcgg aggttgaagg tgacaaacag   4380
ttggcagagg cttatgagtc catcgctaag attgtcaacg ataacaatta caagtcagta   4440
gcgattccac tgttgtccac cggcatcttt tccgggaaca aagatcgact aacccaatca   4500
ttgaaccatt tgctgacagc tttagacacc actgatgcag atgtagccat atactgcagg   4560
gacaagaaat gggaaatgac tctcaaggaa gcagtggcta ggagagaagc agtgaggag   4620
atatgcatat ccgacgactc ttcagtgaca gaacctgatg cagagctggt gagggtgcat   4680
ccgaagagtt ctttggctgg aaggaagggc tacagcacaca gcgatggcaa aactttctca   4740
tatttggaag ggaccaagtt tcaccaggcg gccaaggata tagcagaaat taatgccatg   4800
```

-continued

```
tggcccgttg caacggaggc caatgagcag gtatgcatgt atatcctcgg agaaagcatg   4860
agcagtatta ggtcgaaatg ccccgtcgaa gagtcggaag cctccacacc acctagcacg   4920
ctgccttgct tgtgcatcca tgccatgact ccagaaagag tacagcgcct aaaagcctca   4980
cgtccagaac aaattactgt gtgctcatcc tttccattgc cgaagtatag aatcactggt   5040
gtgcagaaga tccaatgctc ccagcctata ttgttctcac cgaaagtgcc tgcgtatatt   5100
catccaagga agtatctcgt ggaaacacca ccggtagacg agactccgga gccatcggca   5160
gagaaccaat ccacagaggg gacacctgaa caaccaccac ttataaccga ggatgagacc   5220
aggactagaa cgcctgagcc gatcatcatc gaagaggaag aagaggatag cataagtttg   5280
ctgtcagatg gcccgaccca ccaggtgctg caagtcgagg cagacattca cgggccgccc   5340
tctgtatcta gctcatcctg gtccattcct catgcatccg actttgatgt ggacagttta   5400
tccatacttg acaccctgga gggagctagc gtgaccagcg gggcaacgtc agccgagact   5460
aactcttact tcgcaaagag tatggagttt ctggcgcgac cggtgcctgc gcctcgaaca   5520
gtattcagga accctccaca tcccgctccg cgcacaagaa caccgtgcact tgcacccagc   5580
agggcctgct cgagaaccag cctagtttcc accccgccag tgcgtgaatag ggtgatcact   5640
agagaggagc tcgaggcgct tacccccgtca cgcactccta gcaggtcggt ctcgagaacc   5700
agcctggtct ccaacccgcc aggcgtaaat agggtgatta caagagagga gtttgaggcg   5760
ttcgtagcac aacaacaatg acggtttgat gcgggtgcat acatctttc ctccgacacc   5820
ggtcaagggc atttacaaca aaaatcagta aggcaaacgg tgctatccga agtggtgttg   5880
gagaggaccg aattggagat ttcgtatgcc ccgcgcctcg accaagaaaa agaagaatta   5940
ctacgcaaga aattacagtt aaatcccaca cctgctaaca gaagcagata ccagtccagg   6000
aaggtggaga acatgaaagc cataacagct agacgtattc tgcaaggcct agggcattat   6060
ttgaaggcag aaggaaaagt ggagtgctac cgaaccctgc atcctgttcc tttgtattca   6120
tctagtgtga accgtgcctt ttcaagcccc aaggtcgcag tggaagcctg taacgccatg   6180
ttgaaagaga actttccgac tgtggcttct tactgtatta ttccagagta cgatgcctat   6240
ttggacatgg ttgacggagc ttcatgctgc ttagacactg ccagtttttg ccctgcaaag   6300
ctgcgcagct ttccaaagaa acactcctat ttggaaccca caatacgatc ggcagtgcct   6360
tcagcgatcc agaacacgct ccagaacgtc ctggcagctg ccacaaaaag aaattgcaat   6420
gtcacgcaaa tgagagaatt gcccgtattg gattcggcgg cctttaatgt ggaatgcttc   6480
aagaaatatg cgtgtaataa tgaatattgg gaaacgtttta aagaaaaccc catcaggctt   6540
actgaagaaa acgtggtaaa ttacattacc aaattaaaag gaccaaaagc tgctgctctt   6600
tttgcgaaga cacataattt gaatatgttg caggacatac caatggacag gtttgtaatg   6660
gacttaaaga gagacgtgaa agtgactcca ggaacaaaac atactgaaga acggcccaag   6720
gtacaggtga tccaggctgc cgatccgcta gcaacagcgt atctgtgcgg aatccaccga   6780
gagctggtta ggagattaaa tgcggtcctg cttccgaaca ttcatacact gtttgatatg   6840
tcggctgaag actttgacgc tattatagcc gagcacttcc agcctgggga ttgtgttctg   6900
gaaactgaca tcgcgtcgtt tgataaaagt gaggacgacg ccatggctct gaccgcgtta   6960
atgattctgg aagacttagg tgtggacgca gagctgttga cgctgattga ggcggctttc   7020
ggcgaaattt catcaataca tttgcccact aaaactaaat ttaaattcgg agccatgatg   7080
aaatctgaca tgttcctcac actgtttgtg aacacagtca ttaacattgt aatcgcaagc   7140
agagtgttga gagaacggct aaccggatca ccatgtgcag cattcattgg agatgacaat   7200
atcgtgaaag gagtcaaatc ggacaaatta atggcagaca ggtgcgccac ctggttgaat   7260
atggaagtca agattataga tgctgtggtg ggcgagaaag cgccttattt ctgtggaggg   7320
tttattttgt gtgactccgt gaccggcaca gcgtgccgtg tggcagaccc cctaaaaagg   7380
ctgtttaagc ttggcaaacc tctggcagca gacgatgaac atgatgatga caggagaagg   7440
gcattgcatg aagagtcaac acgctggaac cgagtgggta ttctttcaga gctgtgcaag   7500
gcagtagaat caaggtatga aaccgtagga acttccatca tagttatggc catgactact   7560
ctagctagca gtgttaaatc attcagctac ctgagagggg cccctataac tctctacggc   7620
taacctgaat ggactacgac atagtctagt ccgccaagnn nnnnnnnnnn nnnnnnnnnn   7680
nnnnnnnnnn nnnnnnnnnn nnnnnnnnnn nnnnnnnnnn nnnnnnnnnn nnnnnnnnnn   7740
nnnnnnnnnn nnnnnnnnnn nnnnnnnnnn nnnnnnnnnn nnnnnnnnnn tctagcagga   7800
gagtcccgac ctccaggaga gaccagggcc acccttaagn nnnnnnnnnn nnnnnnnnnn   7860
nnnnnnnnnn nnnnnnnnnn nnnnnnnnnn nnnnnnnnnn nnnnnnnnnn nnnnnnnnnn   7920
nnnnnnnnnn nnnnnnnnnn nnnnnnnnnn nnnnnnnnnn nnnnnnnnnn ngccgccacc   7980
atggttagca aaggcgagga agacaacatg gctattatta aagagttcat gcgcttcaag   8040
gtgcacatgg agggctccgt gaacggccac gagttcgaga tcgagggcga gggcgagggc   8100
cgcccctacg agggcaccca gaccgccaag ctgaaggtga ccaagggtgg ccccctgccc   8160
ttcgcctggg acatcctgtc ccctcagttc atgtacggct ccaaggccta cgtgaagcac   8220
cccgccgaca tccccgacta cttgaagctg tccttccccg agggcttcaa gtgggagcgc   8280
gtgatgaact tcgaggacgg cggcgtggtg accgtgaccc aggactcctc cctgcaggac   8340
ggcgagttca tctacaaggt gaagctgcgc ggcaccaact tcccctccga cggccccgta   8400
atgcagaaga gaccatgggc ctgggaggcc tcctccgagc ggatgtaccc cgaggacggc   8460
gccctgaagg cgagatcaa gcagaggctg aagctgaagg acggcggcca ctacgacgct   8520
gaggtcaaga ccacctacaa ggccaagaag cccgtgcagc tgcccggcgc ctacaacgtc   8580
aacatcaagt tggacatcac ctcccacaac gaggactaca ccatcgtgga acagtacgaa   8640
cgcgccgagg gccgccactc caccggcggc atggacgagc tgtacaagag atctcgagct   8700
caagcttcga attctgcagt cgacggtacc gcgggcccgg gatccaccgg atctagataa   8760
taacatnnnn nnnnnnnnnn nnnnnnnnnn nnnnnnnnnn nnnnnnnnnn nnnnnnnnnn   8820
nnnnnnnnnn nnnnnnnnnn nnnnnnnnnn nnnnnnnnnn nnnnnnnnnn nnnnnnnnnn   8880
nnnnnnnnnn nnnnnnnnat ggaattggca agctgcttac atagaactcg cggcgattgg   8940
catgccgcct taaaattttt attttatttt ttcttttctt ttccgaatcg gattttgttt   9000
ttaatatttc                                                          9010
```

SEQ ID NO: 378          moltype = DNA  length = 99
FEATURE                  Location/Qualifiers
source                    1..99
                          mol_type = other DNA
                          organism = synthetic construct
SEQUENCE: 378
tacacttacc atacccgcg cgtcctggat tcgcggaaac gcgtacatcc agctgacgag   60

-continued

```
tcccaaatag gacgaaacgc gcccccacaa tttcaacaa                       99

SEQ ID NO: 379         moltype = DNA   length = 88
FEATURE                Location/Qualifiers
source                 1..88
                       mol_type = other DNA
                       organism = synthetic construct
SEQUENCE: 379
tacacttacc ataccccgcg cgtctggatt cgcggaaacg cgtacatcca ggtcccaaat  60
aggacacgcg cccccacaat ttcaacaa                                    88

SEQ ID NO: 380         moltype = DNA   length = 99
FEATURE                Location/Qualifiers
source                 1..99
                       mol_type = other DNA
                       organism = synthetic construct
SEQUENCE: 380
tacacttacc ataccccgcg cgtttcgtcc tatttgggac tcgtcagctg gatgtacgcg  60
tttccgcgaa tccaggacgc gcccccacaa tttcaacaa                        99

SEQ ID NO: 381         moltype = DNA   length = 99
FEATURE                Location/Qualifiers
source                 1..99
                       mol_type = other DNA
                       organism = synthetic construct
SEQUENCE: 381
tacacttacc ataccccgcg cgtcctggat tcgcggaaac gcgtacatcc agctgacgag  60
tcccaaatag gacgaaacgc gcccccacaa tttcaacaa                        99

SEQ ID NO: 382         moltype = DNA   length = 88
FEATURE                Location/Qualifiers
source                 1..88
                       mol_type = other DNA
                       organism = synthetic construct
SEQUENCE: 382
tacacttacc ataccccgcg cgtctggatt cgcggaaacg cgtacatcca ggtcccaaat  60
aggacacgcg cccccacaat ttcaacaa                                    88

SEQ ID NO: 383         moltype = DNA   length = 99
FEATURE                Location/Qualifiers
source                 1..99
                       mol_type = other DNA
                       organism = synthetic construct
SEQUENCE: 383
tacacttacc ataccccgcg cgtttcgtcc tatttgggac tcgtcagctg gatgtacgcg  60
tttccgcgaa tccaggacgc gcccccacaa tttcaacaa                        99

SEQ ID NO: 384         moltype = DNA   length = 99
FEATURE                Location/Qualifiers
source                 1..99
                       mol_type = other DNA
                       organism = synthetic construct
SEQUENCE: 384
tacacttacc ataccccgcg cgtcctggat tcgcggaaac gcgtacatcc agctgacgag  60
tcccaaatag gacgaaacgc gcccccacaa tttcaacaa                        99

SEQ ID NO: 385         moltype = DNA   length = 88
FEATURE                Location/Qualifiers
source                 1..88
                       mol_type = other DNA
                       organism = synthetic construct
SEQUENCE: 385
tacacttacc ataccccgcg cgtctggatt cgcggaaacg cgtacatcca ggtcccaaat  60
aggacacgcg cccccacaat ttcaacaa                                    88

SEQ ID NO: 386         moltype = DNA   length = 99
FEATURE                Location/Qualifiers
source                 1..99
                       mol_type = other DNA
                       organism = synthetic construct
SEQUENCE: 386
tacacttacc ataccccgcg cgtttcgtcc tatttgggac tcgtcagctg gatgtacgcg  60
tttccgcgaa tccaggacgc gcccccacaa tttcaacaa                        99

SEQ ID NO: 387         moltype = DNA   length = 127
FEATURE                Location/Qualifiers
source                 1..127
                       mol_type = other DNA
                       organism = synthetic construct
```

```
SEQUENCE: 387
cacgtggatc tgagatccaa ttaggtcgtg cgtttcgtcc tatttgggac tcgtcagctg   60
gatgtacgcg tttccgcgaa tccaggacgc acggctgatg ctcgtgcgtg agaggtgggg   120
aaaagag                                                            127

SEQ ID NO: 388          moltype = DNA   length = 132
FEATURE                 Location/Qualifiers
source                  1..132
                        mol_type = other DNA
                        organism = synthetic construct
SEQUENCE: 388
cacgtggatc tgagatccaa ttaggtgtgc cgtttcgtcc tatttgggac tcgtcagctg   60
gatgtacgcg tttccgcgaa tccaggacgg cacgaagcca tatcttctgt gccggagagg   120
tggggaaaag ag                                                      132

SEQ ID NO: 389          moltype = DNA   length = 127
FEATURE                 Location/Qualifiers
source                  1..127
                        mol_type = other DNA
                        organism = synthetic construct
SEQUENCE: 389
cacgtggatc tgagatccaa ttaggtcgtg cgtttcgtcc tatttgggac tcgtcagctg   60
gatgtacgcg tttccgcgaa tccaggacgc acggctgatg ctcgtgcgtg agaggtgggg   120
aaaagag                                                            127

SEQ ID NO: 390          moltype = DNA   length = 132
FEATURE                 Location/Qualifiers
source                  1..132
                        mol_type = other DNA
                        organism = synthetic construct
SEQUENCE: 390
cacgtggatc tgagatccaa ttaggtgtgc cgtttcgtcc tatttgggac tcgtcagctg   60
gatgtacgcg tttccgcgaa tccaggacgg cacgaagcca tatcttctgt gccggagagg   120
tggggaaaag ag                                                      132

SEQ ID NO: 391          moltype = DNA   length = 127
FEATURE                 Location/Qualifiers
source                  1..127
                        mol_type = other DNA
                        organism = synthetic construct
SEQUENCE: 391
cacgtggatc tgagatccaa ttaggtcgtg cgtttcgtcc tatttgggac tcgtcagctg   60
gatgtacgcg tttccgcgaa tccaggacgc acggctgatg ctcgtgcgtg agaggtgggg   120
aaaagag                                                            127

SEQ ID NO: 392          moltype = DNA   length = 131
FEATURE                 Location/Qualifiers
source                  1..131
                        mol_type = other DNA
                        organism = synthetic construct
SEQUENCE: 392
cacgtggatc tgagatccaa ttaggttgcc gtttcgtcct atttgggact cgtcagctgg   60
atgtacgcgt ttccgcgaat ccaggacggc acgaagccat atcttctgtg ccggagaggt   120
ggggaaaaga g                                                       131

SEQ ID NO: 393          moltype = DNA   length = 132
FEATURE                 Location/Qualifiers
source                  1..132
                        mol_type = other DNA
                        organism = synthetic construct
SEQUENCE: 393
cacgtggatc tgagatccaa ttaggtgtgc cgtttcgtcc tatttgggac tcgtcagctg   60
gatgtacgcg tttccgcgaa tccaggacgg cacgaagcca tatcttctgt gccggagagg   120
tggggaaaag ag                                                      132

SEQ ID NO: 394          moltype = RNA   length = 94
FEATURE                 Location/Qualifiers
source                  1..94
                        mol_type = other RNA
                        organism = synthetic construct
SEQUENCE: 394
gcgctcgtgt agctcattag ctccgagcgc gtcctggatt cgcggaaacg cgtacatcca   60
gctgacgagt cccaaatagg acgaaacgcg ctcg                              94

SEQ ID NO: 395          moltype = AA   length = 9
FEATURE                 Location/Qualifiers
source                  1..9
                        mol_type = protein
                        organism = synthetic construct
```

-continued

SEQUENCE: 395
GGGGSGGGG                                                                  9

What is claimed herein is:

1. An RNA molecule comprising:

a) an open reading frame (ORF) encoding at least one cargo polypeptide; and b) at least one untranslated region (UTR) comprising at least one Aptamer and Ribozyme Equilibrium Shifting (ARES) region, which comprises:

i) a protein-binding aptamer that specifically binds to a target protein; and ii) a ribozyme.

2. The RNA molecule of claim 1, wherein the aptamer is selected from the group consisting of: a MS2 aptamer, a PP7 aptamer, a bovine immunodeficiency virus (BIV) transactivation response (Tar) aptamer, and a P22 aptamer; and/or wherein the target protein is selected from:

a) MS2 coat protein (MCP), which specifically binds to the MS2 aptamer;

b) PP7 coat protein (PCP), which specifically binds to the PP7 aptamer;

c) BIV trans-activator of transcription (Tat), which specifically binds to the BIV Tar aptamer; and d) a P22 N protein, which specifically binds to the P22 aptamer.

3. The RNA molecule of claim 1, wherein the ribozyme is a self-cleaving ribozyme selected from the group consisting of: hammerhead ribozyme (HHR), hepatitis delta virus (HDV) ribozyme, hairpin ribozyme, Varkud satellite (VS) ribozyme, glmS ribozyme, twister ribozyme, twister sister ribozyme, Pistol ribozyme, Hatchet ribozyme, and Hovlinc ribozyme.

4. The RNA molecule of claim 1, wherein the aptamer is 5' of the ribozyme in the ARES region, or wherein the aptamer is 3' of the ribozyme in the ARES region.

5. The RNA molecule of claim 1, wherein the at least one ARES region is located in the UTR 5' of the ORF (5' UTR), and/or wherein the at least one ARES region is located in the UTR 3' of the ORF (3' UTR).

6. The RNA molecule of claim 1, wherein the at least one ARES region modulates the stability of the RNA molecule and/or modulates translation of the at least one cargo polypeptide encoded by the ORF.

7. The RNA molecule of claim 1, wherein the at least one ARES region is an ON-switch ARES region structured such that either the aptamer or the ribozyme, but not both, can form at one time in the RNA molecule; wherein in an RNA molecule comprising the ON-switch ARES region:

a) in the presence of the target protein, the aptamer is stabilized, the ribozyme cannot form, the RNA molecule is not cleaved, and the ORF can be translated (ON); and/or b) in the absence of the target protein, the aptamer is not stabilized, the ribozyme can form, the RNA molecule is cleaved, and the ORF cannot be translated (OFF).

8. The RNA molecule of claim 7, wherein the ON-switch ARES region comprises:

a) the aptamer comprising:

i) a first (a) region and a complementary (a*) region that can hybridize to the first (a) region; and ii) a primary second (b1) region and a complementary (b*) region that can hybridize to the primary second (b1) region or to a secondary second (b2) region in the ribozyme; and b) the ribozyme comprising:

i) the secondary second (b2) region and the complementary (b*) region; and ii) a third (c) region and a complementary (c*) region that can hybridize to the third (c) region.

9. The RNA molecule of claim 8, wherein the ON-switch ARES region comprises from 5' to 3':

a) the primary second (b1) region;

b) the first (a) region;

c) the complementary (a*) region that can hybridize to the first (a) region;

d) the complementary (b*) region that can hybridize to the primary second (bi) region in the aptamer or to a secondary second (b2) region in the ribozyme;

e) the third (c) region;

f) the complementary (c*) region that can hybridize to the third (c) region; and g) the secondary second (b2) region; or wherein the ON-switch ARES region comprises from 5' to 3':

a) the secondary second (b2) region;

b) the third (c) region;

c) the complementary (c*) region that can hybridize to the third (c) region;

d) the complementary (b*) region that can hybridize to the secondary second (b2) region in the ribozyme or to a primary second (bi) region in the aptamer;

e) the first (a) region;

f) the complementary (a*) region that can hybridize to the first (a) region; and g) the primary second (b1) region.

10. The RNA molecule of claim 1, wherein the at least one ARES region is a stabilization/degradation ARES region, which comprises in the 3' UTR, from 5' to 3':

a) a stabilization domain;

b) an ON-switch ARES region structured such that either the aptamer or the ribozyme, but not both, can form at one time in the RNA molecule; and c) a degradation domain;

wherein in an RNA molecule comprising a stabilization/ degradation ARES region:

i) in the presence of the target protein, the aptamer is stabilized, the ribozyme cannot form, the RNA molecule is not cleaved, the degradation domain is retained, the RNA molecule is degraded, and the ORF cannot be translated (OFF); and/or ii) in the absence of the target protein, the aptamer is not stabilized, the ribozyme can form, the RNA molecule is cleaved, the degradation domain is not retained, the stabilization domain protects the RNA molecule from degradation, and the ORF can be translated (ON).

11. The RNA molecule of claim 1, wherein the at least one ARES region is an OFF-switch ARES region structured such that either both the aptamer and the ribozyme, or at least one stabilization stem, can form at one time in the RNA molecule;

wherein in an RNA molecule comprising the OFF-switch ARES region:

a) in the presence of the target protein, the aptamer is stabilized, the ribozyme can form, the at least one stabilization stem cannot form, the RNA molecule is cleaved, and the ORF cannot be translated (OFF); and/or b) in the absence of the target protein, the aptamer is not stabilized, the ribozyme cannot form, the at least one stabilization stem can form, the RNA molecule is not cleaved, and the ORF can be translated (ON).

12. The RNA molecule of claim 11, wherein the OFF-switch ARES region comprises:

a) the aptamer comprising:

i) a first (a) region and a complementary (a*) region that can hybridize to the first (a) region; and ii) a primary second (b1) region and a primary complementary (b1*) region that can hybridize to the primary second (b1) region or to a secondary second (b2) region;

b) the ribozyme comprising:

i) the secondary second (b2) region and a secondary complementary (b2*) region that can hybridize to the secondary second (b2) region; and ii) a third (c) region and a complementary (c*) region that can hybridize to the third (c) region; and c) the at least one stabilization stem comprising:

i) a fourth (d) region and a complementary (d*) region that can hybridize to the fourth (d) region; and ii) the secondary second (b2) region of the ribozyme and the primary complementary (b1*) region of the aptamer.

13. The RNA molecule of claim 12, wherein the OFF-switch ARES region comprises from 5' to 3':

a) the primary second (bi) region;

b) the first (a) region;

c) the complementary (a*) region that can hybridize to the first (a) region;

d) the primary complementary (b1*) region that can hybridize to the primary second (b1) region or to a secondary second (b2) region;

e) the fourth (d) region;

f) the complementary (d*) region that can hybridize to the fourth (d) region;

g) the secondary second (b2) region;

h) the third (c) region;

i) the complementary (c*) region that can hybridize to the third (c) region; and j) the secondary complementary (b2*) region that can hybridize to the secondary second (b2) region; or wherein the OFF-switch ARES region comprises from 5' to 3':

a) the secondary second (b2) region;

b) the third (c) region;

c) the complementary (c*) region that can hybridize to the third (a) region;

d) the secondary complementary (b2*) region that can hybridize to the secondary second (b2) region or to a primary second (bi) region;

e) the fourth (d) region;

f) the complementary (d*) region that can hybridize to the fourth (d) region;

g) the primary second (b1) region;

h) the first (a) region;

i) the complementary (a*) region that can hybridize to the first (a) region; and j) the primary complementary (b1*) region that can hybridize to the primary second (b1) region.

14. The RNA molecule of claim 11, wherein the OFF-switch ARES region comprises:

a) the aptamer comprising:

i) a first (a) region and a complementary (a*) region that can hybridize to the first (a) region; and ii) a primary second (b1) region and a primary complementary (b1*) region that can hybridize to the primary second (b1) region or to a secondary second (b2) region;

b) the ribozyme comprising:

i) the secondary second (b2) region and a secondary complementary (b2*) region that can hybridize to the secondary second (b2) region; and ii) a third (c) region and a complementary (c*) region that can hybridize to the third (c) region;

c) a first stabilization stem comprising:

i) a primary fourth (d1) region and a complementary (d1*) region that can hybridize to the primary fourth (d1) region; and ii) the secondary second (b2) region of the ribozyme and the primary complementary (b1*) region of the aptamer; and d) a second stabilization stem comprising:

i) a secondary fourth (d2) region and a complementary (d2*) region that can hybridize to the secondary fourth (d2) region; and ii) the primary second (b1) region of the aptamer and a tertiary complementary (b3*) region that can hybridize to the primary second (b1) region.

15. The RNA molecule of claim 14, wherein the OFF-switch ARES region comprises from 5' to 3':

a) the tertiary complementary (b3*) region that can hybridize to the primary second (bi) region;

b) the complementary (d2*) region that can hybridize to the secondary fourth (d2) region;

c) the secondary fourth (d2) region;

d) the primary second (b1) region;

e) the first (a) region;

f) the complementary (a*) region that can hybridize to the first (a) region;

g) the primary complementary (b1*) region that can hybridize to the primary second (b1) region or to the secondary second (b2) region;

h) the primary fourth (d1) region;

i) the complementary (d1*) region that can hybridize to the primary fourth (d1) region;

j) the secondary second (b2) region;

k) the third (c) region;

l) the complementary (c*) region that can hybridize to the third (c) region; and m) the secondary complementary (b2*) region that can hybridize to the secondary second (b2) region.

16. The RNA molecule of claim 11, wherein the OFF-switch ARES region comprises:

a) the ribozyme comprising:

i) a first (a) region and a complementary (a*) region that can hybridize to the first (a) region; and ii) a primary second (b1) region and a primary complementary (b1*) region that can hybridize to the primary second (bi) region or to a secondary second (b2) region;

b) the aptamer comprising:

i) the secondary second (b2) region and a secondary complementary (b2*) region that can hybridize to the secondary second (b2) region; and ii) a third (c) region and a complementary (c*) region that can hybridize to the third (c) region;

c) a first stabilization stem comprising:
  i) a primary fourth (d1) region and a complementary (d1*) region that can hybridize to the primary fourth (d1) region; and
  ii) the secondary second (b2) region of the aptamer and the primary complementary (b1*) region of the ribozyme; and
d) a second stabilization stem comprising:
  i) a secondary fourth (d2) region and a complementary (d2*) region that can hybridize to the secondary fourth (d2) region; and
  ii) the primary second (b1) region of the ribozyme and a tertiary complementary (b3*) region that can hybridize to the primary second (b1) region.

17. The RNA molecule of claim 16, wherein the OFF-switch ARES region comprises from 5' to 3':
  a) the tertiary complementary (b3*) region that can hybridize to the primary second (b1) region;
  b) the complementary (d2*) region that can hybridize to the secondary fourth (d2) region; c) the secondary fourth (d2) region;
  d) the primary second (b1) region;
  e) the first (a) region;
  f) the complementary (a*) region that can hybridize to the first (a) region;
  g) the primary complementary (b1*) region that can hybridize to the primary second (b1) region or to the secondary second (b2) region;
  h) the primary fourth (d1) region;
  i) the complementary (d1*) region that can hybridize to the primary fourth (d1) region;
  j) the secondary second (b2) region;
  k) the third (c) region;
  l) the complementary (c*) region that can hybridize to the third (c) region; and
  m) the secondary complementary (b2*) region that can hybridize to the secondary second (b2) region.

18. The RNA molecule of claim 1, wherein the at least cargo polypeptide is selected from:
  a) a detectable marker;
  b) an antigen
  c) an antibody;
  d) a cytokine;
  e) a cell therapy protein;
  f) a tumor suppressor protein;
  g) a programmed cell death protein;
  h) a site-specific nuclease; or
  i) a therapeutic protein.

19. The RNA molecule of claim 18, wherein:
  a) the detectable marker is a fluorescent polypeptide;
  b) the antigen is severe acute respiratory syndrome coronavirus 2 (SARS-CoV-2) spike gene, respiratory syncytial virus (RSV) F protein, influenza hemagglutinin, or a tumor-associated antigen;
  c) the antibody is a monoclonal antibody; and/or the antibody is an anti-claudin 18 isoform 2 (anti-CLDN18.2) antibody, an anti-cytotoxic T-lymphocyte-associated protein 4 (anti-CTLA-4) antibody, or an anti-glucocorticoid-induced tumor necrosis factor receptor (TNFR)-related protein (anti-GITR) antibody;
  d) the cytokine is interleukin-2 (IL-2), interleukin-7 (IL-7), interleukin-12 (IL-12), Tumor necrosis factor receptor superfamily, member 4 (TNFRSF4) ligand (OX40L), interleukin-23 (IL-23));
  e) the cell therapy protein is claudin-6 (CLDN6), a chimeric antigen receptor (CAR) protein, or a T cell receptor;
  f) the tumor suppressor protein is tumor protein 53 (p53), breast cancer gene 1 (BRCA1), or breast cancer gene 2 (BRCA2);
  g) the programmed cell death protein is B-cell lymphoma 2 (Bcl-2)-associated X protein (Bax) or a caspase;
  h) the site-specific nuclease is Prime Editor 2 (PE2), Prime Editor 3 (PE3), Prime Editor 4 (PE4), Prime Editor 5 (PE5), Prime Editor 2 Max (PE2max), or Prime Editor 3 Max (PE3max); or
  i) the therapeutic protein is vascular endothelial growth factor (VEGF), Glucagon-like peptide-1, or insulin.

20. The RNA molecule of claim 19, wherein the tumor-associated antigen is New York esophageal squamous cell carcinoma 1 for melanoma or kallikrein-2 for prostate cancer.

21. The RNA molecule of claim 1, which is a messenger RNA (mRNA), further comprising a 5' cap and a 3' polyA tail.

22. A self-amplifying RNA (saRNA) comprising from 5' to 3':
  a) a 5' conserved sequence element (CSE);
  b) a first open reading frame (ORF) encoding an RNA-dependent RNA polymerase (RdRP), operably linked to a promoter in the 5' CSE;
  c) a subgenomic promoter (SGP);
  d) a second ORF encoding at least one cargo polypeptide, operably linked to the SGP; and
  e) a 3' CSE; and
wherein the 5' CSE, a region between the first and second ORFs, and/or the 3' CSE further comprises at least one Aptamer and Ribozyme Equilibrium Shifting (ARES) region in a sense or anti-sense orientation, wherein the ARES region comprises:
  i) a protein-aptamer that specifically binds to a target protein; and
  ii) a ribozyme.

* * * * *